United States Patent
Selvakumar et al.

(10) Patent No.: US 7,160,912 B2
(45) Date of Patent: Jan. 9, 2007

(54) HETEROCYCLIC COMPOUNDS HAVING ANTIBACTERIAL ACTIVITY: PROCESS FOR THEIR PREPARATION AND PHARMACEUTICAL COMPOSITIONS CONTAINING THEM

(75) Inventors: Natesan Selvakumar, Hyderabad (IN); Jagattaran Das, Hyderabad (IN); Sanjay Trehan, Hyderabad (IN); Javed Iqbal, Hyderabad (IN); Magadi Sitaram Kumar, Hyderabad (IN); Ramanujam Rajagopalan, Hyderabad (IN); Mamidi Naga Venkata Srinivasa Rao, Hyderabad (IN)

(73) Assignees: Dr.Reddy's Laboratories Ltd., Hyderabad (IN); Dr. Reddy's Laboratories, Inc., Bridgewater, NJ (US)

( * ) Notice: Subject to any disclaimer, the term of this patent is extended or adjusted under 35 U.S.C. 154(b) by 44 days.

(21) Appl. No.: 10/613,414

(22) Filed: Jul. 3, 2003

(65) Prior Publication Data
US 2004/0102494 A1    May 27, 2004

Related U.S. Application Data

(63) Continuation-in-part of application No. 10/032,392, filed on Dec. 21, 2001.

(30) Foreign Application Priority Data

Dec. 26, 2000 (IN) .................. 1124/MAS/2000
Jan. 4, 2001 (IN) .................. 15/MAS/2001

(51) Int. Cl.
 A61K 31/421  (2006.01)
 C07D 263/04  (2006.01)
 C07D 413/12  (2006.01)

(52) U.S. Cl. .............. 514/376; 548/225; 548/229; 544/106; 544/132; 544/139; 544/358; 544/370; 546/268.1; 546/272.7

(58) Field of Classification Search .......... 548/229; 544/139, 132, 370; 514/376; 546/272.7
See application file for complete search history.

(56) References Cited

U.S. PATENT DOCUMENTS

| 2,987,505 | A | | 6/1961 | Werner et al. ............. 260/77.5 |
| 3,651,079 | A | | 3/1972 | Skorez et al. |
| 3,963,706 | A | | 6/1976 | Pfirrmann |
| 4,174,958 | A | | 11/1979 | Pilgram |
| 4,910,341 | A | | 3/1990 | Lang et al. |
| 5,883,093 | A | * | 3/1999 | Hutchinson et al. ... 514/210.02 |
| 6,124,334 | A | | 9/2000 | Hutchinson |
| 6,277,985 | B1 | * | 8/2001 | Gadwood et al. ............. 544/60 |
| 6,512,112 | B1 | * | 1/2003 | Gadwood et al. ........... 540/543 |
| 6,515,135 | B1 | * | 2/2003 | Gadwood et al. ........... 548/231 |
| 6,525,193 | B1 | * | 2/2003 | Gadwood et al. .......... 544/58.2 |

FOREIGN PATENT DOCUMENTS

| DE | 2357591 | 5/1974 |
| DE | 3536066 | 4/1986 |
| JP | 11-322729 | 11/1999 |
| WO | 95/07271 | 3/1995 |
| WO | 96/13502 | 5/1996 |
| WO | 97/27188 | 7/1997 |
| WO | 01/09107 | 2/2001 |
| WO | 03/011859 | 2/2003 |

OTHER PUBLICATIONS

U.S. Patent 4,910,341 corresponding to German Publication DE 3536066, dated Apr. 17, 1986.
U.S. Patent 3,963,706 corresponding to German Publication DE 2357591, dated May 22, 1974.
Melissaris, A. P. and J. A. Mikroyannidis. "Thermally Stable Polymers Based on Bismaleimides Containing Amide, Imide and Ester Linkages", *J. Polymer Science: Polymer Chemistry Part A* (1989), 27: 245-262.
Artico, M. et al. "Research on Compounds with Antiblastic Activity", *Il Farmaco—Ed. Sci.*, (1969), 24(2): 179-190.
Ueda, Minoru et al. "Syntheses and Novel Bioactivites of Artificial Leaf-Opening Substances of *Lespedeza cuneata* G. Don, Designed for the Bioorganic Studies of Nyctinasty", *Tetrahedron* (1999), 55: 10925-10936.
Ricca, Jean-Marc and David H.G. Crout. "Selectivity and Specificity in Substrate Binding to Proteases: Novel Hydrolytic Reactions Catalysed by α-Chymotrypsin . . . " *J. Chem. Soc. Perkin Trans. I* (1993), 1225-1233.
Braun, et al 1979, Liebigs, Annalen der Chemie, 2, 200-9.
Sorokin, et al, 1987, Khimicheskaya Tekhnologiya, 24(5), 561-5.

* cited by examiner

*Primary Examiner*—Golam M. M. Shameem
(74) *Attorney, Agent, or Firm*—Milagros A. Cepeda; Edward D. Pergament

(57) ABSTRACT

The present invention relates to novel oxazolidinone compounds of formula (I), their stereoisomers, their salts and pharmaceutical compositions containing them.

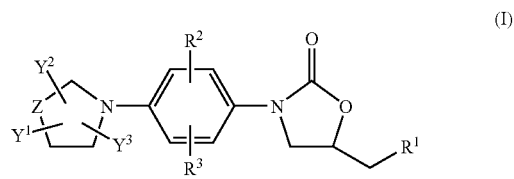

The present invention also relates to a process for the preparation of the above said novel compounds, their stereoisomers, their salts and pharmaceutical compositions.

32 Claims, No Drawings

HETEROCYCLIC COMPOUNDS HAVING ANTIBACTERIAL ACTIVITY: PROCESS FOR THEIR PREPARATION AND PHARMACEUTICAL COMPOSITIONS CONTAINING THEM

This application is a continuation-in-part of copending application Ser. No. 10/032,392 filed on Dec. 21, 2001.

FIELD OF THE INVENTION

The present invention relates to novel oxazolidinone compounds of formula (I), their stereoisomers, their salts and pharmaceutical compositions containing them.

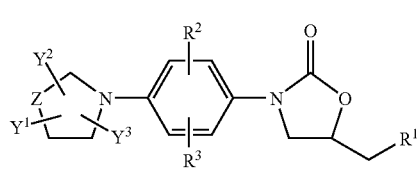

The present invention also relates to a process for the preparation of the above said novel compounds, their stereoisomers, their salts and pharmaceutical compositions.

BACKGROUND OF THE INVENTION

Since the discovery of penicillin, pharmaceutical companies have produced more than one hundred antibacterial agents to combat a wide variety of bacterial infections. In the past several years, there has been rapid emergence of bacterial resistance to several of these antibiotics. The multi-drug resistance among these bacterial pathogens may also be due to mutation leading to more virulent clinical isolations. The most disturbing milestone has been the acquisition of resistance to vancomycin, an antibiotic generally regarded as the agent of last resort for serious Gram-positive infections. It is believed that the proliferation of multidrug resistant bacteria is brought on by a wide spread use, or rather misuse, of existing antibacterials, further exacerbated by the use of antibacterials as feed supplements in farm animals and poultry.

Bacterial infection is a long-term problem that requires innovative new therapeutics. Moreover, in view of the increasing reports of vancomycin-resistant bacterial isolates and growing problem of bacterial resistance, there is an urgent need for new molecular entities effective against the emerging bacterial organisms. The growing problem of multidrug resistance has intensified the search for new antibiotics. Yet new drugs are difficult to develop and bacterial strains resistant to new drugs may quickly emerge. For example, soon after introduction of Linezolid (Zyovx™, Pharmacia Upjohn), a representative of a first entirely new class of antibacterials released into the market over the past 30 years, clinics reported cases of resistance (Lancet 2001, 358(9277): 207–8). Resistant strains have been selected in the lab where a target site alteration was found to reduce drug binding (Antimicrob. Agents Chemother. 2001, 3(3): 288–294).

Oxazolidinones, a class of compounds that includes Linezolid, contain an oxazolidinone moiety

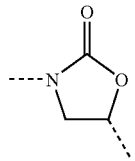

For example, compounds of the generalized structure

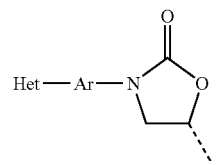

are known in the prior art. In these compounds, a heterocyclic moiety (Het) is connected to the oxazolidinone moiety through an aromatic nucleus (Ar). Specific examples of oxazolidinone compounds are disclosed in International publication nos. WO 01/09107, WO 97/27188, WO 96/13502 and WO 96/13502. Certain oxazolidinones are believed to be useful as antibacterials (J. Med. Chem., 1996, 39, 673), antihistamines and anti allergic agents (EP 291, 244), anticonvulsants (DE 3,915,184), as well as for treating cognition disorders, anti psychotics, anti platelet aggregators, antidepressants, sedatives, hypnotics, and as monoamine oxidase inhibitors (WO 97/13768).

SUMMARY OF THE INVENTION

In accordance with one aspect, the invention provides compounds that are new oxazolidinone derivatives, or salts thereof, or stereoisomers thereof, the molecules of which include a) a heterocyclic moiety containing a 5-membered heterocyclic skeleton that is at least partially saturated; b) a benzene ring, which may be substituted or unsubstituted; and c) an oxazolidinone moiety, wherein the heterocycliclic moiety is connected to the oxazolidinone moiety through the benzene ring. Specific embodiments are described in detail.

In accordance with others aspects, the invention also provide a method of using various oxazolidinone compounds, processes for their preparation, and pharmaceutical compositions containing such compounds.

DETAILED DESCRIPTION OF THE INVENTION

The present invention provides a novel oxazolidinone compounds having the general formula (I),

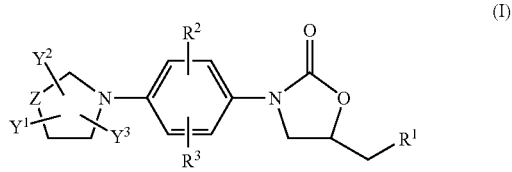

or a salt thereof or a stereoisomer thereof, where $R^1$ is halo, azido, isothiocyano, thioalcohol, —$OR^4$, —$NHR^4$ or —$N(R^4)_2$, where $R^4$ represents hydrogen atom, or substituted or unsubstituted groups selected from (C$_1$–C$_{10}$)alkyl, (C$_1$–C$_{10}$)acyl, thio(C$_1$–C$_{10}$)acyl, —C(=O)—(C$_1$–C$_{10}$)alkoxy, —C(=S)—(C$_3$–C$_8$)cycloalkoxy, —C(=O)—(C$_2$–C$_{10}$)alkenyloxy, —C(=O)—(C$_2$–C$_{10}$)alkenyl, —C(=O)-aryloxy, —C(=S)—C$_1$–C$_{10}$)alkoxy, —C(=S)—(C$_2$–C$_{10}$)alkenyloxy, —C(=S)-aryloxy, —C(=O)—C(=O)—(C$_1$–C$_{10}$)alkyl, —C(=O)—C(=O)-aryl, —C(=O)—C(=O)—(C$_1$–C$_{10}$)alkoxy, —C(=O)—C(=O)-aryloxy, —(C=S)—S—(C$_1$–C$_{10}$)alkyl, —(C=S)—NH$_2$, —(C=S)—NH—(C$_1$–C$_{10}$)alkyl, —C(=S)—N—((C$_1$–C$_{10}$)alkyl)$_2$, —C(=S)—NH—(C$_2$–C$_{10}$)alkenyl, (C=S)—(C=O)—(C$_1$–C$_{10}$)alkoxy, —(C=S)—(C=O)-aryloxy, —C(=S)—O—(C=O)—(C$_1$–C$_{10}$)alkyl, C(=S)—C(=S)—(C$_1$–C$_{10}$)alkyl, —C(=S)—C(=S)-aryl, thiomorpholinyl-C(=S)— or pyrrolidinyl-C(=S)—;

R$^2$ and R$^3$, which may be the same or different, are each independently hydrogen, halogen, (C$_1$–C$_{10}$)alkyl, halogenated (C$_1$–C$_{10}$)alkyl, cyano, nitro, SR$^a$, NR$^a$, or OR$^a$, in which R$^a$ is hydrogen, (C$_1$–C$_{10}$)alkyl or halogenated (C$_1$–C$_{10}$)alkyl;

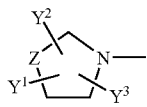

is a heterocyclic moiety in which

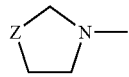

is a 5-membered heterocyclic skeleton, Z represents O, S, =CH, —CH$_2$ or NR$^6$, where R$^b$ is hydrogen or a moiety, which may be substituted or unsubstituted, straight chain or branched, selected from the group consisting of (C$_1$–C$_{10}$)alkyl, (C$_2$–C$_{10}$)alkenyl, (C$_3$–C$_8$)cycloalkyl, hydroxy (C$_1$–C$_{10}$)alkyl, (C$_1$–C$_{10}$)alkylhydroxy, (C$_1$–C$_{10}$)alkylamino, amino(C$_1$–C$_{10}$)alkyl, (C$_1$–C$_{10}$)alkoxy, aryl, aralkyl, aryloxy, (C$_1$–C$_{10}$)alkylcarbonyl, arylcarbonyl, (C$_1$–C$_{10}$)alkoxycarbonyl and aryloxycarbonyl;

Y$^1$ represents =O or =S group and Y$^2$ and Y$^3$ independently represent hydrogen, halogen, cyano, nitro, formyl, hydroxy, amino, =O, =S group or substituted or unsubstituted groups selected from (C$_1$–C$_{10}$)alkyl, hydroxy(C$_1$–C$_{10}$)alkyl, (C$_1$–C$_{10}$)alkylhydroxy, (C$_1$–C$_{10}$)alkoxy C$_1$–C$_{10}$alkyl, (C$_1$–C$_{10}$)alkylcarbonyl, (C$_1$–C$_{10}$)alkoxycarbonyl, arylcarbonyl, carboxy(C$_1$–C$_{10}$)alkyl, (C$_1$–C$_{10}$)alkylsulfonyl, (C$_1$–C$_{10}$)alkylcarbonyl (C$_1$–C$_{10}$)alkyl, arylcarbonylamino (C$_1$–C$_{10}$)alkyl, (C$_1$–C$_{10}$)alkylcarbonyloxy (C$_1$–C$_{10}$)alkyl, amino(C$_1$–C$_{10}$)alkyl, mono(C$_1$–C$_{10}$)alkylamino, di(C$_1$–C$_{10}$) alkylamino, arylamino, (C$_1$–C$_{10}$)alkoxy, aryl, aryloxy, aralkyl, heteroaryl, heteroaralkyl, heterocyclyl or heterocycloalkyl; Y$^2$ and Y$^3$ when present on adjacent carbon atoms together may also form a substituted or unsubstituted 5 or 6 membered aromatic or non-aromatic cyclic structure, optionally containing one or two hetero atoms selected from oxygen, sulfur or nitrogen.

Suitable groups represented by R$^4$ may be selected from hydrogen atom, (C$_1$–C$_{10}$)alkyl group such as methyl, ethyl, propyl, butyl and the like, which may be substituted; (C$_1$–C$_{10}$)acyl group of the formula —C(=O)R$^z$ where R$^z$ is hydrogen, (C$_1$–C$_{10}$)alkyl, aryl or heteroaryl wherein aryl is a group such as phenyl, naphthyl and the like; and heteroaryl is a group such as pyridyl, pyrrolidinyl, piperidinyl, indolyl, furyl and the like; wherein the acyl group is a group such as —C(=O)H, —C(=O)CH$_3$, —C(=O)CH$_2$CH$_3$, —C(=O)(CH$_2$)$_2$CH$_3$, —C(=O)(CH$_2$)$_3$CH$_3$, —C(=O)(CH$_2$)$_4$CH$_3$, —C(=O)(CH$_2$)$_5$CH$_3$, —C(=O)Ph and the like, the acyl group may be substituted; thio(C$_1$–C$_{10}$)acyl group of the formula —C(=S)R$^z$ where R$^z$ is hydrogen, (C$_1$–C$_{10}$)alkyl, aryl or heteroaryl wherein aryl is a group such as phenyl, naphthyl and the like; and heteroaryl is a group such as pyridyl, pyrrolidinyl, piperidinyl, indolyl, furyl and the like wherein the thioacyl group is a group such as —C(=S)H, —C(=S)CH$_3$, —C(=S)CH$_2$CH$_3$, —C(=S)Ph and the like, the thioacyl group may be substituted; —C(=O)—(C$_1$–C$_{10}$) alkoxy group, containing (C$_1$–C$_{10}$)alkyl group which may be linear or branched, such as —C(=O)-methoxy, —C(=O)-ethoxy, —C(=O)-propoxy, —C(=O)-isopropoxy and the like, the —C(=O)—(C$_1$–C$_{10}$)alkoxy group may be substituted; —C(=S)-cyclo(C$_3$–C$_8$)alkoxy group such as —C(=S)-cyclopropoxy, —C(=S)-cyclobutoxy, —C(=S)-cyclopentoxy, —C(=S)-cyclohexoxy and the like, the —C(=S)-cyclo(C$_3$–C$_6$)alkoxy may be substituted; —C(=O)—(C$_2$–C$_6$)alkenyl such as —C(=O)-ethenyl, —C(=O)-propenyl, —C(=O)-butenyl and the like, the —C(=O)—(C$_2$–C$_{10}$)alkenyl may be substituted; —C(=O)—(C$_2$–C$_{10}$)alkenyloxy group such as —C(=O)-ethenyloxy, —C(=O)-propenyloxy, —C(=O)-butenyloxy and the like, the —C(=O)—(C$_2$–C$_6$)alkenyloxy may be substituted; —C(=O)-aryloxy group such as —C(=O)-phenoxy, —C(=O)-benzyloxy group and the like, the —C(=O)-aryloxy group may be substituted; —C(=S)—(C$_1$–C$_{10}$)alkoxy group such as CH$_3$O—C(=S)—, C$_2$H$_5$O—C(=S)—C$_3$H$_7$O—C(=S)—, isopropoxy-C(=S)— and the like, which may be substituted; —C(=S)—(C2–C10)alkenyloxy group such as —C(=S)-ethenyloxy, —C(=S)-propenyloxy, —C(=S)-butenyloxy and the like, the —C(=S)—(C$_2$–C$_{10}$)alkenyloxy group may be substituted; —C(=S)-aryloxy group such as phenyl-O—C(=S)—, benzyl-O—C(=S)— and the like, which may be substituted; —C(=O)—C(=O)—(C$_1$–C$_{10}$)alkyl group such as —C(=O)—C(=O)methyl, —C(=O)—C(=O)ethyl, —C(=O)—C(=O)propyl, —C(=O)—C(=O)butyl and the like, which may be substituted; —C(=O)—C(=O)-aryl group such as —C(=O)—C(=O)phenyl, —C(=O)—C(=O)naphthyl and the like, which may be substituted; —C(=O)—C(=O)—(C$_1$–C$_{10}$)alkoxy group such as —C(=O)—C(=O)methoxy, —C(=O)—C(=O)ethoxy, —C(=O)—C(=O)propyloxy and the like, which may be substituted; —C(=O)—C(=O)-aryloxy group such as —C(=O)—C(=O)phenoxy, —C(=O)—C(=O)benzyloxy, which may be substituted; —(C=S)—S—(C$_1$–C$_{10}$) alkyl such as —(C=S)—S-methyl, —(C=S)—S-ethyl, —(C=S)—S-propyl and the like, which may be substituted; —(C=S)—NH$_2$; —(C=S)—NH—(C$_1$–C$_{10}$)alkyl such as —(C=S)—NH-methyl, —(C=S)—NH-ethyl, —(C=S)—NH-propyl and the like, which may be substituted; —C(=S)—N—((C$_1$–C$_{10}$)alkyl)$_2$ such as —C(=S)—N-(methyl)$_2$, —C(=S)—N-(ethyl)$_2$, —C(=S)—N-(propyl)$_2$ and the like, which may be substituted; —C(=S)—NH—(C$_2$–C$_{10}$)alkenyl such as —C(=S)—NH-ethenyl, —C(=S)—NH-propenyl, —C(=S)—NH-butenyl and the like, which may be substituted; —(C=S)—(C=O)—(C$_1$–C$_{10}$)alkoxy such as —(C=S)—(C=O)-methoxy, —(C=S)—(C=O)-ethoxy, —(C=S)—(C=O)-propoxy and the like, which may be substituted; —(C=S)—(C=O)-aryloxy such as —(C=S)—(C=O)-phenoxy, —(C=S)—(C=O)-naphthyloxy and the like, which may be substituted;

—C(=S)—O—(C=O)—(C$_1$–C$_{10}$)alkyl such as —C(=S)—O—(C=O)-methyl, —C(=S)—O—(C=O)-ethyl, —C(=S)—O—(C=O)-propyl and the like, which may be substituted; —C(=S)—C(=S)—(C$_1$–C$_{10}$)alkyl group such as —C(=S)—C(=S)methyl, —C(=S)—C(=S)ethyl, —C(=S)—C(=S)propyl and the like, which may be substituted; —C(=S—)—C(=S)aryl group such as —C(=S)—C(=S)phenyl, —C(=S)—C(=S)naphthyl and the like, which may be substituted; thiomorpholinyl-C(=S)— which may be substituted; or pyrrolidinyl-C(=S)— which may be substituted.

When the groups represented by R$^4$ are substituted, the substituents may be selected from halogen atom such as chlorine, fluorine, bromine and iodine; hydroxy, amino, mono(C$_1$–C$_{10}$)alkylamino such as methylamino, ethylamino, propylamino and the like, di(C$_1$–C$_{10}$)alkylamino such as dimethylamino, diethylamino, methylethylamino, dipropylamino, ethylpropylamino and the like, cyano, nitro, (C$_1$–C$_{10}$)alkoxy, aryl such as phenyl, naphthyl and the like; hydroxyaryl, pyridyl, hydroxy(C$_1$–C$_{10}$)alkyl, (C$_1$–C$_{10}$)alkyl hydroxy, (C$_1$–C$_{10}$)alkoxyaryl or carboxyl and its derivatives such as amides like CONH$_2$, CONHMe, CONMe$_2$, CONHEt, CONEt$_2$, CONHPh and the like, and esters such as COOMe, COOEt and the like.

Suitable groups represented by R$^2$ and R$^3$ may be selected from hydrogen, halogen atom such as fluorine, chlorine or bromine; (C$_1$–C$_{10}$)alkyl group such as methyl, ethyl, n-propyl, isopropyl, n-butyl, iso-butyl, t-butyl, n-pentyl, isopentyl, n-hexyl and the like; halo(C$_1$–C$_{10}$)alkyl group such as halomethyl, haloethyl, halopropyl, trihalomethyl and the like, wherein the halo group is selected from fluorine, chlorine, bromine or iodine; cyano, nitro; SR$^a$, NR$^a$, OR$^a$ where R$^a$ represents hydrogen or substituted or unsubstituted (C$_1$–C$_{10}$)alkyl group such as methyl, ethyl, propyl, isopropyl and the like; halo(C$_1$–C$_{10}$)alkyl such as halomethyl, haloethyl, halopropyl, haloisopropyl and the like, where the halo group is selected from fluro, chloro, bromo or iodo.

The substituents on R$^a$ are selected from hydroxy, halogen, nitro, amino, (C$_1$–C$_{10}$)alkoxy, carboxyl or cyano.

Suitable groups represented by Z may be selected from S, O, =CH or NR$^b$ where R$^b$ represents hydrogen or substituted or unsubstituted (C$_1$–C$_{10}$)alkyl such as methyl, ethyl, propyl, butyl, pentyl and the like, which may be substituted; (C$_2$–C$_{10}$)alkenyl such as ethenyl, propenyl, butenyl and the like, which may be substituted; (C$_3$–C$_8$)cycloalkyl such as cyclopropyl, cyclobutyl, cyclopentyl, cyclohexyl and the like, which may be substituted; hydroxy(C$_1$–C$_{10}$)alkyl such as hydroxymethyl, hydroxyethyl, hydroxypropyl, propyldihydroxy and the like, which may be substituted; (C$_1$–C$_{10}$) alkylhydroxy such as methylhydroxy, ethylhydroxy, propyl hydroxy. propyldihydroxy and the like, which may be substituted; (C$_1$–C$_{10}$)alkylamino such as methylamino, ethylamino, propylamino, butylamino and the like, which may be substituted, amino(C$_1$–C$_{10}$)alkyl such as aminomethyl, aminoethyl, aminopropyl, aminobutyl and the like, which may be substituted; (C$_1$–C$_{10}$)alkoxy such as methoxy, propoxy, isopropoxy and the like, which may be substituted; aryl group such as phenyl, naphthyl and the like, which may be substituted; aralkyl such as benzyl, phenethyl and the like, which may be substituted; aryloxy such as phenyloxy, naphthyloxy and the like, which may be substituted; (C$_1$–C$_{10}$)alkylcarbonyl such as methylcarbonyl, ethylcarbonyl, propylcarbonyl and the like, which may be substituted; arylcarbonyl such as phenylcarbonyl, naphthylcarbonyl and the like, which may be substituted; (C$_1$–C$_{10}$)alkoxycarbonyl such as methoxycarbonyl, ethoxycarbonyl, propoxycarbonyl and the like, which may be substituted; or aryloxycarbonyl such as phenyloxycarbonyl, naphthyloxycarbonyl and the like, which may be substituted.

The substituents on R$^b$ are selected from hydroxy, halogen, pyrrolidinyl-C(=S)—, nitro, amino, (C$_1$–C$_{10}$)alkyl, (C$_1$–C$_{10}$)alkoxy, carboxyl, oxo, thiooxo or cyano.

Y$^1$ represents =O or =S group, Y$^2$ and Y$^3$ are selected from hydrogen, halogen such as fluorine, chlorine, bromine or iodine; cyano, nitro, formyl, hydroxy, amino, =O, =S group, substituted or unsubstituted (C$_1$–C$_{10}$)alkyl such as methyl, ethyl, n-propyl, isopropyl, n-butyl, iso-butyl, t-butyl and the like; hydroxy(C$_1$–C$_{10}$)alkyl such as hydroxymethyl, hydroxyethyl, hydroxypropyl, propyldihydroxy and the like, which may be substituted; (C$_1$–C$_{10}$)alkylhydroxy such as methyl hydroxy, ethylhydroxy, propylhydroxy. propyldihydroxy and the like, which may be substituted; (C$_1$–C$_{10}$)alkoxy(C$_1$–C$_{10}$)alkyl group such as methoxymethyl, methoxyethyl, ethoxyethyl, ethoxymethyl, methoxypropyl, propoxymethyl, propoxyethyl and the like, which may be substituted; (C$_1$–C$_{10}$)alkylcarbonyl group such as methylcarbonyl, ethylcarbonyl and the like, which may be substituted; arylcarbonyl group such as phenylcarbonyl, naphtylcarbonyl and the like, which may be substituted; (C$_1$–C$_{10}$)alkoxycarbonyl group such as methoxycarbonyl, ethoxycarbonyl and the like, which may be substituted; carboxy(C$_1$–C$_{10}$)alkyl such as CH$_3$—COO, CH$_3$—CH$_2$—COO and the like, which may be substituted; (C$_1$–C$_{10}$)alkylsulfonyl group such as methylsulfonyl, ethylsulfonyl and the like, which may be substituted; (C$_1$–C$_{10}$)alkylcarbonylamino(C$_1$–C$_{10}$)alkyl groups such as methylcarbonylaminomethyl, ethylcarbonylaminomethyl, methylcarbonylaminoethyl, ethylcarbonylaminoethyl and the like, which may be substituted; arylcarbonylamino(C$_1$–C$_{10}$)alkyl such as phenylcarbonylaminomethyl, phenylcarbonylaminoethyl, naphtylcarbonylaminomethyl, naphthylcarbonylaminoethyl and the like, which may be substituted; (C$_1$–C$_{10}$)alkylcarbonyloxy(C$_1$–C$_{10}$)alkyl group such as methylcarbonyloxymethyl, ethylcarbonylxoymethyl, methylcarbonyloxyethyl, propylcarbonyloxymethyl, propylcarbonyloxyethyl, propylcarbonyloxypropyl and the like, which may be substituted; amino(C$_1$–C$_{10}$)alkyl such as aminomethyl, aminoethyl, aminopropyl and the like, which may be substituted; mono(C$_1$–C$_{10}$)alkylamino such as methylamino, ethylamino, propylamino and the like, which may be substituted; di(C$_1$–C$_{10}$)alkylamino sich as dimethylamino, diethylamino, methylethylamino, dipropylamino, ethylpropylamino and the like, which may be substituted; arylamino such as phenylamino, benzylamino and the like, which may be substituted; (C$_1$–C$_{10}$)alkoxy group such as methoxy, ethoxy, propoxy, isopropoxy and the like, which may be substituted; aryl group such as phenyl, naphthyl and the like, which may be substituted; aryloxy group such as phenoxy, naphthyloxy and the like, the aryloxy group may be substituted; aralkyl such as benzyl, phenethyl, C$_6$H$_5$CH$_2$CH$_2$CH$_2$, naphthylmethyl and the like, the aralkyl group may be substituted; heteroaryl groups such as pyridyl, thienyl, furyl, pyrrolyl, oxazolyl, thiazolyl, pyrazolyl, imidazolyl, oxadiazolyl, tetrazolyl, benzopyranyl, benzofuranyl and the like, which may be substituted; heteroaralkyl such as imidazolemethyl, imidazoleethyl, pyridylmethyl, furyl methyl, oxazolemethyl, imidazolyl and the like, which may be substituted; heterocyclyl group such as pyrrolidinyl, piperidinyl, morpholinyl, piperazinyl and the like; heterocycloalkyl groups such as pyrrolidinemethyl, piperidinemethyl, morpholinemethyl, piperazinemethyl and the like, which may be substituted.

When the groups represented by $Y^2$ and $Y^3$ are substituted, the substituents may be selected from hydroxy, nitro, cyano, amino, (tert-butyldimethylsilyloxy) TBSO, halogen atom, $(C_1-C_{10})$alkyl, $(C_1-C_{10})$alkoxy, $(C_3-C_8)$cycloalkyl, aryl group such as phenyl, naphthyl and the like, benzyloxy, acyl group such as formyl, acetyl, and the like, carboxyl or acyloxy group such as formyloxy, acetyloxy and the like.

Suitable cyclic structure formed by $Y^2$ and $Y^3$ when present on adjacent carbon atoms which they are attached may be selected from substituted or unsubstituted benzene, pyridine, pyrrolidine, furan, thiophene, morpholine, piperazine, pyrrole and the like. The substituents on the cyclic structure formed by $Y^2$ and $Y^3$ are selected from halogen, hydroxyl, amino, cyano, nitro, oxo, thioxo, $(C_1-C_{10})$alkyl or $(C_1-C_{10})$alkoxy, where $(C_1-C_{10})$alkyl and $(C_1-C_{10})$alkoxy groups are as defined earlier.

When the groups $R^1$, $R^4$, $R^b$, $Y^2$ and $Y^3$ are substituted, they may be mono- or di- or tri substituted.

The invention provides separate embodiments of the compounds of the invention, which are however not necessarily exclusive of one another. In one embodiment, there are provided oxazolidinone derivatives of the structure in accordance with the formula (I).

Oxazolidinone derivatives of one group of this embodiment have the structure

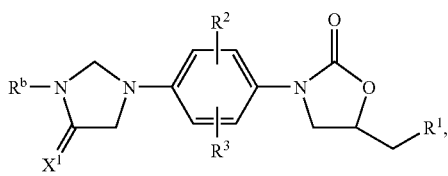

wherein $X^1$ is oxygen or sulfur.

Oxazolidinone derivatives of another group of this embodiment have the structure

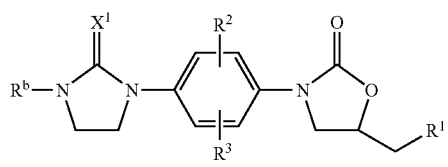

wherein $X^1$ is oxygen or sulfur.

Oxazolidinone derivatives of yet another group of this embodiment have the structure

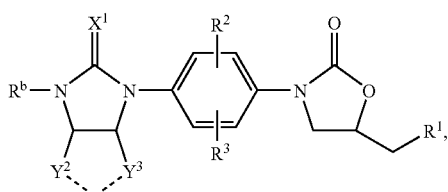

wherein $X^1$ is oxygen or sulfur, and

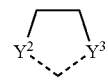

is a substituted or unsubstituted 5- or 6-membered aromatic or non-aromatic cyclic structure optionally having one or two hetero atoms, formed by $Y^2$ and $Y^3$.

Oxazolidinone derivatives of another group of this embodiment have the structure

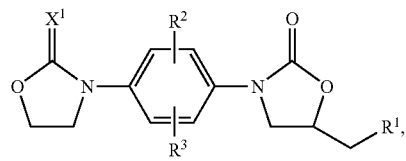

wherein $X^1$ is oxygen or sulfur.

Oxazolidinone derivatives of another group of this embodiment have the structure

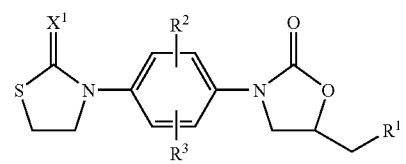

wherein $X^1$ is oxygen or sulfur.

In another embodiment, the invention also provides oxazolidinone derivatives that have the structure, in accordance with the compound of formula (I)

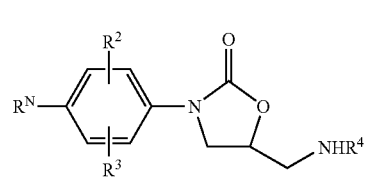

(Ia)

or a salt thereof or a stereoisomer thereof, where $R^N$ is

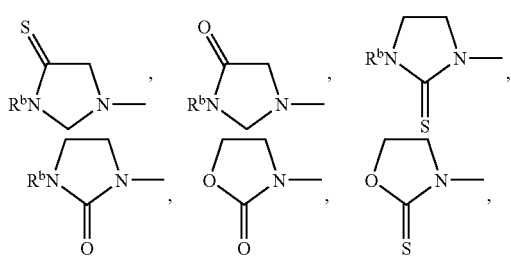

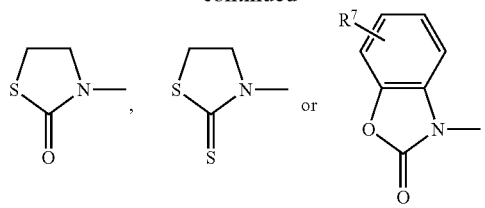

wherein $R^b$ is hydrogen or a moiety, which may be substituted or unsubstituted, straight chain or branched, selected from the group consisting of $(C_1-C_{10})$alkyl, $(C_2-C_{10})$alkenyl, $(C_3-C_8)$cycloalkyl, $(C_1-C_{10})$alkoxy, aryl, aralkyl, aryloxy, $(C_1-C_{10})$alkylhydroxy, hydroxy$(C_1-C_{10})$ alkyl, $(C_1-C_{10})$alkylcarbonyl, $(C_1-C_{10})$alkylamino, amino $(C_1-C_{10})$alkyl, arylcarbonyl, $(C_1-C_{10})$alkoxycarbonyl or aryloxycarbonyl; $R^7$ represents hydrogen, $(C_1-C_{10})$alkyl or $(C_1-C_{10})$alkoxy;

$R^2$ and $R^3$, which may be same or different, are each independently hydrogen, halo, $(C_1-C_{10})$alkyl, halogenated $(C_1-C_{10})$alkyl, hydroxyl or $(C_1-C_{10})$alkoxy; and $R^4$ represents hydrogen atom, or substituted or unsubstituted groups selected from $(C_1-C_{10})$acyl, thio$(C_1-C_{10})$acyl, —C(=O)—$(C_1-C_{10})$alkoxy, —C(=S)-cyclo$(C_3-C_8)$ alkoxy, —C(=O)—$(C_2-C_{10})$alkenyloxy, —C(=O)—$(C_2-C_{10})$alkenyl, —C(=O)-aryloxy, —C(=S)—$(C_1-C_{10})$ alkoxy, —C(=S)—$(C_2-C_{10})$alkenyloxy, —C(=S)-aryloxy, —C(=O)—C(=O)—$(C_1-C_{10})$alkyl, —C(=O)—C(=O)-aryl, —C(=O)—C(=O)—$(C_1-C_{10})$alkoxy, —C(=O)—C(=O)-aryloxy, —(C=S)—S—$(C_1-C_{10})$alkyl, —(C=S)—NH$_2$, —(C=S)—NH—$(C_1-C_{10})$alkyl, —C(=S)—N—$((C_1-C_{10})$alkyl$)_2$, —C(=S)—NH—$(C_2-C_{10})$alkenyl, (C=S)—C(=O)—$(C_1-C_{10})$alkoxy, —(C=S)—(C=O)-aryloxy, —C(=S)—O—(C=O)—$(C_1-C_{10})$alkyl, C(=S)—C(=S)—$(C_1-C_{10})$alkyl, —C(=S)—C(=S)-aryl, thiomorpholinyl-C(=S)— or pyrrolidinyl-C(=S)—. In one embodiment $R^2$ and $R^3$ are each independently hydrogen, fluoro or trifluoromethyl. Oxazolidinone derivatives of another group of this embodiment have the above structure, wherein $R^N$ is

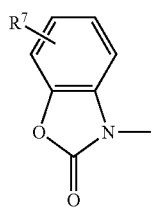

In another embodiment $R''$ is

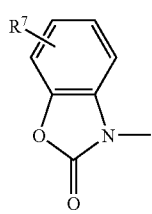

and $R^7$ is hydrogen, $(C_1-C_{10})$alkyl or $(C_1-C_{10})$alkoxy.

Oxazolidinone derivatives of one group of this embodiment have the above structure (Ia), wherein $R^N$ is

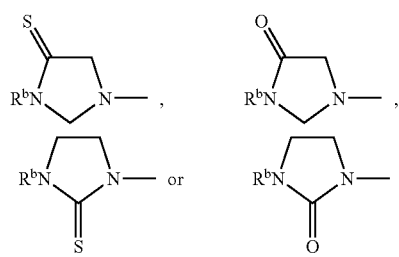

in which $R^b$ is hydrogen, substituted or unstubstituted $(C_1-C_{10})$alkyl, halogenated $(C_1-C_{10})$alkyl, $(C_2-C_{10})$alkenyl, $(C_1-C_{10})$alkylhydroxy, hydroxy$(C_1-C_{10})$alkyl, halogenated $(C_1-C_{10})$alkylhydroxy, halogenated hydroxy$(C_1-C_{10})$ alkyl, $(C_1-C_{10})$alkylamino or amino $(C_1-C_{10})$alkyl, the group of the structure

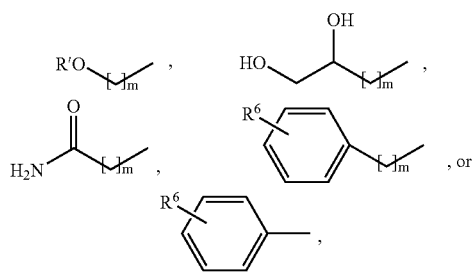

the group of the structure the group of the structure the group of the structure the group of the structure in which R' is hydrogen, $(C_1-C_{10})$alkyl or carboxy $(C_1-C_{10})$ alkyl; $R^6$ is hydrogen, halogen or $(C_1-C_{10})$alkoxy and m is ranging from 1 to 4. Specific non-limiting examples of the group $R^b$ are

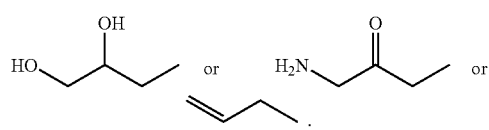

or $R^b$ has the structure

in which $R^6$ is hydrogen, fluoro or methoxy group, or $R^b$ has the structure

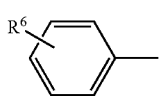

where $R^6$ is hydrogen, fluoro or methoxy group.

Oxazolidinone derivatives of another group of this embodiment have the above structure, wherein $R^N$ is

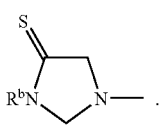

In another embodiment $R^N$ is

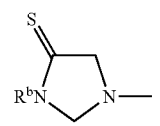

and $R^b$ is hydrogen or methyl.

Oxazolidinone derivatives of another group of this embodiment have the above structure, wherein $R^N$ is

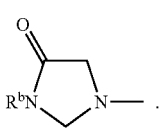

In another embodiment $R^N$ is

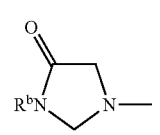

and $R^b$ is hydrogen, methyl, benzyl, p-methoxybenzyl, n-butyl, propenyl or methylhydroxy or Rb has the structure

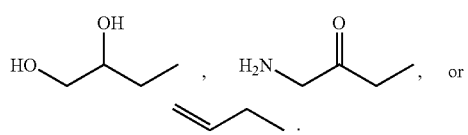

Oxazolidinone derivatives of another group of this embodiment have the above structure, wherein $R^N$ is

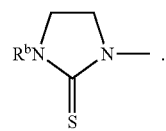

In another embodiment $R^N$ is

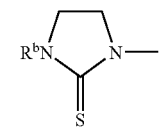

and Rb is methyl.

Oxazolidinone derivatives of another group of this embodiment have the above structure, wherein $R^N$ is

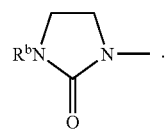

In another embodiment $R^N$ is

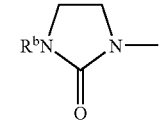

and Rb is methyl, benzyl, p-fluorobenzyl, p-fluorophenyl or phenyl.

Oxazolidinone derivatives of another group of this embodiment have the above structure, wherein $R^N$ is

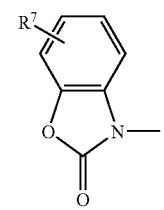

and $R^7$ is hydrogen, $(C_1-C_{10})$alkyl or $(C_1-C_{10})$alkoxy.

The moiety $R^N$ also has the structure

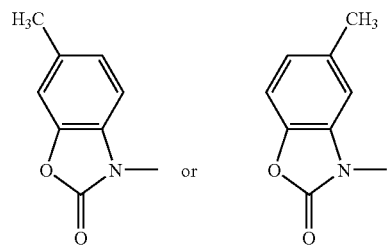

Oxazolidinone derivatives of another group of this embodiment have the above structure, wherein $R^N$ is

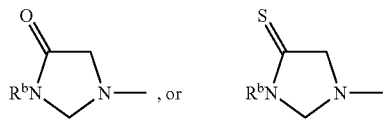

, or in which $R^b$ is hydrogen, substituted or unsubstituted $(C_1-C_{10})$alkyl, halogenated $(C\ C_1-C_{10})$alkyl, $(C_2-C_{10})$alkenyl, aralkyl, $(C_1-C_{10})$alkylcarbonyl, $(C_1-C_{10})$alkoxy $(C_1-C_{10})$alkyl, $(C\ C_1-C_{10})$alkylhydroxy, hydroxy$(C_1-C_{10})$alkyl, dihydroxy$(C_1-C_{10})$alkyl halogenated $(C_1-C_{10})$alkylhydroxy, halogenated hydroxy$(C_1-C_{10})$alkyl; wherein $R^4$ is —C(=O)—H, substituted or unsubstituted —C(=O)—$(C_1-C_{10})$alkyl, —C(=O)—$(C_1-C_{10})$alkylhydroxy, —C(=O)-halogenated$(C_1-C_{10})$alkyl, —C(=O)—$(C_2-C_{10})$alkenyl, —C(=S)—H, —C(=S)—$(C_1-C_{10})$alkyl, —C(=S)—$(C_1-C_{10})$alkoxy, —C(=S)—$NH_2$, —C(=S)—$(C\ C_1-C_{10})$alkylhydroxy, —C(=S)-halogenated$(C_1-C_{10})$alkyl, —C(=S)-phenyl; and $R^2$ and $R^3$ are each independently hydrogen, fluoro or trifluoromethyl group.

Oxazolidinone derivatives of yet another group of this embodiment have the above structure, wherein $R^N$ is

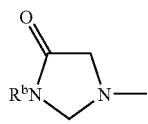

in which $R^b$ is hydrogen, methyl, ethyl, propyl, n-butyl, benzyl, p-methoxybenzyl, hydroxy ethyl (ethylhydroxy), methoxyethyl, propenyl,

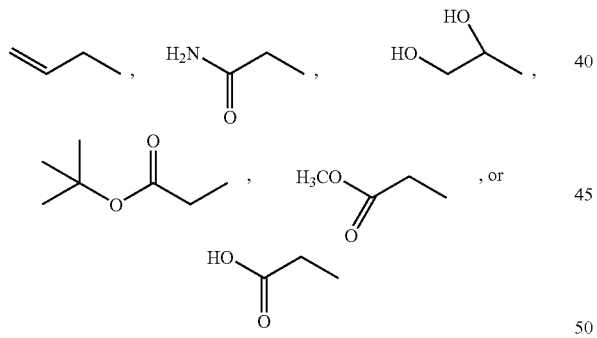

and $R^4$ is —C(=O)—H, —C(=O)—$CH_3$—C(=S)—$CH_3$, —C(=S)—$OCH_3$, —C(=S)—$OCH_2CH_3$. —C(=S)-(isopropoxy) or —C(=S)—NH(pyridyl).

Oxazolidinone derivatives of yet another group of this embodiment have the above structure, wherein $R^N$ is

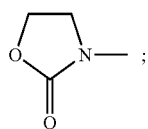

$R^4$ is —C(=O)—H, substituted or unsubstituted —C(=O)—$(C_1-C_{10})$alkyl, —C(=O)-halogenated $(C_1-C_{10})$alkyl, —C(=O)—$(C_2-C_{10})$alkenyl, —C(=O)—C(=O)—$(C_1-C_{10})$alkoxy, —C(=O)—$(C_1-C_{10})$alkoxy, —C(=S)—$(C_1-C_{10})$alkyl, —C(=S)-halogenated $(C_1-C_{10})$ alkyl, —C(=S)—S—$(C_1-C_{10})$alkyl, —C(=S)—$(C_1-C_{10})$ alkoxy, —C(=S)—O—C(=O)—$(C_1-C_{10})$alkyl, —C(=S)—$(C_3-C_8)$cycloalkoxy, —C(=S)—$(C_2-C_{10})$alkenyloxy, —C(=S)-pyrrolidinyl, —C(=S)—$NH_2$, —C(=S)—N$((C_1-C_{10})$alkyl$)_2$, —C(=S)—NH—$(C_2-C_{10})$ alkenyl, —C(=S)-thiomorpholinyl; and $R^2$ and $R^3$ are each independently hydrogen, fluoro or trifluoromethyl group.

Oxazolidinone derivatives of another embodiment have the above structure, where $R''$ has the structure

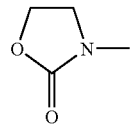

and $R^2$ and $R^3$ are each independently hydrogen, fluoro or trifluoromethyl group and $R^4$ is —C(=S)—$CH_3$, —C(=S)—$CH_2$—$CH_3$, —C(=S)—$CH_2$—$CF_3$, —C(=S)—S—$CH_3$, —C(=S)—O—$CH_3$, —C(=S)—O—$CH_2$—$CH_3$, —C(=S)—O—$CH_2$—$CH_2$—$CH_3$, —C(=S)—O-(iso-propyl), —C(=S)—O—$CH_2$—$CF_3$, —C(=S)—O-cyclohexyl, —C(=S)—O—$CH_2$—CH=$CH_2$, —C(=S)—$CH_2$—$CH_2$—N$(CH_3)_2$, —C(=S)—O—$CH_2$—$CH_2$OH, —C(=S)—$CH_2$—$CH_2$—$OCH_3$, —C(=S)—O—C(=O)—$CF_3$, —C(=S)—$NH^2$, —C(=S)—NH—$CH_2$, C(=S)—NH—$CH_2$—$CH_2$—OH, —C(=S)—N$(CH_2CH_3)_2$, —C(=S)—NH—$CH_2$—CH=$CH_2$, —C(=S)—NH-benzyl, —C(=S)—NH-pyridyl, —C(=S)—NH-(p-methoxybenzyl), —C(=S)—NH—$CH_2$-pyridyl, —C(=S)-thiomorpholinyl, —C(=S)—O—$CH_2$—$CH_2$—, $\overset{+}{N}HCl^-$, or

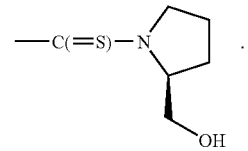

.

Pharmaceutically acceptable salts forming part of this invention include salts derived from inorganic bases such as Li, Na, K, Ca, Mg, Fe, Cu, Zn, Mn; salts of organic bases such as N,N'-diacetylethylenediamine, betaine, caffeine, 2-diethylaminoethanol, 2-dimethylaminoethanol, N-ethylmorpholine, N-ethylpiperidine, glucamine, glucosamine, hydrabamine, isopropylamine, methylglucamine, morpholine, piperazine, piperidine, procaine, purines, theobromine, triethylamine, trimethylamine, tripropylamine, tromethamine, diethanolamine, meglumine, ethylenediamine, N,N'-diphenylethylenediamine, N,N'-dibenzylethylenediamine, N-benzyl phenylethylamine, choline, choline hydroxide, dicyclohexylamine, metformin, benzylamine, phenylethylamine, dialkylamine, trialkylamine, thiamine, aminopyrimidine, aminopyridine, purine, spermidine, and the like; chiral bases like alkylphenylamine, glycinol, phenyl glycinol and the like, salts of natural amino acids such as glycine, alanine, valine, leucine, isoleucine, norleucine, tyrosine, cystine, cysteine, methionine, proline, hydroxy proline, histidine, ornithine, lysine, arginine, serine, threonine, phenylalanine; unnatural amino acids such as D-isomers or substituted amino acids; guanidine, substituted guanidine wherein the substituents are selected from nitro, amino, alkyl such as methyl, ethyl, propyl and the like; alkenyl such as ethenyl, propenyl, butenyl and the like; alkynyl such as ethynyl, propynyl and the like; ammonium or substituted ammonium salts and aluminum salts. Salts may include acid addition salts where appropriate which are, sulphates, nitrates, phosphates, perchlorates, borates, halides, acetates, tartrates, maleates, citrates, succinates, palmoates, methanesulphonates, benzoates, salicylates, hydroxynaphthoates, benzenesulfonates, ascorbates, glycerophosphates, ketoglutarates and the like. Pharmaceutically acceptable solvates may be hydrates or comprising other solvents of crystallization such as alcohols.

The compounds which are provided by way of illustration only and therefore should not be construed to limit the scope of the invention are:

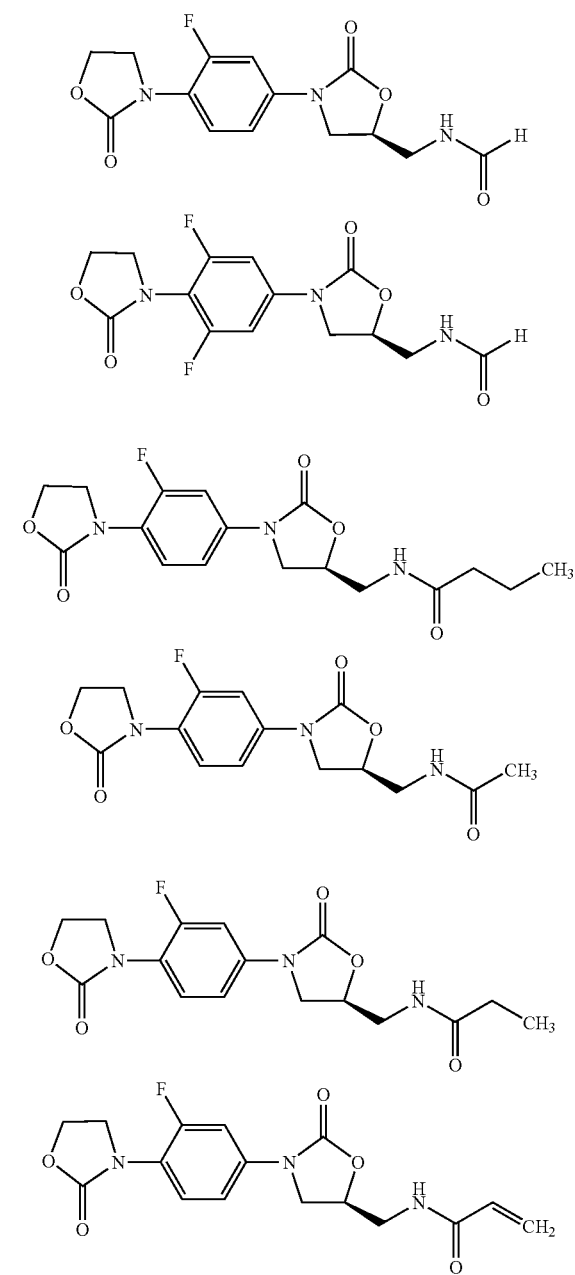

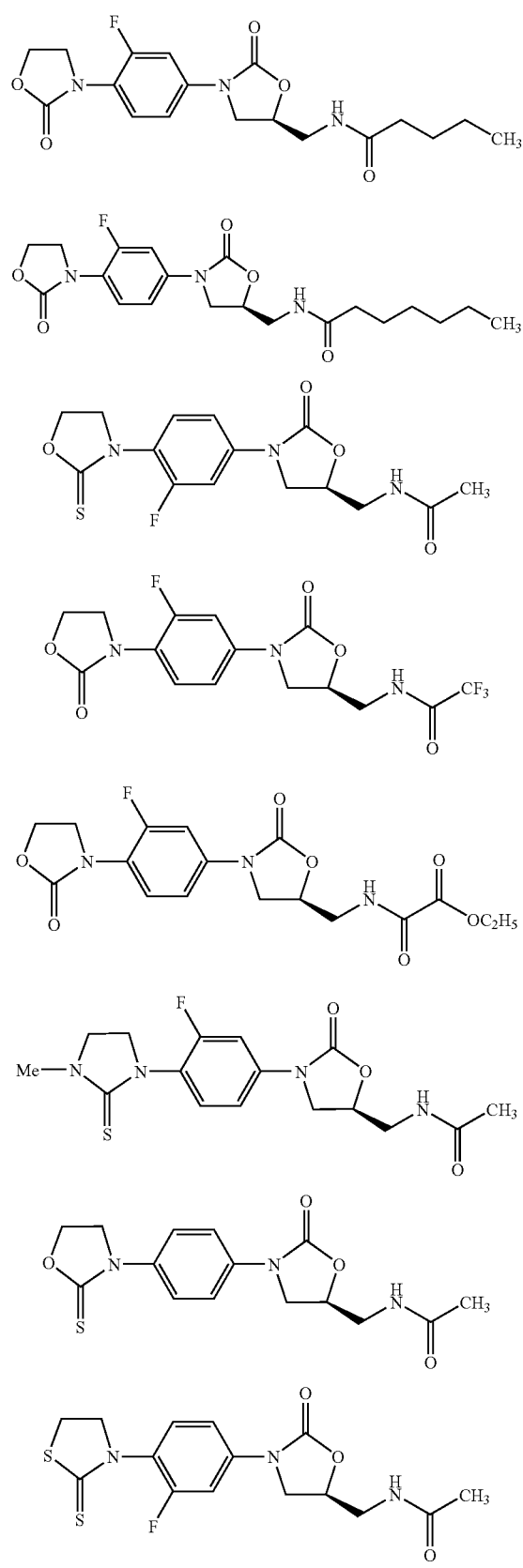

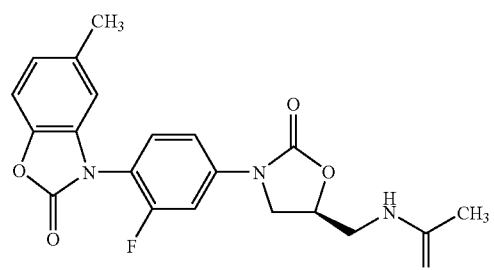
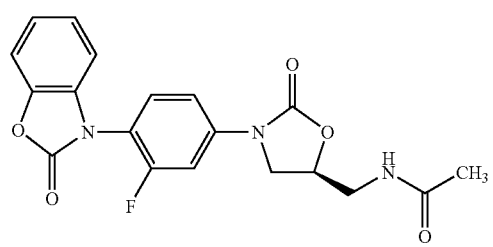
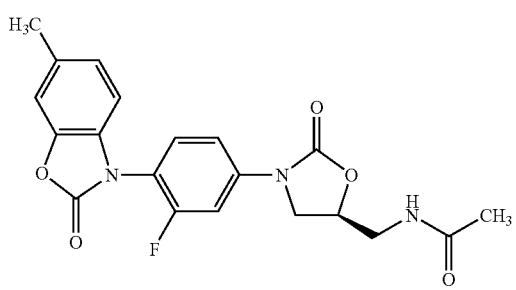
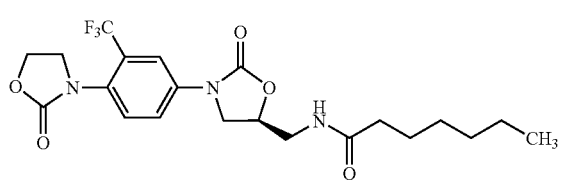
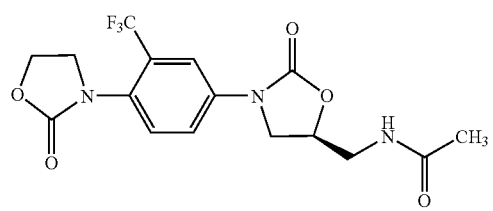
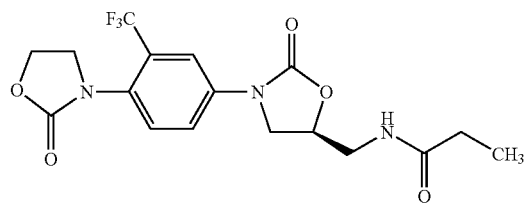
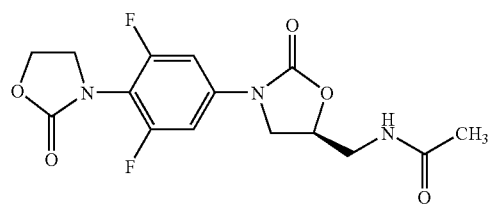
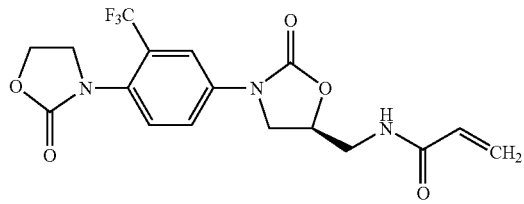
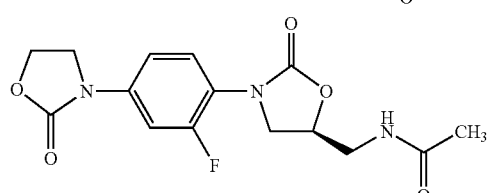
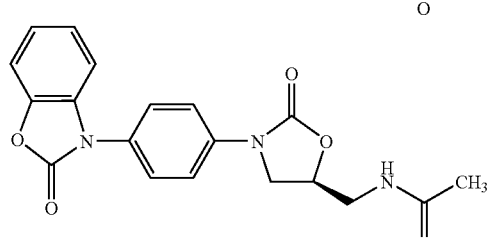
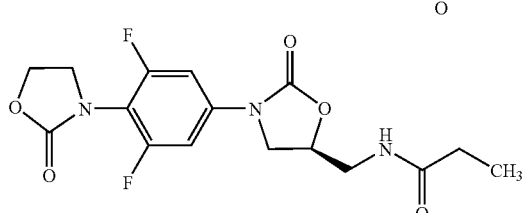
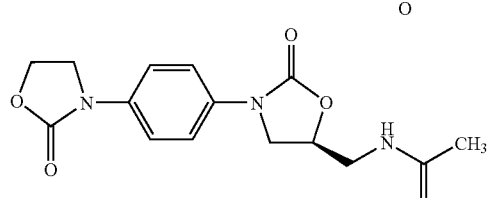
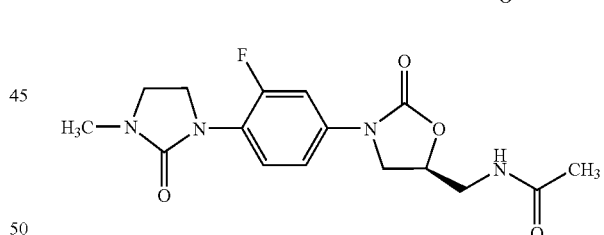
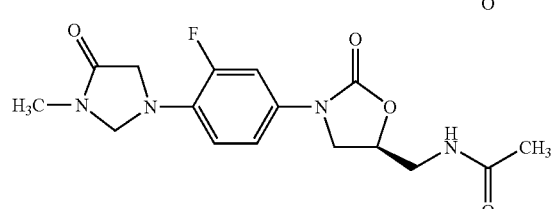
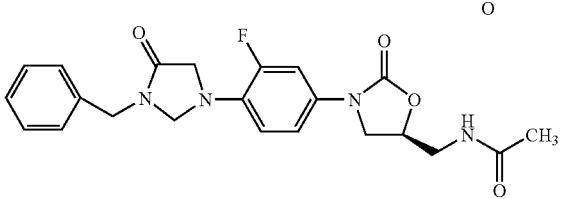

-continued
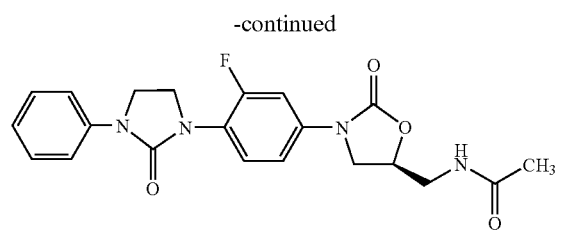
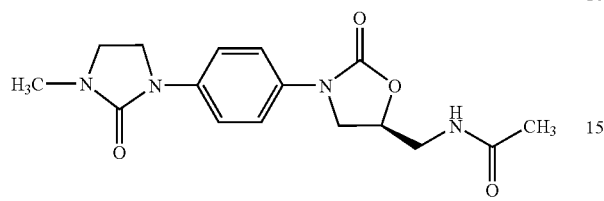
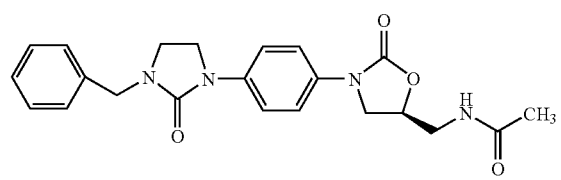
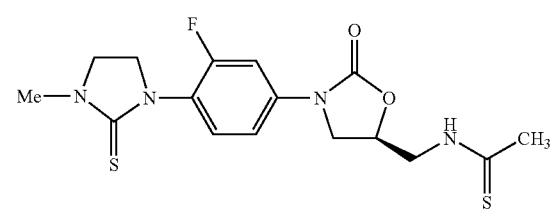
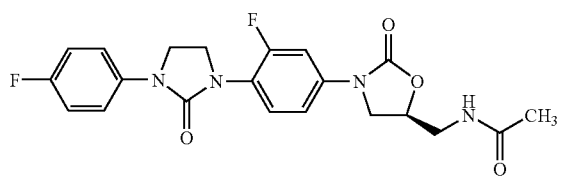
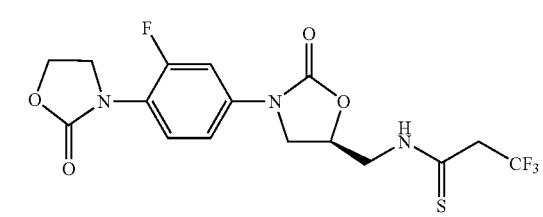
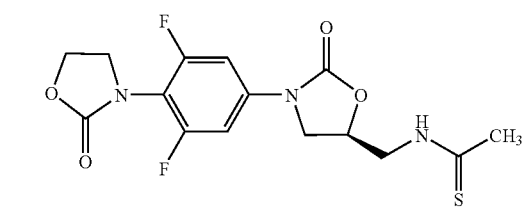
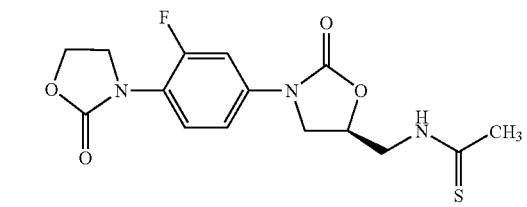
-continued
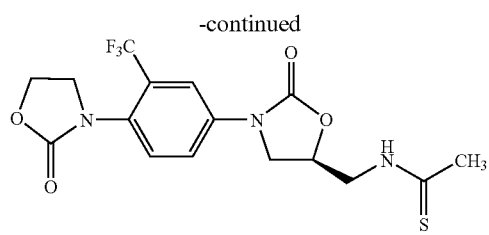
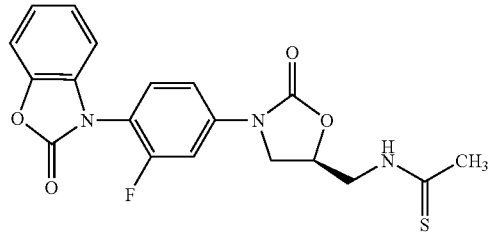
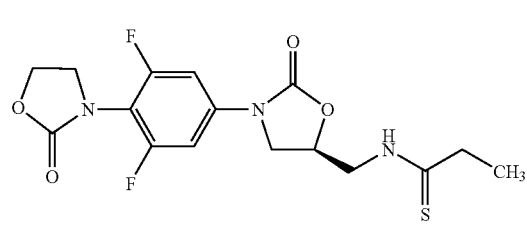
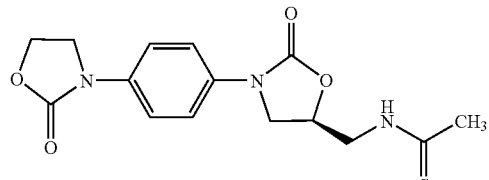
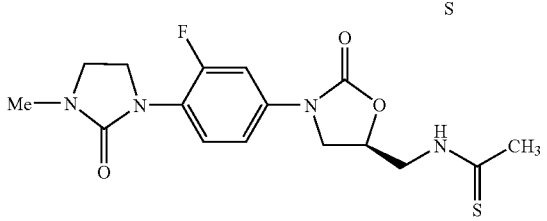
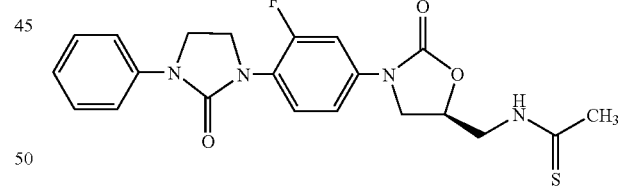
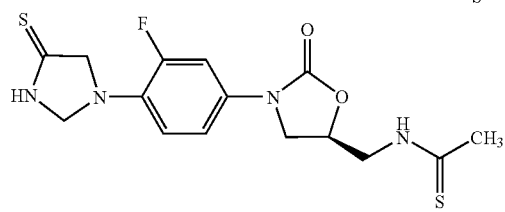
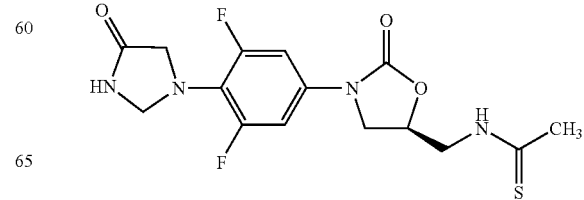

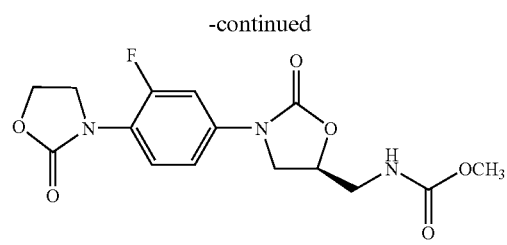
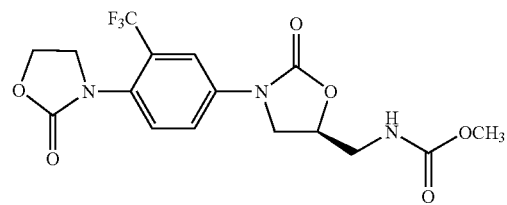
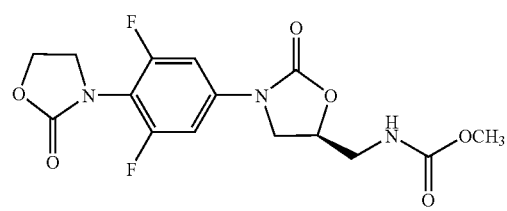
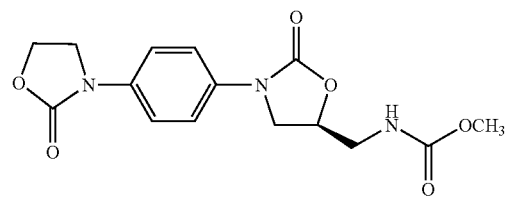
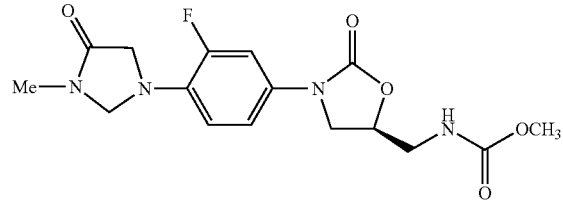
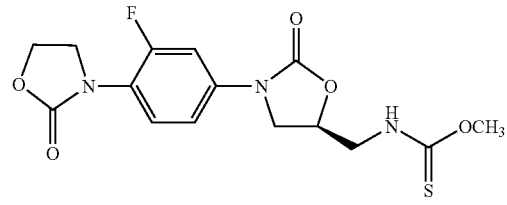
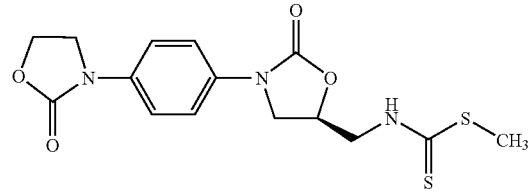
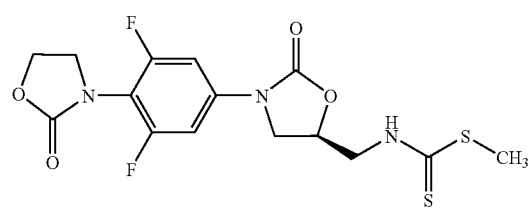
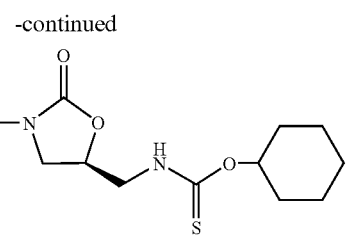
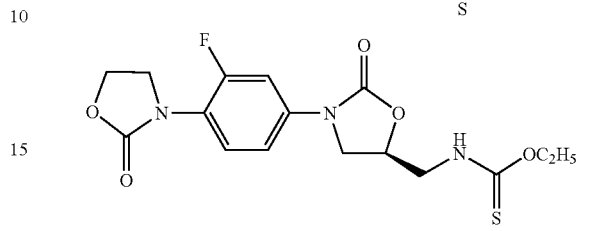
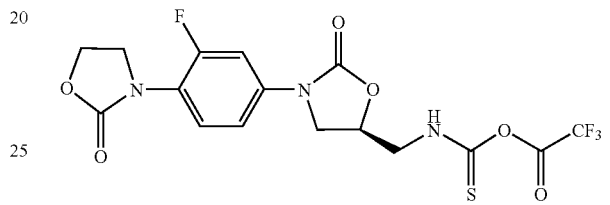
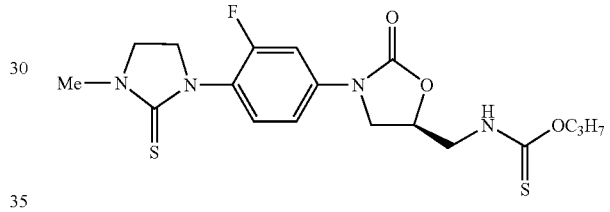
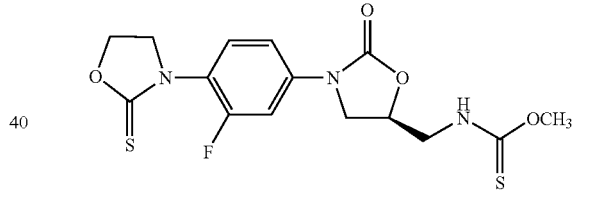
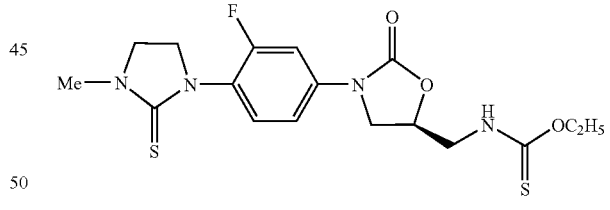
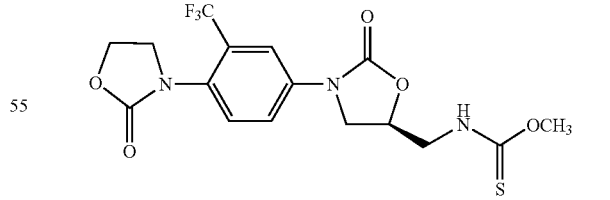
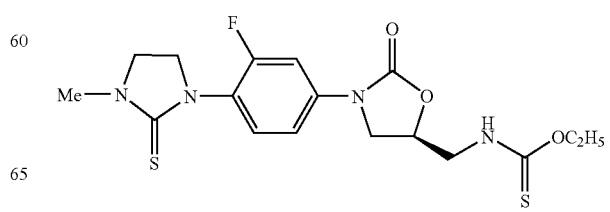

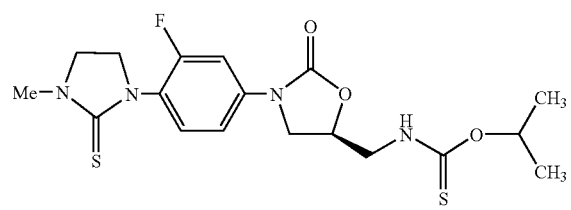
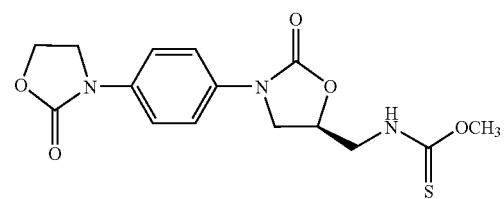
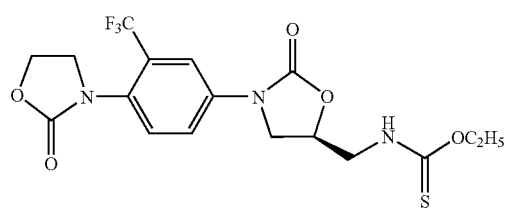
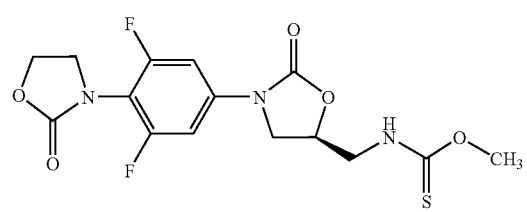
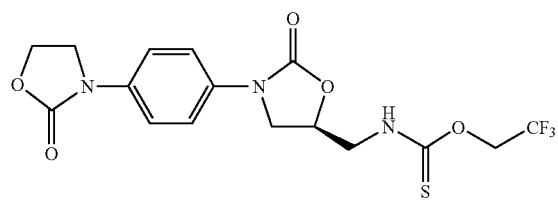
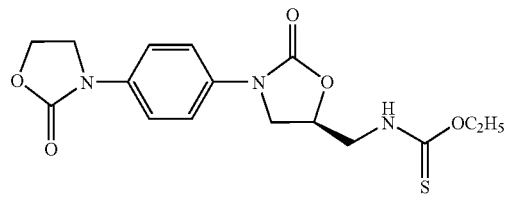
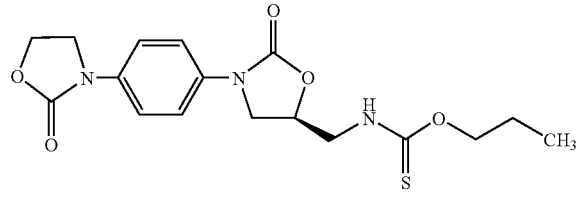
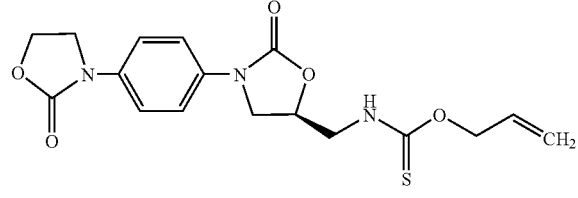
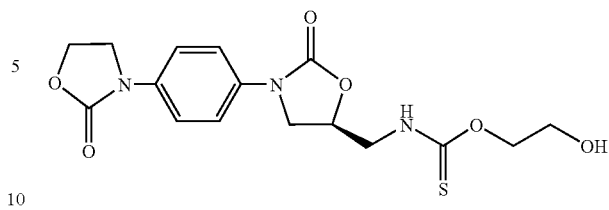
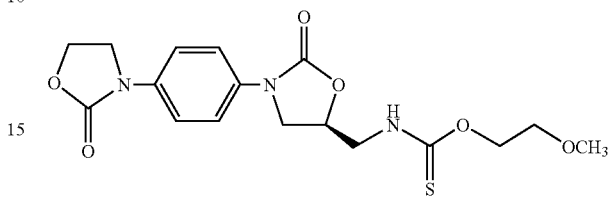
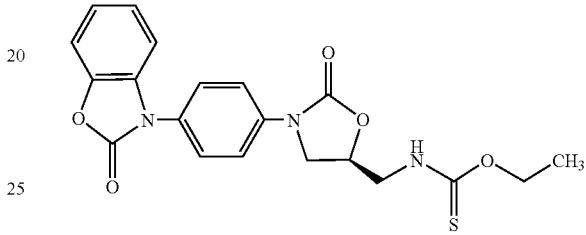
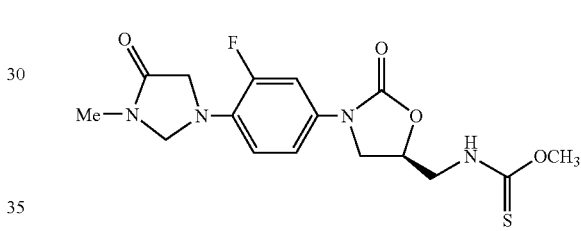
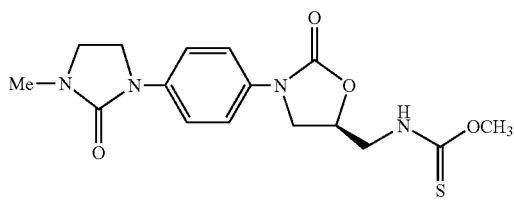
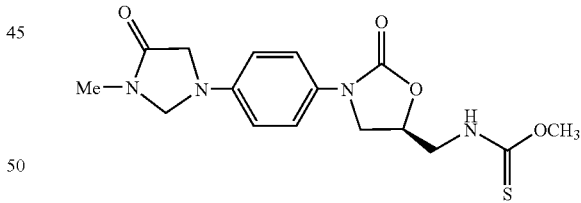
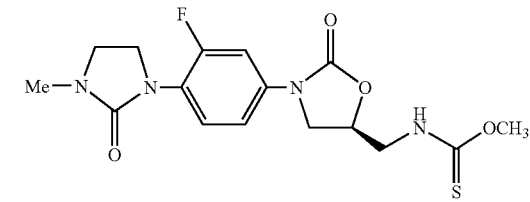
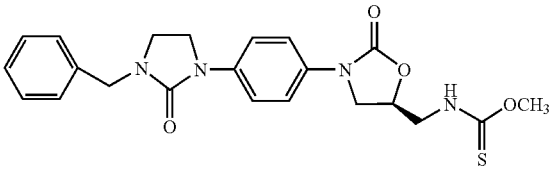

-continued
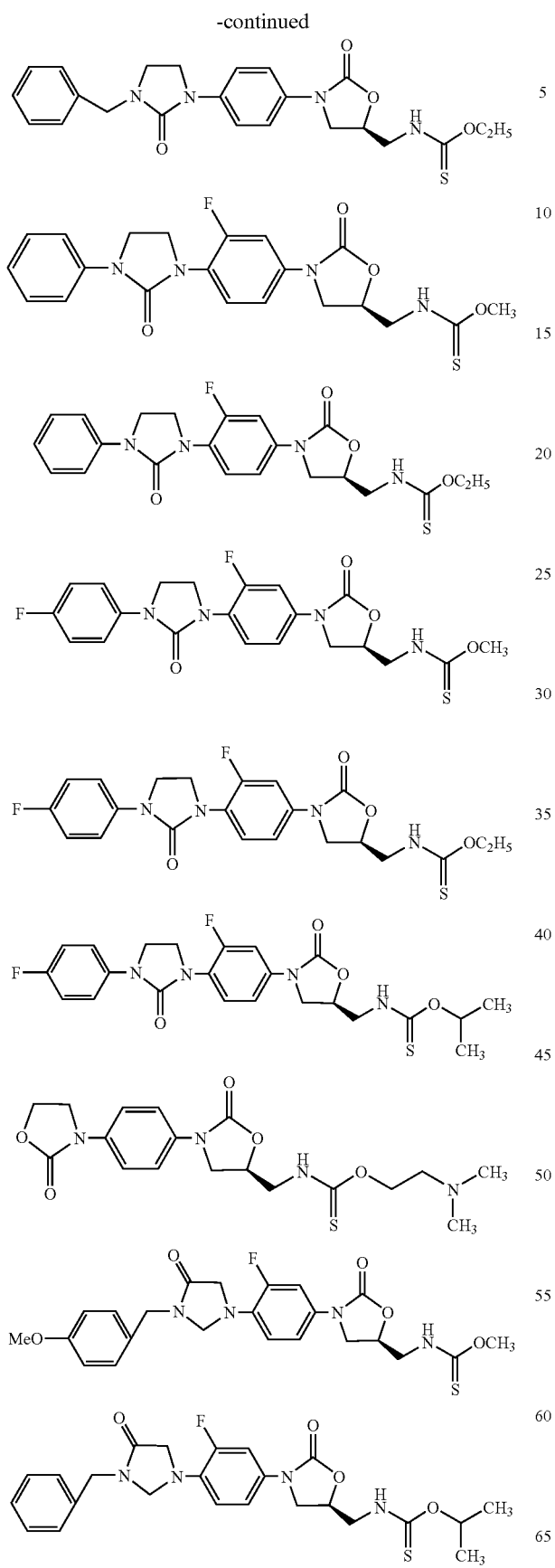
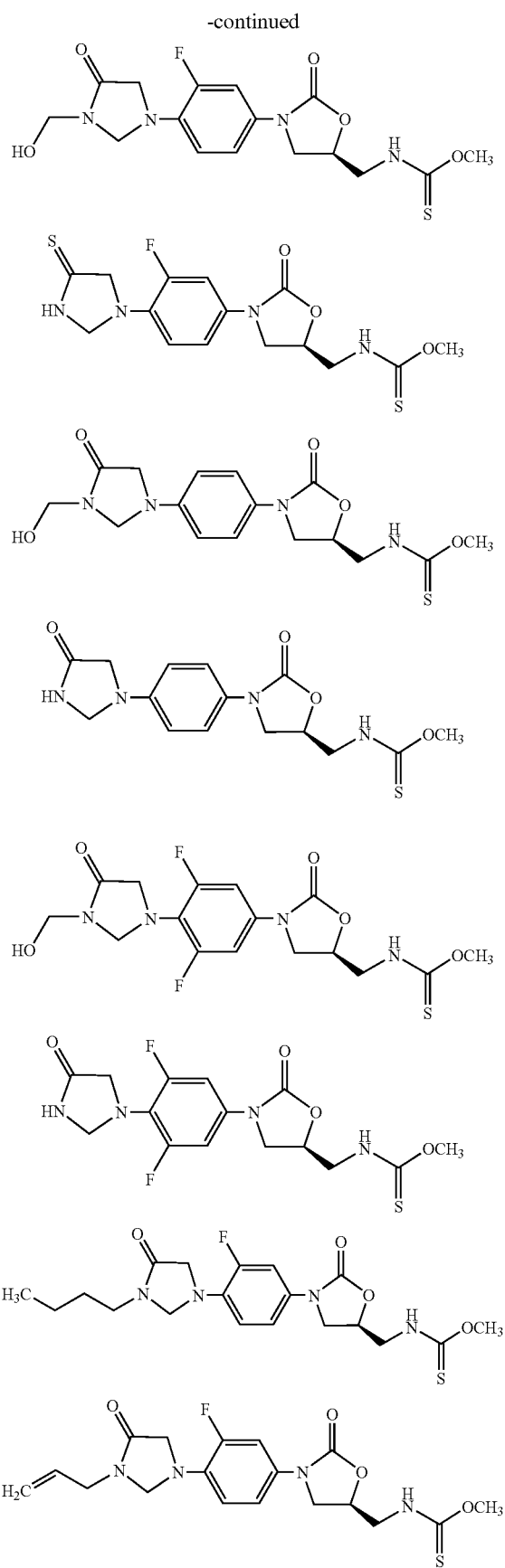

-continued
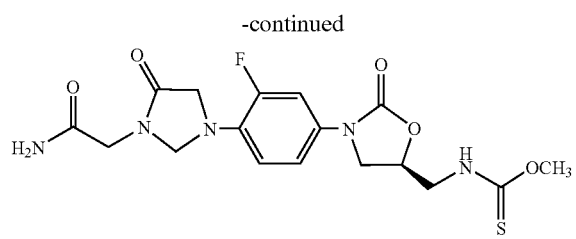
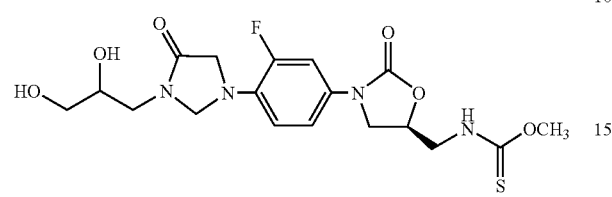
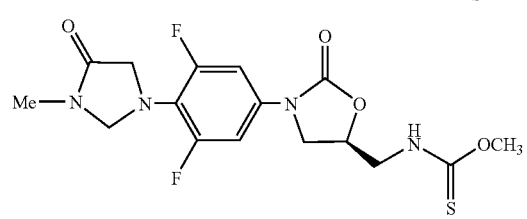
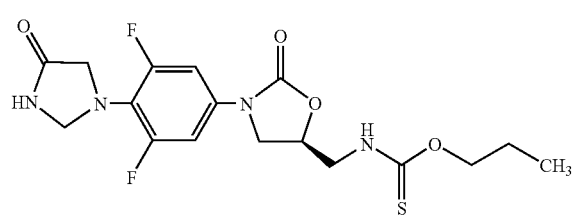
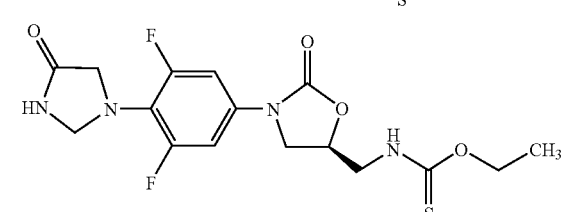
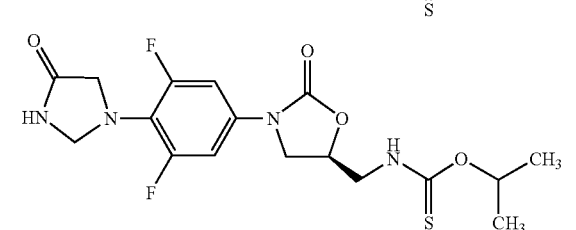
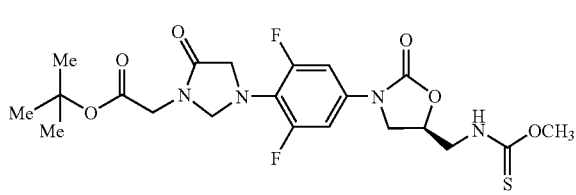
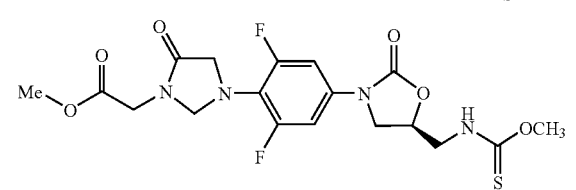
-continued
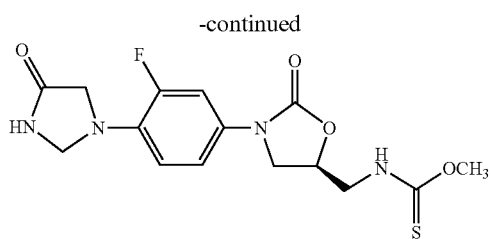
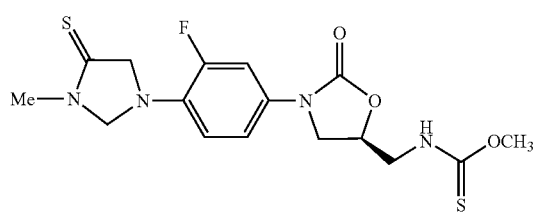
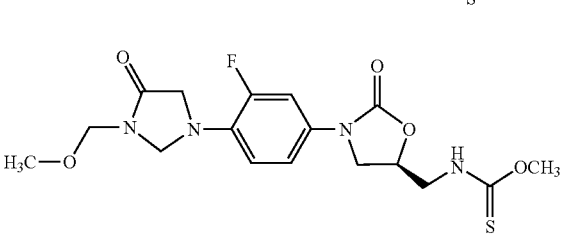
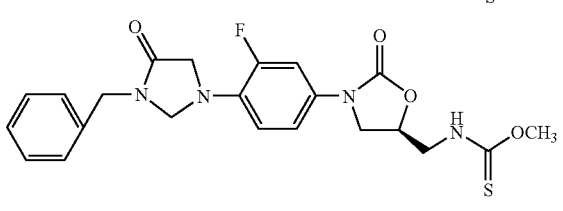
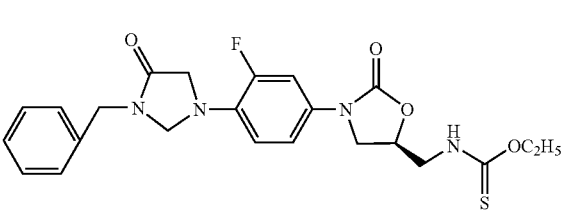
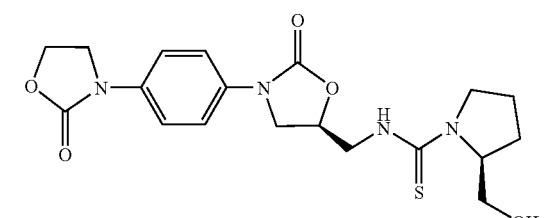
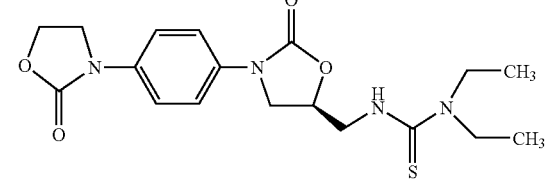
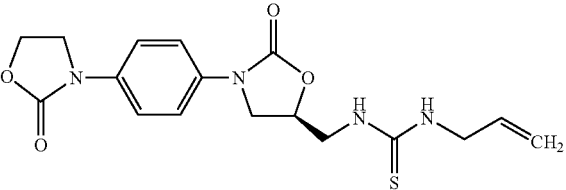

-continued

-continued

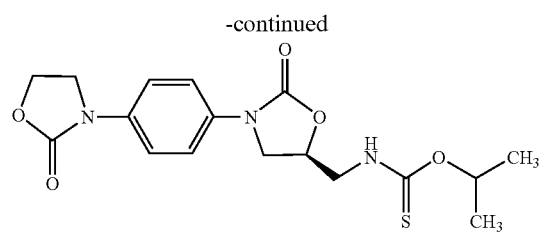
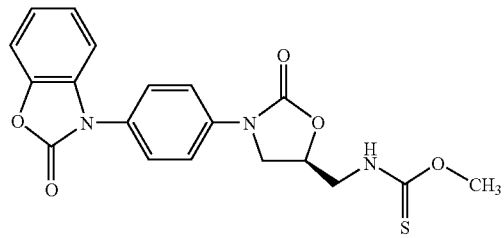
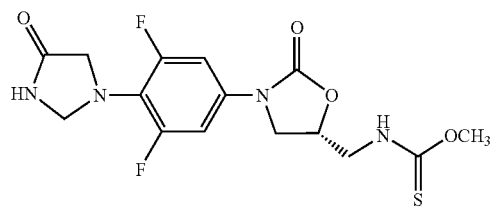
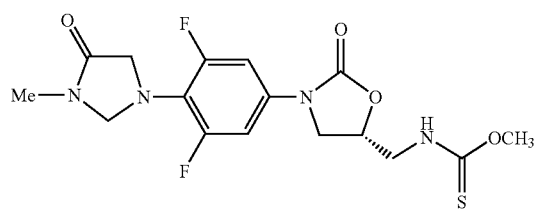
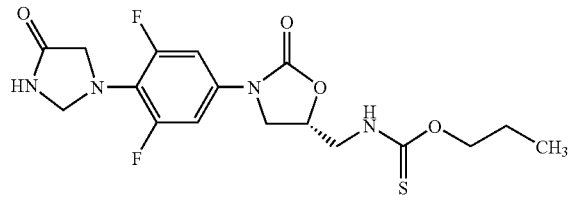
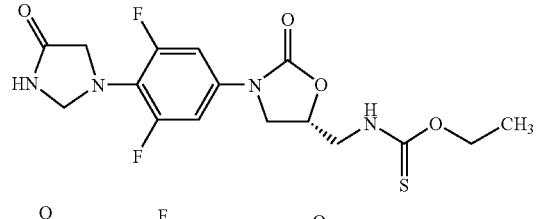
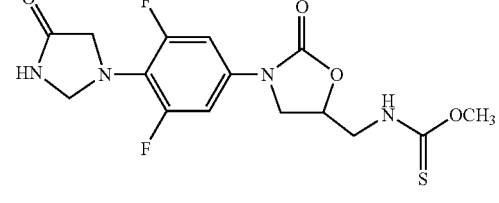
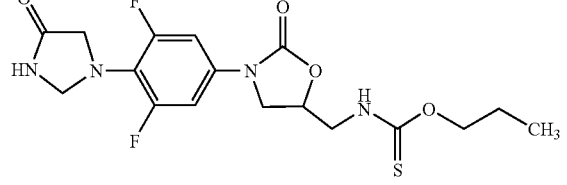

-continued

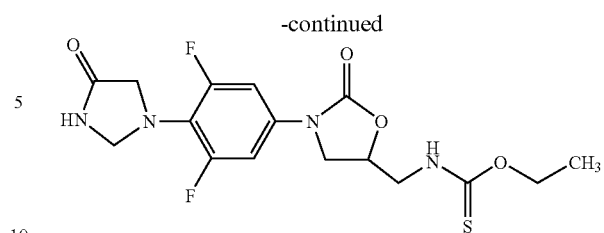
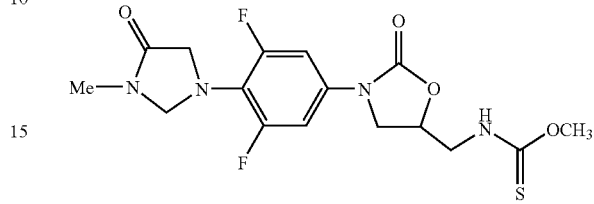

or its steroisomers like (R) or mixture of (R) and (S) isomers; or pharmaceutically acceptable salts thereof.

Me represent methyl
Et represent ethyl
Pro represents propyl.

In the structures described herein whenever an open ended bond is present that represents a methyl group.

THP represent tetrahydropyranyl

The present invention also relates to a process for the preparation of the compound of formula (I) where $R^1$ represents —$NHR^4$, wherein $R^4$ represents hydrogen atom and all other symbols are as defined earlier, which comprises:

(i) reacting a compound of formula (III)

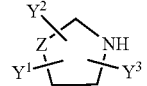
(III)

where all the symbols are as defined earlier, with a compound of formula (IV)

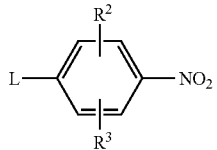
(IV)

where L represents a leaving group such as halogen atom, $(C_1-C_{10})$alkoxy, such as methoxy, ethoxy, propoxy and the like; sulfonyl groups such as methylsulfonyl, ethylsulfonyl, p-toluenesulfonyl and the like; $R^2$ and $R^3$ are as defined earlier, to produce a compound of formula (V)

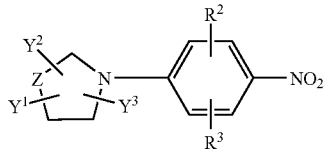
(V)

where $Y^1$, $Y^2$, $Y^3$, $R^2$, $R^3$ and Z are as defined earlier, (ii) reducing the compound of formula (V) to produce a compound of formula (VI)

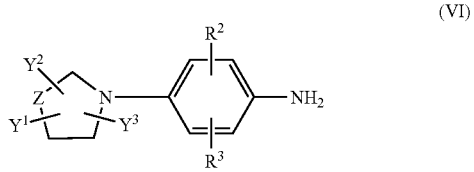
(VI)

where $Y^1$, $Y^2$, $Y^3$, $R^2$, $R^3$ and Z are as defined earlier, (iii) reacting the compound of formula (VI) with alkylchloroformate, to produce a compound of formula (VII)

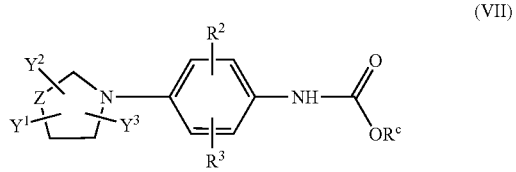
(VII)

where $R_c$ represents $(C_1-C_{10})$alkyl group such as methyl, ethyl, propyl, and the like, or aralkyl group such as benzyl, allyl group and the like; $Y^1$, $Y^2$, $Y^3$, $R^2$, $R^3$ and Z are as defined earlier, (iv) reacting the compound of formula (VII) with a compound of formula (VIII)

(VIII)

where $R^{12}$ represents $(C_1-C_{10})$alkyl group such as methyl, ethyl, propyl and the like, in the presence of a base to produce a compound of formula (I)

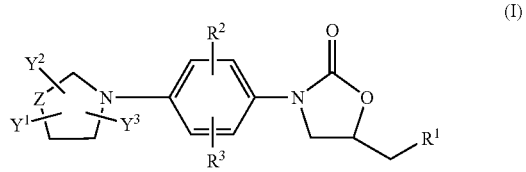
(I)

where $R^1$ represents hydroxy; $Y_1$, $Y^2$, $Y^3$, $R^2$, $R^3$ and Z are as defined earlier, (v) reacting the compound of formula (I) with $(C_1-C_{10})$ alkylsulfonyl chloride or aryl sulfonyl chloride to produce a compound of formula (I), where $R^1$ represents alkyl sulfonyl or aryl sulfonyl, which in turn was reacted with $NaN_3$ to produce compound of formula (I)

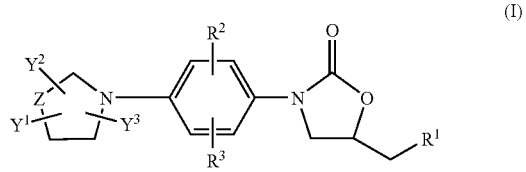
(I)

where $R^1$ represents azido; $Y^1$, $Y^2$, $Y^3$, $R^2$, $R^3$ and Z are as defined earlier and (vi) reducing the compound of formula (I) wherein $R^1$ represents azido group, to produce compound of formula (I)

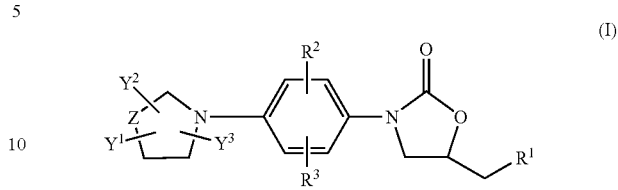
(I)

where $R^1$ represents —$NHR^4$ wherein $R^4$ represents hydrogen atom; $Y^1$, $Y^2$, $Y^3$, $R^2$, $R^3$ and Z are as defined earlier.

The reaction of a compound of formula (III) with a compound of formula (IV) to produce a compound of formula (V) may be carried out using a base such as potassium hydroxide (KOH), sodium hydroxide (NaOH), potassium carbonate ($K_2CO_3$), sodium carbonate ($Na_2CO_3$), sodium hydride (NaH), potassium hydride (KH), triethylamine, diisopropylethyl amine and the like. The reaction may be carried out using a solvent such as dimethylsulfoxide (DMSO), dimethylformamide (DMF), tetrahydrofuran (THF), acetonitrile, chloroform and the like or mixtures thereof. The reaction may be carried out in inert atmosphere, which may be maintained using inert gases such as nitrogen ($N^2$) or argon (Ar). The reaction may be carried out at a temperature in the range of 20 to 100° C., preferably at a temperature in the range of ambient to 80° C. The reaction time may range from 1 to 15 h, preferably from 6 to 12 h.

The reduction of a compound of formula (V) to produce a compound of formula (VI) may be carried out in the presence of gaseous hydrogen and a catalyst such as Ru, Pd, Rh, Pt, Ni on solid beads such as charcoal, alumina, asbestos and the like. The reduction may be conducted in the presence of a solvent such as dioxane, acetic acid, ethyl acetate, THF, alcohol such as methanol, ethanol and the like or mixtures thereof. A pressure between atmospheric pressure to 60 psi may be used. The reaction may be carried out at a temperature in the range of 25 to 60° C., preferably at room temperature. The reaction time ranges from 2 to 48 h. The reduction may also be carried out by employing metal in mineral acids such as Sn/HCl, Fe/HCl, Zn/HCl, $Zn/CH_3CO_2H$ and the like.

The conversion of compound of formula (VI) to compound of formula (VII) may be carried out with alkylchloroformates such as methychloroformate, ethylchlorofor-mate, propylchloroformate, benzylchloroformate and the like. The solvent of the reaction may be selected from water, acetone, THF, acetonitrile, dichloromethane (DCM) and the like or mixtures thereof. The reaction may be carried out in the presence of base such as $K_2CO_3$, $Na_2CO_3$, NaH, KOH, triethylamine ($Et_3N$) and the like. The temperature of the reaction may be carried out in the presence of 0 to 60° C., preferably at 0° C. to room temperature. The time of the reaction is maintained in the range of 1–12 h, preferably in the range of 1–4 h.

The reaction of a compound of formula (VII) with a compound of formula (VIII) to produce a compound of formula (I), where $R^1$ represents hydroxy group, defined above may be carried out in the presence of a base such as alkali metal hydrides like NaH or KH or organolithiums like methyllithium ($CH_3Li$), butyllithium (BuLi), lithium diisopropylamide (LDA) and the like or alkoxides such as sodiummethoxide (NaOMe), sodiumethoxide (NaOEt), potassium tert-butoxide (t-BuOK). The reaction may be carried out in the presence of a solvent such as THF, dioxane, DMF, DMSO, ethylene glycol dimethylether (DME) and the like or mixtures thereof. Hexamethylphosphamide (HMPA) may be used as a cosolvent. The reaction temperature may range from −78 to 150° C., preferably at a temperature in the range of −78 to 30° C. The duration of the reaction may range from 3 to 12 h.

The compound of formula (I) where $R^1$ represents OH is converted to compound of formula (I) where $R^1$ represents alkylsulfonyl or arylsulfonyl by treating with alkylsulfonylchloride or arylsulfonylchloride such as methanesulfonyl chloride, p-toluenesulfonyl chloride and the like. The reaction may be carried out in the presence of chloroform, DCM, THF, dioxane and the like or mixtures thereof. The base used in the reaction may be selected from Et3N, diisopropyl ethylamine, $Na_2CO_3$, $K_2CO_3$ and the like. The temperature of the reaction is maintained in the range of 0 to 50° C., preferably in the range of 0 to room temperature. The time of the reaction should be maintained in the range of 1–12 h, preferably in the range of 1–4 h. The compound of formula (I) where $R^1$ represents alkylsulfonyl or arylsulfonyl is converted to compound of formula (I) where $R^1$ represents azido group, by treating with sodium azide ($NaN_3$) or lithium azide ($LiN_3$). The solvent used in the reaction may be selected from DMF, DMSO, acetonitrile and the like. The temperature of the reaction is maintained in the range of room temperature to 120° C., preferably room temperature to 80° C. The time of the reaction is maintained in the range of 1–12 h, preferably 1–4 h.

The reduction of a compound of formula (I) where $R^1$ represents azido group, to produce a compound of formula (I) where $R^1$ represents —$NHR^4$ wherein $R^4$ represents hydrogen atom, may be carried out in the presence of gaseous hydrogen and a catalyst such as Ru, Pd, Rh, Pt, Ni on solid beads such as charcoal, alumina, asbestos and the like. The reduction may be conducted in the presence of a solvent such as dioxane, acetic acid, ethyl acetate, THF, alcohol such as methanol, ethanol and the like or mixtures thereof. A pressure between atmospheric pressure to 60 psi may be used. The reaction may be carried out at a temperature in the range of 25 to 60° C., preferably at room temperature. The reaction time ranges from 2 to 48 h. The reduction may also be carried out by employing $PPh_3$ in water.

In still another embodiment of the present invention there is provided another process for the preparation of compound of formula (I) where $R^1$ represents hydroxy and all the symbols are as defined earlier, which comprises:

(i) reacting the compound of formula (VI)

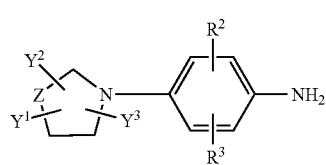

(VI)

where all the symbols are as defined earlier, with a compound of formula (IX)

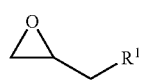

(IX)

where $R^1$ represents hydroxy, to produce a compound of formula (X)

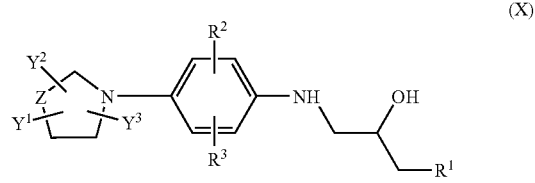

(X)

where $R^1$ represents hydroxy; $Y^1$, $Y^2$, $Y^3$, $R^2$, $R^3$ and Z are as defined earlier, and (ii) carbonylating the compound of formula (X) with a suitable carbonylating agent to produce the compound of formula (I) where $R^1$ represents hydroxy and all other symbols are as defined above.

The reaction of a compound of formula (VI) defined above with a compound of formula (IX) defined above to produce a compound of formula (X) may be carried out in the presence or absence of a base such as $K_2CO_3$, NaH, t-BuOK and the like or mixtures thereof. The reaction may be carried out in the presence of a solvent such as DMF, toluene, THF, acetonitrile and the like or mixtures thereof. The reaction may also be carried out in the presence of Lewis acids such as $BF_3.OEt_2$, $ZnC_{12}$, $Ti(OiPr)_4$, lanthanide metal complexes and the like in the presence of dichloroethylene (DCE), DMF, THF and the like or mixtures thereof. The reaction temperature may be in the range of 0 to 120° C., preferably at a temperature in the range of 0 to 100° C. The reaction time may range from 3 to 24 h, preferably from 4 to 12 h.

The conversion of compound of formula (X) to a compound of formula (I) may be carried out using a carbonylating agent such as dialkyl carbonate, dihalo carbonyl, 1,1'-carbonyldiimidazole and the like in the presence or absence of a base. The base may be selected from triethylamine, tributylamine, diisopropylethylamine, 1,4-diazabicyclo[2.2.2]octane (DABCO), 1,8-diazabicyclo[5.4.0]undec-7-ene (DBU), 1,1,5-diazabicyclo[4.3.0]non-5-ene (DBN), alkoxides like NaOMe, NaOEt and the like or the inorganic base such as NaOH, KOH and the like. The reaction may be carried out in the presence of a solvent such as dichloromethane, THF, DMF, ethyl acetate and the like or mixtures thereof. The reaction temperature may be in the range of −20 to 135° C., preferably at a temperature in the range of 15 to 80° C. The reaction time may range from 2 to 72 h, preferably from 2 to 50 h.

In still another embodiment of the present invention there is provided yet another process for the preparation of compound of the formula (I) where $R^1$ represents azido and all other symbols are as defined earlier, which comprises:

(i) reacting a compound of formula (VII)

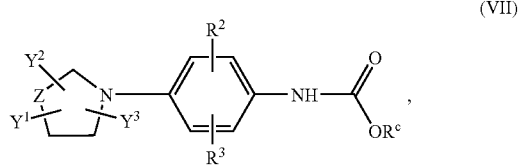

(VII)

where $R^c$ represents ($C_1$–$C_{10}$)alkyl group such as methyl, ethyl, propyl, and the like; or aralkyl group such as benzyl, allyl group and the like; and all other symbols are as defined earlier, with a compound of formula (XI)

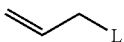

where L represents a leaving group such as halogen atom, $(C_1–C_{10})$alkoxy group such as methoxy, ethoxy, propoxy and the like, or sulphonyl group such as methylsulfonyl, ethylsulfonyl, p-toluenesulfonyl and the like; to produce a compound of formula (XII)

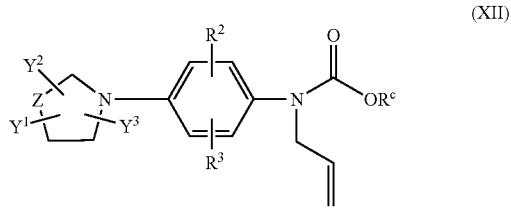

where $R^c$, $Y^1$, $Y^2$, $Y^3$, $R^2$, $R^3$ and Z are as defined earlier, (ii) converting the compound of formula (XII) defined above to a compound of formula (XIII)

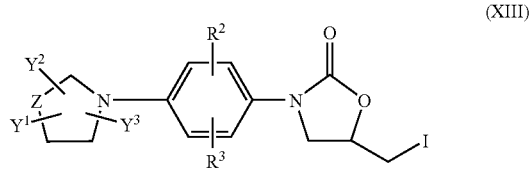

where $Y^1$, $Y^2$, $Y^3$, $R^2$, $R^3$ and Z are as defined earlier, and (iii) converting the compound of formula (XIII) defined above to a compound of formula (I) by reacting with organic or inorganic azide,

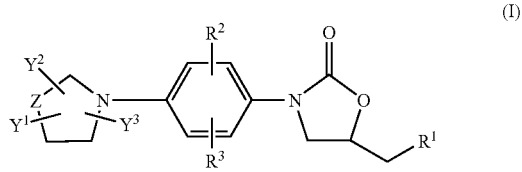

where $R^1$ represents azido group; $Y^1$, $Y^2$, $Y^3$, $R^2$, $R^3$ and Z are as defined earlier.

The reaction of a compound of formula (VII) with a compound of formula (XI) may be carried out in the presence of base such as NaH, KH, $K_2CO_3$, t-BuOK, LDA, NaOMe, with or without phase transfer catalyst such as tetrabutylammonium halide and the like. The reaction may be carried out in the presence of a suitable solvent such as THF, DMF, DMSO, benzene and the like or mixtures thereof. The reaction may be carried out at a temperature in the range of –78 to 120° C., preferably at –78 to 60° C. The reaction time may range from 2 to 20 h, preferably from 4 to 10 h.

The conversion of a compound of formula (XII) to a compound of formula (XIII) defined above may be carried in the presence of reagents such as $I_2$, KI, or NaI. The reaction may be carried out in the presence of a solvent such as chloroform ($CHCl_3$), dichloromethane ($CH_2Cl_2$), THF, DMF, DMSO, acetonitrile and the like or mixtures thereof. The reaction temperature may be in the range of 0 to 100° C., preferably at ambient temperature. The reaction time may range from 2 to 24 h, preferably from 2 to 12 h.

The conversion of a compound of formula (XIII) to a compound of formula (I) where $R^1$ represents azido group, may be carried out in the presence of one or more equivalents of metal azide such as $LiN_3$, $NaN_3$ or trialkyl silylazide. The reaction may be carried out in the presence of solvent such as THF, acetone, DMF, DMSO and the like or mixtures thereof. The reaction may be carried out in inert atmosphere, which may be maintained using $N_2$ or Ar. The reaction may be carried out at a temperature in the range of ambient temperature to reflux temperature of the solvent, preferably at a temperature in the range of 50 to 80° C. The reaction time may range from 0.5 to 18 h, preferably 1 to 4 h.

In yet another embodiment of the present invention, there is provided a process for the preparation of compound of formula (I), where $R^1$ represents hydroxy group and all other symbols are as defined earlier, which comprises:

(i) reacting a compound of formula (VII)

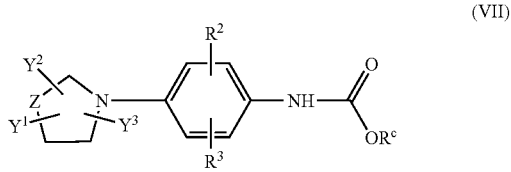

where all the symbols are as defined earlier, with a compound of formula (XIV)

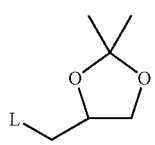

where L represents a leaving group such as halogen atom, $(C_1–C_{10})$alkoxy group such as methoxy, ethoxy, propoxy and the like, sulphonyl group such as methylsulfonyl, ethylsulfonyl, p-toluenesulfonyl and the like; to produce a compound of formula (XV)

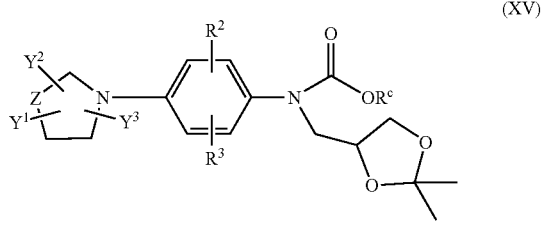

where $R^c$, $Y^1$, $Y^2$, $Y^3$, $R^2$, $R^3$ and Z are as defined earlier, (ii) hydrolysing the acetonide moiety in the compound of formula (XV) using conventional methods to produce a compound of formula (XVI)

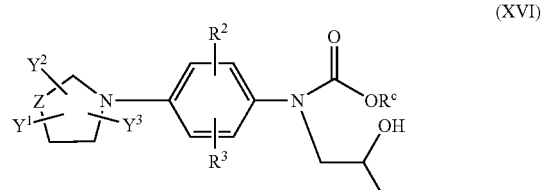

where $R^c$, $Y^1$, $Y^2$, $Y^3$, $R^2$, $R^3$ and Z are as defined earlier, and (iii) cyclising the compound of formula (XVI) with or without a base to a compound of formula (I)

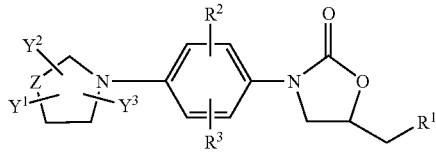
(I)

where $R^1$ represents hydroxy group and all other symbols are as defined earlier.

The reaction of a compound of formula (VII) with a compound of formula (XIV) to produce a compound of formula (XV) may be carried out in the presence of a base. The base employed may be selected from $K_2CO_3$, NaH, t-BuOK, LDA and the like. The reaction may be carried out in the presence of a solvent such as DMF, THF, DMSO, methanol, ethanol, propanol, iso-propanol and the like. The reaction may be carried at a temperature in the range of −78 to 120° C., preferably at a temperature in the range of −78 to 100° C. The reaction time may range from 2 to 24 h, preferably from 2 to 20 h.

The hydrolysis of a compound of formula (XV) to produce a compound of formula (XVI) may be carried out using dilute mineral acid such as hydrochloric acid (HCl), sulfuric acid ($H_2SO_4$) and the like, organic acids such as aqueous acetic acid, p-toluene sulfonic acid, camphorsulfonic acid, trifluoro acetic acid and the like. The reaction may be carried out in the presence of suitable solvent such as water, methanol, THF, dioxane and the like or mixtures thereof. The reaction may be carried at a temperature in the range of 30 to 100° C., preferably in the range of 30 to 60° C. The reaction time may range from 10 min to 5 h, preferably from 30 min to 2.5 h.

The conversion of a compound of formula (XVI) to a compound of formula (I) where $R^1$ represents hydroxy group, may be carried out by using a base such as NaOMe, $K_2CO_3$, NaH and the like, in presence of the a solvent such as methanol, ethanol, propanol, isopropanol, DMF, THF, and the like. The duration and temperature of the reaction are maintained in the range of 2 to 4 h and room temperature to 150° C. respectively.

In still another embodiment of the present invention there is provided yet another process for the preparation of compound of the formula (I) where $R^1$ represents hydroxy group and all other symbols are as defined earlier, which comprises:

(i) converting the compound of formula (XII)

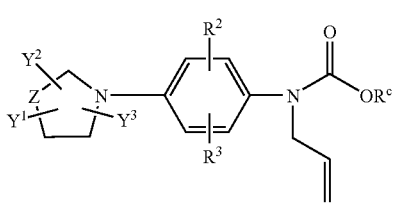
(XII)

where $R^c$, $Y^2$, $Y^3$, $R^2$, $R^3$ and Z are as defined earlier, to a compound of formula (XVI)

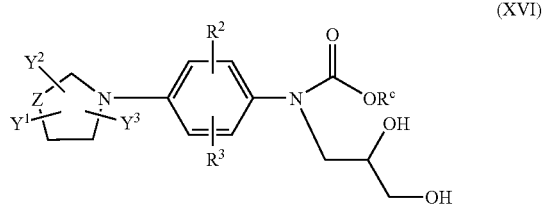
(XVI)

where $R^c$, $Y^1$, $Y^2$, $Y^3$, $R^2$, $R^3$ and Z are as defined earlier, and (ii) cyclising the compound of formula (XVI) with or without a base to a compound of formula (I)

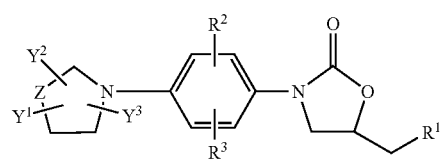
(I)

where $R^1$ represents hydroxy group and all other symbols are as defined earlier.

The conversion of a compound of (XII) to a compound of formula (XVI) may be carried out by treating with $OsO_4$, $KMnO_4$ and the other related reagents. The reaction may be carried out in the presence of co-oxidant such as N-methylmorpholine N-oxide, t-butylhydroperoxide, barium chloride and the like.

The conversion of a compound of formula (XVI) to a compound of formula (I) where $R^1$ represents hydroxy group, may be carried out by using a base such as NaOMe, $K_2CO_3$, NaH and the like, in presence of the a solvent such as methanol, ethanol, propanol, isopropanol, DMF, THF, and the like. The duration and temperature of the reaction are maintained in the range of 2 to 4 h and room temperature to 150° C. respectively.

In still another embodiment of the present invention there is provided a process for the preparation of compounds of formula (I) where $R^1$ represents azido group and all other symbols are as defined earlier, which comprises:

(i) reacting a compound of formula (VII)

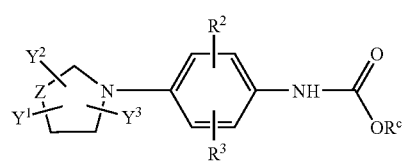
(VII)

where all the symbols are as defined earlier, with a compound of formula (XVII)

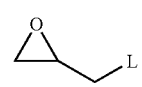
(XVII)

where L represents a leaving group such as halogen atom, ($C_1$–$C_{10}$)alkoxy group such as methoxy, ethoxy, propoxy and the like, or sulphonyl group such as methylsulfonyl, ethylsulfonyl, p-toluenesulfonyl and the like; to produce a compound of formula (XVIII)

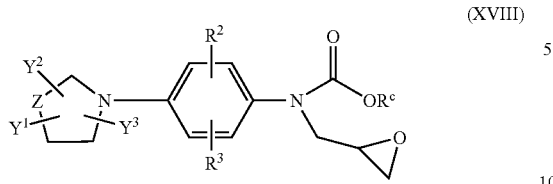
(XVIII)

where $R^c$, $Y^1$, $Y^2$, $Y_3$, $R^2$, $R^3$ and Z are as defined earlier, and
(ii) converting the compound of formula (XVIII) defined above to a compound of formula (I) by reacting with an organic or an inorganic azide,

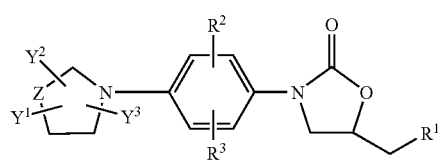
(I)

where $R^1$ represents azido group; $Y^1$, $Y^2$, $Y^3$, $R^2$, $R^3$ and Z are as defined earlier, The reaction of a compound of formula (VII) defined above with a compound of formula (XVII) defined above may be carried out in the presence of a base such as NaH, NaOMe, $K_2CO_3$, n-BuLi, LDA and the like. The reaction may be carried out in the presence of a solvent such as DMF, THF, DMSO, benzene and the like or mixtures thereof. The reaction may be carried out at a temperature in the range of −78 to 70° C. preferably at a temperature in the range of −78 to 50° C. The reaction time may range from 1 to 15 h preferably 1 to 10 h.

The conversion of a compound of formula (XVIII) to a compound of formula (I) where $R^1$ represents azido group, may be carried out in the presence of one or more equivalent of metal azide such as $LiN_3$, $NaN_3$ or trialkyl silylazide. The reaction may be carried out in the presence of solvent such as THF, acetone, DMF, DMSO and the like or mixtures thereof. The reaction may be carried out in inert atmosphere, which may be maintained by using $N_2$ or Ar. The reaction may be carried out at a temperature in the range of ambient temperature to reflux temperature of the solvent, preferably at a temperature in the range of 50 to 80° C. The reaction time may range from 0.5 to 18 h, preferably 1 to 4 h.

In still another embodiment of the present invention there is provided yet another process for the preparation of compound of the formula (I), where $R^1$ represents —$NHR^4$, wherein $R^4$ represents acetyl group and all other symbols are as defined earlier, which comprises:
(i) reacting a compound of formula (VII)

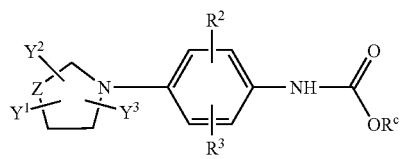
(VII)

where all the symbols are as defined earlier, with a compound of formula (XIX)

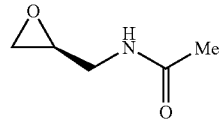
(XIX)

to produce a compound of formula (I)

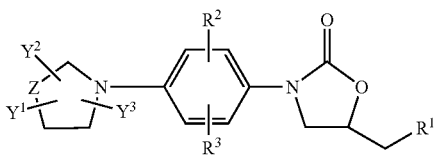
(I)

where $R^1$ represents —$NHR^4$, where $R^4$ represents acetyl group; and $Y^1$, $Y^2$, $Y^3$, $R^2$, $R^3$ and Z are as defined earlier.

The compound of formula (VII) defined above may be converted to a compound of formula (I) defined above, by reacting with compound of formula (XIX) in presence of a base such as NaH, LDA, BuLi and the like. The reaction may be carried out at a temperature in the range of −78 to 100° C., preferably in the range of −78 to 80° C. The reaction time may range from 3 to 10 h.

Another embodiment of the present invention provides a process for the preparation of compound of formula (I), which comprises:
(i) reacting the compound of formula (VI),

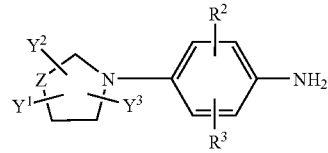
(VI)

where all symbols are as defined earlier, to a compound of formula (VIa)

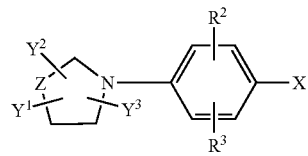
(VIa)

where X represents halogen atom such as fluorine, chlorine, bromine or iodine and all other symbols are as defined earlier,
(ii) reacting the compound of formula (VIa), with a compound of formula (IXa)

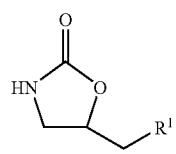
(IXa)

where R1 is as defined earlier, to obtain a compound of formula (I)

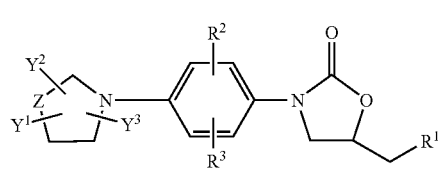
(I)

where all symbols are as defined earlier.

The compound of formula (VI) is converted to a compound of formula (VIa), by reacting with sodium nitrite, in the presence of acid and cuprous halide such as cuprous bromide and the like. The temperature of the reaction is maintained in the range of 0 to 60° C., preferably 10° C. The duration of the reaction is maintained in the range of 1 to 12 h, preferably 1–2 h.

The compound of formula (VIa) is reacted with a compound of formula (IXa), to obtain a compound of formula (I), in the presence of solvent such as dioxane, DMF, THF and the like. The reaction may be carried out in the presence of amine ligand such as cyclohexane-1,2-diamine, ethylene diamine and the like. The temperature of the reaction is maintained in the range of 60 to 140° C., preferably reflux temperature of the solvent used. The duration of the reaction is maintained in the range of 2 to 24 h, preferably 12 h.

In yet another embodiment of the present invention there is provided a process for the preparation of compound of formula (I), where $R^1$ represents —$NHR^4$, wherein $R^4$ represents formyl group; from compound of formula (I) where $R^1$ represents —$NHR^4$ wherein $R^4$ represents hydrogen atom,

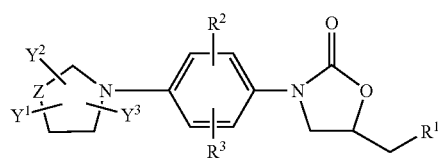
(I)

where all other symbols are as defined earlier.

The reaction of compound of formula (I) where $R^1$ represents —$NHR^4$ wherein $R^4$ represents hydrogen atom, to produce a compound of formula (I), where $R^1$ represents —$NHR^4$, wherein $R^4$ represents formyl group, may be carried out in presence of alkyl formates such as methyl formate, ethyl formate and the like. The duration of the reaction may range from 4 to 48 h, prefereably 12 to 24 h. The reaction may be carried out at a temperature in the range of 60 to 120° C., preferably at reflux temperature.

In another embodiment of the present invention there is provided a process for the preparation of compound of formula (I), where $R^1$ represents —$NHR^4$, wherein $R^4$ represents —$C(=O)$—$R^{4a}$, where $R^{4a}$ represents ($C_1$–$C_{10}$) alkyl, ($C_1$–$C_{10}$)lkoxy, ($C_2$–$C_{10}$)alkenyl, halo($C_1$–$C_{10}$)alkyl, aryloxy, ($C_2$–$C_{10}$)alkenyloxy, aryloxy-C(=O)— or ($C_1$–$C_{10}$)alkoxy-C(=O)—; from a compound of formula (I) where $R^1$ represents —$NHR^4$ wherein $R^4$ represents hydrogen atom,

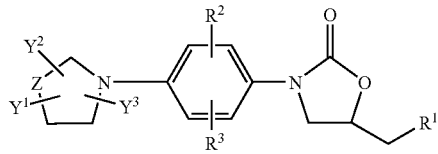
(I)

where all other symbols are as defined earlier.

The above conversion may be carried out by treating the starting material with appropriate halide such as acetyl chloride like acetyl chloride, propionyl chloride and the like; ($C_1$–$C_{10}$)alkylchloroformate like methylchloroformate, ethylchloroformate and the like; aralkylchloroformate like benzylchloroformate and the like. The reaction may be carried out in the presence of a solvent such as $CH_2Cl_2$, $CHCl_3$, toluene, THF and the like or mixtures thereof. The reaction may be carried out in the presence of a base like $Et_3N$, diisopropyl ethylamine, $K_2CO_3$, NaH, KOt-Bu and the like. The reaction may be carried at a temperature in the range of –20 to 60° C., preferably at a temperature in the range of 0 to room temperature. The reaction time may range from 1 to 12 h, preferably from 1 to 4 h.

Alternatively, the compound of formula (I), where $R^1$ represents —$NHR^4$ wherein $R^4$ represents acetyl group, may be prepared by reacting compound of formula (I) where $R^1$ represents azido group, by treating with thioacetic acid.

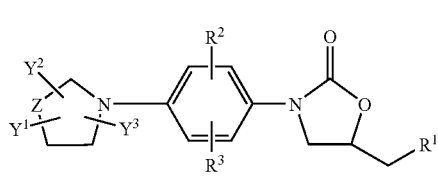
(I)

The compound of formula (I) where $R^1$ represents azido group may be converted to a compound of formula (I) where $R^1$ represents $NHR^4$ wherein $R^4$ represents acetyl group by using thioacetic acid, with or without using a solvent such as THF, DMF, toluene and the like. The reaction may be carried out at a temperature in the range of 25 to 40° C., preferably at room temperature. The reaction may range from 3 to 24 h, preferably from 4 to 12 h.

In another embodiment of the present invention there is provided a process for the preparation of compound of formula (I), where $R^1$ represents $NHR^4$, wherein $R^4$ represents —$C(=S)$—$R^{4b}$, wherein $R^{4b}$ represents ($C_1$–$C_{10}$) alkyl, halo($C_1$–$C_{10}$)alkyl, —$C(=O)$—($C_1$–$C_{10}$)alkoxy, —$C(=O)$-aryloxy, —$C(=S)$—($C_1$–$C_{10}$)alkyl or —$C(=S)$-aryl; from compound of formula (I), where $R^1$ represents $NHR^4$, wherein $R^4$ represents —$C(=O)$—$R^{4b}$, wherein $R^{4b}$ represents ($C_1$–$C_{10}$)alkyl, halo($C_1$–$C_{10}$)alkyl, C(=O)— ($C_1$–$C_{10}$)alkoxy, —$C(=O)$-aryloxy, —$C(=S)$—($C_1$–$C_{10}$) alkyl or —$C(=S)$-aryl.

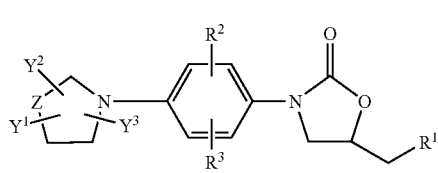
(I)

where all symbols are as defined earlier.

The above conversion may be carried out by taking a solution of the amide and Lawesson's reagent (2,4-bis(methoxyphenyl)-1,3-dithia-2,4-diphosphetane-2,4-disulfide) in dry dioxane, toluene, THF, DMF and the like. The reaction may be carried at a temperature in the range of room temperature to 130° C., preferably at a temperature in the range of 55 to 90° C. The reaction time may range from 3 to 24 h, preferably from 3 to 10 h.

In another embodiment of the present invention there is provided a process for the preparation of compound of formula (I), where $R^1$ represents —$NHR^4$, wherein $R^4$ represents —C(=S)—$SR^{4c}$, wherein $R^{4c}$ represents ($C_1$–$C_{10}$)alkyl group; from compound of formula (I) where $R^1$ represents —$NHR^4$ wherein $R^4$ represents hydrogen atom,

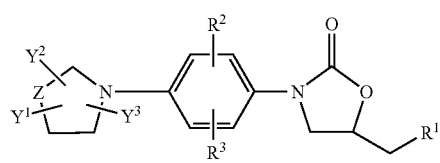
(I)

where all other symbols are as defined earlier.

The compound of fomula (I), where $R^1$ represents —$NHR^4$, wherein $R^4$ represents —C(=S)—$SR^{4c}$, wherein $R^{4c}$ represents ($C_1$–$C_{10}$)alkyl group, may be prepared from compound of formula (I) where $R^1$ represents —$NHR^4$ wherein $R^4$ represents hydrogen atom, by using $CS_2$ in the presence of a base such as $Et_3N$, diisopropyl ethylamine, $K_2CO_3$, NaH, t-BuOK and the like, followed by the appropriate alkylhalide such as methyliodide, ethylbromide, propylbromide and the like. The reaction may be carried out in the presence of a solvent such as water, ethanol, methanol, isopropanol, acetonitrile and the like, or mixtures thereof. The reaction may be carried at a temperature in the range of room temperature to 60° C., preferably at room temperature. The reaction time may range from 6 to 24 h.

In another embodiment of the present invention there is provided a process for the preparation of compound of formula (I), where $R^1$ represents —$NHR^4$, wherein $R^4$ represents —C(=S)—$OR^{4d}$, $R^{4d}$ represents ($C_1$–$C_{10}$)alkyl, ($C_3$–$C_8$)cycloalkyl, —(C=O)—($C_1$–$C_{10}$)alkyl group substituted with fluorine; aryl such as phenyl or napthyl and the like; halo($C_1$–$C_{10}$)alkyl, hydroxy($C_1$–$C_{10}$)alkyl, ($C_1$–$C_{10}$)alkoxy($C_1$–$C_{10}$)alkyl or ($C_2$–$C_{10}$)alkenyl, which comprises:

(i) converting the compound of formula (I) where $R^1$ represents —$NHR^4$ wherein $R^4$ represents hydrogen atom, to a compound of formula (I) where $R^1$ represents isothiocyanate group,

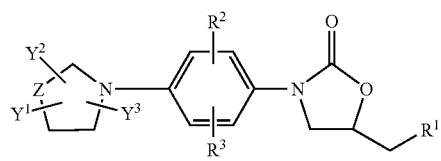
(I)

where all other symbols are as defined earlier, (ii) converting the compound of formula (I) where $R^1$ represents isothiocyanate group, to a compound of formula (I) where $R^1$ represents —$NHR^4$, wherein $R^4$ represents —C(=S)—$OR^{4d}$, wherein $R^{4d}$ represents ($C_1$–$C_{10}$)alkyl, ($C_3$–$C_8$)cycloalkyl, —(C=O)—(C1–C10)alkyl group substituted with fluorine; aryl, halo($C_1$–$C_{10}$)alkyl, hydroxy($C_1$–$C_{10}$)alkyl, ($C_1$–$C_{10}$)alkoxy(C1–C10)alkyl or ($C_2$–$C_{10}$)alkenyl group and all other symbols are as defined earlier.

The compound of fomula (I) where $R^1$ represents isothiocyanate group, may be prepared from compound of formula (I) where $R^1$ represents —$NHR^4$ wherein $R^4$ represents hydrogen atom, by using thiophosgene, in the presence of a base such as $Et_3N$, $K_2CO_3$, NaOH and the like. The reaction may be carried out in the presence of a solvent such as ethanol, methanol, isopropanol, $CH_2Cl_2$, acetonitrile and the like. The reaction may be carried at a temperature in the range of 0 to 60° C., preferably at 0° C. The reaction may be carried out in an inert atmosphere using argon or any other inert gas. The reaction time may range from 3 to 24 h.

The compound of formula (I) where $R^1$ represents —$NHR^4$, wherein $R^4$ represents —C(=S)—$OR^{4d}$, wherein $R^{4d}$ represents ($C_1$–$C_{10}$)alkyl, ($C_3$–$C_8$)cycloalkyl, —(C=O)—($C_1$–$C_{10}$)alkyl group substituted with fluorine; aryl, halo($C_1$–$C_{10}$)alkyl, hydroxy($C_1$–$C_{10}$)alkyl, ($C_1$–$C_{10}$)alkoxy($C_1$–$C_{10}$)alkyl or ($C_2$–$C_{10}$)alkenyl, is prepared from the compound of formula (I) where $R^1$ represents isothiocyanate group, by using respective alcohol such as methanol, ethanol, propanol, cylcohexanol and the like, in the presence of a base such as NaH, KH and the like. The reaction may be carried out in the presence of a solvent such as THF, toluene, DMF and the like. The reaction may be carried at a temperature in the range of room temperature to 130° C., preferably at reflux temperature of the solvent used. The reaction time may range from 6 to 24 h.

In another embodiment of the present invention there is provided a process for the preparation of compound of formula (I), where $R^1$ represents —$NHR^4$, wherein $R^4$ represents —C(=S)—N(R'R''), wherein R' represents hydrogen, ($C_1$–$C_{10}$)alkyl, ($C_2$–$C_{10}$)alkenyl, substituted or unsubstituted aralkyl, heteroaralkyl, hydroxy($C_1$–$C_{10}$)alkyl, R' represents hydrogen or ($C_1$–$C_{10}$)alkyl or the two R' and R'' groups together form a 5 or 6 membered cyclic structures containing one or two hetero atoms; from a compound of formula (I) where $R^1$ represents isothiocyanate group,

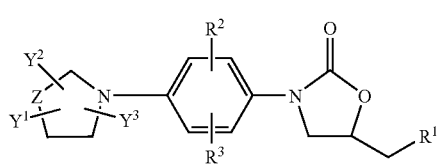
(I)

where all other symbols are as defined earlier.

The compound of formula (I), where $R^1$ represents —$NHR^4$, wherein $R^4$ represents —C(=S)—N(R'R''), where in R' and R'' independently represent hydrogen, is prepared by passing ammonia gas into a solution of compound of formula (I) where $R^1$ represents isothiocyanate group, by using a solvent such as THF, toluene, and the like. The reaction may be carried at a temperature in the range of –10° C. to room temperature, preferably at –10° C. The reaction time may range from 20 min to 4 h, preferably 30 min. The compound of formula (I), where $R^1$ represents —$NHR^4$, wherein $R^4$ represents —C(=S)—N(R'R''), R' represents hydrogen, ($C_1$–$C_{10}$)alkyl, alkenyl, substituted or unsubstituted aralkyl, heteroaralkyl, hydroxy($C_1$–$C_{10}$)alkyl, R'' represents hydrogen or alkyl or R' and R'' groups together form a 5 or 6 membered cyclic structures containing one or two hetero atoms, is prepared by treating compound of formula (I) where R¹ represents isothiocyanate group, by using appropriate amine such as methylamine, ethylamine, dimethylamine, diethylamine, benzylamine, aniline, proline, morpholine, thiomorpholine, pyridiylmethylamine and the like, in the presence of a solvent such as THF, DMF, toluene, and the like. The reaction may be carried at a temperature in the range of room temperature to 140° C., preferably at 60 to 100° C. The reaction time may range from 1 to 24 h, preferably 4 to 12 h.

In yet another embodiment of the present invention there is provided a process for the preparation of compound of formula (I) where Z represents $NR^b$ wherein $R^b$ represents hydrogen, $Y^1$ represents '=O' group, $Y^2$ and $Y^3$ independently represent hydrogen atom, from a compound of formula (I) where Z represents $NR^b$ wherein $R^b$ represents ($C_1$–$C_{10}$)alkyl group substituted with hydroxy group, $Y^1$ represents '=O group', $Y^2$ and $Y^3$ independently represent hydrogen atom,

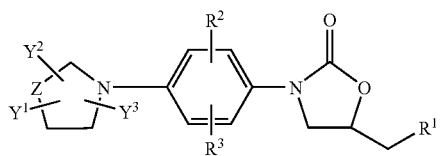

(I)

where all other symbols are as defined earlier.

The compound of formula (I) where Z represents $NR^b$ wherein $R^b$ represents hydrogen, $Y^1$ represents '=O' group, $Y^2$ and $Y^3$ independently represent hydrogen atom, from a compound of formula (I) wherein Z represents $NR^b$ wherein $R^b$ represents ($C_1$–$C_{10}$)alkyl group substituted with hydroxy group at the α-position, $Y^1$ represents '=O group', $Y^2$ and $Y^3$ independently represent hydrogen atom, may be prepared by treating with a base such as triethylamine, di-isopropylamine, di-isopropylethylamine, pyridine, piperidine, 4-dimethylaminopyridine (DMAP), 1,8-diazabicyclo[5.4.0]undec-7-ene (DBU), LDA, potassium bis-(trimethyl silyl)amide, BuLi, $Na_2CO_3$, $K_2CO_3$, NaOH, KOH, NaOMe, NaOEt, NaOiPr, t-BuOK, NaH, KH and the like. The solvents used in the reaction may be selected from THF, ether, dioxane, toluene, benzene, DMF, DMSO, acetonitrile and the like. The temperature of the reaction may be maintained in the range of –20 to 150° C., preferably in the range of –10 to 100° C. The duration of the reaction may be in the range of 0.2 to 64 h, preferably in the range of 1 to 48 h.

In still another embodiment of the present invention there is provided a process for the preparation of compound of formula (I), where Z represents $NR^b$ wherein $R^b$ represents substituted or unsubstituted ($C_1$–$C_{10}$)alkyl or aralkyl, $Y^1$ represents '=O group', $Y^2$ and $Y^3$ independently represent hydrogen atom; from a compound of formula (I) where Z represents $NR^b$ wherein $R^b$ represents hydrogen, $Y^1$ represents '=O' group, $Y^2$ and $Y^3$ independently represent hydrogen atom,

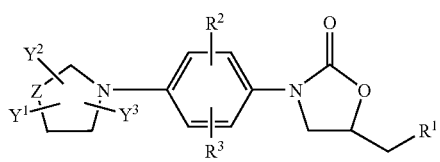

(I)

where all other symbols are as defined earlier.

The compound of formula (I), wherein Z represents $NR^b$ wherein $R^b$ represents substituted or unsubstituted ($C_1$–$C_{10}$) alkyl or aralkyl, $Y^1$ represents '=O group', $Y^2$ and $Y^3$ independently represent hydrogen atom, from a compound of formula (I) wherein Z represents $NR^b$ wherein $R^b$ represents hydrogen, $Y^1$ represents '=O' group, $Y^2$ and $Y^3$ independently represent hydrogen atom, may be carried out in the presence of a base such as triethylamine, di-isopropylamine, di-isopropylethylamine, pyridine, piperidine, DMAP, 1,8-diazabicyclo[5.4.0]undec-7-ene (DBU), LDA, potassium bis-(trimethyl silyl)amide, BuLi, $Na_2CO_3$, $K_2CO_3$, NaOH, KOH, NaOMe, NaOEt, NaOiPr, t-BuOK, NaH, KH and the like, followed by reacting with alkyl halide such as methyliodide, methoxymethylchloride, allylbromide, benzylbromide and the like. The solvent used in the reaction may be selected from DMF, DMSO, THF, dioxane, benzene, toluene and the like. The temperature of the reaction may be maintained in the range of –5 to 150° C., preferably in the range of 0° C. to reflux temperature of the solvent. The duraion of the reaction may be in the range of 0.2 to 48 h, preferably in the range of 0.5 to 24 h.

In another embodiment of the present invention there is provided a process for the preparation of a compound of formula (I) where R¹ represents halogen, from compound of formula (I) where R¹ represents hydroxy group,

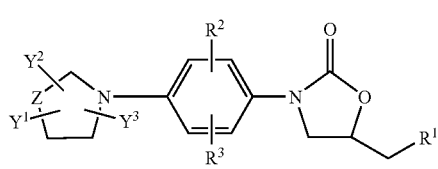

(I)

where all other symbols are as defined above.

The compound of formula (I) where R¹ represents halogen is prepared from compound of formula (I) where R¹ represents hydroxy group may be carried out by treating with tetrahalomethane group such as $CBr_4$, $CCl_4$ and the like, in the presence of $PPh_3$, $P(alkyl)_3$ and the like. The reaction may be carried out in the presence of a solvent such as dry dichloromethane, chloroform, tetrachloromethane, benzene, DMF, DMSO, THF and the like. The temperature of the reaction may be maintained in the range of 0 to 60° C., preferably at room temperature. The duration of the reaction may be in the range of 2 to 24 h, preferably 8 to 13 h.

In another embodiment of the present invention there is provided a process for the preparation of a compound of formula (I) where R¹ represents 'SH', from compound of formula (I) where R¹ represents halogen atom,

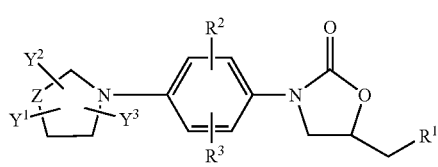

(I)

where all other symbols are as defined above, which comprises (i) reacting the compound of formula (I) where R¹ represents halogen atom, to produce a compound of formula (XX),

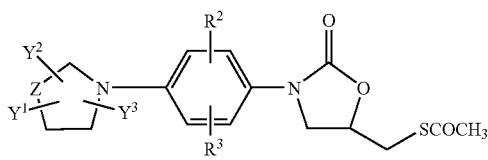
(XX)

where all other symbols are as defined earlier, with a base and thioacetic acid, (ii) reacting the compound of formula (XX), to produce a compound of formula (I) where $R^1$ represents 'SH' group and all other symbols are as defined earlier, with base.

The compound of formula (XX) is prepared from compound of formula (I) where $R^1$ represents hydroxy group is prepared by using thioacetic acid in the presence of a base such as triethylamine, di-isopropylamine, di-isopropylethylamine, pyridine, piperidine, DMAP, DBU, LDA, potassium bis-(trimethyl silyl)amide, BuLi, $Na_2CO_3$, $K_2CO_3$, NaOH, KOH, NaOMe, NaOEt, NaOiPr, t-BuOK, NaH, KH and the like. The solvent used in the reaction may be seleceted from THF, benzene, dioxane and the like. The temperature of the reaction is maintained in the range of room temperature to reflux temperature, preferably at reflux temperature. The duration of the reaction is maintained in the range of 2 to 24 h, preferably 6 h.

The compound of formula (I), where $R^1$ represents 'SH' group is prepared from compound of formula (XX) by reacting with a base such as $K_2CO_3$, NaOH, KOH, BuLi and the like. The reaction may be carried out at a temperature in the range of room temperature to reflux temprature. The duration of the reaction may be in the range of 1 to 24 h.

In still another embodiment of the present invention there is provided a novel intermediate of the formula (VII)

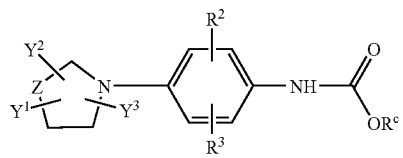
(VII)

where $R^c$ represents $(C_1-C_{10})$alkyl group such as methyl, ethyl, propyl, and the like; aralkyl group such as benzyl, allyl group and the like; $R^2$ and $R^3$, which may be the same or different, are each independently hydrogen, halogen, $(C_1-C_{10})$alkyl, halogenated $(C_1-C_{10})$alkyl, cyano, nitro, $SR^a$, $NR^a$, or $OR^a$, in which $R^a$ is hydrogen, $(C_1-C_{10})$alkyl or halogenated $(C_1-C_{10})$alkyl;

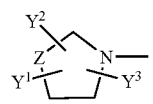

is a heterocyclic moiety in which

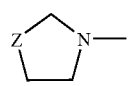

is a 5-membered heterocyclic skeleton, Z represents O, S, =CH, —$CH_2$ or $NR^b$, $R^b$ is hydrogen or a moiety, which may be substituted or unsubstituted, straight chain or branched, selected from the group consisting of $(C_1-C_{10})$ alkyl, $(C_2-C_{10})$alkenyl, $(C_3-C_8)$cycloalkyl, hydroxy $(C_1-C_{10})$alkyl, $(C_1-C_{10})$alkylhydroxy, $(C_1-C_{10})$alkylamino, amino$(C_1-C_{10})$alkyl, $(C_1-C_{10})$alkoxy, aryl, aralkyl, aryloxy, $(C_1-C_{10})$alkylcarbonyl, arylcarbonyl, $(C_1-C_{10})$alkoxycarbonyl and aryloxycarbonyl;

$Y^1$ represents =O or =S group and $Y^2$ and $Y^3$ independently represent hydrogen, halogen, cyano, nitro, formyl, hydroxy, amino, =O, =S group or substituted or unsubstituted groups selected from $(C_1-C_{10})$alkyl, hydroxy$(C_1-C_{10})$alkyl, $(C_1-C_{10})$alkylhydroxy, $(C_1-C_{10})$alkoxy$(C_1-C_{10})$alkyl, $(C_1-C_{10})$alkylcarbonyl, $(C_1-C_{10})$alkoxycarbonyl, arylcarbonyl, carboxy$(C_1-C_{10})$alkyl, $(C_1-C_{10})$alkylsulfonyl, $(C_1-C_{10})$alkylcarbony$(C_1-C_{10})$alkyl, arylcarbonylamino$(C_1-C_{10})$alkyl, $(C_1-C_{10})$alkylcarbonyloxy$(C_1-C_{10})$ alkyl, amino$(C_1-C_{10})$alkyl, mono$(C_1-C_{10})$alkylamino, di$(C_1-C_{10})$alkylamino, arylamino, $(C_1-C_{10})$alkoxy, aryl, aryloxy, aralkyl, heteroaryl, heteroaralkyl, heterocyclyl or heterocycloalkyl; $Y^2$ and $Y^3$ when present on adjacent carbon atoms together may also form a substituted or unsubstituted 5 or 6 membered aromatic or non-aromatic cyclic structure, optionally containing one or two hetero atoms selected from oxygen, sulfur or nitrogen.

The novel intermediate of formula (VII) may be prepared by a process, which comprises:

(i) reacting a compound of formula (III)

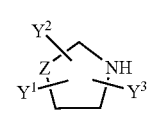
(III)

where all the symbols are as defined earlier, with a compound of formula (IV)

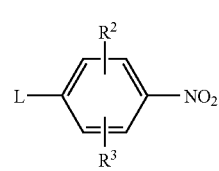
(IV)

where L represents a leaving group such as halogen atom, $(C_1-C_{10})$alkoxy group such as methoxy, ethoxy, propoxy and the like, or sulphonyl group such as methylsulfonyl, ethylsulfonyl, p-toluenesulfonyl and the like; and the like; $R^2$ and $R^3$ are as defined earlier, to produce a compound of formula (V)

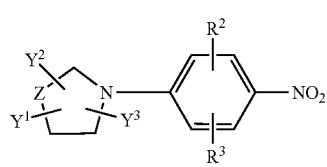
(V)

where $Y^1$, $Y^2$, $Y^3$, $R^2$, $R^3$ and Z are as defined earlier, (ii) reducing the compound of formula (V) to produce a compound of formula (VI)

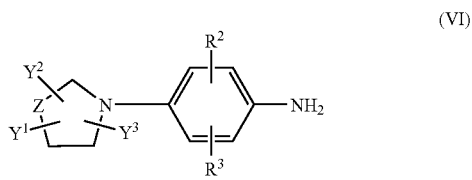
(VI)

where $Y^1$, $Y^2$, $Y^3$, $R^2$, $R^3$ and Z are as defined earlier, (iii) reacting the compound of formula (VI) with alkylchloroformate, to produce a compound of formula (VII)

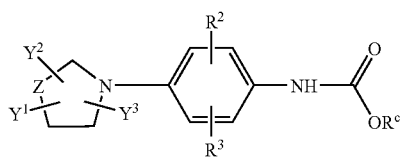
(VII)

where $R^c$, $Y^1$, $Y^2$, $Y^3$, $R^2$, $R^3$ and Z are as defined above,

The reaction of a compound of formula (III) with a compound of formula (IV) to produce a compound of formula (V) may be carried out using a base such as KOH, NaOH, $K_2CO_3$, $Na_2CO_3$, NaH, KH, triethylamine, diisopropylethyl amine and the like. The reaction may be carried out using a solvent such as DMSO, DMF, THF, acetonitrile, chloroform and the like or mixtures thereof. The reaction may be carried out in inert atmosphere, which may be maintained using inert gases such as $N_2$ or Ar. The reaction may be carried out at a temperature in the range of 20° C.–100° C., preferably at a temperature in the range of ambient to 80° C. The reaction time may range from 1 to 15 h, preferably from 6 to 12 h.

The reduction of a compound of formula (V) to produce a compound of formula (VI) may be carried out in the presence of gaseous hydrogen and a catalyst such as Ru, Pd, Rh, Pt, Ni on solid beads such as charcoal, alumina, asbestos and the like. The reduction may be conducted in the presence of a solvent such as dioxane, acetic acid, ethyl acetate, THF, alcohol such as methanol, ethanol and the like or mixtures thereof. A pressure between atmospheric pressure to 60 psi may be used. The reaction may be carried out at a temperature from 25 to 60° C., preferably at room temperature. The reaction time ranges from 2 to 48 h. The reduction may also be carried out by employing metal in mineral acids such Sn/HCl, Fe/HCl, Zn/HCl, $Zn/CH_3CO_2H$ and the like.

The conversion of compound of formula (VI) to compound of formula (VII) may be carried out with an alkylchloroformate such as methychloroformate, ethylchloroformate, propylchloroformate, benzylchloroformate and the like. The solvent of the reaction may be selected from water, acetone, tetrahydrofuran (THF), acetonitrile, dichloromethane (DCM) and the like or mixtures thereof. The reaction may be carried out in the presence of base such as $K_2CO_3$, $Na_2CO_3$, NaOH, KOH, triethylamine and the like. The temperature of the reaction may be carried out in the presence of 0 to 60° C., preferably at 0° C. to room temperature. The time of the reaction is maintained in the range of 1–12 h, preferably in the range of 1–4 h.

In still another embodiment of the present invention there is provided a novel intermediate of formula (VI)

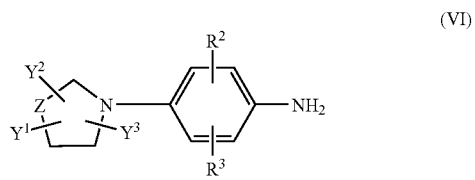
(VI)

where $R^2$ and $R^3$, which may be the same or different, are each independently hydrogen, halogen, $(C_1-C_{10})$alkyl, halogenated $(C_1-C_{10})$alkyl, cyano, nitro, $SR^a$, $NR^a$, or $OR^a$, in which $R^a$ is hydrogen, $(C_1-C_{10})$alkyl or halogenated $(C_1-C_{10})$alkyl;

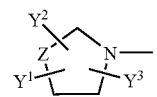

is a heterocyclic moiety in which

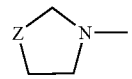

is a 5-membered heterocyclic skeleton, Z represents O, S, =CH, $-CH_2$ or $NR^b$, where $R^b$ is hydrogen or a moiety, which may be substituted or unsubstituted, straight chain or branched, selected from the group consisting of $(C_1-C_{10})$ alkyl, $(C_2-C_{10})$alkenyl, $(C_3-C_8)$cycloalkyl, hydroxy $(C_1-C_{10})$alkyl, $(C_1-C_{10})$alkylhydroxy, $(C_1-C_{10})$alkylamino, amino$(C_1-C_{10})$alkyl, $(C_1-C_{10})$alkoxy, aryl, aralkyl, aryloxy, $(C_1-C_{10})$alkylcarbonyl, arylcarbonyl, $(C_1-C_{10})$alkoxycarbonyl and aryloxycarbonyl;

$Y^1$ represents =O or =S group and $Y^2$ and $Y^3$ independently represent hydrogen, halogen, cyano, nitro, formyl, hydroxy, amino, =O, =S group or substituted or unsubstituted groups selected from $(C_1-C_{10})$alkyl, hydroxy$(C_1-C_{10})$ alkyl, $(C_1-C_{10})$alkylhydroxy, $(C_1-C_{10})$alkoxy$(C_1-C_{10})$ alkyl, $(C_1-C_{10})$alkylcarbonyl, $(C_1-C_{10})$alkoxycarbonyl, arylcarbonyl, carboxy$(C_1-C_{10})$alkyl, $(C_1-C_{10})$alkylsulfonyl, $(C_1-C_{10})$alkylcarbony$(C_1-C_{10})$alkyl, arylcarbonylamino$(C_1-C_{10})$alkyl, $(C_1-C_{10})$ alkylcarbonyloxy$(C_1-C_{10})$ alkyl, amino$(C_1-C_{10})$alkyl, mono$(C_1-C_{10})$alkylamino, di$(C_1-C_{10})$alkylamino, arylamino, $(C_1-C_{10})$alkoxy, aryl, aryloxy, aralkyl, heteroaryl, heteroaralkyl, heterocyclyl or heterocycloalkyl; $Y^2$ and $Y^3$ when present on adjacent carbon atoms together may also form a substituted or unsubstituted 5 or 6 membered aromatic or non-aromatic cyclic structure, optionally containing one or two hetero atoms selected from oxygen, sulfur or nitrogen.

The novel intermediate of formula (VI) may be prepared by a process, which comprises:

(i) reacting a compound of formula (III)

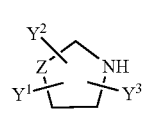
(III)

where all the symbols are as defined earlier, with a compound of formula (IV)

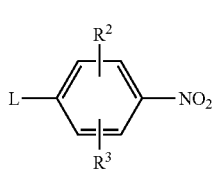

(IV)

where L represents a leaving group such as halogen atom, (C$_1$–C$_{10}$)alkoxy group such as methoxy, ethoxy, propoxy and the like, or sulphonyl group such as methylsulfonyl, ethylsulfonyl, p-toluenesulfonyl and the like; R$^2$ and R$^3$ are as defined earlier, to produce a compound of formula (V)

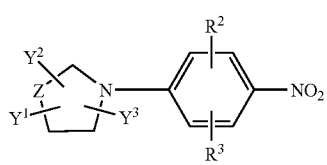

(V)

where Y$^1$, Y$^2$, Y$^3$, R$^2$, R$^3$ and Z are as defined earlier, and (ii) reducing the compound of formula (V) to produce a compound of formula (VI)

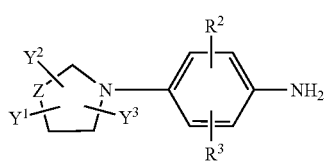

(VI)

where Y$^1$, Y$^2$, Y$^3$, R$^2$, R$^3$ and Z are as defined earlier,

The reaction of a compound of formula (III) with a compound of formula (IV) to produce a compound of formula (V) may be carried out using a base such as KOH, NaOH, K$_2$CO$_3$, Na$_2$CO$_3$, NaH, KH, triethylamine, diisopropylethyl amine and the like. The reaction may be carried out using a solvent such as DMSO, DMF, THF, acetonitrile, chloroform and the like or mixtures thereof. The reaction may be carried out in inert atmosphere, which may be maintained using inert gases such as N$_2$ or Ar. The reaction may be carried out at a temperature in the range of 20° C.–100° C., preferably at a temperature in the range of ambient-80° C. The reaction time may range from 1 to 15 h, preferably from 6 to 12 h.

The reduction of a compound of formula (V) to produce a compound of formula (VI) may be carried out in the presence of gaseous hydrogen and a catalyst such as Ru, Pd, Rh, Pt, Ni on solid beads such as charcoal, alumina, asbestos and the like. The reduction may be conducted in the presence of a solvent such as dioxane, acetic acid, ethyl acetate, THF, alcohol such as methanol, ethanol and the like or mixtures thereof. A pressure between atmospheric pressure to 60 psi may be used. The reaction may be carried out at a temperature from 25 to 60° C., preferably at room temperature. The reaction time ranges from 2 to 48 h. The reduction may also be carried out by employing metal in mineral acids such Sn/HCl, Fe/HCl, Zn/HCl, Zn/CH$_3$CO$_2$H and the like.

In yet another embodiment of the present invention there is provided a novel intermediate of formula (X)

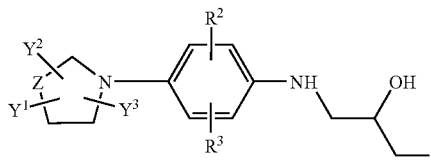

(X)

where R$^1$ is halo, azido, isothiocyano, thioalcohol, —OR$^4$, —NHR$^4$ or —N(R$^4$)$_2$, where R$^4$ represents hydrogen atom, or substituted or unsubstituted groups selected from (C$_1$–C$_{10}$)alkyl, (C$_1$–C$_{10}$)acyl, thio(C$_1$–C$_{10}$)acyl, —C(=O)—(C$_1$–C$_{10}$)alkoxy, —C(=S)—(C$_3$–C$_8$)cycloalkoxy, —C(=O)—(C$_2$–C$_{10}$)alkenyloxy, —C(=O)—(C$_2$–C$_{10}$)alkenyl, —C(=O)-aryloxy, —C(=S)—(C$_1$–C$_{10}$)alkoxy, —C(=S)—(C$_2$–C$_{10}$)alkenyloxy, —C(=S)-aryloxy, —C(=O)—C(=O)—(C$_1$–C$_{10}$)alkyl, —C(=O)—C(=O)-aryl, —C(=O)—C(=O)—(C$_1$–C$_{10}$)alkoxy, —C(=O)—C(=O)-aryloxy, —C(=S)—S—(C$_1$–C$_{10}$)alkyl, —(C=S)—NH$_2$, —(C=S)—NH—(C$_1$–C$_{10}$)alkyl, —C(=S)—N((C$_1$–C$_{10}$)alkyl)$_2$, —C(=S)—NH—(C$_2$–C$_{10}$)alkenyl, (C=S)—(C=O)—(C$_1$–C$_{10}$)alkoxy, —(C=S)—(C=O)-aryloxy, —C(=S)—O—(C=O)—(C$_1$–C$_{10}$)alkyl, C(=S)—C(=S)—(C$_1$–C$_{10}$)alkyl, —C(=S)—C(=S)-aryl, thiomorpholinyl-C(=S)— or pyrrolidinyl-C(=S)—;

R$^2$ and R$^3$, which may be the same or different, are each independently hydrogen, halogen, (C$_1$–C$_{10}$)alkyl, halogenated (C$_1$–C$_{10}$)alkyl, cyano, nitro, SR$^a$, NR$^a$, or OR$^a$, in which R$^a$ is hydrogen, (C$_1$–C$_{10}$)alkyl or halogenated (C$_1$–C$_{10}$)alkyl;

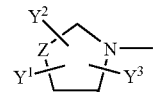

is a heterocyclic moiety in which

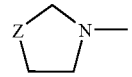

is a 5-membered heterocyclic skeleton, Z represents O, S, =CH, —CH$_2$ or NR$^b$ where R$^b$ is hydrogen or a moiety, which may be substituted or unsubstituted, straight chain or branched, selected from the group consisting of (C$_1$–C$_{10}$) alkyl, (C$_2$–C$_{10}$)alkenyl, (C$_3$–C$_8$)cycloalkyl, hydroxy (C$_1$–C$_{10}$)alkyl, (C$_1$–C$_{10}$)alkylhydroxy, (C$_1$–C$_{10}$)alkylamino, amino(C$_1$–C$_{10}$)alkyl, (C$_1$–C$_{10}$)alkoxy, aryl, aralkyl, aryloxy, (C$_1$–C$_{10}$)alkylcarbonyl, arylcarbonyl, (C$_1$–C$_{10}$)alkoxycarbonyl and aryloxycarbonyl;

Y$^1$ represents =O or =S group and Y$^2$ and Y$^3$ independently represent hydrogen, halogen, cyano, nitro, formyl, hydroxy, amino, =O, =S group or substituted or unsubstituted groups selected from (C$_1$–C$_{10}$)alkyl, hydroxy(C$_1$–C$_{10}$) alkyl, (C$_1$–C$_{10}$)alkylhydroxy, (C$_1$–C$_{10}$)alkoxy(C$_1$–C$_{10}$) alkyl, (C$_1$–C$_{10}$)alkylcarbonyl, (C$_1$–C$_{10}$)alkoxycarbonyl, arylcarbonyl, carboxy(C$_1$–C$_{10}$)alkyl, (C$_1$–C$_{10}$)alkylsulfonyl, (C$_1$–C$_{10}$)alkylcarbony(C$_1$–C$_{10}$)alkyl, arylcarbonylamino(C$_1$–C$_{10}$)alkyl, (C$_1$–C$_{10}$)alkylcarbonyloxy (C$_1$–C$_{10}$) alkyl, amino(C$_1$–C$_{10}$)alkyl, mono(C$_1$–C$_{10}$)alkylamino, di(C$_1$–C$_{10}$)alkylamino, arylamino, (C$_1$–C$_{10}$)alkoxy, aryl, aryloxy, aralkyl, heteroaryl, heteroaralkyl, heterocyclyl or heterocycloalkyl; $Y^2$ and $Y^3$ when present on adjacent carbon atoms together may also form a substituted or unsubstituted 5 or 6 membered aromatic or non-aromatic cyclic structure, optionally containing one or two hetero atoms selected from oxygen, nitrogen or sulfur.

The novel intermediate of formula (X) may be prepared by a process, which comprises:

(i) reacting a compound of formula (III)

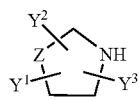

(III)

where all the symbols are as defined earlier, with a compound of formula (IV)

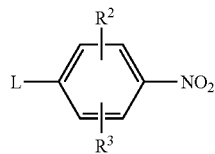

(IV)

where L represents a leaving group such as halogen atom, $(C_1-C_{10})$alkoxy, such as methoxy, ethoxy, propoxy and the like or sulfonyl groups such as methylsulfonyl, ethylsulfonyl, p-toluenesulfonyl and the like; $R^2$ and $R^3$ are as defined earlier, to produce a compound of formula (V)

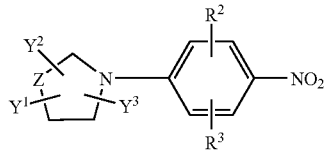

(V)

where $Y^1$, $Y^2$, $Y^3$, $R^2$, $R^3$ and Z are as defined earlier, (ii) reducing the compound of formula (V) to produce a compound of formula (VI)

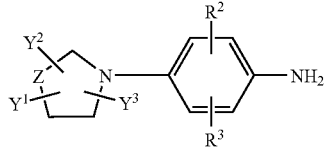

(VI)

where $Y_1$, $Y^2$, $Y^3$, $R^2$, $R^3$ and Z are as defined earlier, and (iii) reacting the compound of formula (VI) with a compound of formula (IX)

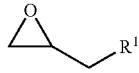

(IX)

where $R^1$ represents —$NHR^4$ or —$N(R^4)_2$, where $R^4$ represents hydrogen atom, or substituted or unsubstituted groups selected from $(C_1-C_{10})$alkyl, $(C_1-C_{10})$acyl, thio$(C_1-C_{10})$ acyl, —C(=O)—$(C_1-C_{10})$alkoxy, —C(=S)—$(C_3-C_8)$cycloalkoxy, —C(=O)—$(C_2-C_{10})$alkenyloxy, —C(=O)—$(C_2-C_{10})$alkenyl, —C(=O)-aryloxy, —C(=S)—$(C_1-C_{10})$alkoxy, —C(=S)—$(C_2-C_{10})$alkenyloxy, —C(=S)-aryloxy, —C(=O)—C(=O)—$(C_1-C_{10})$alkyl, —C(=O)—C(=O)-aryl, —C(=O)—C(=O)—$(C_1-C_{10})$alkoxy, —C(=O)—C(=O)-aryloxy, —C(=S)—S—$(C_1-C_{10})$alkyl, —C(=S)—$NH_2$, —C(=S)—NH—$(C_1-C_{10})$alkyl, —C(=S)—N—$((C_1-C_{10})$alkyl$)_2$, —C(=S)—NH—$(C_2-C_{10})$alkenyl, (C=S)—C(=O)—$(C_1-C_{10})$alkoxy, —C(=S)—C(=O)-aryloxy, —C(=S)—O—C(=O)—$(C_1-C_{10})$alkyl, C(=S)—C(=S)—$(C_1-C_{10})$alkyl, —C(=S)—C(=S)-aryl, thiomorpholinyl-C(=S)— or pyrrolidinyl-C(=S)—, to produce a compound of formula (X)

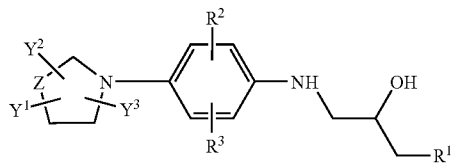

(X)

where $Y^1$, $Y^2$, $Y^3$, $R^2$, $R^3$ and Z are as defined above.

The reaction of a compound of formula (III) with a compound of formula (IV) to produce a compound of formula (V) may be carried out using a base such as KOH, NaOH, $K_2CO_3$, $Na_2CO_3$, NaH, KH, triethylamine, diisopropylethyl amine and the like. The reaction may be carried out using a solvent such as DMSO, DMF, THF, acetonitrile, chloroform and the like or mixtures thereof. The reaction may be carried out in inert atmosphere, which may be maintained using inert gases such as $N_2$ or Ar. The reaction may be carried out at a temperature in the range of 20 to 100° C., preferably at a temperature in the range of ambient to 80° C. The reaction time may range from 1 to 15 h, preferably from 6 to 12 h.

The reduction of a compound of formula (V) to produce a compound of formula (VI) may be carried out in the presence of gaseous hydrogen and a catalyst such as Ru, Pd, Rh, Pt, Ni on solid beads such as charcoal, alumina, asbestos and the like. The reduction may be conducted in the presence of a solvent such as dioxane, acetic acid, ethyl acetate, THF, alcohol such as methanol, ethanol and the like or mixtures thereof. A pressure between atmospheric pressure to 60 psi may be used. The reaction may be carried out at a temperature from 25 to 60° C., preferably at room temperature. The reaction time ranges from 2 to 48 h. The reduction may also be carried out by employing metal in mineral acids such Sn/HCl, Fe/HCl, Zn/HCl, Zn/$CH_3CO_2H$ and the like.

The reaction of a compound of formula (VI) defined above with a compound of formula (IX) defined above to produce a compound of formula (X) may be carried out in the presence or absence of a base such as $K_2CO_3$, NaH, t-BuOK and the like or mixtures thereof. The reaction may be carried out in the presence of a solvent such as toluene, DMF, THF, or acetonitrile. The reaction may also be carried out in the presence of Lewis acids such as $BF_3.OEt_2$, $ZnCl_2$, $Ti(OiPr)_4$, lanthanide metal complexes and the like in the presence of DCE, DMF, THF or the like or mixtures thereof. The reaction temperature may be in the range of 0 to 120° C., preferably at a temperature in the range of 0 to 100° C. The reaction time may range from 3 to 24 h, preferably from 4 to 12 h.

In yet another embodiment of the present invention there is provided a novel intermediate of formula (XVI)

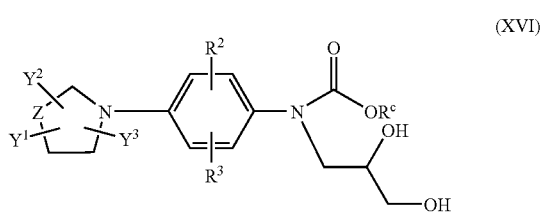

(XVI)

where $R^c$ represents $(C_1–C_{10})$alkyl group such as methyl, ethyl, propyl, and the like, or aralkyl such as benzyl, allyl group and the like; $R^2$ and $R^3$, which may be the same or different, are each independently hydrogen, halogen, $(C_1–C_{10})$alkyl, halogenated $(C_1–C_{10})$alkyl, cyano, nitro, $SR^a$, $NR^a$, or $OR^a$, in which $R^a$ is hydrogen, $(C_1–C_{10})$alkyl or halogenated $(C_1–C_{10})$alkyl;

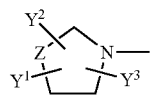

is a heterocyclic moiety in which

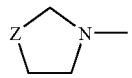

is a 5-membered heterocyclic skeleton, Z represents O, S, =CH, —CH$_2$ or NR$^b$, where R$^b$ is hydrogen or a moiety, which may be substituted or unsubstituted, straight chain or branched, selected from the group consisting of $(C_1–C_{10})$ alkyl, $(C_2–C_{10})$alkenyl, $(C_3–C_8)$cycloalkyl, hydroxy $(C_1–C_{10})$alkyl, $(C_1–C_{10})$alkylhydroxy, $(C_1–C_{10})$alkylamino, amino$(C_1–C_{10})$alkyl, $(C_1–C_{10})$alkoxy, aryl, aralkyl, aryloxy, $(C_1–C_{10})$alkylcarbonyl, arylcarbonyl, $(C_1–C_{10})$alkoxycarbonyl and aryloxycarbonyl;

Y$^1$ represents =O or =S group and Y$^2$ and Y$^3$ independently represent hydrogen, halogen, cyano, nitro, formyl, hydroxy, amino, =O, =S group or substituted or unsubstituted groups selected from $(C_1–C_{10})$alkyl, hydroxy$(C_1–C_{10})$ alkyl, $(C_1–C_{10})$alkylhydroxy, $(C_1–C_{10})$alkoxy$(C_1–C_{10})$ alkyl, $(C_1–C_{10})$alkylcarbonyl, $(C_1–C_{10})$alkoxycarbonyl, arylcarbonyl, carboxy$(C_1–C_{10})$alkyl, $(C_1–C_{10})$alkylsulfonyl, $(C_1–C_{10})$alkylcarbony$(C_1–C_{10})$alkyl, arylcarbonylamino$(C_{1-C10})$alkyl, $(C_1–C_{10})$alkylcarbonyloxy$(C_1–C_{10})$ alkyl, amino$(C_1–C_{10})$alkyl, mono$(C_1–C_{10})$alkylamino, di$(C_1–C_{10})$alkylamino, arylamino, $(C_1–C_{10})$alkoxy, aryl, aryloxy, aralkyl, heteroaryl, heteroaralkyl, heterocyclyl or heterocycloalkyl; Y$^2$ and Y$^3$ when present on adjacent carbon atoms together may also form a substituted or unsubstituted 5 or 6 membered aromatic or non-aromatic cyclic structure, optionally containing one or two hetero atoms selected from oxygen, sulfur or nitrogen.

The novel intermediate of formula (XVI) may be prepared by a process, which comprises:

(i) reacting a compound of formula (VII)

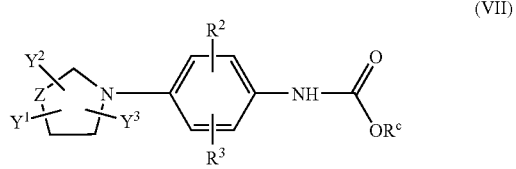

(VII)

where all the symbols are as defined earlier, with a compound of formula (XIV)

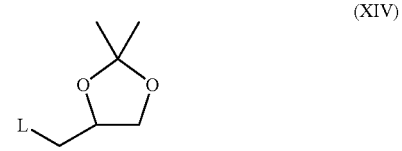

(XIV)

where L represents a leaving group such as halogen atom, $(C_1–C_{10})$alkoxy group such as methoxy, ethoxy, propoxy and the like, or sulphonyl group such as methylsulfonyl, ethylsulfonyl, p-toluenesulfonyl and the like; to produce a compound of formula (XV)

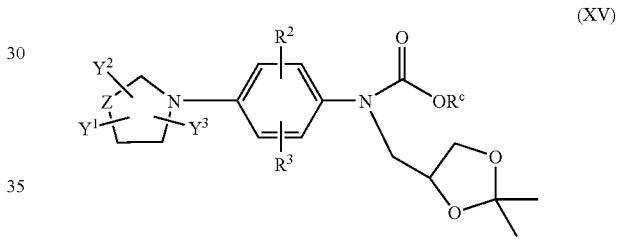

(XV)

where $R^c$, $Y^1$, $Y^2$, $Y^3$, $R^2$, $R^1$ and Z are as defined earlier and (ii) hydrolysing the acetonide moiety in the compound of formula (XV) using conventional methods to produce a compound of formula (XVI)

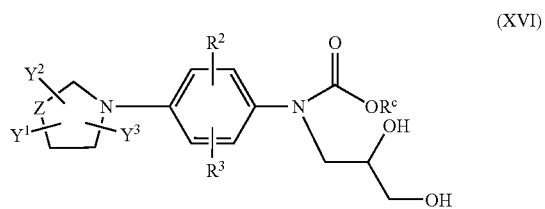

(XVI)

where $R^c$, $Y^1$, $Y^2$, $Y^3$, $R^2$, $R^3$ and Z are as defined earlier.

The reaction of a compound of formula (VII) with a compound of formula (XIV) to produce a compound of formula (XV) may be carried out in the presence of a base. The base employed may be selected from K$_2$CO$_3$, NaH, t-BuOK, LDA and the like. The reaction may be carried out in the presence of a solvent such as DMF, THF, DMSO, methanol, ethanol, propanol and the like. The reaction may be carried at a temperature in the range of −78 to 120° C., preferably at a temperature in the range of −78 to 100°C. The reaction time may range from 2 to 24 h, preferably from 2 to 20 h.

The hydrolysis of a compound of formula (XV) to produce a compound of formula (XVI) may be carried out using dilute mineral acid such as HCl, $H_2SO_4$ and the like, organic acids such as aqueous acetic acid, p-toluene sulfonic acid, camphor sulfonic acid, trifluoro acetic acid and the like. The reaction may be carried out in the presence of suitable solvent such as water, methanol, ethanol, propanol, THF, dioxane and the like or mixtures thereof. The reaction may be carried at a temperature in the range of 30 to 100° C., preferably at a temperature in the range of 30 to 60° C. The reaction time may range from 10 min to 5 h, preferably from 30 min to 2.5 h.

In yet another embodiment of the present invention there is provided a novel intermediate of formula (XVIII)

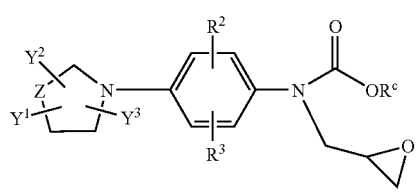

(XVIII)

wherein $R^c$ represents $(C_1-C_{10})$alkyl group such as methyl, ethyl, propyl, and the like or aralkyl such as benzyl, allyl group and the like; $R^2$ and $R^3$, which may be the same or different, are each independently hydrogen, halogen, $(C_1-C_{10})$alkyl, halogenated $(C_1-C_{10})$alkyl, cyano, nitro, $SR^a$, $NR^a$, or $OR^a$, in which $R^a$ is hydrogen $(C_1-C_{10})$alkyl or halogenated $(C_1-C_{10})$alkyl;

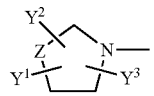

is a heterocyclic moiety in which

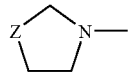

is a 5-membered heterocyclic skeleton, Z represents O, S, =CH, —$CH_2$ or $NR^b$, where $R^b$ is hydrogen or a moiety, which may be substituted or unsubstituted, straight chain or branched, selected from the group consisting of $(C_1-C_{10})$ alkyl, $(C_2-C_{10})$alkenyl, $(C_3-C_8)$cycloalkyl, hydroxy $(C_1-C_{10})$alkyl, $(C_1-C_{10})$alkylhydroxy, $(C_1-C_{10})$alkylamino, amino$(C_1-C_{10})$alkyl, $(C_1-C_{10})$alkoxy, aryl, aralkyl, aryloxy, $(C_1-C_{10})$alkylcarbonyl, arylcarbonyl, $(C_1-C_{10})$alkoxycarbonyl and aryloxycarbonyl;

$Y^1$ represents =O or =S group and $Y^2$ and $Y^3$ independently represent hydrogen, halogen, cyano, nitro, formyl, hydroxy, amino, =O, =S group or substituted or unsubstituted groups selected from $(C_1-C_{10})$alkyl, hydroxy$(C_1-C_{10})$ alkyl, $(C_1-C_{10})$alkylhydroxy, $(C_1-C_{10})$alkoxy$(C_1-C_{10})$ alkyl, $(C_1-C_{10})$alkylcarbonyl, $(C_1-C_{10})$alkoxycarbonyl, arylcarbonyl, carboxy$(C_1-C_{10})$alkyl, $(C_1-C_{10})$alkylsulfonyl, $(C_1-C_{10})$alkylcarbony$(C_1-C_{10})$alkyl, arylcarbonylamino$(C_1-C_{10})$alkyl, $(C_1-C_{10})$alkylcarbonyloxy $(C_1-C_{10})$ alkyl, amino$(C_1-C_{10})$alkyl, mono$(C_1-C_{10})$alkylamino, di$(C_1-C_{10})$alkylamino, arylamino, $(C_1-C_{10})$alkoxy, aryl, aryloxy, aralkyl, heteroaryl, heteroaralkyl, heterocyclyl or heterocycloalkyl; $Y^2$ and $Y^3$ when present on adjacent carbon atoms together may also form a substituted or unsubstituted 5 or 6 membered aromatic or non-aromatic cyclic structure, optionally containing one or two hetero atoms.

The novel intermediate of formula (XVIII) may be prepared by a process, which comprises: reacting a compound of formula (VII)

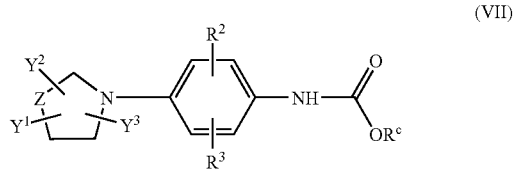

(VII)

where all the symbols are as defined earlier, with a compound of formula (XVII)

(XVII)

where L represents a leaving group such as halogen atom $(C_1-C_{10})$alkoxy group such as methoxy, ethoxy, propoxy and the like, or sulphonyl group such as methylsulfonyl, ethylsulfonyl, p-toluenesulfonyl and the like; produce a compound of formula (XVIII)

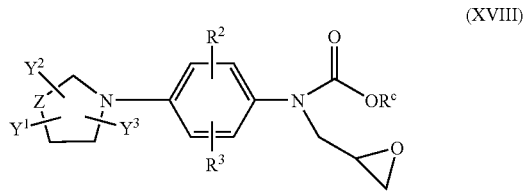

(XVIII)

where $R^c$, $Y^1$, $Y^2$, $Y^3$, $R^2$, $R^3$ and Z are as defined earlier.

The reaction of a compound of formula (VII) defined above with a compound of formula (XVII) defined above may be carried out in the presence of a base such as NaH, NaOMe, $K_2CO_3$, n-BuLi, LDA and the like. The reaction may be carried out in the presence of a solvent such as DMF, THF, DMSO, benzene and the like or mixtures thereof. The reaction may be carried out at a temperature in the range of −78 to 70° C. preferably at a temperature in the range of −78 to 50° C. The reaction time may range from 1 to 15 h preferably 1 to 10 h.

It is appreciated that in any of the above-mentioned reactions, any reactive group in the substrate molecule may be protected according to conventional chemical practice. Suitable protecting groups in any of the above mentioned reactions are tertiarybutyldimethylsilyl, methoxymethyl, triphenyl methyl, benzyloxycarbonyl, tetrahydropyran (THP) etc, to protect hydroxyl or phenolic hydroxy group; N-tert-butoxycarbonyl (N-Boc), N-benzyloxycarbonyl (N-Cbz), N-9-fluorenyl methoxy carbonyl (—N-FMOC), benzophenoneimine, propargyloxy carbonyl (POC) etc, for protection of amino or anilino group, acetal protection for aldehyde, ketal protection for ketone and the like. The methods of formation and removal of such protecting groups are those conventional methods appropriate to the molecule being protected.

The compounds of this invention may be optically active. The compounds of this invention may be racemic mixtures or tautomers.

The stereoisomers includes enatiomers and geometrical isomers such as (R), (S), a mixture of (R) and (S), (E), (Z)

or a mixture of (E) and (Z), may be prepared by using reactants in such a way to obtain single isomeric form in the process wherever applicable or by conducting the reaction in the presence of reagents or catalysts in their single enantiomeric form. The single enantiomer, wherever applicable, may be prepared by resolving the racemic mixture by conventional methods. The stereoisomers of the compounds forming part of this invention may be prepared by using reactants in their single enantiomeric form in the process wherever possible or by conducting the reaction in the presence of reagents or catalysts in their single enantiomer form or by resolving the mixture of stereoisomers by conventional methods. Some of the preferred methods include use of microbial resolution, resolving the diastereomeric salts formed with chiral acids such as mandelic acid, camphorsulfonic acid, tartaric acid, lactic acid, and the like wherever applicable or chiral bases such as brucine, cinchona alkaloids and their derivatives and the like. Commonly used methods are compiled by Jaques et al in "Enantiomers, Racemates and Resolution" (Wiley Interscience, 1981). Where appropriate the compounds of formula (I) may be resolved by treating with chiral amines, aminoacids, aminoalcohols derived from aminoacids; conventional reaction conditions may be employed to convert acid into an amide; the diastereomers may be separated either by fractional crystallization or chromatography and the stereoisomers of compound of formula (I) may be prepared by hydrolyzing the pure diastereomeric amide.

The prodrugs such as esters and amides of the compounds of formula (I) can be prepared by conventional methods.

The metabolites, which are formed inside the body of the mammal are formed by the reaction of various enzymes present in the body with the compounds of formula (I).

The invention includes in vivo hydrolysable precursors of the compounds of formula (I). The hydrolysable precursors of the compounds of formula (I) may be esters.

The pharmaceutically acceptable salts are prepared by reacting the compounds of formula (I) wherever applicable with 1 to 4 equivalents of a base such as sodium hydroxide, sodium methoxide, sodium hydride, potassium t-butoxide, calcium hydroxide, magnesium hydroxide and the like, in solvent like ether, THF, methanol, t-butanol, dioxane, isopropanol, ethanol and the like. Mixture of solvents may be used. Organic bases like lysine, arginine, diethanolamine, choline, tromethamine, guanidine and their derivatives etc. may also be used. Alternatively, acid addition salts wherever applicable are prepared by treatment with acids such as hydrochloric acid, hydrobromic acid, nitric acid, sulfuric acid, phosphoric acid, p-toluenesulphonic acid, methanesulfonic acid, acetic acid, citric acid, maleic acid salicylic acid, hydroxynaphthoic acid, ascorbic acid, palmitic acid, succinic acid, benzoic acid, benzenesulfonic acid, tartaric acid and the like in solvents like ethyl acetate, ether, alcohols, acetone, THF, dioxane etc. Mixture of solvents may also be used. The salts of amino acid groups and other groups may be prepared by reacting the compounds of formula (I) with the respective groups in solvent like alcohols, ketones, ether and the like. Mixture of solvents may be used.

Various polymorphs of a compound of general formula (I) forming part of this invention may be prepared by crystallization of compound of formula (I) under different conditions. For example, using different solvents commonly used or their mixtures for recrystallization; crystallizations at different temperatures; various modes of cooling, ranging from very fast to very slow cooling during crystallizations. Heating or melting the compound followed by gradual or fast cooling may also obtain polymorphs. The presence of polymorphs may be determined by solid probe nmr spectroscopy, IR spectroscopy, differential scanning calorimetry, powder X-ray diffraction or such other techniques.

The present invention also provides pharmaceutical compositions, containing compounds of the general formula (I), as defined above, their derivatives, their analogs, their tautomeric forms, their stereoisomers, their polymorphs, their pharmaceutically acceptable salts, their prodrugs, their metabolites, or their pharmaceutically acceptable solvates in combination with the usual pharmaceutically employed carriers, diluents and the like. The present invention also provides pharmaceutical compositions made using compounds of the general formula (I) as defined above, their stereoisomers, their polymorphs, or their pharmaceutically salts in combination with the usual pharmaceutically employed carriers, diluents and the like. The pharmaceutical compositions according to this invention can be used for the prevention or treatment of bacterial infections. They can also be used for the prevention or treatment of bacterial infections associated with multidrug resistance.

Pharmaceutically acceptable solvates of compound of formula (I) forming part of this invention may be prepared by conventional methods such as dissolving the compounds of formula (I) in solvents such as water, methanol, ethanol etc., preferably water and recrystallizing by using different crystallization techniques.

The pharmaceutical compositions may be in the forms normally employed, such as tablets, capsules, powders, syrups, solutions, suspensions and the like, may contain flavorants, sweeteners etc. in suitable solid or liquid carriers or diluents, or in suitable sterile media to form injectable solutions or suspensions. Such compositions typically contain from 0.5 to 20%, preferably 0.5 to 10% by weight of active compound, the remainder of the composition being pharmaceutically acceptable carriers, diluents or solvents.

Suitable pharmaceutically acceptable carriers include solid fillers or diluents and sterile aqueous or organic solutions. The active compounds will be present in such pharmaceutical compositions in the amounts sufficient to provide the desired dosage in the range as described above. Thus, for oral administration, the compounds can be combined with a suitable solid, liquid carrier or diluent to form capsules, tablets, powders, syrups, solutions, suspensions and the like. The pharmaceutical compositions, may, if desired, contain additional components such as flavorants, sweeteners, excipients and the like. For parenteral administration, the compounds can be combined with sterile aqueous or organic media to form injectable solutions or suspensions. For example, solutions in sesame or peanut oil, aqueous propylene glycol and the like can be used, as well as aqueous solutions of water-soluble pharmaceutically-acceptable acid addition salts or salts with base of the compounds. The injectable solutions prepared in this manner can then be administered intravenously, intraperitoneally, subcutaneously, or intramuscularly, with intramuscular administration being preferred in humans.

A method of treating or preventing an infectious disorder in a subject is provided by administering an effective amount of oxazolidinone as disclosed herein to the subject, wherein the infectious disorder is characterized by the presence of microbial infection caused by pathogens such as Gram-positive, Gram-negative, aerobic and anerobic bacteria such as Methicillin-Resistant *Staphylococcus Aureas* (MRSA), *Pseudomonas aeruginosa, Escherischia* spp., *Streptococci* including *Str. pneumoniae, Str. pyogenes, Enterococci* as well as anaerobic organisms such as *Bacteroides* spp., Clostridia spp. species and Acid-fast organisms such as *Mycobacterium tuberculosis, Mycobacterium avium* and *Mycobacterium* spp. Fastidious Gram negative organisms, *Hemophilus influenzae* (*H. influenzae*), *Morexella catarrhalis* (*M. catarrhalis*) and several other bacteria resistant to fluoroquinolone, macrolide, Vancomycin, aminoglycosides, Streptogramin, Lincosamides and β lactam resistant species. Such disorders include infections of the middle, internal and external ear including otitis media, infections of the cranial sinuses, eye infections, infections of the oral cavity, central nervous system infections, infections of teeth and gums, infections of the mucosa, respiratory tract infections, genitourinary tract infections, gastro-intestinal infections, septicemia, bone and joint infections, skin and soft infections, bacterial endocarditis, burns, nosocomical infections, pre- and postsurgical infections, opportunistic infections in the immune compromised, intracellular infections such as Chlamydia and Mycoplasma. A method of preventing an infectious disorder in a subject who is at risk for developing an infectious disorder is provided by administering to the subject an amount of an oxazolidinone as disclosed herein sufficient to prevent the infectious disorders. Examples of a subject who is at risk for developing an infectious disorder are, but are not limited to, a subject who has or will undergo a surgical procedure, will be hospitalized, a health care worker or provider, a person who will be exposed to another who has an infectious disorder and the like. A method for treating or preventing an infectious disorder may result from inhibiting the growth of bacteria or killing the bacteria.

In addition to the compounds of formula (I) the pharmaceutical compositions of the present invention may also contain or be co-administered with one or more known drugs selected from other clinically useful antibacterial agents such as β-lactams, aminoglycosides, other oxazolidinones, such as linezolid, fluoroquinolines, macrolides or any other suitable antiinfective agent. These may include penicillins such as oxacillin or flucloxacillin and carbapenems such as meropenem or imiphenem to broaden the therapeutic effectiveness against, for example, methicillin-resistant staphylococci. Compounds of the formula (I) of the present invention may also contain or be co-admistered with bactericidal/permeability-increasing protein product (BPI) or efflux pump inhibitors to improve activity against gram negative bacteria and bacteria resistant to antimicrobial agents.

The compounds of the formula (I), as defined above are clinically administered to mammals, including human beings, via either oral, rectal, vaginal, topical or parenteral routes. Administration by the oral route is preferred, being more convenient and avoiding the possible pain and irritation of injection. However, in circumstances where the patient cannot swallow the medication, or absorption following oral administration is impaired, as by disease or other abnormality, it is essential that the drug be administered accordingly by an alternate route. By either oral or parenteral route, the dosage is in the range of about 0.5 mg/kg to about 50 mg/kg body weight of the subject per day administered singly or as divided doses 1–4 times/day. However, the optimum dosage for the individual subject being treated will be determined by the person responsible for treatment, generally smaller doses being administered initially and thereafter increments made to determine the most suitable dosage. The amount(s) that is administered should be effective to elicit the biological or medical response sought.

The invention is explained in detail in the examples given below which are provided by way of illustration only and therefore should not be construed to limit the scope of the invention.

General Procedure for the Preparations 1–12

A mixture of appropriate nitro compound such as 4-fluoronitrobenzene and the like, a five membered heterocyclic group, containing two heteroatoms selected from oxygen, nitrogen or sulfur, and is substituted by an =O or =S group, the heterocycle may also be fused with substituted or unsubstituted phenyl group, (1.1 eq) and anhydrous $K_2CO_3$ (2.0 eq) in dry DMF was stirred at temperature ranging from 0 to 100° C. (depending on the substrate) overnight. Cold water was added to the reaction mixture and the solid formed was filtered. The filtered solids were dried to yield pure compound. Yield: 50–85%.

REPRESENTATIVE PREPARATIONS

Preparation 1

1-(2-Fluoro-4-nitrophenyl)-4-imidazolidinone

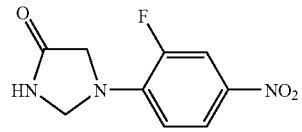

A solution of 4-imidazolidinone (9.5 g, 110.5 mmol), 3,4-difluoro nitrobenzene (12.2 ml, 110.5 mmol) and diisopropyl ethylamine (28.6 ml, 165 mmol) in dry DMF (80 ml) was heated to 60° C. overnight under argon. The reaction mixture was allowed to cool to room temperature and ice pieces were added. The solid formed was filtered and washed with water. The solid was dried under air to yield the nitro compound (19.5 g, 78.5%) as yellow crystals.

$^1$H NMR (DMSO, 200 MHz): δ 8.81 (bs, 1H), 8.07–7.96 (m, 2H), 6.82 (t, J=8.8 Hz, 1H), 4.97 (s, 2H), 4.06 (s, 2H). Mass (CI method): 226, 185, 152.

Preparation 2

1-(4-nitrophenyl)-4-imidazolidinone

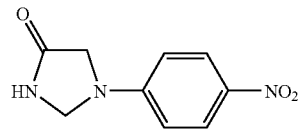

A solution of 4-imidazolidinone (9.5 g, 110.5 mmol), 4-nitrobenzene (1 eq) and diisopropyl ethylamine (28.6 mL, 165 mmol) in dry DMF (80 mL) was heated to 60° C. overnight under argon. The reaction mixture was allowed to cool to room temperature and ice pieces were added. The solid formed was filtered and washed with water. The solid was air dried to yield the nitro compound as yellow crystals.

$^1$H NMR (DMSO-d$^6$, 200 MHz): δ 8.83 (bs, 1H), 8.13 (d, J=8.8 Hz, 2H), 6.70 (d, J=8.8 Hz, 2H), 4.82 (s, 2H), 3.92 (s, 2H); Mass (CI method): 208, 167; IR (KBr, cm$^{-1}$): 1709, 1602, 1308.

Preparation 3

1-(2,6-difluoro-4-nitrophenyl)-4-imidazolidinone

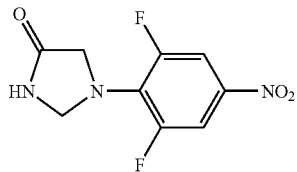

A solution of 4-imidazolidinone (9.5 g, 110.5 mmol), 3,4,5-trifluoronitrobenzene (1 eq) and diisopropyl ethylamine (28.6 mL, 165 mmol) in dry DMF (80 mL) was heated to 60° C. overnight under argon. The reaction mixture was allowed to cool to room temperature and ice pieces were added. The solid formed was filtered and washed with water. The solid was air dried to yield the nitro compound as yellow crystals.

$^1$H NMR (DMSO-d$^6$, 200 MHz): δ 8.76 (s, 1H), 7.97 (dd, J=2.6 Hz & 7.0 Hz, 2H), 5.1 (s, 2H), 4.2 (s, 2H); Mass (CI method): 244, 187; IR (KBr, cm−1): 3188, 3063, 2360, 1715, 1609, 1514, 1449, 1398, 1293, 1157.

Similarly preparations 4–12 have been prepared by a person skilled in the art according to the methodology as described in preparations 1–3

| S. No. | Preparation | Analytical data |
|---|---|---|
| 4 | | 1HNMR(CDCl3, 200MHz): δ 8.25(d, J=9.2Hz, 2H), 7.72(d, J=9.2Hz, 2H), 4.57(t, J=7.3Hz, 2H), 4.18(t, J=7.3Hz, 2H). Mass(CI method): 209. |
| 5 | | 1HNMR(CDCl3, 200MHz): δ 8.12–7.93(m, 3H), 4.56(t, J=7.3Hz, 2H), 4.23(t, J=7.3Hz, 2H). Mass(CI method): 227. |
| 6 | | 1HNMR(CDCl3, 200MHz): δ 7.92(d, J=7.8Hz, 2H), 4.64(t, J=7.4Hz, 2H), 4.07(t, J=7.4Hz, 2H). Mass(CI method): 245, 215. |
| 7 | | 1HNMR(CDCl3, 200MHz): δ 8.00(m, 1H), 7.15(m, 2H), 4.56(t, J=7.4Hz, 2H), 4.06(t, J=7.4Hz, 2H). Mass(CI method): 226, 180, 164, 152, 135, 109, 94. |
| 8 | | 1HNMR(CDCl3, 200MHz): δ 8.64–8.48(m, 2H), 7.69(d, J=8.8Hz, 1H), 4.60(t, J=7.3Hz, 2H), 4.01(t, J=7.3Hz, 2H). Mass(CI method): 276, 232, 217, 171, 144. |
| 9 | | 1HNMR(CDCl3, 200MHz): δ 8.14–8.04(m, 2H), 7.90(t, J=7.6Hz, 1H), 4.76(t, J=8.4Hz, 2H), 4.23(t, J=8.4Hz, 2H). Mass(CI method): 242, 223, 167, 121, 94. |
| 10 | | 1HNMR(CDCl3, 200MHz): δ 8.14–8.07(m, 2H), 7.72(t, J=7.6Hz, 1H), 4.43(t, J=7.6Hz, 2H), 3.57(t, J=7.6Hz, 2H). Mass(CI method): 258, 239, 212, 193, 108. |

| S. No. | Preparation | Analytical data |
|---|---|---|
| 11 | 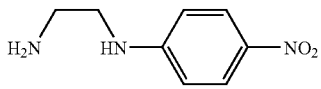 | 1HNMR(CDCl3, 200MHz): δ 8.11–8.02(m, 2H), 7.96(t, J=7.8Hz, 1H), 4.09–3.83(2t, 4H), 3.27(s, 2H). Mass(CI method): 255, 236, 209, 190. |
| 12 | 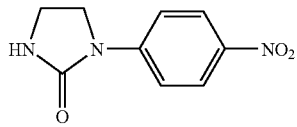<br>R = 4-Me | 1HNMR(CDCl3, 200MHz): δ 8.23(m, 2H), 7.81(t, J=7.4Hz, 1H), 7.22(t, J=7.4Hz, 1H), 7.03(d, J=8.4Hz, 1H). Mass(CI method): 288, 258, 243, 197, 94. |

Preparation 13

N1-(2-aminoethyl)-4-nitroaniline

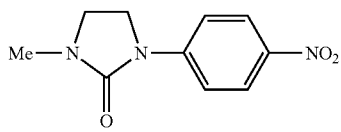

A solution of 4-fluoronitrobenzene (5 g, 35.4 mmol) in CH3CN (250 ml) was at room temperature under argon overnight. The reaction mixture was filtered and the was concentrated. The residue obtained was suspended in pet. ether and filtered. The ere collected to afford the nitro compound (4.1 g, 64%) as yellow crystals.

$^1$H NMR (DMSO+CDCl$_3$, 200 MHz): δ 7.97 (d, J=9.3 Hz, 2H), 7.09 (bs, 1H), 6.62 (d, J=9.3 Hz, 2H), 2.80–3.40 (m, 6H). Mass(CI method): 181, 152, 135, 105.

Preparation 14

1-(4-Nitrophenyl)-2-imidazolidinone

A solution of phosgene (20% in toluene, 13 ml, 26.5 mmol) in toluene was added drop wise to a solution of the diamine (4 g, 22 mmol) (obtained in preparation 13) and Et$_3$N (7.6 ml, 55 mmol) in dichloromethane (100 ml) at 0° C. under argon. After being stirred at same temperature for 1 h, the reaction mixture was poured in water and extracted with dichloromethane (4×150 ml). The combined organic extracts were washed with water, brine and dried. The residue obtained upon evaporation of the solvents was passed through a column of silica gel to afford the product (3 g, 66%) as yellow solid.

$^1$H NMR (CDCl$_3$, 200 MHz): δ 8.17 (d, J=9.3 Hz, 2H), 7.75 (d, J=9.2 Hz, 2H), 7.07 (bs, 1H), 4.00 (t, J=8.8 Hz, 2H), 3.59 (t, J=8.8 Hz, 2H). Mass(CI method): 207, 151, 105.

Preparation 15

1-Methyl-3-(4-nitrophenyl)-2-imidazolidinone

Sodium hydride (60% in oil, 138 mg, 5.3 mmol) was added portion wise to a solution of the nitro compound (1 g, 4.8 mmol) (obtained in preparation 14) in dry DMF (15 ml) under argon at 0° C. Stirred the reaction mixture at the same temperature for 15 min. Methyl iodide (MeI) (0.68 g, 4.8 mmol) was added and the reaction mixture was stirred for 1 h. Ice pieces were added to the reaction mixture and the solid formed was filtered to afford the product (900 mg, 84%) as yellow crystals.

$^1$H NMR (CDCl$_3$, 200 MHz): δ 8.19 (d, J=9.3 Hz, 2H), 7.70 (d, J=9.3 Hz, 2H), 3.88 (t, J=8.8 Hz, 2H), 3.54 (t, J=8.8 Hz, 2H), 2.93 (s, 3H). Mass(CI method): 222.

Preparation 16

N1-phenyl-2-azidoacetamide

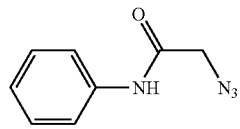

Chloroacetyl chloride (5.1 ml, 64.5 mmol) was added drop wise to a solution of aniline (5 g, 53.7 mmol) and Et$_3$N (18.7 ml, 134.3 mmol) in dichloromethane (150 ml) at 0° C. under argon. After the completion of reaction (TLC control), the reaction mixture was diluted with dichloromethane (300 ml). The resultant mixture was washed with water, brine and dried. The residue obtained upon evaporation of solvent was taken up in dry DMF (40 ml), added NaN$_3$ (6.15 g, 94.6 mmol) and the resultant mixture was stirred at 80° C. for 2 h. The reaction mixture was diluted with ethyl acetate and washed with water, brine and dried. The residue obtained upon evaporation of the solvent was chromatographed over silica gel to afford the azide (6 g, 63%).

Preparation 17

N1-phenyl-2-(2-fluoro-4-nitroanilino)acetamide

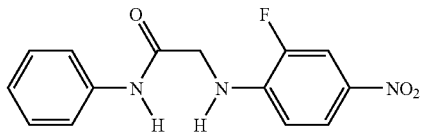

A solution of the azide (6 g, 34 mmol) obtained in preparation 16, was taken in MeOH (60 ml) and the resultant solution was hydrogenated over 10% Pd on charcoal (2.5 g) overnight. The reaction mixture was filtered on a celite pad and the filtrate was concentrated. To this residue dry DMF (40 ml) was added followed by diisopropyl ethyl amine (16.7 ml, 93.8 mmol) and 3,4-difluoronitro benzene (3.8 ml, 37.5 mmol). The resultant solution was kept at 80° C. overnight with continuous monitoring by TLC. Ice-cold water was added to the reaction mixture and the solid separated was filtered to afford the nitro compound as a yellow solid (6 g, 61%).

$^1$H NMR (DMSO+CDCl$_3$, 200 MHz): δ 9.74 (bs, 1H), 7.84–8.00 (m, 2H), 7.58 (d, J=8.3 Hz, 2H), 7.30 (d, J=8.3 Hz, 2H), 7.08 (m, 1H), 6.66 (t, J=8.8 Hz, 1H), 6.45 (bs, 1H), 4.09 (d, J=5.4 Hz, 2H). Mass (CI Method): 290.

Preparation 18

N1-(2-anilinoethyl)-2-fluoro-4-nitroaniline

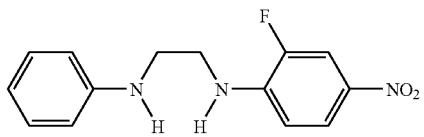

A 1 M solution of BH$_3$.THF (45 ml, 45 mmol) was added drop wise to a solution of the nitro compound (4.5 g, 15.5 mmol) (obtained in preparation 17) in dry THF (30 ml) at 0° C. under argon. The reaction mixture was stirred overnight at room temperature and then water was added cautiously to quench the excess borane. The volatiles were removed from the reaction mixture under vacuum and the residue was taken up in ethyl acetate (400 ml). The organic layer was washed with water, brine and dried. The residue obtained upon evaporation of the solvent was passed through column to afford the product (4 g, 93%).

$^1$H NMR (CDCl$_3$, 200 MHz): δ 8.02–7.86 (m, 2H), 7.26–7.18 (m, 2H), 682–6.62 (m, 4H), 4.94 (bs, 1H), 3.83 (bs, 1H), 3.51 (s, 4H). Mass (CI method): 274.

Preparation 19

1-(2-Fluoro-4-nitrophenyl)-3-phenyl-2-imidazolidinone

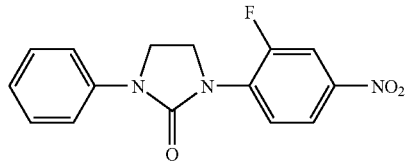

A solution of phosgene (20% in toluene, 7.4 ml, 14.7 mmol) was added drop wise to a solution of the diamine (4 g, 14.5 mmol) (obtained in preparation 18) and Et3N (5.6 ml, 40.4 mmol) in dichloromethane (50 ml) at 0° C. under argon. Stirred for 2 h at the same temperature the reaction mixture was diluted with dichloromethane (300 ml) and washed with water, brine and dried. The crystals obtained upon evaporation of the solvents were suspended in petroleum ether and filtered. The product was isolated as yellow crystals (4 g, 91.4%).

$^1$H NMR (CDCl$_3$, 200 MHz): δ 8.10–7.11 (m, 8H), 4.22–4.00 (m, 4H). Mass (CI Method): 302, 106.

Preparation 20

1-(2-Fluoro-4-nitrophenyl)-3-hydroxymethyl-4-imidazolidinone

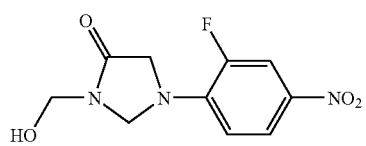

A mixture of nitro compound (9 g, 40 mmol) (obtained in preparation 1) and 40% solution of formaldehyde (100 mL) was heated to reflux for 4 h. The reaction mixture was allowed to cool to room temperature and ice water mixture was added. The precipitated solid was filtered and dried to give the product as yellow solid (8.5 g, 83% yield).

$^1$H NMR (DMSO-d6, 200 MHz): δ 8.10–7.95 (m, 2H), 6.90–6.80 (m, 1H), 6.20 (t, J=6.8 Hz, 1H), 5.13 (d, J=2.9 Hz, 2H), 4.77 (d, J=7.3 Hz, 2H), 4.19 (s, 2H). Mass (CI method): 226.

Preparation 21

1-(2-Fluoro-4-nitro-phenyl)-3-tetrahydro-pyran-2-yloxymethyl)-imidazolidin-4-one

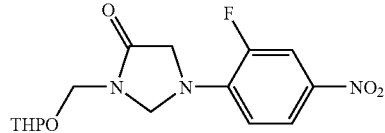

A solution of nitro compound (6.7 g, 26.2 mmol) (obtained in preparation 20), pyridinium p-toluenesulphonate (PPTS) (65 mg, 0.39 mmol) and 3,4-dihydro-2H-pyran (3.6 mL, 39.4 mmol) in dichloromethane (100 mL) was stirred at room temperature under argon overnight. The reaction mixture was diluted with dichloromethane (400 mL), washed with half-saturated brine (2×100 mL) and dried. The residue obtained upon evaporation of solvent was passed through a column of silica gel to afford the product as yellow solid (7 g, 79%).

$^1$H NMR (CDCl3, 200 MHz): δ 8.05–7.85 (m, 2H), 6.60–6.45 (m, 1H), 5.30–4.70 (m, 5H), 4.17 (s, 2H), 4.20–3.30 (m, 4H), 2.00–1.40 (m, 6H). Mass (CI method): 340, 256, 237.

Preparation 22

1-(2,6-difluoro-4-nitrophenyl)-3-hydroxymethyl-4-imidazolidinone

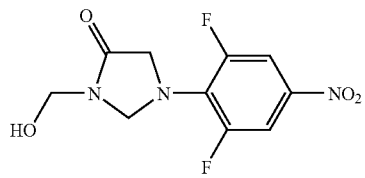

A solution of nitro compound (26 g, 106.9 mmol), obtained in preparation 3, in formalin (37–41% w/v in water, 150 mL) was refluxed overnight. Ice water was added to the reaction mixture and the solid obtained was filtered. The dried title compound was further dried azeotropically with toluene (2×100 mL) to afford the product as a pale yellow solid (26 g, 89.3%). Mp 140–143° C.

1H NMR (DMSO-d6, 200 MHz): δ 7.99 (dd, J=2.4 Hz & 9.8 Hz, 2H), 6.22 (t, J=7.3, 1H), 5.25 (s, 2H), 4.76 (d, J=7.0, 2H), 4.35 (s, 2H); Mass (CI method): 244, 214; IR (KBr, cm$^{-1}$): 3438, 1721, 1519.

Preparation 23

2-(2,6-Difluoro-4-nitro-phenylamino)-acetamide

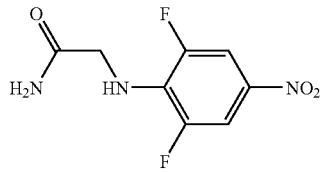

To a stirred solution of glycinamide hydrochloride (45 g, 407 mmol) in DMF (500 mL) was added successively triethylamine (197 mL, 1.43 mol) followed by 3,4,5-trifluoronitrobenzene (72 g, 407 mmol) at room temperature over 15 min. The reaction mixture was heated to 80° C. overnight and then allowed to cool to room temperature. Ice pieces suspended in water were added to the reaction mixture and the solid obtained was filtered. The solid was dried to afford title compound (62 g, 67%) that was taken up directly for the next step without further purification. Mp 160–162° C.

$^1$H NMR (DMSO-d$_6$, 200 MHz): δ 7.90 (dd, J=2.4 Hz & 8.1 Hz, 2H), 7.47 (s, 1H), 7.13 (s, 1H), 6.87 (bs, 1H), 3.96–3.92 (m, 2H); Mass (CI method): 232, 200; IR (KBr, cm$^{-1}$): 1686, 1616, 1333.

Preparation 24

1-(2,6-difluoro-4-nitrophenyl)-3-hydroxymethyl-4-imidazolidinone

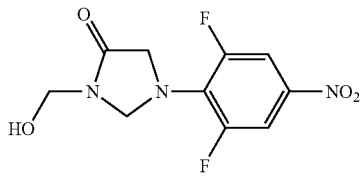

A solution of nitro compound (60 g, 283 mmol), obtained in preparation 23, in formalin (37–41% w/v in water, 180 mL) and water (700 mL) was refluxed overnight. Ice water was added to the reaction mixture and the solid obtained was filtered. The dried title compound was further dried azeotropically with toluene (2×300 mL) to afford the product as a pale yellow solid (60 g, 96%).

Preparation 25

1-(2,6-Difluoro-4-nitro-phenyl)-3-(tetrahydro-pyran-2-yloxymethyl)-imidazolidin-4-one

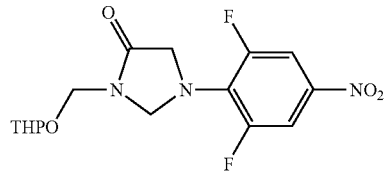

A solution of 1-(2,6-difluoro-4-nitrophenyl)-3-hydroxymethyl-4-imidazolidinone (60 g, 220.6 mmol), obtained in preparation 24, 3,4-dihydro-2H-pyran (24 mL, 264.7 mmol) and pyridinium p-toluene sulfonate (5.5 g, 22 mmol) in dichloromethane (500 mL) was stirred at room temperature overnight. The reaction mixture was concentrated (100 mL) and directly loaded on a column of silica gel. Elution with 1:1 ethyl acetate-pet.ether gave the protected compound 5 (70 g, 89.7%) as a yellow solid. Mp 106–108° C.

1H NMR (DMSO-d6, 200 MHz): δ 7.88–7.73 (m, 2H), 5.33–4.76 (m, 5H), 4.43 (s, 2H), 3.92–3.55 (m, 2H), 1.82–1.58 (m, 6H); Mass (CI method): 358, 274, 244; IR (KBr, cm–1): 1719, 1520, 1338.

Preparation 26

General procedure for the conversion of

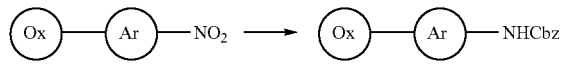

where 'Ox' represents a five membered heterocyclic group, containing at least one nitrogen atom and one more heteroatom selected from oxygen, nitrogen or sulfur. In which, the said atleast one nitrogen atom connecting said heterocyclic moiety 'Ox' to the 'Ar' moiety. The heterocyclic moiety is substituted by an =O or =S. The heterocycle may also be substituted by one or two additional substituents which are as defined on the heterocyclic moiety of formula (I). The heterocycle may also be fused with substituted or unsubstituted phenyl group. 'Ar' represents substituted or unsubstituted phenyl ring, the substituents are as defined on the phenyl ring of the formula (I).

A solution of the nitro compound in THF was hydrogenated over 10% Pd on charcoal (catalytic amount) overnight. After the complete consumption of starting material, a 5% solution of $Na_2CO_3$ (2.2 eq) in water was added followed benzyl chloroformate (1.2 eq) at 0° C. After stirring the reaction mixture for 3 h at room temperature, it was filtered over celite bed and washed with ethyl acetate. The organic layer was separated from the filtrate and washed with water twice followed by brine. The organic extract was dried, evaporated and purified on a column of silica gel.

Reference Example of the Above Procedure

Preparation 26A

{3,5-Difluoro-4-[4-oxo-3-(tetrahydro-pyran-2-yloxymethyl)-imidazolidin-1-yl]-phenyl}-carbamic acid benzyl ester

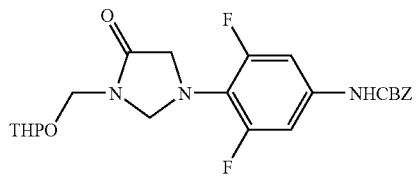

A solution of $Na_2CO_3$ (10 g) in water (100 mL) was added to a solution of nitro (65 g, 182 mmol), obtained in preparation 25, in THF (400 mL) and the reaction mixture was hydrogenated over 10% Pd on charcoal (20 g) overnight. The resultant mixture was filtered on a pad of celite and the filtrate was concentrated. The residue obtained upon evaporation of solvent was taken up in acetone (400 mL) and to that was added a solution of $Na_2CO_3$ (77.7 g, 720 mmol) in water (400 mL). The reaction mixture was cooled in an ice bath at this stage and benzyl chloroformate (50% in toluene, 73 mL, 216 mmol) was added dropwise over 30 min. After stirring for a further 30 min, ice pieces were added to the reaction mixture. The solid obtained was filtered and dried azeotropically with toluene (2×300 mL) to give the title compound (66 g, 78.3%) as a tan colored solid. Mp 116–118° C.

1H NMR (DMSO-d6, 200 MHz): δ 10.07 (s, 1H), 7.40–7.13 (m, 7H), 5.15–4.70 (m, 7H), 3.89 (s, 2H), 3.79–3.34 (m, 2H), 1.67–1.46 (m, 6H); Mass (CI method): 461, 378, 270; IR (KBr, cm−1): 1696, 1517, 1239.

Preparation 27

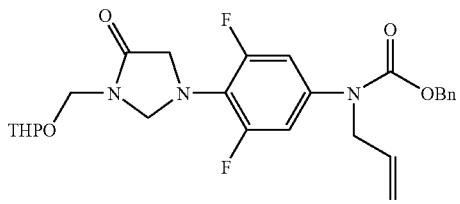

Sodium hydride (0.312 g, 7.8 mmol) and allyl bromide (0.73 mL, 8.5 mmol) were added sequentially to a solution of starting material (3 g, 6.5 mmol) in dry DMF (25 mL) at 0° C. under argon. The reaction mixture was stirred for 12 h at rt and then diluted with ethyl acetate. The organic layer was washed with water, brine and dried. The residue obtained upon evaporation of solvent was chromatographed over silica gel to afford the product (3.1 g, 95%).

1H NMR (DMSO-d6, 500 MHz) δ 7.38–7.30 (m, 5H), 7.11 (d, J=11.6 Hz, 2H), 5.86–5.79 (m, 1H), 5.14–5.10 (m, 4H), 5.01–4.93 (m, 3H), 4.74–4.70 (m, 2H), 4.27 (d, J=5.2 Hz, 2H), 4.08–4.01 (m, 2H), 3.78–3.75 (m, 1H), 3.47–3.44 (m, 1H), 1.71–1.40 (m, 6H). Mass (CI method): 502, 418, 400. IR (KBr, cm−1): 1717, 1516, 1023.

Preparation 28

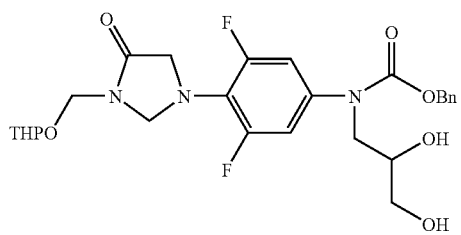

N-Methylmorpholine N-oxide (0.135 g, 0.99 mmol) and osmium tetroxide (0.25 wt. % in 2-methylpropan-2-ol, 0.65 mL, 0.05 mmol), were added sequentially to a solution of starting material (0.5 g, 0.99 mmol) obtained by preparation 27 in 10:1 acetone:water mixture (50 mL) at 20–35° C. The reaction mixture was stirred for 48 h at 20–35° C. The residue obtained upon evaporation of volatiles was chromatographed over silica gel to afford the product (0.454 g, 80%).

1H NMR (DMSO-d6, 400 MHz) δ 7.38–7.30 (m, 5H), 7.18 (d, J=12.2 Hz, 2H), 5.11 (s, 2H), 5.02–4.52 (m, 8H), 4.04 (s, 2H), 3.79–3.44 (m, 5H), 1.80–1.40 (m, 6H). Mass (CI method): 427, 344, 326. IR (Neat, cm−1): 3436, 1708, 1516.

EXAMPLES

A. General procedure for the conversion of

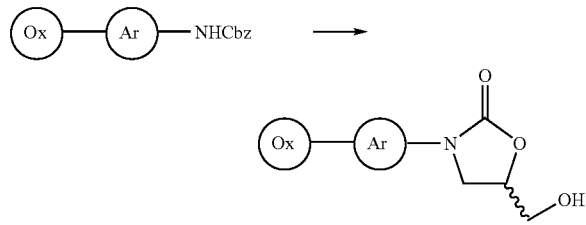

where 'Ox' represents a five membered heterocyclic group, containing at least one nitrogen atom and one more heteroatom selected from oxygen, nitrogen or sulfur. In which, the said atleast one nitrogen atom connecting said heterocyclic moiety 'Ox' to the 'Ar' moiety. The heterocyclic moiety is substituted by an ═O or ═S. The heterocycle may also be substituted by one or two additional substituents which are as defined on the heterocyclic moiety of formula (I). The heterocycle may also be fused with substituted or unsubstituted phenyl group. 'Ar' represents substituted or unsubstituted phenyl ring, the substituents are as defined on the phenyl ring of the formula (I).

To a solution of the starting material in dry THF at −78° C. under argon was added 1.6 M BuLi (1.2 eq) drop wise. The reaction mixture was stirred for 45 min at the same temperature and then R(−)-glycidyl butyrate or S(+)-glycidyl butyrate (1.2 eq ) was added. Stirred for 1 h at −78° C. Then the cold bath was removed while monitoring with TLC. After 3–12 h, the reaction mixture was quenched with saturated NH4Cl solution and extracted with ethyl acetate. The combined organic extracts were washed with water, brine and dried. The residue obtained upon evaporation of solvents was chromatographed over silica gel to afford the product.

Reference Example of the Above Procedure

Example 1

(S)-3-{3,5-Difluoro-4-[4-oxo-3-(tetrahydro-pyran-2-yloxymethyl)-imidazolidin-1-yl]-phenyl}-5-hydroxymethyl-oxazolidin-2-one

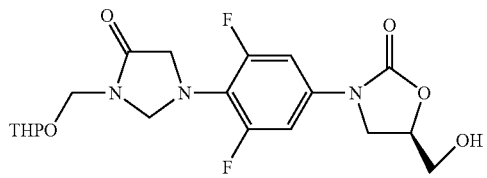

To a solution of {3,5-difluoro-4-[4-oxo-3-(tetrahydro-pyran-2-yloxymethyl)-imidazolidin-1-yl]-phenyl}-carbamic acid benzyl ester (40 g, 86.8 mmol), obtained in preparation 26A, in dry THF (600 mL) at −78° C. under argon atmosphere was added butyl lithium (1.6 M in hexanes, 70 mL, 104.2 mmol) dropwise over a period of 5 min. The reaction mixture was stirred at −78° C. for 1 h followed by addition of (R) (−)-glycidylbutyrate (14.7 mL, 104.2 mmol). The reaction mixture was stirred initially at −78° C. for 1 h and then at room temperature for overnight. The reaction mixture was quenched by addition of saturated NH₄Cl solution and then extracted with ethyl acetate. The combined organic extracts were washed with water, brine and dried. The residue obtained upon evaporation of solvent was chromatographed over silica gel and eluted with ethyl acetate to give the title compound as a cream colored gummy solid (24 g, 63.5% yield).

1H NMR (CDCl3, 400 MHz): δ 7.19–7.10 (m, 2H), 5.19–4.71 (m, 6H), 4.17–3.53 (m, 8H), 1.80–1.46 (m, 6H); Mass (CI method): 427, 344; IR (neat, cm−1): 3421, 1721, 1518, 1023.

Example 2

(R)-3-{3,5-Difluoro-4-[4-oxo-3-(tetrahydro-pyran-2-yloxymethyl)-imidazolidin-1-yl]-phenyl}-5-hydroxymethyl-oxazolidin-2-one

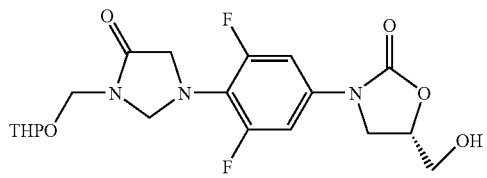

To a solution of {3,5-difluoro-4-[4-oxo-3-(tetrahydro-pyran-2-yloxymethyl)-imidazolidin-1-yl]-phenyl}-carbamic acid benzyl ester (40 g, 86.8 mmol), obtained in preparation 26A, in dry THF (600 mL) at −78° C. under argon atmosphere was added butyl lithium (1.6 M in hexanes, 70 mL, 104.2 mmol) dropwise over a period of 5 min. The reaction mixture was stirred at −78° C. for 1 h followed by addition of (S)(+)-glycidylbutyrate (14.7 mL, 104.2 mmol). The reaction mixture was stirred initially at −78° C. for 1 h and then at room temperature for overnight. The reaction mixture was quenched by addition of saturated NH₄Cl solution and then extracted with ethyl acetate. The combined organic extracts were washed with water, brine and dried. The residue obtained upon evaporation of solvent was chromatographed over silica gel and eluted with ethyl acetate to give the title compound as a cream colored gummy solid (24 g, 63.5% yield).

1H NMR (CDCl3, 400 MHz): δ 7.19–7.10 (m, 2H), 5.19–4.71 (m, 6H), 4.17–3.53 (m, 8H), 1.80–1.46 (m, 6H); Mass (CI method): 427, 344; IR (neat, cm−1): 3421, 1721, 1518, 1023.

Example 3

(RS)-3-{3,5-Difluoro-4-[4-oxo-3-(tetrahydro-pyran-2-yloxymethyl)-imidazolidin-1-yl]-phenyl}-5-hydroxymethyl-oxazolidin-2-one

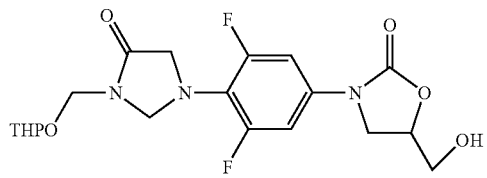

A mixture of potassium carbonate (0.2 g, 1.5 mmol) and starting material (0.5 g, 0.93 mmol), obtained in preparation 28, in DMF (5 mL) was heated to 60° C. for 30 min. The reaction mixture was allowed to cool to 25 to 35° C. and then worked up by adding aq. NH₄Cl followed by extraction with ethyl acetate. The organic layer was washed with water, brine and dried. The residue obtained upon evaporation of solvent was directly used in the next step (0.367 g, 92%).

1H NMR (CDCl₃, 400 MHz): δ 7.19–7.10 (m, 2H), 5.19–4.71 (m, 6H), 4.17–3.53 (m, 8H), 1.80–1.46 (m, 6H); Mass (CI method): 427, 344; IR (neat, cm⁻¹): 3421, 1721, 1518, 1023.

Similarly Examples 4–22, 23–24 and 25–26 have been prepared by a person skilled in the art according to the methodology as described in Examples 1, 2 and 3 respectively.

| Example No. | Structure | Analytical Data |
|---|---|---|
| 4 | 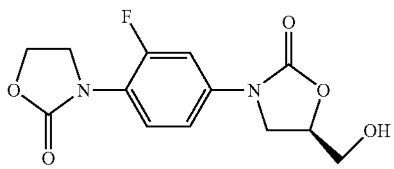 | 1HNMR(DMSO-d6, 200MHz): δ 7.68–7.50(m, 2H), 7.38(d, J=8.8Hz, 1H), 5.23(t, J=5.8Hz, 1H), 4.73–4.72(m, 1H), 4.47(t, J=7.4Hz, 2H), 4.14–3.80(m, 4H), 3.68–3.56(m, 2H). |
| 5 | 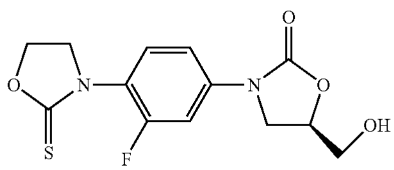 | 1HNMR(CDCl3, 200MHz): δ 7.73(d, J=11.6Hz, 1H), 7.52(t, J=8.8Hz, 1H), 7.29(d, J=8.8Hz, 1H), 4.89(bs, 1H), 4.76(t, J=2H), 4.17(t, J=8.8Hz, 2H), 3.93–3.68(m, 4H). |
| 6 | 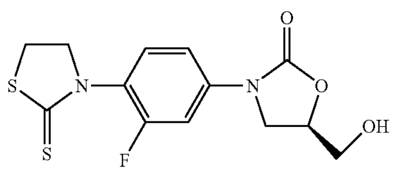 | 1HNMR(CDCl3, 200MHz): δ 7.70(dd, J=12.7Hz and 2.2Hz, 1H), 7.44–7.26(m, 2H), 4.75–4.68(m, 2H) 4.37(t, J=7.8Hz, 2H), 4.04–3.56(m, 4H), 3.48(t, J=7.8Hz, 2H). |
| 7 | 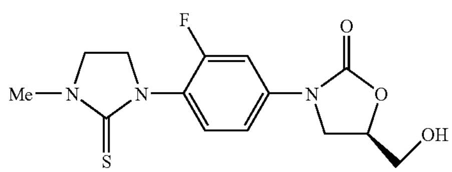 | 1HNMR(CDCl3, 200MHz): δ 7.62(dd, J=2.4Hz and 12.7Hz, 1H), 7.47(t, J=8.4Hz, 1H), 7.24–7.20(m, 1H), 4.77–4.69(m, 1H), 4.10–3.81(m, 5H), 3.77–3.68(m, 4H), 3.23(s, 3H). |
| 8 | 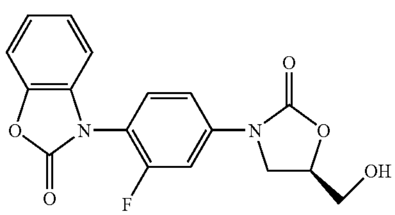 | 1HNMR(CDCl3, 200MHz): δ 7.85–7.79(m, 1H), 7.58(t, J=8.0Hz, 1H), 7.46–7.42(m, 1H), 7.30–7.18(m, 4H), 6.90–6.87(m, 1H), 4.90–4.75(m, 1H), 4.15–4.07(m, 3H), 3.87–3.81(m, 1H). |
| 9 | 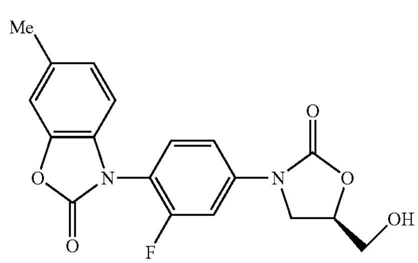 | 1HNMR(CDCl3, 200MHz): δ 7.76(dd, J=2.4Hz and 12.2Hz, 1H), 7.53–7.26(m, 2H), 7.11(s, 1H), 6.97(d, J=8.4Hz, 1H), 6.72(d, J=7.8Hz, 1H), 4.81–4.65(m, 1H), 4.09–3.82(m, 4H), 2.41(s, 3H), 2.09(hump, 1H). |
| 10 | 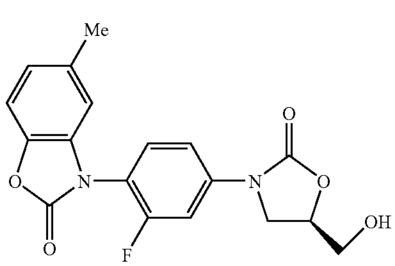 | 1HNMR(CDCl3, 200MHz): δ 7.77(d, J=10.4Hz, 1H), 7.57–7.26(m, 3H), 6.96(d, J=7.8Hz, 1H), 6.64(s, 1H), 4.82–4.71(m, 1H), 4.14–4.05(m, 3H), 3.84–3.78(m, 2H), 2.35(s, 3H). |

-continued

| Example No. | Structure | Analytical Data |
|---|---|---|
| 11 | 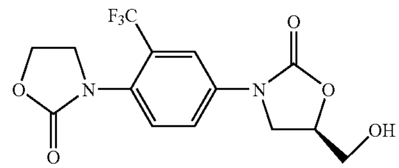 | 1HNMR(CDCl3, 200MHz): δ 7.92–7.89(m, 2H), 7.44(d, J=7.8Hz, 1H), 7.80–7.71(m, 1H), 4.54(t, J=7.2Hz, 2H), 4.08–3.89(m, 6H), 2.16(s, 1H). |
| 12 | 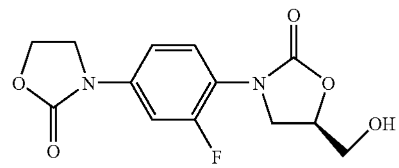 | 1HNMR(CDCl3, 200MHz): δ 7.69–7.48(m, 2H), 7.23(d, J=8.8Hz, 1H), 4.81–4.72(m, 1H), 4.54(t, J=7.4Hz, 2H), 4.13–3.69(m, 6H). |
| 13 | 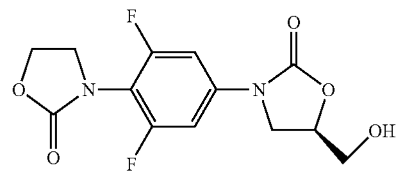 | 1HNMR(CDCl3, 200MHz): δ 7.29(d, J=10.8Hz, 2H), 4.80–4.73(m, 1H), 4.57(t, J=15.6Hz, 2H), 4.00–3.73(m, 8H). |
| 14 | 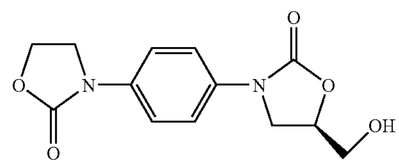 | 1HNMR(CDCl3, 200MHz): δ 7.59(s, 4H), 5.24(t, J=5.4Hz, 1H), 4.67(bs, 1H), 4.45(t, J=7.4Hz, 2H), 4.13–4.02(m, 3H), 3.88–3.54(m, 3H). |
| 15 | 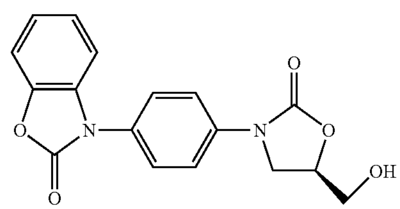 | 1HNMR(CDCl3, 200MHz): δ 7.79(d, J=9.2Hz, 2H), 7.72(d, J=9.2Hz, 2H), 7.59–7.03(m, 4H), 5.18(t, J=5.8Hz, 1H), 4.80–4.71(m, 1H), 4.18–4.02(m, 2H), 3.98–3.68(m, 2H). |
| 16 | | 1HNMR(CDCl3, 200MHz): δ 2.9(s, 3H), 4.1(t, 1H), 3.9(m, 6H), 4.7(m, 1H), 4.8(s, 2H), 6.8(t, 1H), 7.2(d, 1H). |
| 17 | 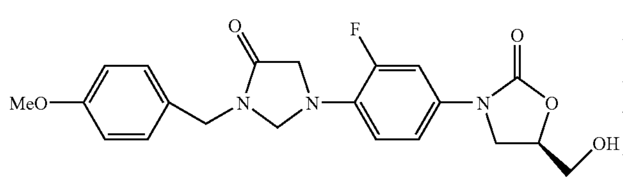 | 1HNMR(CDCl3, 200MHz): δ 7.4(dd, J=2Hz and 15.4Hz, 1H), 7.2(d, J=8.8Hz, 2H), 7.0(d, J=9.4Hz, 1H), 6.85(d, J=8.4Hz, 2H), 6.5(t, J=9.2Hz, 1H), 4.75(s, 3H), 4.50(s, 2H), 3.95(m, 6H), 3.8(s, 3H). |
| 18 | 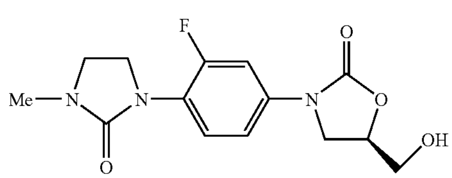 | 1HNMR(CDCl3, 200MHz): δ 7.55(dd, J=2.4Hz and 13.4Hz, 1H), 7.45(t, J=8.8Hz, 1H), 7.10(dd, J=2.2Hz and 13.0Hz, 1H), 4.66(m, 1H), 3.81(m, 6H), 3.47(t, 2H), 2.8(s, 3H). |
| 19 | 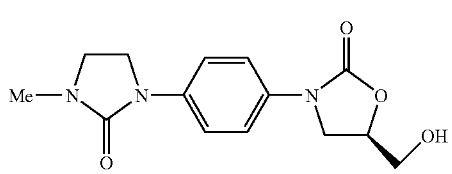 | 1HNMR(CDCl3, 200MHz): δ 2.8(s, 3H), 3.4(m, 3H), 4.7(m, 1H), 7.5(m, 4H). |

-continued
| Example No. | Structure | Analytical Data |
|---|---|---|
| 20 | 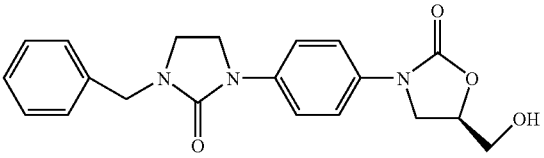 | 1HNMR(CDCl3, 200MHz): δ 7.7–7.2(m, 9H), 4.8–4.6(m, 1H), 4.5(s, 2H), 4.1–3.7(m, 6H). 3.4(t, J=8.8Hz, 2H) |
| 21 | 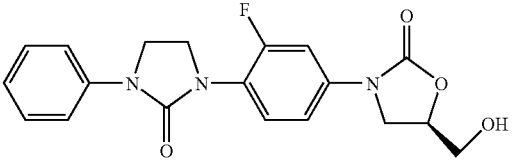 | 1HNMR(CDCl3, 200MHz): δ 7.5–7.7(m, 4H), 7.3–7.4(m, 2H), 7.2(d, J=8.8Hz, 1H), 7.1(t, 4H), 4.7(m, 1H), 3.9–4.1(m, 6H), 3.9(s, 1H), 3.7(m, 1H). |
| 22 | 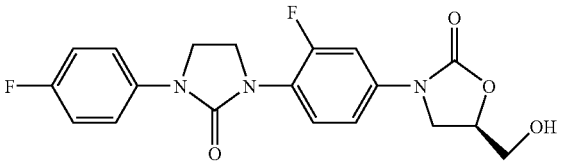 | 1HNMR(CDCl3, 200MHz): δ 7.5(m, 4H), 7.2(m, 1H), 7.0(m, 2H), 4.7(m, 2H), 4.0(m, 7H), 3.8(m, 1H). |
| 23 | 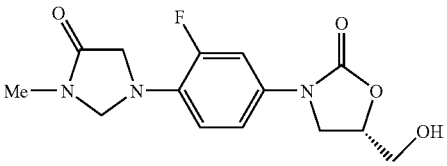 | 1HNMR(CDCl3, 200MHz): δ 2.9(s, 3H), 4.1(t, 1H), 3.9(m, 6H), 4.7(m, 1H), 4.8(s, 2H), 6.8(t, 1H), 7.2(d, 1H). |
| 24 | 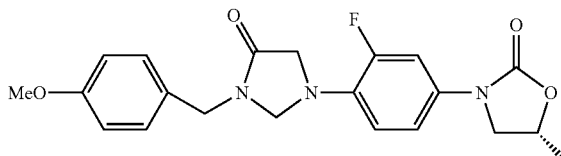 | 1HNMR(CDCl3, 200MHz): δ 7.4(dd, J=2Hz and 15.4Hz, 1H), 7.2(d, J=8.8Hz, 2H), 7.0(d, J=9.4Hz, 1H), 6.85(d, J=8.4Hz, 2H), 6.5(t, J=9.2Hz, 1H), 4.75(s, 3H), 4.50(s, 2H), 3.95(m, 6H), 3.8(s, 3H). |
| 25 | 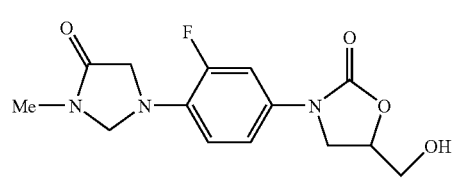 | 1HNMR(CDCl3, 200MHz): δ 2.9(s, 3H), 4.1(t, 1H), 3.9(m, 6H), 4.7(m, 1H), 4.8(s, 2H), 6.8(t, 1H), 7.2(d, 1H). |
| 26 | 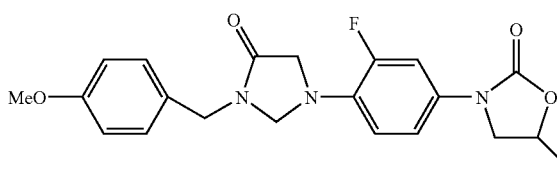 | 1HNMR(CDCl3, 200MHz): δ 7.4(dd, J=2Hz and 15.4Hz, 1H), 7.2(d, J=8.8Hz, 2H), 7.0(d, J=9.4Hz, 1H), 6.85(d, J=8.4Hz, 2H), 6.5(t, J=9.2Hz, 1H), 4.75(s, 3H), 4.50(s, 2H), 3.95(m, 6H), 3.8(s, 3H). |

B. General procedure for the conversion of

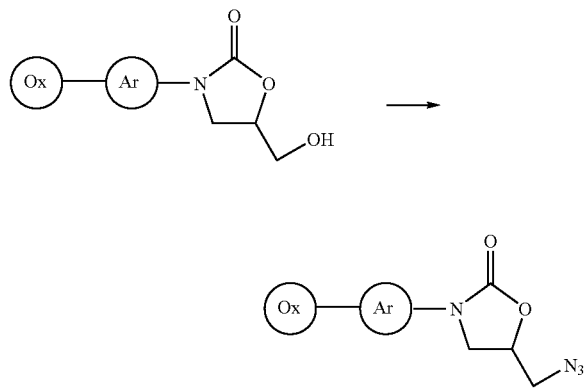

where 'Ox' represents a five membered heterocyclic group, containing at least one nitrogen atom and one more heteroatom selected from oxygen, nitrogen or sulfur. In which, the said atleast one nitrogen atom connecting said heterocyclic moiety 'Ox' to the 'Ar' moiety. The heterocyclic moiety is substituted by an =O or =S. The heterocycle may also be substituted by one or two additional substituents which are as defined on the heterocyclic moiety of formula (I). The heterocycle may also be fused with substituted or unsubstituted phenyl group. 'Ar' represents substituted or unsubstituted phenyl ring, the substituents are as defined on the phenyl ring of the formula (I)

To a solution of the alcohol, triethylamine (2.2 eq) in dry dichloromethane, methane sulfonylchloride (1.1 eq) was added at 0° C. under argon. The reaction mixture was warmed to room temperature over 2 h and then diluted with dichloromethane. The organic layer was washed with water, brine and dried. The residue obtained upon evaporation of the solvent was taken up in dry DMF and then NaN3 (1.5 eq) was added at room temperature. The resultant mixture was heated to 80° C. for 2–5 h while monitoring by TLC. Allowed the reaction mixture to attain room temperature, water was added and extracted with ethyl acetate. The combined organic extracts were washed with water (3 times), brine and dried. The residue obtained upon evaporation of the solvent was passed through column to obtain the azide.

Reference Example of the Above Procedure

Example 27

(S)-5-Azidomethyl-3-{3,5-difluoro-4-[4-oxo-3-(tetrahydro-pyran-2-yloxymethyl)-imidazolidin-1-yl]-phenyl}-oxazolidin-2-one

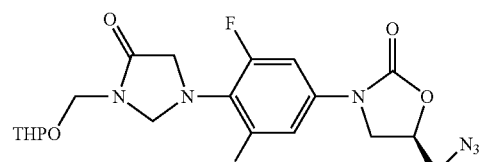

To a solution of (S)-3-{3,5-difluoro-4-[4-oxo-3-(tetrahydro-pyran-2-yloxymethyl)-imidazolidin-1-yl]-phenyl}-5-hydroxymethyl-oxazolidin-2-one (31 g, 72.6 mmol), obtained in Example 1, in dry dichloromethane (500 mL) at 0° C. under argon atmosphere was added triethylamine (30 mL, 223 mmol) followed by methanesulfonylchloride (7 mL, 89.9 mmol) drop wise over a period of 10 min. The reaction mixture was stirred at 0° C. for 1 h and was worked up by adding water followed by extracting with dichloromethane. The combined organic extracts were washed with water, brine and dried. The solvent was evaporated to give the corresponding mesylate as a gum, which was taken up for the next step without any purification.

To a solution of the above crude mesylate in dry DMF (400 mL) under argon atmosphere was added sodium azide (6.76 g, 103.9 mmol) and the resulting mixture was stirred at 80° C. for 2 h. The reaction mixture was allowed to cool to room temperature and worked up by adding water followed by extraction with ethyl acetate. The combined organic extracts were washed with water, brine and dried. The residue obtained upon evaporation of solvent was the title compound (29 g, 92.6% crude yield for two steps) and was directly used for the next step without further purification.

1H NMR (CDCl3, 400 MHz): δ 7.20–7.10 (m, 2H), 5.20–4.75 (m, 6H), 4.15–3.45 (m, 8H), 1.85–1.45 (m, 6H); Mass (CI method): 452, 369, 244; IR (neat, cm−1): 2109, 1756, 1721, 1518.

Similarly Examples 28–41 have been prepared by a person skilled in the art according to the methodology as described in the above Example 27.

| Example No. | Structure | Analytical Data |
|---|---|---|
| 28 | 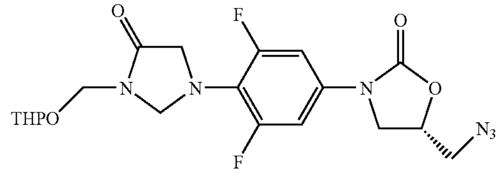 | 1H NMR(CDCl3, 400MHz): δ 7.20–7.10(m, 2H), 5.20–4.75(m, 6H), 4.15–3.45(m, 8H), 1.85–1.45(m, 6H); Mass(CI method): 452, 369, 244; IR (neat, cm−1): 2109, 1756, 1721, 1518. |

| Example No. | Structure | Analytical Data |
|---|---|---|
| 29 | 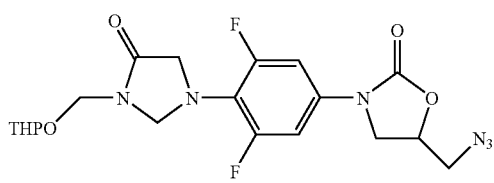 | 1H NMR(CDCl3, 400MHz): δ 7.20–7.10(m, 2H), 5.20–4.75(m, 6H), 4.15–3.45(m, 8H), 1.85–1.45(m, 6H); Mass(CI method): 452, 369, 244; IR (neat, cm-1): 2109, 1756, 1721, 1518. |
| 30 | 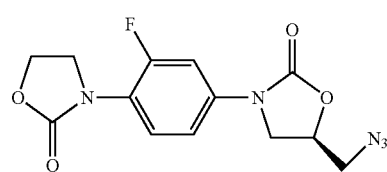 | 1HNMR(DMSO-d6, 200MHz): δ 7.67–7.52(m, 2H), 7.38(d, J=8.8Hz, 1H), 4.95–4.88(m, 1H), 4.47(t, J=7.2Hz, 2H), 4.16(t, J=9.4Hz, 1H), 4.02–3.64(m, 5H). |
| 31 | 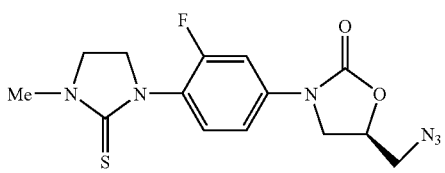 | 1HNMR(CDCl3, 200MHz): δ 7.62(dd, J=2.4Hz and 12.7Hz, 1H), 7.48(t, J=8.4Hz, 1H), 7.22–7.17(m, 1H), 4.85–4.73(m, 1H), 4.16–3.52(m, 8H), 3.22(s, 3H). |
| 32 | 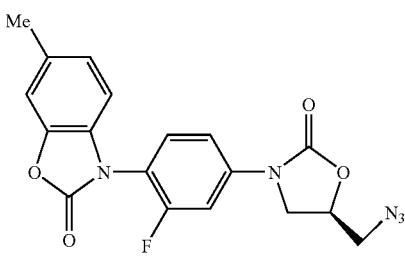 | 1HNMR(CDCl3, 200MHz): δ 7.75(dd. J=2.0Hz and 12.2Hz, 1H), 7.54(t, J=8.8Hz, 1H), 7.40–7.26(m, 1H), 7.10(s, 1H), 6.97(d, J=7.8Hz, 1H), 6.71(d, J=6.8Hz, 1H), 4.87–4.79(m, 1H), 4.17–3.57(m, 4H), 2.41(s, 3H). |
| 33 | 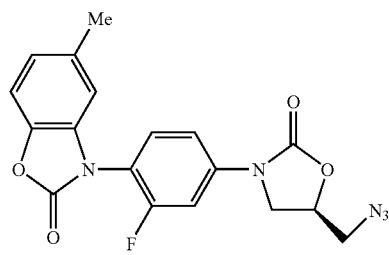 | 1HNMR(CDCl3, 200MHz): δ 7.81(d, 1H), 7.54(t, 1H), 7.45–7.01(m, 3H), 6.67(s, 1H), 4.91–4.79(m, 1H), 3.95–3.47(m, 4H), 2.38(s, 3H). |
| 34 | 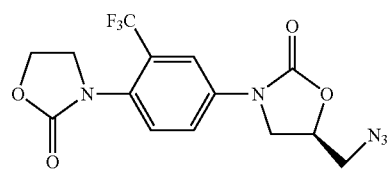 | 1HNMR(CDCl3, 200MHz): δ 7.89(d, J=7.4Hz, 2H), 7.43(d, J=9.4Hz, 1H), 4.87–4.80(m, 1H), 4.54(t, J=7.2Hz, 2H), 4.12(t, J=8.8Hz, 2H), 3.97–3.55(m, 4H). |

| Example No. | Structure | Analytical Data |
|---|---|---|
| 35 | 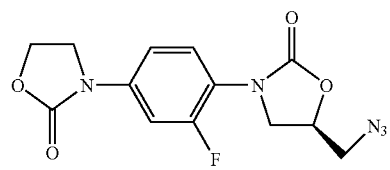 | 1HNMR(CDCl3, 200MHz): δ 7.71–7.50(m, 2H), 7.17(d, J=8.8Hz, 1H), 4.89–4.75(m, 1H), 4.52(t, J=7.2Hz, 2H), 4.47–3.55(m, 6H). |
| 36 | 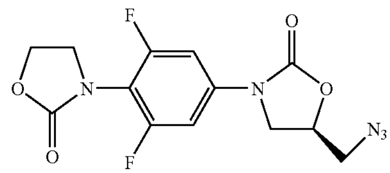 | 1HNMR(CDCl3, 200MHz): δ 7.31(s, 2H), 4.83–4.81(m, 1H), 4.57(t, J=7.8Hz, 2H), 4.09–3.55(m, 6H). |
| 37 | 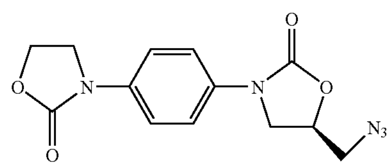 | 1HNMR(DMSO-d6, 200MHz): δ 7.64(s, 4H), 4.98–4.89(m, 1H), 4.50(t, J=7.4Hz, 2H), 4.25–4.07(m, 4H), 3.88–3.70(m, 2H). |
| 38 | | 1HNMR(CDCl3, 200MHz): δ 7.75(d, J=9.2Hz, 2H), 7.59(d, J=9.2Hz, 2H) 7.48–7.03(m, 4H), 4.89–4.81(m, 1H), 4.16(t, J=9.2Hz, 1H), 3.98–3.58(m, 3H). |
| 38 | | $^1$HNMR(CDCl$_3$, 200MHz): δ 7.75(d, J=9.2Hz, 2H), 7.59(d, J=9.2Hz, 2H) 7.48–7.03(m, 4H), 4.89–4.81(m, 1H), 4.16(t, J=9.2Hz, 1H), 3.98–3.58(m, 3H). |
| 39 | 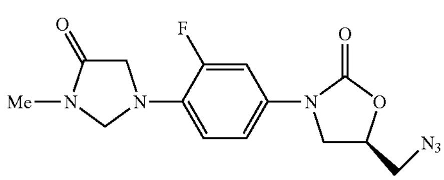 | $^1$HNMR(CDCl$_3$, 200MHz): δ 7.5–7.4(dd, 1H), 7.1(dd, 1H), 6.5(t, 1H), 4.9(s, 2H), 4.8–4.7(m, 1H), 4.1–3.5(m, 6H), 3.0(s, 3H). |
| 40 | 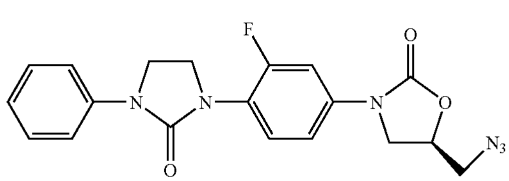 | $^1$HNMR(CDCl$_3$, 200MHz): δ 7.6(m, 4H), 7.35(t, 2H), 7.0–7.2(m, 2H), 4.8(m, 1H), 4.1(m, 1H), 4.0(s, 4H), 3.9(m, 1H), 3.7(m, 2H). |

| Example No. | Structure | Analytical Data |
|---|---|---|
| 41 | 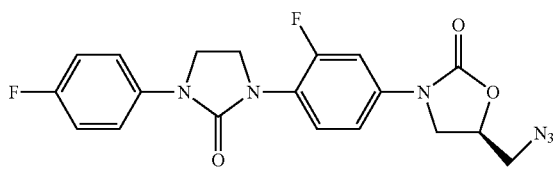 | ¹HNMR(CDCl₃, 200MHz): δ 7.6(m, 4H), 7.2(m, 1H), 7.0(m, 2H), 4.8(m, 1H), 4.1(m, 1H), 4.0(s, 4H), 3.9(m, 1H), 3.6(m, 2H). |

Example 42

(S)-5-Azidomethyl-3-[3,5-difluoro-4-(3-hydroxymethyl-4-oxo-imidazolidin-1-yl)-phenyl]-oxazolidin-2-one

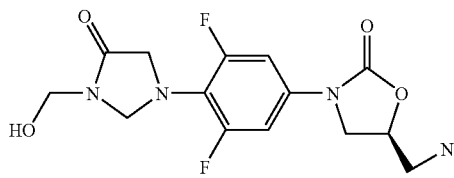

A solution of 5-azidomethyl-3-{3,5-difluoro-4-[4-oxo-3-(tetrahydro-pyran-2-yloxymethyl)-imidazolidin-1-yl]-phenyl}-oxazolidin-2-one (29 g, 64.1 mmol), obtained in example 27, and pyridinium p-toluene sulfonate (1.61 g, 6.4 mmol) in ethanol (300 mL) was refluxed for 4 h. The white solid obtained upon cooling the reaction mixture was filtered and washed with ethanol to afford the title compound (20 g, 86%). Mp. 148–150° C.

¹H NMR (DMSO-d₆, 200 MHz): δ 7.34 (d, J=12.2 Hz, 2H), 6.10 (t, J=6.8 Hz, 1H), 5.00–4.80 (m, 3H), 4.72 (d, J=7.3 Hz, 2H), 3.96 (s, 2H), 4.20–3.60 (m, 4H; Mass (CI method): 339, 311, 214; IR (KBr, cm⁻¹): 3374, 2108, 1737, 1690.

Similarly Examples 43 and 44 have been prepared by a person skilled in the art according to the methodology as described in the Example 42

Example 45

(S)-5-Azidomethyl-3-[3,5-difluoro-4-(4-oxo-imidazolidin-1-yl)-phenyl]-oxazolidin-2-one

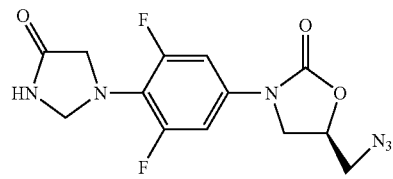

To a solution of 5-azidomethyl-3-[3,5-difluoro-4-(3-hydroxymethyl-4-oxo-imidazolidin-1-yl)-phenyl]-oxazolidin-2-one (15 g, 40.7 mmol), obtained in example 42, in dry THF (200 mL) at 0° C. was added sodium hydride (60% in oil, 4.07 g, 101.9 mmol, washed twice with dry hexane and dried at vacuum) in batches over 30 min. The reaction mixture was allowed to warm to room temperature over 4 h and stirred for a further 16 h before being quenched with aq. NH₄Cl solution at ice bath temperature. The reaction mixture was extracted with ethyl acetate and the combined organic extracts were washed-with brine and dried. Evapo-

| Example No. | Structure | Analytical Data |
|---|---|---|
| 43 | 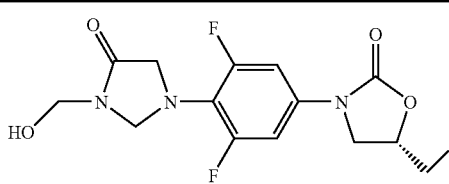 | ¹H NMR(DMSO-d₆, 200MHz): δ 7.34(d, J=12.2Hz, 2H), 6.10(t, J=6.8Hz, 1H), 5.00–4.80(m, 3H), 4.72(d, J=7.3Hz, 2H), 3.96(s, 2H), 4.20–3.60(m, 4H); Mass(CI method): 339, 311, 214; IR(KBr, cm⁻¹): 3374, 2108, 1737, 1690 |
| 44 | 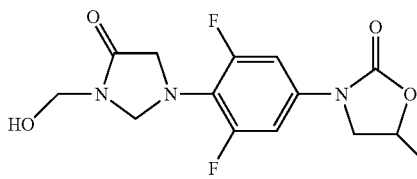 | ¹H NMR(DMSO-d₆, 200MHz): δ 7.34(d, J=12.2Hz, 2H), 6.10(t, J=6.8Hz, 1H), 5.00–4.80(m, 3H), 4.72(d, J=7.3Hz, 2H), 3.96(s, 2H), 4.20–3.60(m, 4H); Mass(CI method): 339, 311, 214; IR(KBr, cm⁻¹): 3374, 2108, 1737, 1690 | ration of the solvent afforded the title compound (13 g, 94% for crude) as a colorless solid. Mp. 186–188° C.

$^1$H NMR (DMSO-$d_6$, 200 MHz): δ 8.59 (bs, 1H), 7.35 (d, J=12.2 Hz, 2H), 5.00–4.80 (m, 1H), 4.75 (s, 2H), 3.85 (s, 2H), 4.20–4.62 (m, 4H); Mass (CI method): 339, 311, 214; IR (KBr, cm$^{-1}$): 2115, 1733, 1526.

Similarly examples 46 and 47 have been prepared by a person skilled in the art according to the methodology as described in the Example 45

| Example No. | Structure | Analytical Data |
|---|---|---|
| 46 | 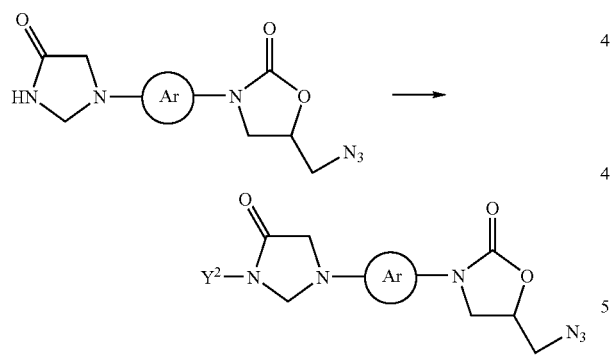 | $^1$H NMR(DMSO-$d_6$, 200MHz): δ 8.59(bs, 1H), 7.35(d, J=12.2Hz, 2H), 5.00–4.80(m, 1H), 4.75(s, 2H), 3.85(s, 2H), 4.20–4.62(m, 4H); Mass(CI method): 339, 311, 214; IR(KBr, cm$^{-1}$): 2115, 1733, 1526. |
| 47 | 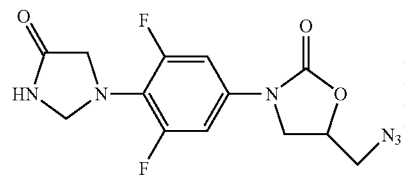 | $^1$H NMR(DMSO-$d_6$, 200MHz): δ 8.59(bs, 1H), 7.35(d, J=12.2Hz, 2H), 5.00–4.80(m, 1H), 4.75(s, 2H), 3.85(s, 2H), 4.20–4.62(m, 4H); Mass(CI method): 339, 311, 214; IR(KBr, cm$^{-1}$): 2115, 1733, 1526. |

Example C

General procedure for the conversion of

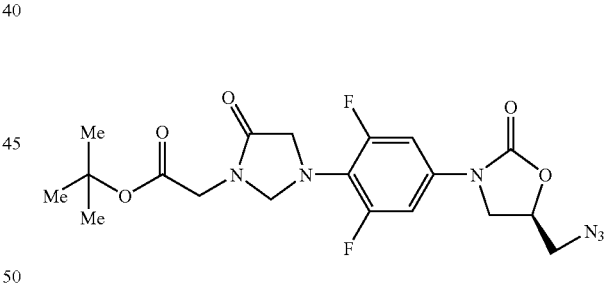

where $Y^2$ is as defined for formula (I); 'Ar' represents substituted or unsubstituted phenyl ring, the substituents are as defined on the phenyl ring of the formula (I).

Sodium hydride (1 eq.) was added to a solution of the starting azide (1 eq.) in dry DMF. The reaction mixture was stirred for 30 min and then quenched with appropriate alkyl halide. After stirring for a further 2 h, the reactioin mixture was added to ice cold water and extracted with ethyl acetate. The organic layer was washed with water, brine and dried. The residue obtained upon evaporation of solvent was passed through a column of silica gel to afford the respective alkylated azide.

Reference Example of the Above Procedure

Example 48

(S)-Methoxythiocarbonylaminomethyl-2-oxo-oxazolidin-3-yl]-phenyl}-5-oxo-imidazolidin-1-yl)-acetic acid tert-butyl ester Sodium hydride (0.17 g, 4.3 mmol)) was added to a solution of the starting azide (1.2 g, 3.6 mmol), obtained in example 45, in dry DMF. The reaction mixture was stirred for 30 min and then quenched with appropriate alkyl halide. After stirring for a further 2 h, the reaction mixture was added to ice cold water and extracted with ethyl acetate. The organic layer was washed with water, brine and dried. The residue obtained upon evaporation of solvent was passed through a column of silica gel to afford the final compound (Yield: 1.5 g, 94%).

$^1$H NMR (DMSO-$d_6$, 200 MHz): δ 7.32 (d, J=11.7 Hz, 2H), 4.86–4.80 (m, 1H), 4.78 (s, 2H), 4.12–3.60 (m, 8H), 1.40 (s, 9H).

Similarly Example 49 has been prepared by a person skilled in the art according to the methodology as described in the Example 48

| Example No. | Structure | Analytical Data |
|---|---|---|
| 49 | 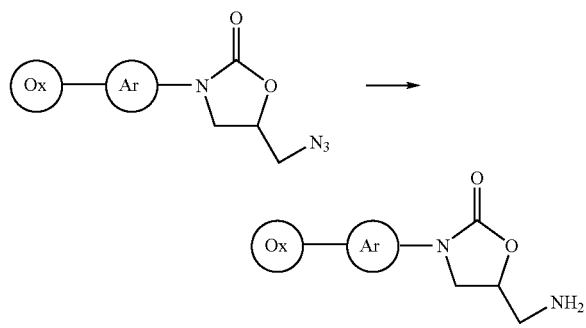 | $^1$H NMR(CDCl$_3$, 200MHz): δ 7.48(dd, J=15.1 & 2.4Hz, 1H), 7.10(d, J=8.3Hz, 1H), 6.70–6.50(m, 1H), 5.00–4.70(m, 3H), 4.10–3.30(m, 8H), 2.00–0.70(m, 7H). |

D. General procedure for the conversion of

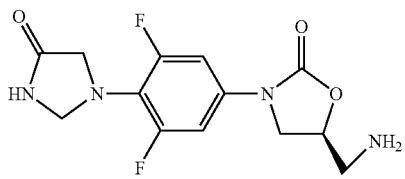

where 'Ox' represents a five membered heterocyclic group, containing at least one nitrogen atom and one more heteroatom selected from oxygen, nitrogen or sulfur. In which, the said at least one nitrogen atom connecting said heterocyclic moiety 'Ox' to the 'Ar' moiety. The heterocyclic moiety is substituted by an =O or =S. The heterocycle may also be substituted by one or two additional substituents which are as defined on the heterocyclic moiety of formula (I). The heterocycle may also be fused with substituted or unsubstituted phenyl group. 'Ar' represents substituted or unsubstituted phenyl ring, the substituents are as defined on the phenyl ring of the formula (I)

Procedure (i)

A solution of the azide in THF: MeOH (1:3) was hydrogenated over 10% Pd on charcoal overnight. The reaction mixture was filtered and the filtrate was concentrated. The residue was crystallized in MeOH to afford the amine.

Procedure (ii)

Triphenyl phosphine (1.3 eq) was added portion wise to a solution of the azide in dry THF and the resultant mixture was stirred at room temperature for 6 h. Water (few drops) was added and the reaction mixture was heated to 60° C. overnight. The solvent was evaporated and the residue was passed through a column of silica gel to afford the amine.

Reference Example of the Above Procedure

Example 50

(5S)-Aminomethyl-3-[3,5-difluoro-4-(4-oxo-imidazolidin-1-yl)-phenyl]-oxazolidin-2-one Triphenyl phosphine (33.5 g, 127.8 mL) was added portion wise to a solution of the azide (36 g, 106.5 mmol), obtained in example 45, in dry THF and the resultant mixture was stirred at room temperature for 6 h. Water (few drops) was added and the reaction mixture was heated to 60° C. overnight. The solvent was evaporated and the residue was passed through a column of silica gel to afford the amine (31 g, 93%).

$^1$H NMR (200 MHz, DMSO-d$_6$) δ: 8.56 (s, 1H), 7.31 (d, J=12.8 Hz, 2H), 4.70–4.62 (m, 3H), 4.02 (t, J=8.8 Hz, 1H), 3.97–3.80 (m, 3H), 3.33 (s, 4H); MP: 192–194° C.

Similarly Examples 51–63 have been prepared by a person skilled in the art according to the methodology as described in the Example 50.

| Example No. | Structure | Analytical Data |
|---|---|---|
| 51 | 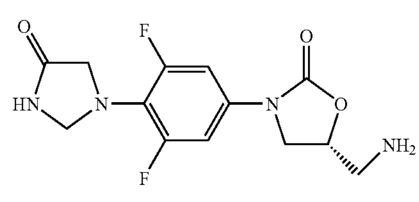 | $^1$H NMR(200MHz, DMSO-d$_6$) δ: 8.56(s, 1H), 7.31(d, J=12.8Hz, 2H), 4.70–4.62(m, 3H), 4.02(t, J=8.8Hz, 1H), 3.97–3.80(m, 3H), 3.33(s, 4H). |

-continued

| Example No. | Structure | Analytical Data |
|---|---|---|
| 52 | 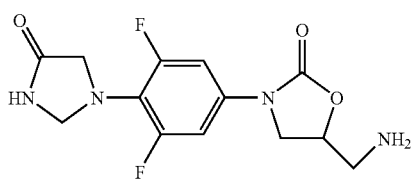 | $^1$H NMR(200MHz, DMSO-d$_6$) δ: 8.56(s, 1H), 7.31(d, J=12.8Hz, 2H), 4.70–4.62(m, 3H), 4.02(t, J=8.8Hz, 1H), 3.97–3.80(m, 3H), 3.33(s, 4H). |
| 53 | 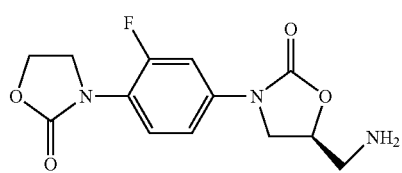 | $^1$HNMR(DMSO-D$^6$, 200MHz): δ 7.66–7.50(m, 2H), 7.37(D, j=9.4Hz, 1H), 4.66–4.60(m, 1H), 4.47(t, J=7.8Hz, 2H), 4.12–3.83(m, 6H), 2.91–2.80(m, 2H) Mp: 147° C. |
| 54 | 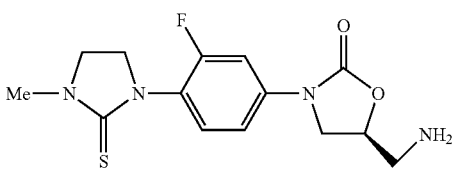 | $^1$HNMR(CDCl$_3$, 200MHz): δ 7.63–7.55(dd, J=2.0Hz and 13.0Hz, 1H), 7.49–7.22(m, 2H), 4.63–4.60(m, 1H) 4.09(t, J=8.8Hz, 1H), 4.03–3.73(m, 4H), 3.32(m, 3H), 3.08(s, 3H). |
| 55 | 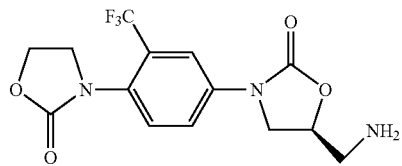 | $^1$HNMR(CDCl$_3$, 200MHz): δ 8.02(s, 2H), 7.87–7.83(m, 2H), 7.64(s, 1H), 7.50(d, J=8.2Hz, 1H), 4.84(s, 1H), 4.54(t, J=7.4Hz, 2H), 4.20–3.90(m, 6H). |
| 56 | 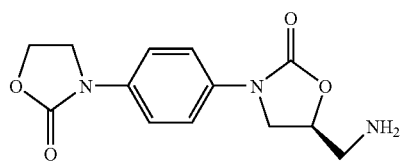 | $^1$HNMR(DMSO-d$^6$, 200MHz): δ 7.57(s, 4H), 4.63–4.61(m, 1H), 4.44(t, J=7.2Hz, 2H), 4.08–3.82(m, 4H), 2.86–2.82(m, 2H). |
| 57 | 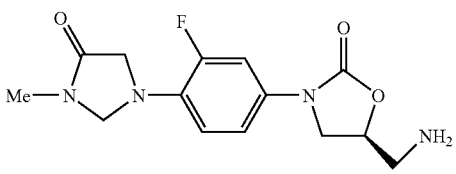 | $^1$HNMR(CDCl$_3$, 200MHz): δ 7.6–7.4(dd, 1H), 7.1(dd, 1H), 6.6(t, 1H), 4.9(s, 1H), 4.6(m, 1H), 4.1–3.7(m, 4H), 3.2–2.8(m, 4H). |
| 58 | 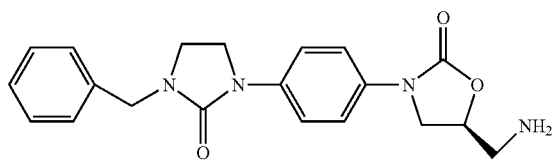 | $^1$HNMR(CDCl$_3$, 200MHz): δ 7.62–7.40(m, 3H), 7.3(s, 5H), 4.7(m, 1H), 4.5(s, 2H), 4.1(t, 1H), 3.9–3.8(m, 4H), 3.4(t, 2H). |

| Example No. | Structure | Analytical Data |
|---|---|---|
| 59 | 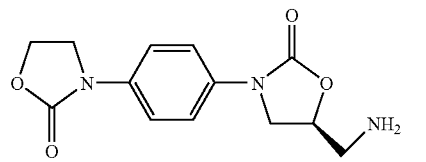 | $^1$H NMR(200MHz, DMSO-d$_6$) δ: 7.55(s, 4H), 4.58–4.55(m, 1H), 4.41(t, J=7.8Hz, 2H), 4.02(t, J=7.0Hz, 2H), 3.83(t, J=6.8Hz, 2H), 3.44–2.78(m, 4H). MP: 189–191° C. |
| 60 | 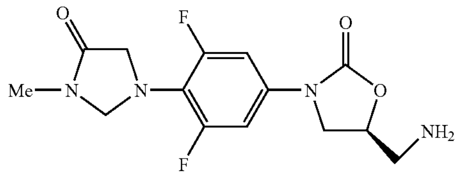 | $^1$H NMR(DMSO-d$_6$, 200MHz): δ 7.32(d, J=12.2Hz, 2H), 4.76(s, 2H), 4.61–4.58(m, 1H), 4.05–3.10(m, 6H), 2.83(s, 3H). |
| 61 | 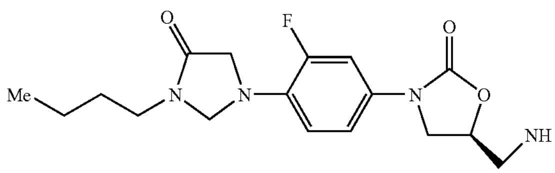 | $^1$H NMR(DMSO-d$_6$, 200MHz): δ 7.50(dd, J=15.8 & 2.2Hz, 1H), 7.20(d, J=8.6Hz, 1H), 6.92–6.80(m, 1H), 4.81(s, 2H), 4.60–4.50(m, 1H), 4.10–3.70(m, 4H), 3.50–3.10(m, 2H), 2.90–2.70(m, 2H), 1.80–1.20(m, 4H), 0.90(t, J=7.3Hz, 3H). |
| 62 | 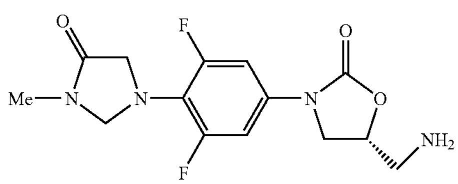 | $^1$H NMR(DMSO-d$_6$, 200MHz): δ 7.32(d, J=12.2Hz, 2H), 4.76(s, 2H), 4.61–4.58(m, 1H), 4.05–3.10(m, 6H), 2.83(s, 3H). |
| 63 | 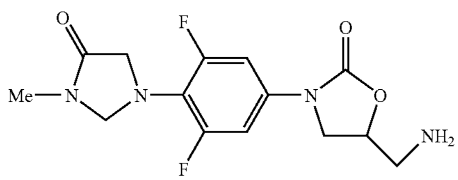 | $^1$H NMR(DMSO-d$_6$, 200MHz): δ 7.32(d, J=12.2Hz, 2H), 4.76(s, 2H), 4.61–4.58(m, 1H), 4.05–3.10(m, 6H), 2.83(s, 3H). |

E. General procedure for the conversion of

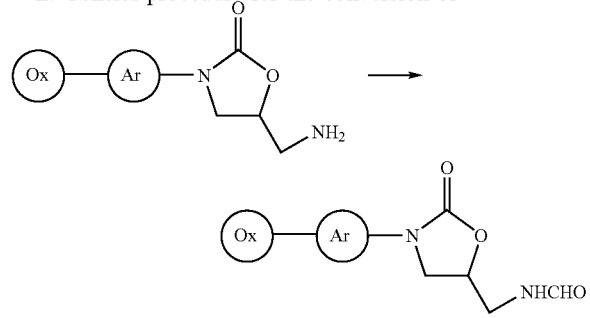

where 'Ox' represents a five membered heterocyclic group, containing at least one nitrogen atom and one more heteroatom selected from oxygen, nitrogen or sulfur. In which, the said atleast one nitrogen atom connecting said heterocyclic moiety 'Ox' to the 'Ar' moiety. The heterocyclic moiety is substituted by an =O or =S. The heterocycle may also be substituted by one or two additional substituents which are as defined on the heterocyclic moiety of formula (I). The heterocycle may also be fused with substituted or unsubstituted phenyl group. 'Ar' represents substituted or unsubstituted phenyl ring, the substituents are as defined on the phenyl ring of the formula (I)

A solution of amine in methyl formate was heated to 80° C. overnight. The volatiles were removed under low pressure and the residue obtained was passed through column to yield formate in very pure form.

Examples 64–66 have been prepared by a person skilled in the art according to the methodology as described in the above procedure E.

| Example No. | Structure | Analytical Data |
|---|---|---|
| 64 | 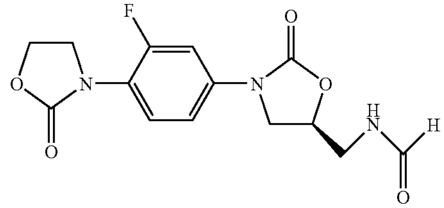 | ¹HNMR(CDCl₃, 200MHz): δ 8.28(s, 1H), 7.66–7.49(m, 2H), 7.15(d, J=8.8Hz, 1H), 6.15(bs, 1H), 4.82(m, 1H), 4.52(t, J=7.4Hz, 2H), 4.48–4.02(m, 3H). |
| 65 | 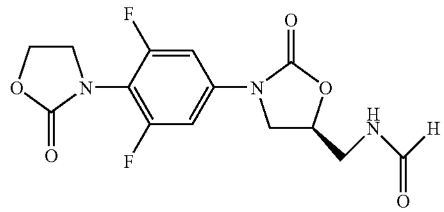 | ¹HNMR(CDCl₃, 200MHz): δ 8.27(s, 1H), 7.26–7.23(m, 2H), 6.32(bs, 1H), 4.82(bs, 1H), 4.58(t, J=7.2Hz, 2H), 4.214–3.68(m, 6H). |

F. General procedure for the conversion of

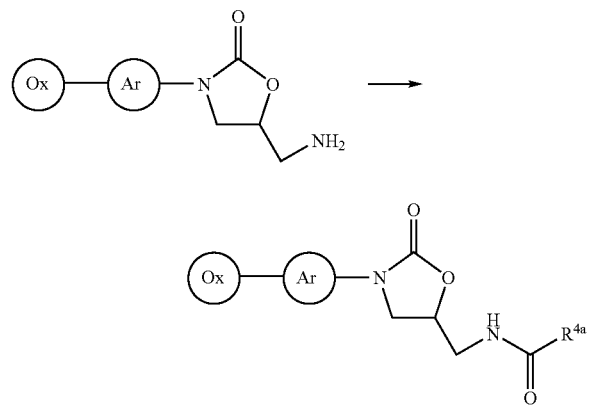

where 'Ox' represents a five membered heterocyclic group, containing at least one nitrogen atom and one more heteroatom selected from oxygen, nitrogen or sulfur. In which, the said at least one nitrogen atom connecting said heterocyclic moiety 'Ox' to the 'Ar' moiety. The heterocyclic moiety is substituted by an =O or =S The heterocycle may also be substituted by one or two additional substituents which are as defined on the heterocyclic moiety of formula (I). The heterocycle may also be fused with substituted or unsubstituted phenyl group. 'Ar' represents substituted or unsubstituted phenyl ring, the substituents are as defined on the phenyl ring of the formula (I); and $R^{4a}$ represents ($C_1$–$C_{10}$) alkyl, ($C_1$–$C_{10}$)alkoxy, ($C_2$–$C_{10}$)alkenyl, halo($C_1$–$C_{10}$)alkyl, aryloxy, ($C_2$–$C_{10}$)alkenyloxy, aryloxycarbonyl or ($C_1$–$C_{10}$) alkoxycarbonyl.

To a solution of the amine (1 eq) in dry dichloromethane at 0° C. under argon was added Et₃N (2.5 eq) followed by respective acid chloride (1.2 eq) drop wise. After being stirred at room temperature for 1 to 6 h (TLC control), the reaction mixture was diluted with dichloromethane and washed with water twice followed by brine. The organic extract was dried, evaporated and was passed through column to afford the acylated product.

Representative examples of the above procedure

Examples 66–96 have been prepared by a person skilled in the art according to the methodology as described in the above procedure F.

| Example No. | Structure | Analytical Data |
|---|---|---|
| 66 | 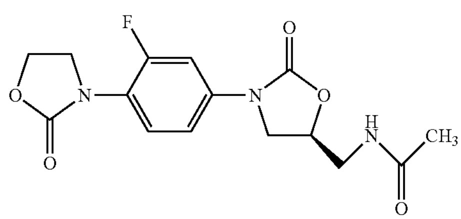 | ¹HNMR(CDCl₃, 200MHz): δ 7.62(dd, J=2.60Hz and 13.4Hz, 1H), 7.52(d, J=8.60Hz, 1H), 7.13–7.17(m, 1H), 5.96–5.99(m, 1H), 4.82–4.76(m, 1H), 4.52(t, J=7.40Hz, 2H), 4.01–4.09(m, 3H), 3.62–3.81(m, 3H), 2.02(s, 3H). |

-continued

| Example No. | Structure | Analytical Data |
|---|---|---|
| 67 | 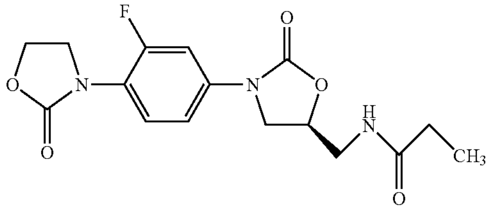 | ¹HNMR(CDCl₃, 200MHz): δ 7.66–7.49(m, 2H), 7.16(d, J=8.8Hz, 1H), 6.03(bs, 1H), 4.82–4.78(m, 1H), 4.52(t, J=7.8Hz, 2H), 4.09–4.0(m, 3H), 3.83–3.65(m, 3H), 2.24(q, J=7.8Hz, 2H), 1.13(t, J=7.8Hz, 3H). Mp: 203° C. |
| 68 | 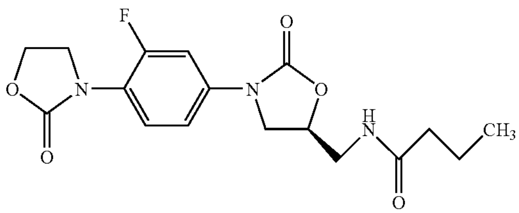 | ¹HNMR(CDCl₃, 200MHz): δ 7.66–7.49(m, 2H), 7.15(d, J=8.8Hz, 1H), 6.01(bs, 1H), 4.81–4.75(m, 1H), 4.52(t, J=7.8Hz, 2H), 4.09–4.01(m, 3H), 3.83–3.65(m, 3H), 2.19(t, J=7.4Hz, 2H), 1.65–1.58(m, 2H), 0.98(t, J=7.4Hz, 3H). Mp: 211° C. |
| 69 | 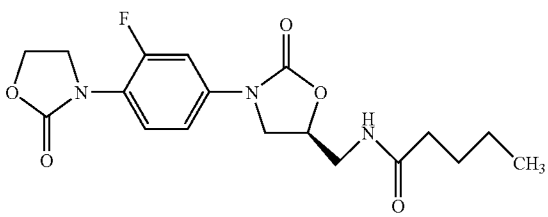 | ¹HNMR(CDCl₃, 200MHz): δ 7.66–7.49(m, 2H), 7.15(d, J=8.8Hz, 1H), 4.82–4.76(m, 1H), 4.52(t, J=7.8Hz, 2H), 4.09–4.01(m, 2H), 3.83–=3.65(m, 3H), 2.21(t, J=7.4Hz, 2H), 1.57–1.49(m, 2H), 1.38–1.20(m, 2H), 0.89(t, 3H). Mp: 187° C. |
| 70 | 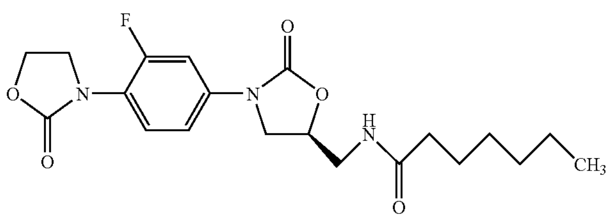 | ¹HNMR(CDCl₃, 200MHz): δ 7.68–7.52(m, 2H), 7.17(d, 8.6Hz, 1H), 5.96(hump, 1H), 4.81(hump, 1H), 4.54(t, J=7.2Hz, 2H), 4.11–3.67(m, 6H), 2.22(t, J=7.4Hz, 2H), 1.60(bs, 8H), 0.87(s, 3H). Mp: 131° C. |
| 71 | 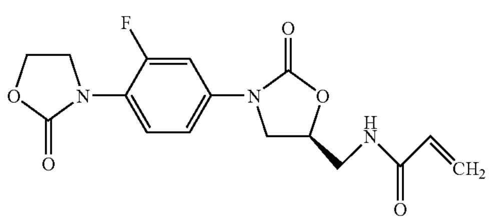 | ¹HNMR(CDCl₃ + DMSO-d⁶, 200MHz): δ 7.97(bs, 1H), 7.6–7.40(m, 2H), 7.10(d, J=8.8Hz, 1H), 6.35–6.15(m, 2H), 5.63(dd, J=4.0Hz and 8.3Hz, 1H), 4.79–4.86(m, 1H), 4.53(t, J=7.8Hz, 2H), 4.05(t, J=6.8Hz, 2H), 3.89–3.56(m, 4H). Mp: 196° C. |
| 72 | 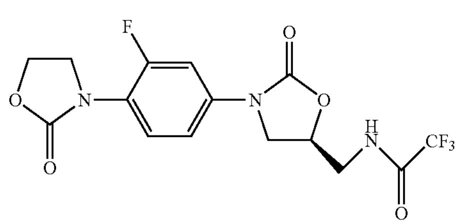 | ¹HNMR(CDCl₃ + DMSO-d⁶, 200MHz): δ 9.38(bs, 1H) 7.67–7.5(m, 2H), 7.20(d, J=8.8Hz, 1H), 4.88–4.87(m, 1H), 4.53(t, J=7.8Hz, 2H), 4.16–4.02(m, 3H), 3.89–3.70(m, 1H), 3.67–3.65(m, 2H). Mp: 194° C. |
| 73 | 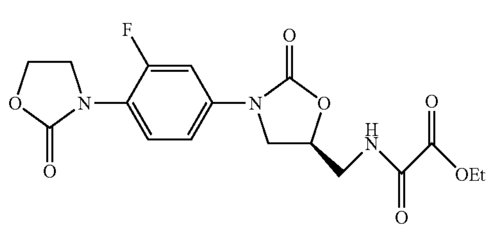 | ¹HNMR(CDCl₃, 200MHz): δ 7.66–7.49(m, 2H), 7.15(d, J=8.8Hz, 1H), 4.85–4.83(m, 1H), 5.55–4.47(m, 2H), 4.37–4.31(m, 2H), 4.14–3.90(m, 3H), 3.88–3.60(m, 3H), 1.42(t, 3H). Mp: 160° C. |

| Example No. | Structure | Analytical Data |
|---|---|---|
| 74 | 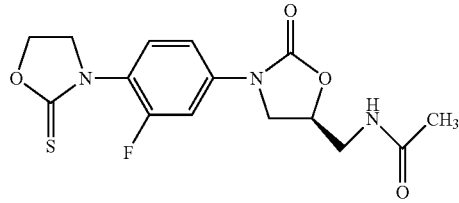 | ¹HNMR(CDCl₃, 200MHz): δ 7.75–7.05(m, 3H), 6.05(bs, 1H), 4.95–4.62(m 2H), 4.52(t, 1H), 4.30–3.32(m, 6H), 2.023(s, 3H). |
| 75 | 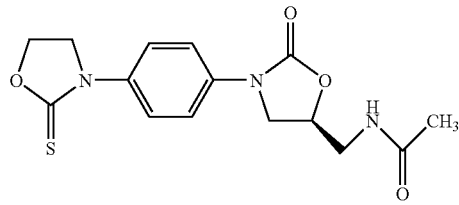 | ¹HNMR(CDCl₃, 200MHz): δ 7.5(d, J=7.81Hz, 2H), 7.3(d, J=7.81Hz, 2eH), 4.8(s, 1H), 4.4(s, 4H), 4.1(t, 1H), 3.8(t, 1H), 3.5(s, 1H), 32.3(s, 1H), 2.0(s, 3H). |
| 76 | 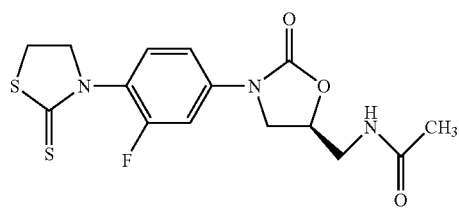 | ¹HNMR(CDCl₃, 200MHz): δ 7.99(hump, 1H), 7./73(d, J=13.0Hz, 1H), 7.43(d, J=8.0Hz, 1H) 7.31(d, J=8.8Hz, 1H), 4.83(hump, 1H), 4.42(t, J=7.6Hz, 2H), 4.15–3.89(m, 3H), 3.62–3.55(m, 4H), 2.0(s, 3H). Mp: 220° C. |
| 77 | 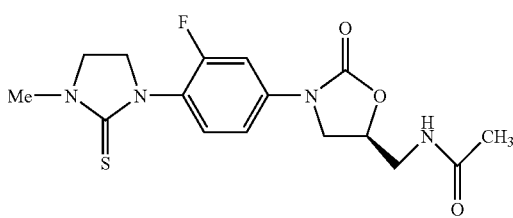 | ¹HNMR(CDCl₃, 200MHz): δ 7.61(dd, J=2.6Hz and 12.7Hz, 1H), 7.48(t, J=8.4Hz, 1H), 7.19(dd, J=2.6Hz and 8.8Hz, 1H), 6.15(t, J=8.4Hz, 1H), 4.79–4.77(m, 1H), 4.05(t, J=8.8Hz, 1H), 3.97–3.88(m, 2H), 3.81–3.74(m, 3H), 3.69–3.61(m, 2H), 3.23(s, 3H), 2.03(s, 3H). Mp: 171° C. |
| 78 | 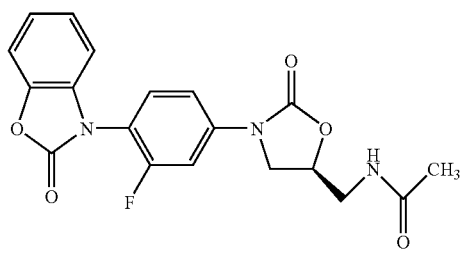 | ¹HNMR(CDCl₃, 200MHz): δ 7.76(dd, J=2.2Hz and 12.0Hz, 1H), 7.53(t, J=8.4Hz, 1H), 7.37–7.14(m, 4H), 6.82(t, J=3.4Hz, 1H), 6.03(t, J=5.4Hz, 1H), 4.83–4.80(m, 1H), 4.10(t, J=9.0Hz, 1H), 3.88–3.80(m, 1H), 3.71–3.66(m, 2H), 2.04(s, 3H). |
| 79 | 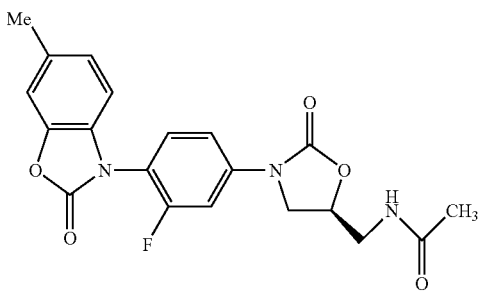 | ¹HNMR(CDCl₃, 200MHz): δ 7.74(dd, J=2.6Hz and 12.2Hz, 1H), 7.53(t, J=8.4Hz, 1H), 7.49–7.26(m, 2H), 7.10–6.95(m, 2H), 6.72–6.68(m, 1H), 6.09–6.01(m, 1H), 4.84(bs, 1H), 4.10(t, J=8.8Hz, 1H), 3.88–3.66(m, 3H), 2.41(s, 3H), 2.04(s, 3H). Mp: 213° C. |

-continued

| Example No. | Structure | Analytical Data |
|---|---|---|
| 80 | (structure) | ¹HNMR(CDCl₃, 200MHz): δ 7.80–6.94(m, 4H), 6.63(s, 1H), 6.0(bs, 1H), 4.82–4.90(m, 1H), 4.11(t, J=9.2Hz, 1H), 3.89–3.66(m, 3H), 2.35(s, 3H), 2.09(s, 3H). Mp: 202° C. |
| 81 | (structure) | ¹HNMR(CDCl₃, 200MHz): δ 7.93(s, 1H), 7.76(d, J=8.8Hz, 1H), 7.42(d, J=8.8Hz, 1H), 6.57(bs, 1H), 4.79(bs, 1H), 4.52(t, J=7.8Hz, 2H), 4.11–3.60(m, 6H), 1.99(s, 3H). Mp: 143° C. |
| 82 | (structure) | ¹HNMR(CDCl₃, 200MHz): δ 7.93–7.79(m, 2H), 7.43(d, J=8.8Hz, 1H), 6.12(bs, 1H), 4.82–4.78(m, 1H), 4.53(t, J=7.4Hz, 2H), 4.09(t, J=9.4Hz, 1H), 3.96–3.66(m, 5H), 2.30–2.17(m, 2H), 1.20(t, J=9.4Hz, 3H). Mp: 143° C. |
| 83 | (structure) | ¹HNMR(CDCl₃, 200MHz): δ 7.91(s, 1H), 7.78(d, J=8.2Hz, 1H), 6.26(bs, 1H), 4.80(bs, 1H), 4.52(t, J=7.2Hz, 2H), 4.06(t, J=9.4Hz, 1H), 3.95–3.67(m, 5H), 2.47–2.05(m, 4H), 1.83–1.54(m, 6H), 0.83–0.78(m, 3H). Mp: hygroscopic |
| 84 | (structure) | ¹HNMR(CDCl₃, 200MHz): δ 7.92(s, 1H), 7.85(d, J=8.2Hz, 1H), 7.45(d, J=8.8Hz, 1H), 6.40–6.07(m, 3H), 5.75(d, J=10.4Hz, 1H), 4.89(hump, 1H), 4.56(t, J=7.8Hz, 2H), 4.13(t, J=9.2Hz, 1H), 3.98–3.78(m, 5H). Mp: 191° C. |
| 85 | (structure) | ¹HNMR(CDCl₃, 200MHz): δ 7.65–7.41(m, 2H), 7.23(d, J=7.2Hz, 1H), 6.12(bs, 1H), 4.80(bs, 1H), 4.52(t, J=7.8Hz, 2H), 4.47–4.00(m, 3H), 3.81–3.59(m, 3H), 2.05(s, 3H). Mp: 120° C. |

-continued

| Example No. | Structure | Analytical Data |
|---|---|---|
| 86 | 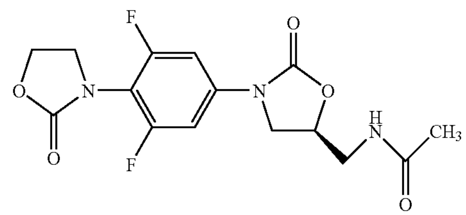 | ¹HNMR(CDCl₃, 200MHz): δ 7.27(d, J=9.8Hz, 2H), 6.01(hump, 1H), 4.80(hump, 1H), 4.57(t, J=7.8Hz, 2H), 4.06–3.67(m, 6H), 2.03(s, 3H). Mp: 219° C. |
| 87 | 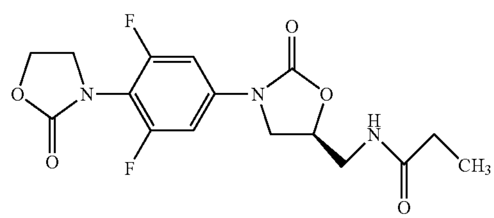 | ¹HNMR(CDCl₃ + DMSO-d⁶, 200MHz): δ 7.32–7.26(m, 2H), 7.09(hump, 1H), 4.81(hump, 1H), 4.58(t, J=7.4Hz, 2H), 4.05–3.62(m, 6H), 2.25–2.18(m, 2H), 1.11(t, J=7.8Hz, 3H). Mp: 224° C. |
| 88 | 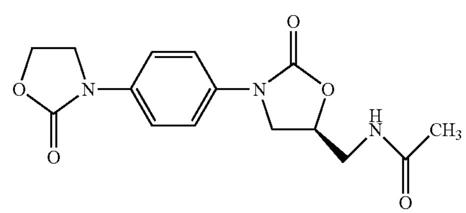 | ¹HNMR(CDCl₃ + DMSO-d6, 200MHz): δ 7.64(s, 2H), 7.55(s, 2H), 7.09–7.25(m, 1H), 4.70–4.85(m, 1H), 4.46(t, 2H), 4.13–3.81(m, 4H), 3.57(bs, 2H), 1.96(s, 3H). Mp: 231° C. |
| 89 | 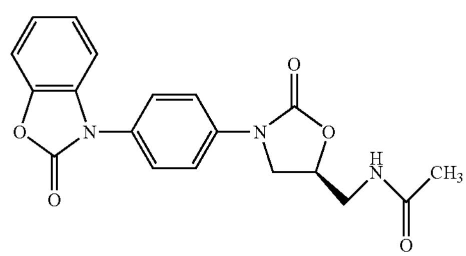 | ¹HNMR(CDCl₃, 200MHz): δ 7.70(d, J=8.8Hz, 2H), 7.54(d, J=8.8Hz, 2H), 7.24–6.99(m, 4H), 6.19(bs, 1H), 4.80(m, 1H), 4.09(t, J=8.8Hz, 1H), 3.85(t, J=7.0Hz, 1H), 3.69–3.63(m, 2H), 2.02(s, 3H). Mp: 229° C. |
| 90 | 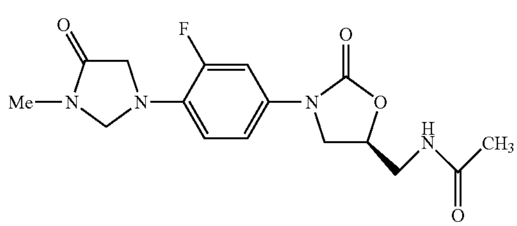 | ¹HNMR(CDCl₃, 200MHz): δ 7.10(d, 1H), 6.6(t, 1H), 6.0(m, 1H), 4.90(s, 2H), 4.9(m, 1H), 4.0(s, 3H), 3.80(m, 3H), 3.0(s, 3H), 2.0(s, 3H). Mp: 230° C. |

-continued

| Example No. | Structure | Analytical Data |
|---|---|---|
| 91 | 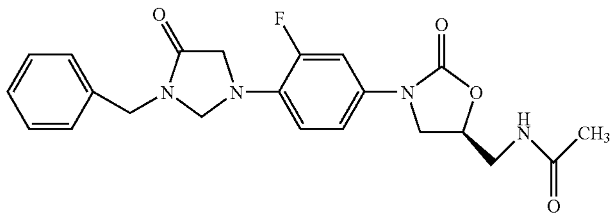 | ¹HNMR(CDCl₃, 200MHz): δ 7.26–7.46(m, 6H), 7.01(d, 1H), 6.63(t, 1H), 6.05(s, 1H), 4.71–4.89(m, 2H), 4.77(s, 1H), 4.60(s, 2H), 3.94–4.04(m, 3H), 3.61–3.76(m, 3H), 2.01(s, 3H). |
| 92 | 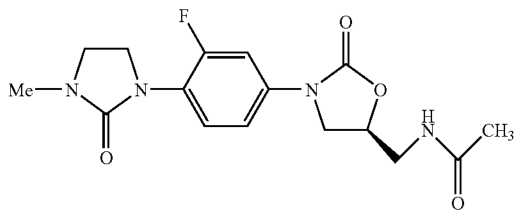 | ¹HNMR(CDCl₃, 200MHz): δ 7.50(m, 2H), 7.10(d, J=8.4Hz, 1H), 6.18(t, 1H), 4.7(m, 1H), 4.0(t, J=9.4Hz, 1H), 3.6(m, 7H), 2.9(s, 3H), 2.0(s, 3H). Mp: 182° C. |
| 93 | 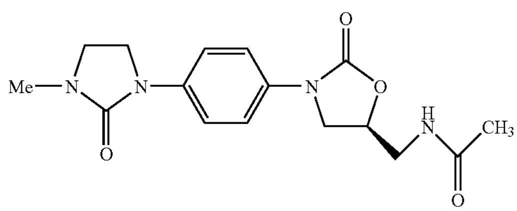 | ¹HNMR(CDCl₃, 200MHz): δ 2.0(s, 3H), 2.8(s, 3H), 4.0(t, 1H), 3.4–3.8(m, 5H), 4.8(m, 1H), 6.2(m, 1H), 7.6(m, 4H). Mp: 217° C. |
| 94 | 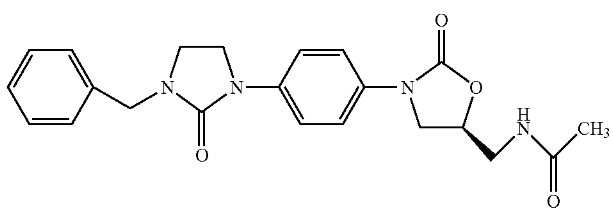 | ¹HNMR(CDCl₃, 200MHz): δ 7.6–7.3(m, 9H), 6.2(bt, 1H), 4.8–4.7(m, 1H), 4.5(s, 2H), 4.06(t, J=9.3Hz, 1H), 3.90–3.3(m, 6H), 2.0(s, 3H). Mp: 204° C. |
| 95 | 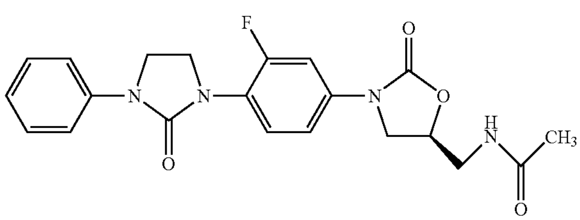 | ¹HNMR(CDCl₃, 200MHz): δ 7.70–7.50(m, 4H), 7.40–7.30(t, 2H), 7.2(d, J=8.8Hz, 1H), 7.1(t, 1H), 4.80(m, 5H), 4.0(m, 5H), 3.8(m, 1H), 3.6(m, 2H), 2.0(s, 3H). Mp: 182° C. |
| 96 | 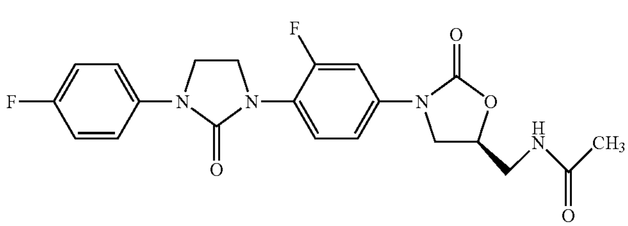 | ¹HNMR(CDCl₃, 200MHz): δ 8.3(m, 1H), 7.6(m, 4H), 7.3(m, 1H), 7.2(t, 2H), 4.7(m, 1H), 4.1(t, 1H), 3.8–4.0(m, 4H), 3.7(t, 1H), 3.0(m, 2H), 1.8(s, 3H). Mp: 194° C. |

G. General procedure for the conversion of

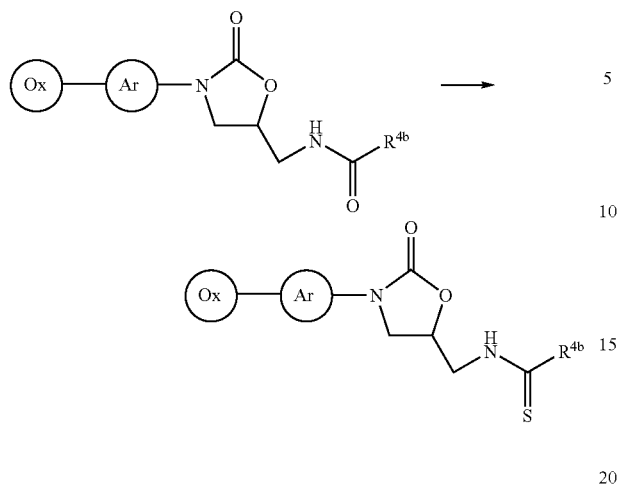

where 'Ox' represents a five membered heterocyclic group, containing at least one nitrogen atom and one more heteroatom selected from oxygen, nitrogen or sulfur. In which, the said atleast one nitrogen atom connecting said heterocyclic moiety 'Ox' to the 'Ar' moiety. The heterocyclic moiety is substituted by an =O or =S. The heterocycle may also be substituted by one or two additional substituents which are as defined on the heterocyclic moiety of formula (I). The heterocycle may also be fused with substituted or unsubstituted phenyl group. 'Ar' represents substituted or unsubstituted phenyl ring, the substituents are as defined on the phenyl ring of the formula (I); and $R^{4b}$ represents $(C_1-C_{10})$ alkyl, halo$(C_1-C_{10})$alkyl, —C(=O)—$(C_1-C_{10})$alkoxy, —C(=O)-aryloxy, —C(=S)—$(C_1-C_{10})$alkyl or —C(=S)-aryl.

A solution of the amide (1 eq) and Lawesson's reagent (0.6 eq) in dry dioxane was heated to 55 to 100° C. over 3 to 10 h (TLC control). The reaction mixture was allowed to cool to room temperature and diluted with ethyl acetate. The resultant mixture was washed with water (4 times) followed by brine and dried. The residue obtained upon evaporation of solvent was passed through column of silica gel to afford the respective thioacetate.

Reference Example of the Above Procedure

Example 97

(5S)-3-[3-Fluoro-4-(3-methyl-2-oxo-1-imidazolidinyl)phenyl]-5-(1-thioxoethylaminomethyl)-1,3-oxazolan-2-one

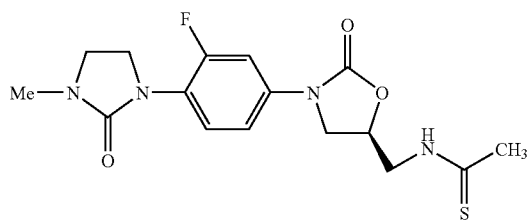

A solution of the amide (100 mg, 0.28 mmol), obtained in example 92, and Lawesson's reagent (69 mg, 0.17 mmol) in dry dioxane was heated to 80 to 90° C. over 3 to 10 h (TLC control). The reaction mixture was allowed to cool to room temperature and diluted with ethyl acetate. The resultant mixture was washed with water (4 times) followed by brine and dried. The residue obtained upon evaporation of solvent was passed through column of silica gel to afford the final compound (Yield: 70 mg, 67%).

$^1$HNMR (CDCl$_3$, 200 MHz): δ 8.4 (1H), 7.5 (m, 2H), 7.0 (d, J=8.8 Hz, 2H), 4.9 (m, 1H), 3.9 (m, 6H), 3.5 (t, J=8.8 Hz, 2H), 2.9 (s, 3H), 2.5 (s, 3H); Mp: 168° C.

Examples 98–108 have been prepared by a person skilled in the art according to the methodology as described in the above Example 97.

| Example No. | Structure | Analytical Data |
|---|---|---|
| 98 | (structure shown) | $^1$HNMR(CDCl$_3$, 200MHz): δ 7.94(bs, 1H), 7.66–7.52 (m, 2H), 7.16(d, J=7.8Hz, 1H), 5.20–4.85(m, 1H), 4.54 (t, J=7.8Hz, 2H), 4.25–3.82 (m, 6H), 2.61(s, 3H). Mp: 171° C. |
| 99 | (structure shown) | $^1$HNMR(CDCl$_3$+DMSO-d6, 200MHz): δ 10.51(s, 1H), 7.64–7.47(m, 2H), 7.16(d, J=8.8Hz, 1H), 5.01(bs, 1H), 4.53(t, J=7.2Hz, 2H), 4.29–3.89(m, 4H), 3.63(q, J=10.2Hz, 2H). Mp: 165° C. |

-continued

| Example No. | Structure | Analytical Data |
|---|---|---|
| 100 | 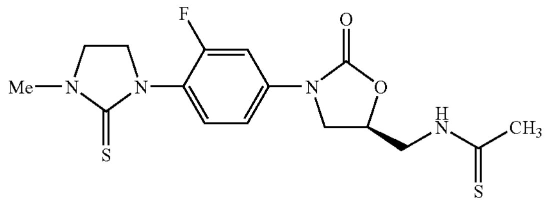 | $^1$HNMR(CDCl$_3$, 200MHz): δ 7.90(bs, 1H), 7.61(dd, J=2.4Hz and 12.8Hz, 1H), 7.50(t, J=8.2Hz, 1H), 7.19 (dd, J=2.4Hz and 12.8Hz, 1H), 5.0(m, 1H), 4.25–3.74 (m, 8H), 3.24(s, 3H), 2.6(s, 3H). Mp: 111°C. |
| 101 | 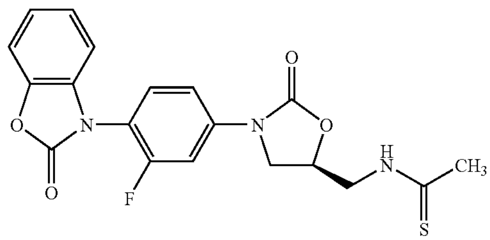 | $^1$HNMR(CDCl$_3$, 200MHz): δ 7.87–7.74(m, 2H), 7.57(t, J=8.2Hz, 1H), 7.39–7.18 (m, 4H), 6.87–6.85(m, 1H), 5.08–5.05(m, 1H), 4.37–4.27 (m, 1H), 4.23–4.06(m, 2H), 3.94(t, J=6.8Hz, 1H), 2.62 (s, 3H) Mp: 137° C. |
| 102 | 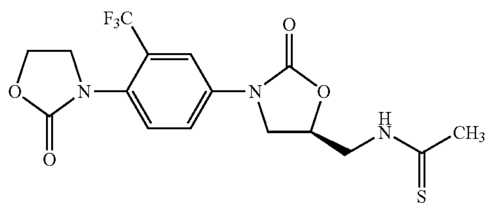 | $^1$HNMR(CDCl$_3$, 200MHz): δ 8.1(s, 1H), 7.9(s, 1H), 7.8 (d, J=8.7Hz, 1H), 7.4(d, J=8.79, 1H), 5.0(s, 1H), 4.6 (t, 2H), 4.0(m, 6H), 2.6(s, 3H). Mp: 154° C. |
| 103 | 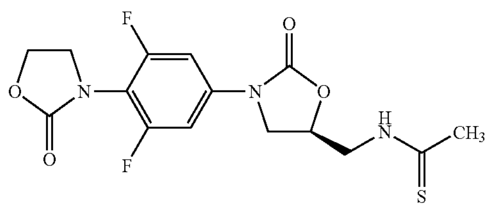 | $^1$HNMR(CDCl$_3$+DMSO-d$^6$, 200MHz): δ 10.37(bs, 1H), 7.50(d, J=10.8Hz, 2H), 4.98(bs, 1H), 4.55(t, J=7.8 Hz, 2H), 4.23–3.78(m, 6H), 2.50(s, 3H). Mp: 108° C. |
| 104 | 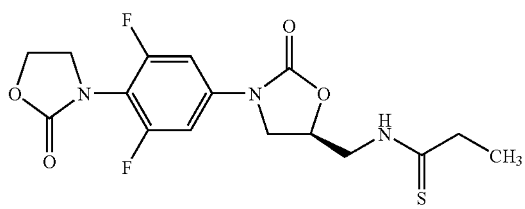 | $^1$HNMR(CDCl$_3$, 200MHz): δ 7.86(bt, 1H), 7.28(d, J=9.6Hz, 2H), 5.02–4.99(m, 1H), 4.58(t, J=7.4Hz, 2H), 4.24–3.80(m, 6H), 2.71(q, J=7.4Hz, 2H), 1.29(t, J=7.8 Hz, 3H). Mp: 168° C. |
| 105 | 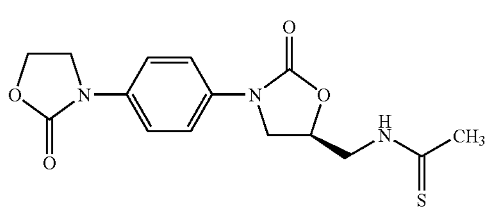 | $^1$HNMR(CDCl$_3$, 200MHz): δ 7.86(hump, 1H), 7.25(d, J=9.6Hz, 2H), 5.02–4.99(m, 1H), 4.58(t, J=7.4Hz, 2H), 4.24–3.80(m, 6H), 2.71(q, J=7.4Hz, 2H), 1.29(t, J=7.8 Hz, 3H). Mp: 195° C. |
| 106 | 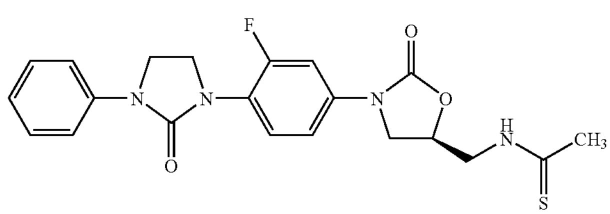 | $^1$HNMR(CDCl$_3$, 200MHz): δ 7.6(m, 4H), 7.4(m, 2H), 7.2(d, J=8.8Hz, 1H), 7.0 (t, 1H), 5.0(m, 1H), 4.0(m, 8H), 2.6(s, 3H). Mp: 165°C. |

| Example No. | Structure | Analytical Data |
|---|---|---|
| 107 | 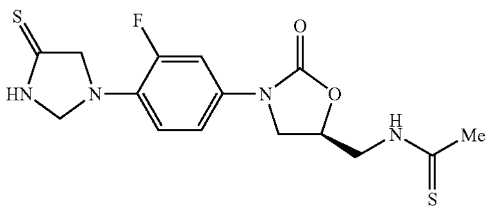 | ¹HNMR(200MHz, DMSO-d₆) δ: 11.10(s, 1H), 10.40 (bs, 1H), 7.47(d, J=15.8Hz, 1H), 7.61(d, J=8.3Hz, 1H), 6.83(t, J=9.4Hz, 1H), 5.00(s, 2H), 4.98–4.91 (m, 1H), 4.30(s, 2H), 4.20–3.65(m, 4H), 2.47(d, J=12.6Hz, 3H). |
| 108 | 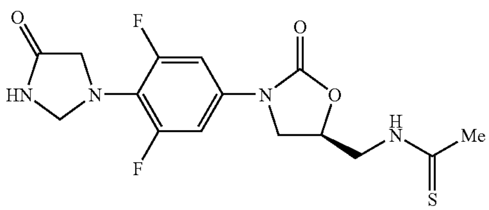 | ¹HNMR(200Mz, DMSO-d₆) δ: 10.38(bs, 1H), 8.58(s, 1H), 7.31(d, J=12.2Hz, 2H), 4.96(bs, 1H), 4.73(s, 2H), 4.14(t, J=9.0Hz, 1H), 3.91–3.75(m, 5H), 2.51(s, 3H). MP: 148–150° C. |

H. General procedure for the conversion of

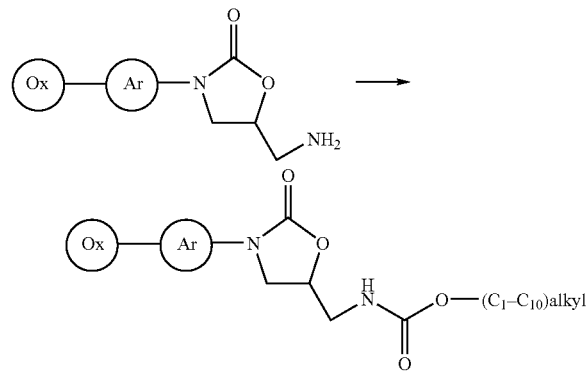

where 'Ox' represents a five membered heterocyclic group, containing at least one nitrogen atom and one more heteroatom selected from oxygen, nitrogen or sulflur. In which, the said atleast one nitrogen atom connecting said heterocyclic moiety 'Ox' to the 'Ar' moiety. The heterocyclic moiety is substituted by an =O or =S. The heterocycle may also be substituted by one or two additional substituents which are as defined on the heterocyclic moiety of formula (I). The heterocycle may also be fused with substituted or unsubstituted phenyl group. 'Ar' represents substituted or unsubstituted phenyl ring, the substituents are as defined on the phenyl ring of the formula (I).

To a solution of the amine (1 eq), Et₃N (2.2 eq) in dry dichloromethane and methyl chloroformate under argon was added at 0° C. (1.2 eq). The reaction mixture was stirred at room temperature overnight and worked up by diluting with dichloromethane followed by washing with water and brine. The residue obtained after evaporation of the dried organic layer was passed through column to afford the carbamate.

Examples 109–113 have been prepared by a person skilled in the art according to the methodology as described in the above procedure H.

| Example No. | Structure | Analytical Data |
|---|---|---|
| 109 | 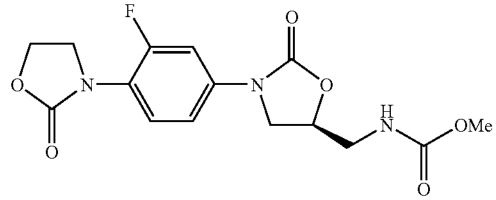 | ¹HNMR(CDCl₃, 200MHz): δ 7.68–7.49(m, 2H), 7.16(d, J=8.4Hz, 1H), 5.16(bs, 1H), 4.78(bs, 1H), 4.52(t, J=7.2 Hz, 2H), 4.09–4.0(m, 3H), 3.84–3.55(m, 6H). Mp: 153° C. |

-continued

| Example No. | Structure | Analytical Data |
|---|---|---|
| 110 | 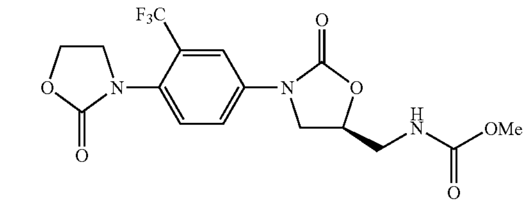 | $^1$HNMR(CDCl$_3$, 200MHz): δ 7.9(m, 2H), 7.4(d, J=8.3Hz, 1H), 5.2(s, 1H), 4.8(s, 1H), 4.5(t, 1H), 4.0(m, 9H). Mp: 148° C. |
| 111 | 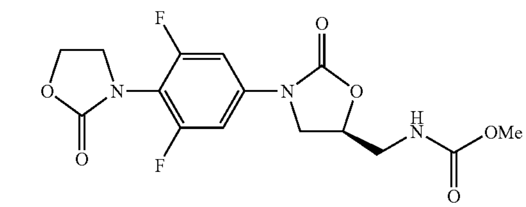 | $^1$HNMR(CDCl$_3$, 200MHz): δ 7.27(d, J=6.8Hz, 2H), 5.16 (bs, 1H), 4.84–4.80(m, 1H), 4.58(t, J=7.2Hz, 2H), 4.07– 3.60(m, 9H). Mp: 157° C. |
| 112 | 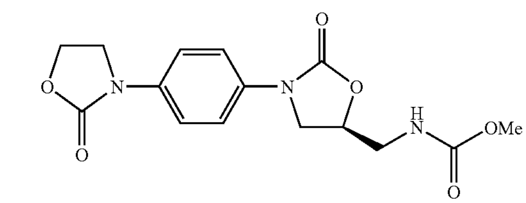 | $^1$HNMR(CDCl$_3$+DMSO-d$^6$, 200MHz): δ 7.57(s, 4H), 6.98 (bs, 1H), 4.96–4.76(m, 1H), 4.51(t, J=7.4Hz, 2H), .4.47 (m, 3H), 3.91–3.84(m, 1H), 3.65(s, 1H), 3.51(bs, 3H). Mp: 195° C. |
| 113 | 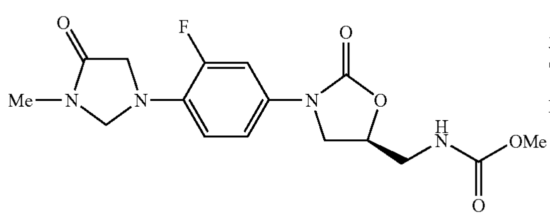 | $^1$HNMR(CDCl$_3$, 200MHz): δ 3.0(s, 3H), 3.8(m, 6H), 4.8 (m, 1H), 4.9(s, 2H), 5.1(m, 1H), 6.6(t, 1H). Mp: 226° C. |

I. General procedure for the conversion of

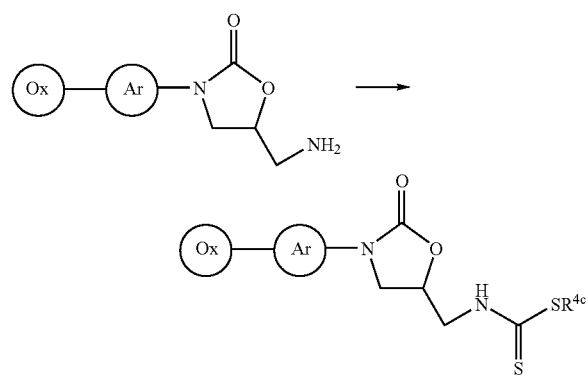

where 'Ox' represents a five membered heterocyclic group, containing at least one nitrogen atom and one more heteroatom selected from oxygen, nitrogen or sulfur. In which, the said atleast one nitrogen atom connecting said heterocyclic moiety 'Ox' to the 'Ar' moiety. The heterocyclic moiety is substituted by an =O or =S. The heterocycle may also be substituted by one or two additional substituents which are as defined on the heterocyclic moiety of formula (I). The heterocycle may also be fused with substituted or unsubstituted phenyl group. 'Ar' represents substituted or unsubstituted phenyl ring, the substituents are as defined on the phenyl ring of the formula (I); and R$^{4c}$ represents (C$_1$–C$_{10}$) alkyl group.

To an ice cold mixture of amine (1 eq), Et$_3$N (2 eq) and water (few drops) in EtOH CS$_2$ (1 eq) was added under argon. Stirred overnight at room temperature, Methyl iodide (MeI) (1.1 eq) in EtOH was added and the stirring was continued for 12 h. The volatiles were removed and the residue was taken up in ethyl acetate. The organic mixture was washed with saturated NaHCO$_3$, water, brine and dried. The residue obtained was passed through column to afford the product.

Examples 114 and 115 have been prepared by a person skilled in the art according to the methodology as described in the above procedure I.

| Example No. | Structure | Analytical Data |
|---|---|---|
| 114 | 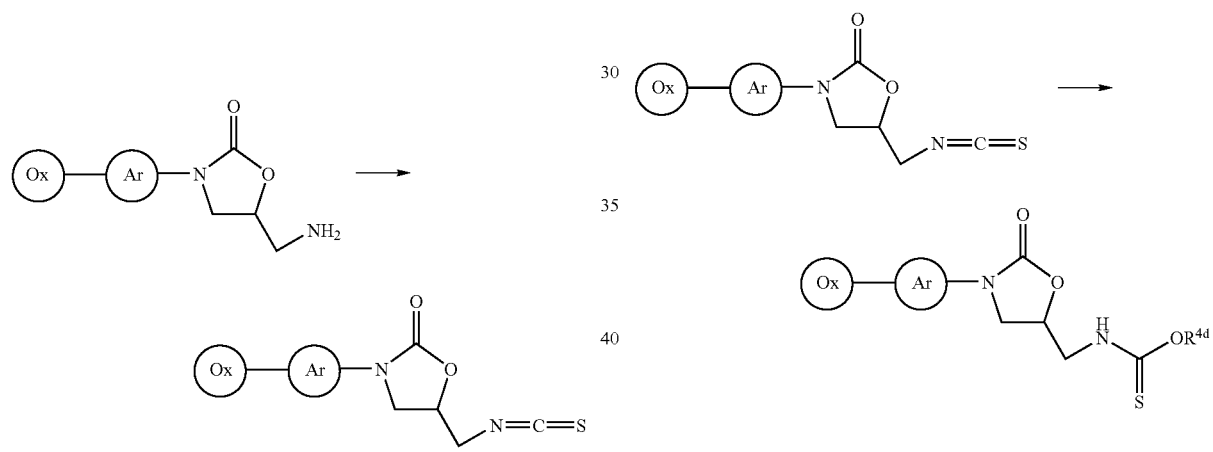 | $^1$HNMR(CDCl$_3$+DMSO-d6, 200MHz): δ 9.98(bt, 1H), 7.55 (s, 4H), 5.05–5.02(m, 1H), 4.50(t, J=7.8Hz, 2H), 4.12–3.87(m, 6H), 2.60(s, 3H). Mp: 161° C. |
| 115 | 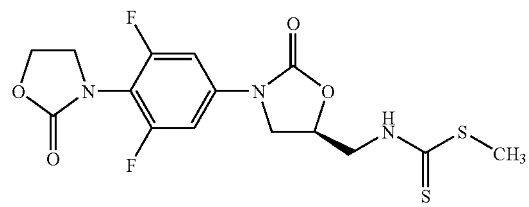 | $^1$HNMR(DMSO-d6, 200MHz): δ7.26(s, 1H), 6.15 (d, J=10.2Hz, 2H), 4.56–4.49 (m, 3H), 4.27–3.83(m, 5H), 3.26–3.15(m, 1H), 2.54(s, 3H). Mp: 147° C. |

J. General procedure for the conversion of

Step (i):

where 'Ox' represents a five membered heterocyclic group, containing at least one nitrogen atom and one more heteroatom selected from oxygen, nitrogen or sulfur. In which, the said atleast one nitrogen atom connecting said heterocyclic moiety 'Ox' to the 'Ar' moiety. The heterocyclic moiety is substituted by an =O or =S. The heterocycle may also be substituted by one or two additional substituents which are as defined on the heterocyclic moiety of formula (I). The heterocycle may also be fused with substituted or unsubstituted phenyl group. 'Ar' represents substituted or unsubstituted phenyl ring, the substituents are as defined on the phenyl ring of the formula (I).

Thiophosgene (1.2 eq) was added drop wise to a solution of the amine (1 eq), Et$_3$N (2.4 eq) in dry dichloromethane at ice bath temperature. The reaction may be carried out in the presence of argon. The reaction mixture was warmed to 20 to 35° C. over 3 h and then the volatiles were removed. The residue obtained was directly charged on to a column of silica gel to afford the product.

Step (ii)

where 'Ox' represents a five membered heterocyclic group, containing at least one nitrogen atom and one more heteroatom selected from oxygen, nitrogen or sulfur. In which, the said atleast one nitrogen atom connecting said heterocyclic moiety 'Ox' to the 'Ar' moiety. The heterocyclic moiety is substituted by an =O or =S. The heterocycle may also be substituted by one or two additional substituents which are as defined on the heterocyclic moiety of formula (I). The heterocycle may also be fused with substituted or unsubstituted phenyl group. 'Ar' represents substituted or unsubstituted phenyl ring, the substituents are as defined on the phenyl ring of the formula (I); and R$^{4d}$ represents (C$_1$–C$_{10}$) alkyl, cyclo(C$_1$–C$_{10}$)alkyl, —(C=O)—(C$_1$–C$_{10}$)alkyl group substituted with fluorine; aryl such as phenyl or naphthyl; halo(C$_1$–C$_{10}$)alkyl, hydroxy(C$_1$–C$_{10}$)alkyl, (C$_1$–C$_{10}$)alkoxy (C$_1$–C$_{10}$)alkyl or (C$_2$–C$_{10}$)alkenyl.

A solution of the isothiocyanate in the respective alcohol was heated to 80 to 100° C. while monitoring by TLC. At the complete consumption of starting material, the reaction mixture was allowed to cool to room temperature. The crystals formed were separated, washed with ether and dried at vacuum to yield the pure product.

Reference Examples of the Above Procedure

Example 116

(S)-{3-[3,5-Difluoro-4-(4-oxo-imidazolidin-1-yl)-phenyl]-2-oxo-oxazolidin-5-ylmethyl}-thiocarbamic acid O-methyl ester

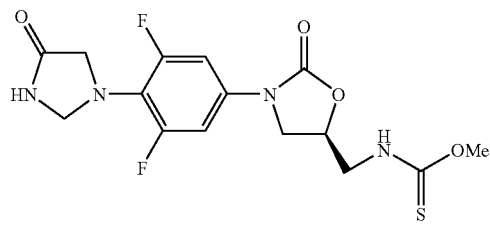

Step (i)

To a solution of the amine (13 g, 41.6 mmol), obtained in example 50, in dichloromethane (100 mL) and DMF (100 mL) was added a solution of NaHCO$_3$ (10.4 g, 124.8 mmol) in water (50 mL) followed by thiophosgene (3.8 mL, 49.9 mmol) at ice bath temperature. The reaction mixture was stirred at 20–35° C. over 30 min and was worked up by adding water followed by extraction of chloroform. The combined organic extracts were washed with brine and the residue obtained upon evaporation of all the solvents was washed with petroleum ether to afford the corresponding isothiocyanate (Yield: 12 g, 87%).

Step (ii)

A solution of the above obtained isothiocynate compound (24 g, 67.7 mmol) in dry methanol (750 mL) was refluxed overnight. The residue obtained upon evaporation of methanol was purified on a column of silica gel to afford the title compound (Yield: 22 g, 84%).

$^1$H NMR (200 MHz, DMSO-d$_6$) δ: 9.53–9.45 (m, 1H), 8.57 (s, 1H), 7.29 (d, J=12.1 Hz, 2H), 4.94–4.87 (m, 1H), 4.71 (s, 2H), 4.16–4.07 (m, 1H), 3.93–3.75 (m, 7H); Mp: 199° C.

Examples 117–175 have been prepared by a person skilled in the art according to the methodology as described in the above Example 116.

| Example No. | Structure | Analytical Data |
|---|---|---|
| 117 | 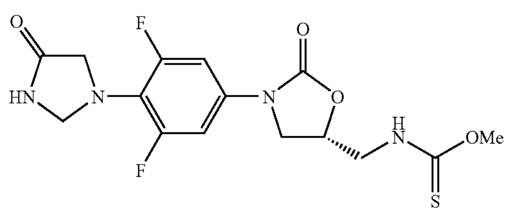 | $^1$HNMR(200MHz, DMSO-d$_6$) δ: 9.53–9.45 (m, 1H), 8.57(s, 1H), 7.29(d, J=12.1Hz, 2H), 4.94–4.87(m, 1H), 4.71 (s, 2H), 4.16–4.07(m, 1H), 3.93–3.75(m, 7H). |
| 118 | 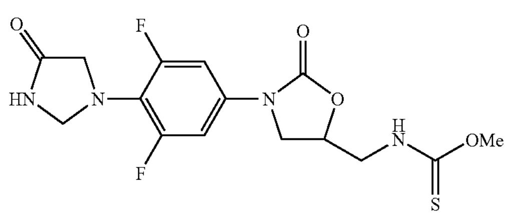 | $^1$HNMR(200MHz, DMSO-d$_6$) δ: 9.53–9.45 (m, 1H), 8.57(s, 1H), 7.29(d, J=12.1Hz, 2H), 4.94–4.87(m, 1H), 4.71 (s, 2H), 4.16–4.07(m, 1H). 393–3.75(m, 7H). |
| 119 | 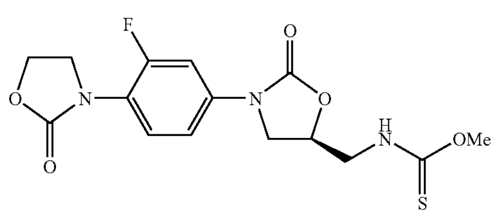 | $^1$HNMR(CDCl$_3$, 200MHz): δ 7.67–7.56 (m, 2H), 7.16(d, J=2.0 Hz, 1H), 6.72(bs, 1H), 4.94(bs, 1H), 4.52(t, J=7.8Hz, 2H), 4.12–3.83 (m, 9H). Mp: 137° C. |
| 120 | 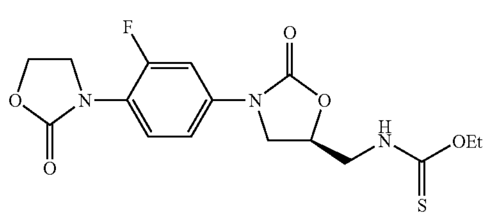 | $^1$HNMR(CDCl$_3$, 200MHz): δ 7.66–7.50 (m, 2H), 7.15(d, J=7.4 Hz, 1H), 6.66(hump, 1H), 4.94(bs, 1H), 4.56–4.43(m, 4H), 4.12–3.84 (m, 6H), 1.32(t, J=6.8 Hz, 3H). Mp: 208° C. |

-continued

| Example No. | Structure | Analytical Data |
|---|---|---|
| 121 | 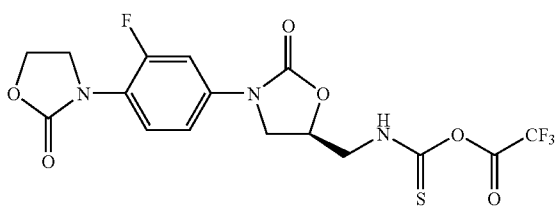 | ¹HNMR (CDCl₃+DMSO-d⁶, 200MHz): δ 8.45(bs, 1H), 7.65–7.46(m, 2H), 7.17(d, J=8.8Hz, 1H), 4.81(bs, 1H), 4.53(t, J=7.4Hz, 2H), 4.09–3.99 (m, 3H), 3.84–3.55(m, 3H), 3.13(q, J=10.4Hz, 2H). Mp: 184° C. |
| 122 | 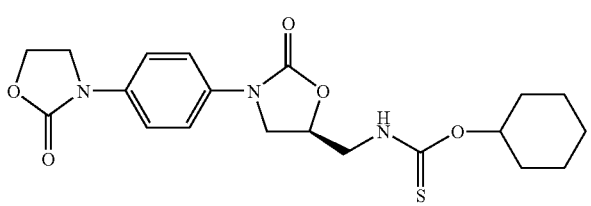 | ¹HNMR(DMSO-d⁶, 200MHz): δ 9.54(m, 1H), 7.57(s, 4H), 4.90–4.80(m, 2H), 4.44(t, J=7.4Hz, 2H), 4.21–4.01 (m, 4H), 3.88–3.77(m, 3H), 3.56–3.53(m, 1H), 1.23–0.97(m, 6H). Mp: 153° C. |
| 123 | 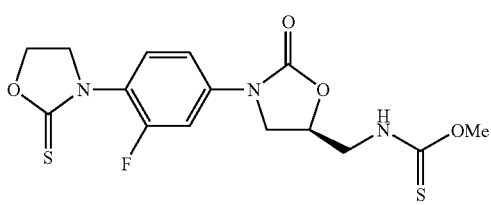 | ¹HNMR(CDCl₃, 200MHz): δ 8.2(m, 1H), 7.7(d, J=10.74Hz, 1H), 7.5(t, 1H), 7.3(d, J=8.79Hz, 1H), 5.0(m, 1H), 4.70(t, 2H), 4.1(m, 9H). Mp: 197° C. |
| 124 | 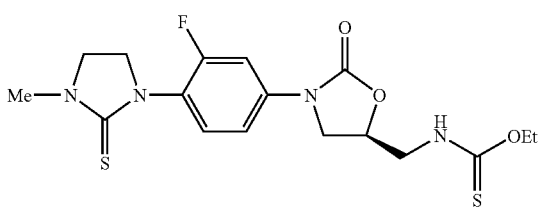 | ¹HNMR(CDCl₃, 200MHz): δ 7.02(dd, J=2.4Hz and 12.8Hz, 1H), 7.49(t, J=8.8Hz and 12.8Hz, 1H), 7.20(dd, J=2.4Hz and 12.8Hz, 1H), 6.63(bs, 1H), 4.93 (m, 1H), 4.54–4.44(q, J=7.4Hz, 2H), 4.13–3.72 (m, 8H), 3.24(s, 3H), 1.32(t, J=7.0Hz, 3H). Mp: 197° C. |
| 125 | 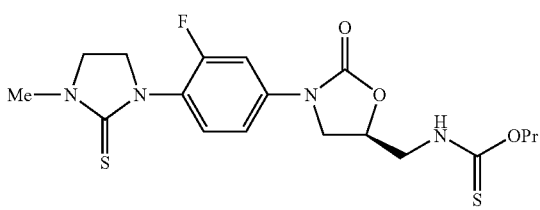 | ¹HNMR(CDCl₃, 200MHz): δ 7.62(dd, J=2.4Hz and 12.6Hz, 1H), 7.49(t, J=8.8Hz, 1H), 7.20(dd, J=2.4Hz and 12.6Hz, 1H), 6.65(bs, 1H), 4.94(m, 1H), 4.38 (t, J=8.8Hz, 2H), 4.13–3.73(m, 8H), 3.24(s, 3H), 1.78–1.63(m, 2H), 0.99(t, 3H). Mp: >200° C. |
| 126 | 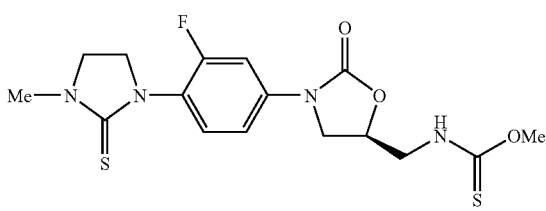 | ¹HNMR(CDCl₃, 200MHz): δ 7.62(dd, J=2.4Hz and 12.7Hz, 1H), 7.49(t, J=8.8Hz, 1H), 7.20(dd, J=2.4Hz and 12.7Hz, 1H), 6.70(bs, 1H), 4.94(m, 1H), 4.13–3.72(m, 11H), 3.24(s, 3H). Mp: 179° C. |

-continued

| Example No. | Structure | Analytical Data |
|---|---|---|
| 127 | 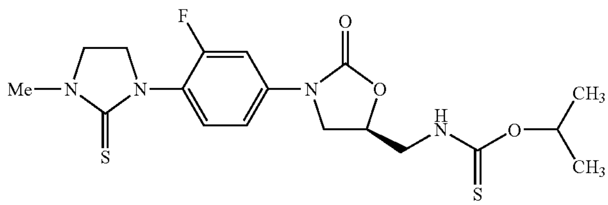 | ¹HNMR(CDCl₃, 200MHz): δ 7.62(dd, J= 2.4Hz and 12.7Hz, 1H), 7.49(t, J=8.8Hz, 1H), 7.20(dd, J=2.4Hz and 13.0Hz, 1H), 6.55(bs, 1H), 5.58–5.49(heptet, 1H), 4.92(m, 1H), 4.13–3.73(m, 8H), 3.24(s, 3H), 1.39–1.25(m, 6H). Mp: 183° C. |
| 128 | 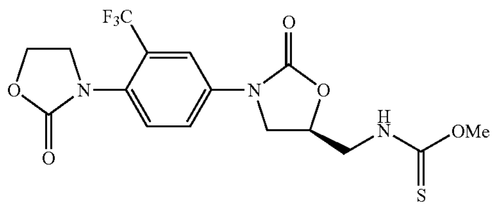 | ¹HNMR(CDCl₃, 200MHz): δ 7.9(m, 2H), 7.5(d, J=8.79Hz, 1H), 6.7(s, 1H), 5.0(s, 1H), 4.5(t, 2H), 4.0(m, 9H). Mp: 146° C. |
| 129 | 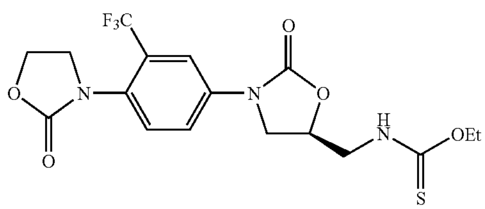 | ¹HNMR(CDCl₃, 200MHz): δ 7.8(m, 2H), 7.4(d, J=8.79Hz, 1H), 6.7(s, 1H), 5.0(s, 1H), 4.5(m, 4H), 4.0(m, 6H), 1.3(m, 3H). Mp: 157° C. |
| 130 | 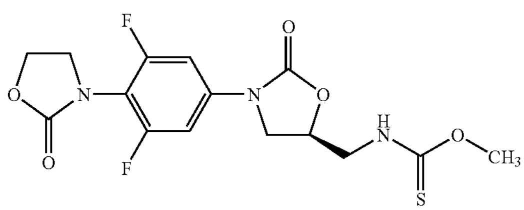 | ¹HNMR(CDCl₃, 200MHz): δ 7.29–7.24 (m, 2H), 6.73(hump, 1H), 4.96(huimp, 1H), 4.58(t, J=7.4Hz, 2H), 4.08–3.83(m, 9H). Mp: 182° C. |
| 131 | 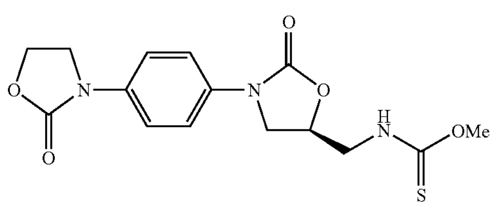 | ¹HNMR(CDCl₃, 200MHz): δ 7.52(s, 4H), 6.81(bs, 1H), 4.91 (hump, 1H), 4.49(t, J= 7.8Hz, 2H), 4.13–3.82 (m, 9H). Mp: 153° C. |
| 132 | 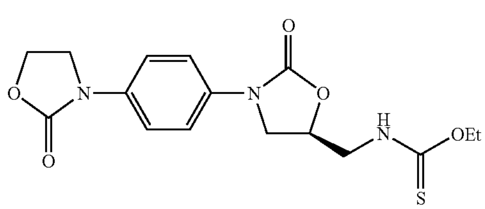 | ¹HNMR(CDCl₃, 200MHz): δ 7.5(s, 4H), 6.7(s, 1H), 4.9(s, 1H), 4.5(m, 4H), 4.0(m, 6H), 1.3(t, J=6.8Hz, 3H). Mp: 168° C. |
| 133 | 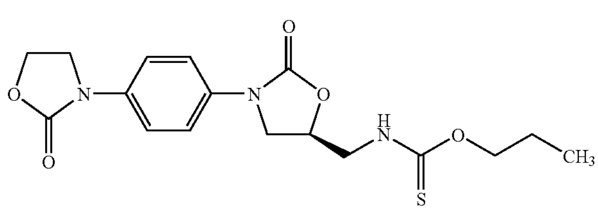 | ¹HNMR(CDCl₃, 200MHz): δ 7.54(s, 4H), 6.7(s, 1H), 4.9(m, 1H), 4.4(m, 4H), 4.0(m, 6H), 1.7(m, 2H), 0.95(t, J= 7.4Hz, 3H). Mp: 176° C. |

-continued

| Example No. | Structure | Analytical Data |
|---|---|---|
| 134 | 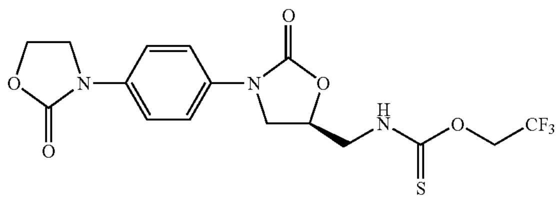 | ¹HNMR(CDCl₃, 200MHz): δ 7.52(s, 4H), 7.26(bs, 1H), 4.96–4.77 (m, 3H), 4.50(t, J=7.2 Hz, 2H), 4.15–3.80(m, 6H).<br>Melting Point(° C.): 181° C. |
| 135 | 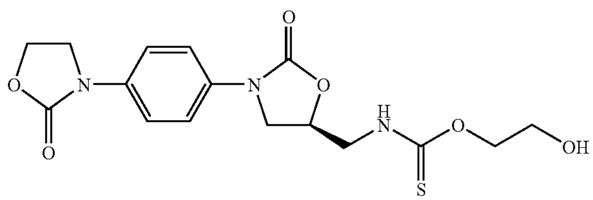 | ¹HNMR(CDCl₃, 200MHz): δ 9.2–8.9(m, 1H), 7.5(s, 4H), 5.0–4.8 (m, 1H), 4.6–4.4(m, 4H), 4.2–3.5(m, 8H).<br>Mp: 141° C. |
| 136 | 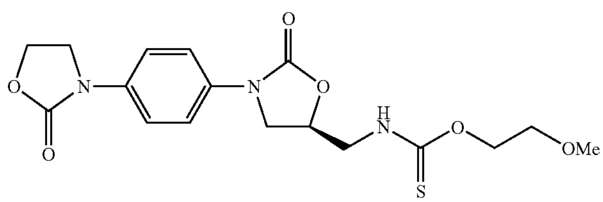 | ¹HNMR(CDCl₃, 200MHz): δ 7.54(s, 4H), 6.81(bt, 1H), 4.91(m, 1H), 4.67–4.58(m, 2H), 4.50(t, J=7.2Hz, 2H), 4.13–3.82(m, 6H), 3.68–3.63(m, 2H), 3.38(s, 3H).<br>Mp: 149° C. |
| 137 | 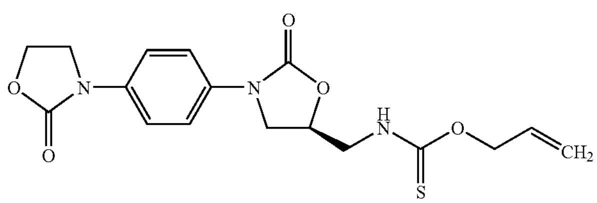 | ¹HNMR(CDCl₃, 200MHz): δ 7.55(s, 4H), 7.26(s, 2H), 6.7(s, 1H), 5.93(m, 1H), 5.29(m, 2H), 4.9(m, 3H), 4.5(t, J= 7.4Hz, 2H), 4.0(m, 6H).<br>Mp: 150° C. |
| 138 | 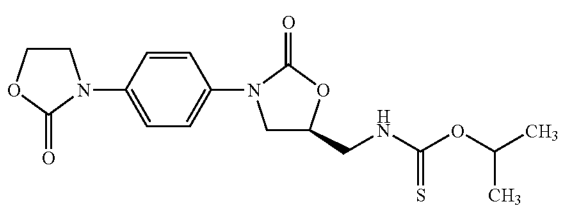 | ¹HNMR(CDCl₃, 200MHz): δ 7.54(s, 4H), 6.57(s, 1H), 5.5(m, 1H), 4.92(m, 1H), 4.5(t, J= 7.4Hz, 2H), 4.0(m, 6H), 1.31(dd, J=10.2Hz and 13.8Hz, 6H).<br>Mp: 140° C. |
| 139 | 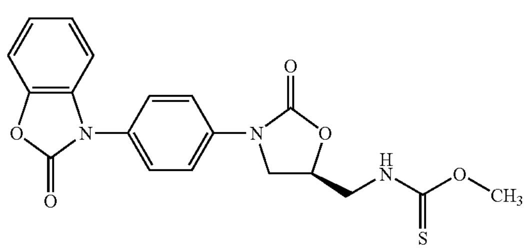 | ¹HNMR(CDCl₃, 200MHz): δ 7.72(d, J= 9.2Hz, 2H), 7.57(d, J= 9.2Hz, 2H), 7.31–7.01 (m, 4H), 6.77(bs, 1H), 4.97–4.96(m, 1H), 4.19–3.91(m, 7H).<br>Mp: 141° C. |
| 140 | 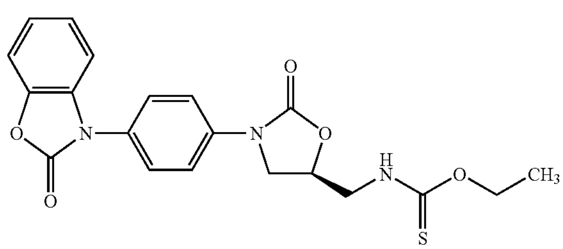 | ¹HNMR(CDCl₃, 200MHz): δ 7.73(d, J= 8.8Hz, 2H), 7.56(d, J= 8.8Hz, 2H), 7.31–7.01 (m, 4H), 6.70(bs, 1H), 4.97(m, 1H), 4.55–4.44 (q, J=6.8Hz, 2H), 4.19–3.92(m, 4H), 1.32(t, J= 7.0Hz, 3H).<br>Mp: 147° C. |

-continued

| Example No. | Structure | Analytical Data |
|---|---|---|
| 141 | 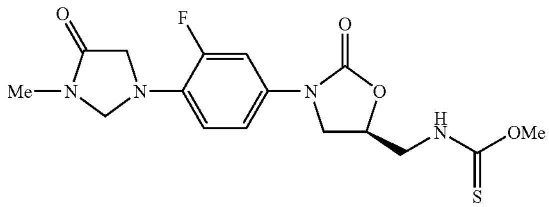 | ¹HNMR(CDCl₃, 200MHz): δ 2.8(s, 3H), 4.8(t, 1H), 3.6(m, 8H), 6.8(t, 1H), 7.2(d, 1H), 7.5(dd, 1H). Mp: 218° C. |
| 142 | 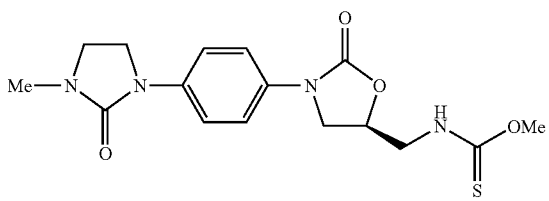 | ¹HNMR(CDCl₃, 200MHz): δ 1.5(s, 3H), 2.9(s, 3H), 3.6(t, 2H), 4.9(m, 1H), 6.8(m, 1H), 7.8(d, 2H). Mp: 209° C. |
| 143 | 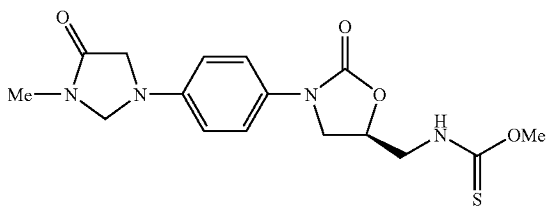 | ¹HNMR(DMSO-d⁶, 200MHz): 9.5(br, 1H), 7.4(d, J=8.8Hz, 2H), 6.6 (d, J=8.8Hz, 2H), 4.90–4.80(m, 1H), 4.7(s, 2H), 4.2–3.4(m, 9H), s, 3H). Mp: 205° C. |
| 144 | 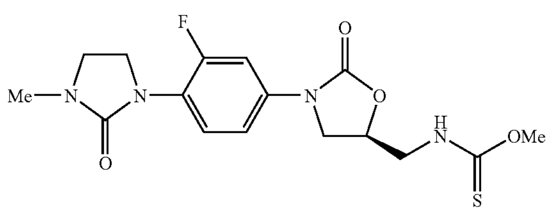 | ¹HNMR(CDCl₃, 200MHz): δ 7.5(m, 2H), 7.1(m, 1H), 6.9(s, 1H), 4.9(m, 1H), 3.8(m, 9H), 3.4(t, J=8.8Hz, 2H), 2.9(s, 3H). Mp: 146° C. |
| 145 | 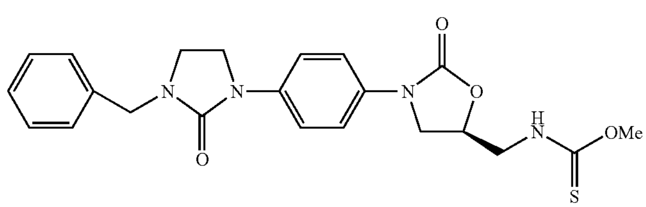 | ¹HNMR(CDCl₃, 200MHz): δ 7.6–7.2(m, 9H), 6.7(bt, 1H), 5.0–4.8 (m, 1H), 4.5(s, 2H), 4.2–3.6(m, 9H), 3.4(t, J=8.8 Hz, 2H). Mp: 170° C. |
| 146 | 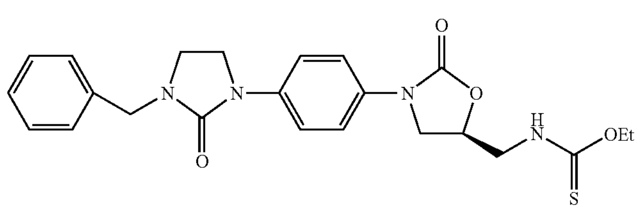 | ¹HNMR(CDCl₃, 200MHz): δ 7.6–7.2(m, 9H), 6.7(bt, 1H), 5.0–4.8 (m, 1H), 4.6–4.4(m, 4H), 4.2–3.6(m, 6H), 3.7(t, J=8.3Hz, 2H), 1.3(t, J=6.8Hz, 3H). Mp: 160° C. |
| 147 | 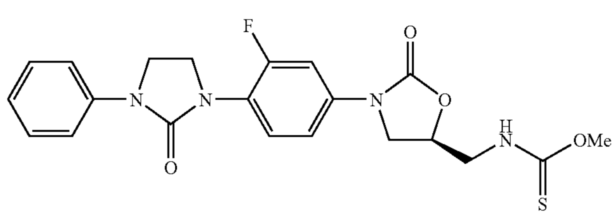 | ¹HNMR(CDCl₃, 200MHz): δ 9.5(m, 1H), 7.6(m, 4H), 7.4(m, 3H), 7.0(m, 1H), 4.9(m, 1H), 4.2(m, 1H), 3.8–4.0(m, 7H), 3.3(s, 3H) Mp: 174° C. |

-continued

| Example No. | Structure | Analytical Data |
|---|---|---|
| 148 | 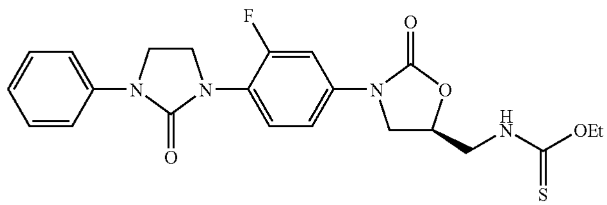 | ¹HNMR(CDCl₃, 200MHz): δ 9.5(m, 1H), 7.6(m, 4H), 7.3(m, 3H), 7.1(t, 1H), 4.8(m, 1H), 4.4(m, 2H), 4.2(m, 1H), 3.7–4.1(m, 5H), 3.5(m, 2H), 1.2(t, 3H). Mp: 195° C. |
| 149 | 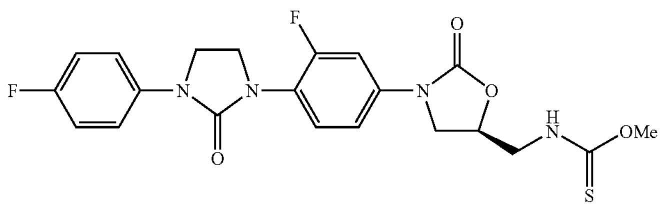 | ¹HNMR(CDCl₃, 200MHz): δ 7.5(m, 4H), 7.0(m, 4H), 4.9(m, 1H), 4.0(11H). Mp: 208° C. |
| 150 | 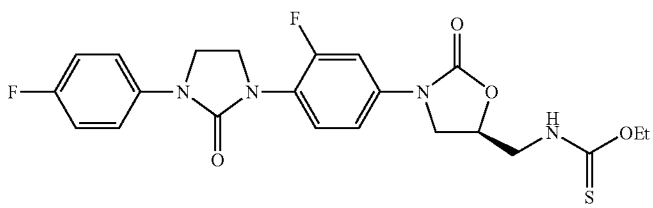 | ¹HNMR(CDCl₃, 200MHz): δ 7.6(m, 4H), 7.0–7.2(m, 3H), 4.9(m, 2H), 4.5(m, 2H), 4.0(m, 8H), 1.3(t, 3H). Mp: 215° C. |
| 151 | 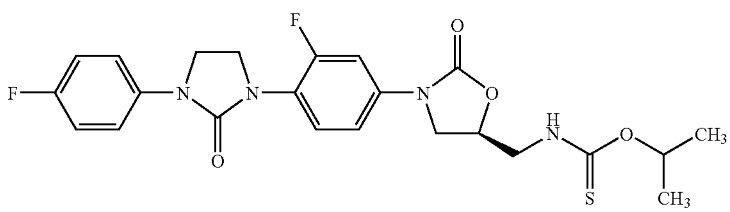 | ¹HNMR(CDCl₃, 200MHz): δ 7.5(m, 4H), 7.0(m, 3H), 5.5(m, 1H), 4.9(m, 1H), 4.0(m, 8H), 1.3(t, 6H). Mp: 220° C. |
| 152 | 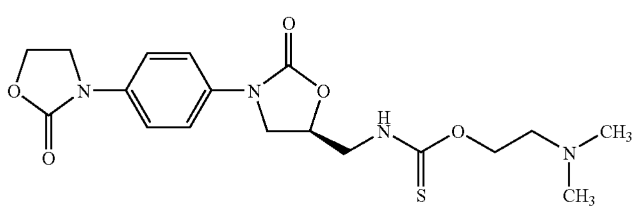 | ¹HNMR(DMSO-d⁶, 200 MHz): δ 9.60–9.40(m, 1H), 7.57(s, 4H), 5.00–4.75(m, 1H), 4.44–3.40 (m, 12H), 2.16(s, 6H). Mp: 161° C. |
| 153 | 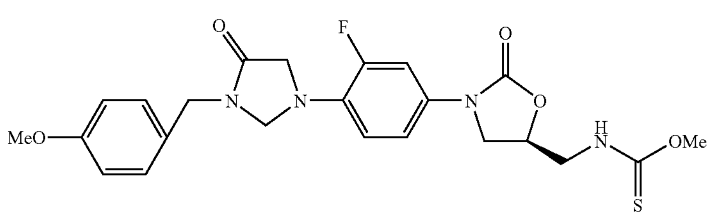 | ¹HNMR(CDCl₃, 200 MHz): δ 7.40(dd, J= 17.6, 2.4Hz, 1H), 7.24 (d, J=9.7Hz, 2H), 7.04 (d, J=8.8Hz, 1H), 6.89 (d, J=8.8Hz, 2H), 6.78 (bt, 1H), 6.58–6.49(m, 1H), 5.00–4.80(m, 1H), 4.75(s, 2H), 4.54(s, 2H), 4.20–3.60(m, 9H), 3.81 (s, 3H) Mp: 158° C. |
| 154 | 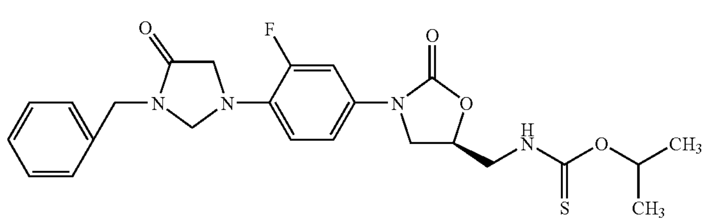 | ¹HNMR(DMSO-d⁶, 200 MHz): δ 9.50–9.35(m, 1H), 7.60–6.60(m, 8H), 5.50–5.30(m, 1H), 4.95–4.70(m, 1H), 4.74(s, 2H), 4.55(s, 2H), 4.20–3.25(m, 6H), 1.40–1.10 (bd, 6H). Mp: 192° C. |

| Example No. | Structure | Analytical Data |
|---|---|---|
| 155 | 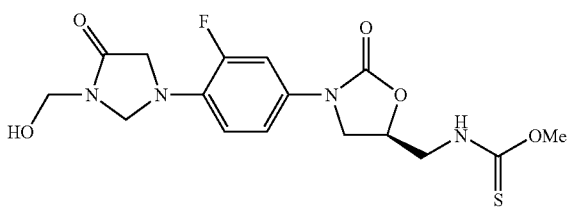 | $^1$HNMR(DMSO-d$^6$, 200 MHz): δ 9.55–9.35(m, 1H), 7.45(d, J=18.1Hz, 1H), 7.15(d, J=8.8Hz, 1H), 6.90–6.80(m, 1H), 6.09(t, J=6.8Hz, 1H), 4.87(s, 2H), 4.90–4.75 (m, 1H), 4.71(d, J=6.8 Hz, 2H), 4.20–3.10(m, 9H). Mp: 184° C. |
| 156 | 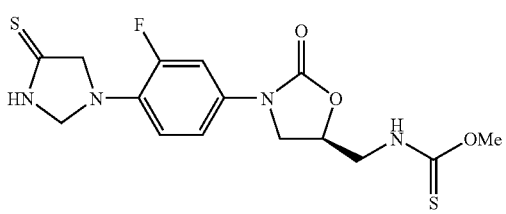 | $^1$HNMR(200MHz, DMSO-d$_6$) δ: 11.10(bs, 1H), 9.55(m, 1H), 7.47 (d, J=15.6Hz, 1H), 7.17 (d, J=8.3Hz, 1H), 6.87 (t, J=9.5Hz, 1H), 5.00 (bs, 2H), 4.85(m, 1H), 4.30(bs, 2H), 4.15–3.40 (m, 7H). |
| 157 | 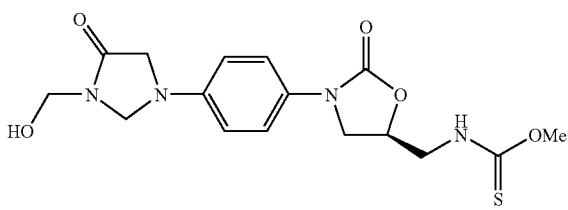 | $^1$HNMR(200MHz, DMSO-d$_6$) δ: 9.55(bs, 1H), 7.41(d, J=8.3Hz, 2H), 6.64(d, J=8.8Hz, 2H), 6.13(t, 1H), 4.79–4.75(m, 5H), 3.93–3.76 (m, 9H). MP: 202–208° C. |
| 158 | 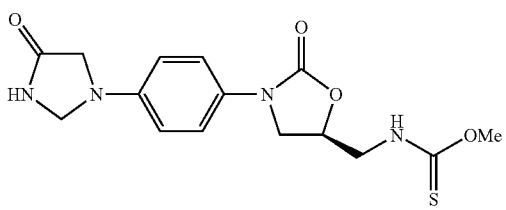 | $^1$HNMR(200MHz, DMSO-d$_6$) δ: 9.50(bs, 1H), 8.64(s, 1H), 7.34 (d, J=8.6Hz, 2H), 6.56 (d, J=8.6Hz, 2H), 4.60 (s, 3H), 3.88–3.67(m, 9H). MP: 205–210° C. |
| 159 | 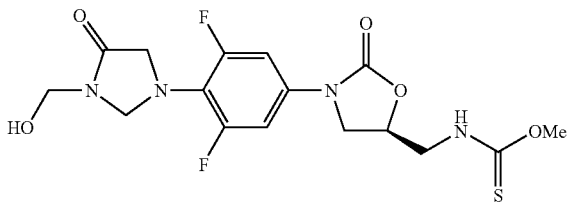 | $^1$HNMR(200MHz, DMSO-d$_6$) δ: 9.55(bs, 1H), 7.32(d, J=12.1 Hz, 2H), 6.12(t, J=7.3Hz, 1H), 4.87(s, 3H), 4.72 (d, J=7.3Hz, 2H), 4.13–3.76(m, 9H). |
| 160 | 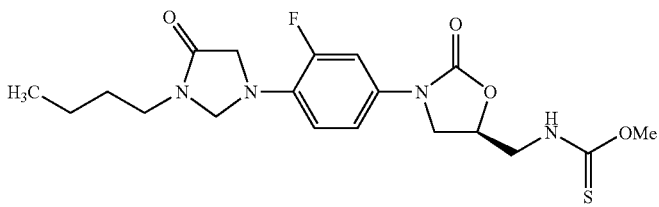 | $^1$HNMR(200MHz, DMSO-d$_6$) δ: 9.55(bs, 1H), 7.52–7.43(m, 1H), 7.17(d, J=9.0Hz, 1H), 6.82(t, J=9.8Hz, 1H), 4.90–4.81(m, 3H), 4.15–3.73(m, 6H), 3.34–3.28 (m, 6H), 1.59–1.09(m, 4H), 0.90(t, J=7.2Hz, 3H). MP: 122° C. |

-continued

| Example No. | Structure | Analytical Data |
|---|---|---|
| 161 | 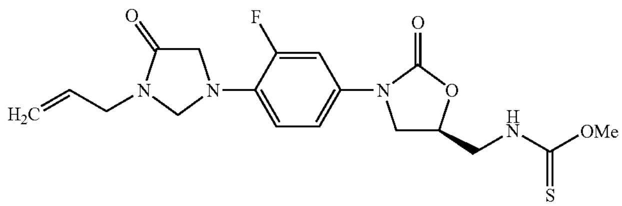 | ¹HNMR(200MHz, DMSO-d₆) δ: 7.45(dd, $J_{2,3}$=12.9Hz & $J_{1,2}$=2.4 Hz, 1H), 7.07(d, J=8.9 Hz, 1H), 6.79–6.70(m, 1H), 6.59(t, J=9.1Hz, 1H), 5.82–5.74(m, 1H), 5.35–5.26(m, 2H), 4.86 (s, 3H), 4.20–4.01(m, 11H). MP: 86° C. |
| 162 | 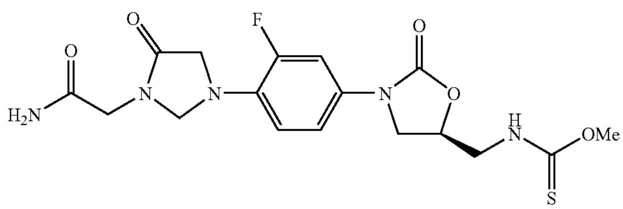 | ¹HNMR(200MHz, DMSO-d₆) δ: 9.55(bs, 1H), 7.55(d, J=13.4Hz, 2H), 7.44(s, 1H), 6.83(t, 1H), 4.87(s, 3H), 4.11–3.76(m, 11H). |
| 163 | 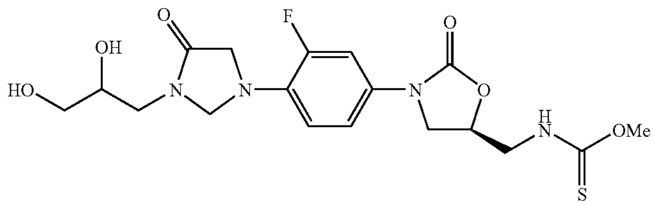 | ¹HNMR(200MHz, DMSO-d₆) δ: 9.35(bs, 1H), 7.51(d, 1H), 7.08 (d, J=8.3Hz, 1H), 6.60 (t, 1H), 5.10–4.65(m, 3H), 4.20–3.45(m, 14H). |
| 164 | 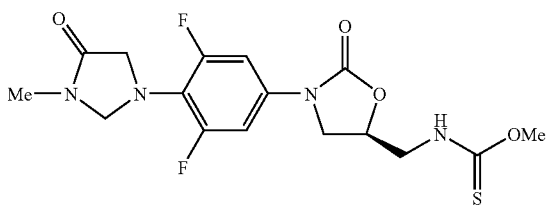 | ¹HNMR(200MHz, DMSO-d₆) δ: 9.53(bs, 1H), 7.29(d, J=12.4Hz, 2H), 4.88–4.76(m, 3H), 4.15–4.06(m, 1H), 3.91–3.74(m, 8H), 2.81(s, 3H). |
| 165 | 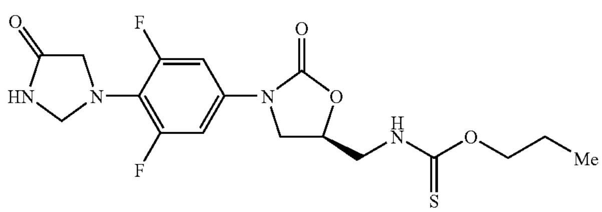 | ¹HNMR(400MHz, DMSO-d₆) δ: 9.47(bs, 1H), 8.53(s, 1H), 4.94–4.71(m, 3H), 4.35–4.22 (m, 2H), 4.14–4.08(m, 1H), 3.81–3.63(m, 4H), 3.52–3.45(m, 1H), 1.71–1.60(m, 2H), 0.93–0.84 (m, 3H). MP: 186–188° C. |
| 166 | 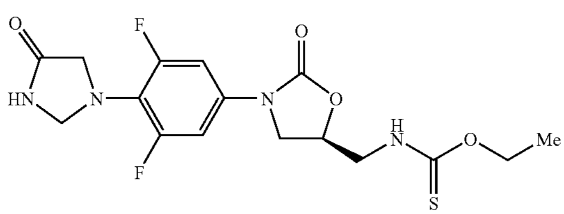 | ¹HNMR(400MHz, DMSO-d₆) δ: 9.42(t, J= 5.4Hz, 1H), 8.51(s, 1H), 4.88(m, 1H), 4.69(s, 2H), 4.44–4.35(m, 2H), 4.19–4.02(m, 2H), 3.79–3.68(m, 4H), 3.49–3.46 (m, 1H), 3.37–3.33(m, 1H), 1.32–1.21(m, 3H). MP: 178–180° C. |
| 167 | 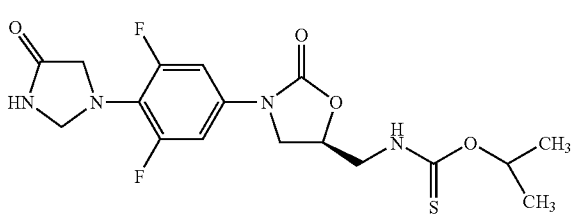 | ¹HNMR(400MHz, DMSO-d₆) δ: 9.34(bs, 1H), 8.51(s, 1H), 7.29 (dd, $J_{2,3}$=10.3Hz & $J_{1,2}$= 3.9Hz, 2H), 5.43–5.37 (m, 1H), 4.91–4.85(m, 1H), 4.76–4.69(m, 2H), 4.19–4.03(m, 2H), 3.93–3.62(m, 4H), 1.25–1.17 (m, 6H). MP: 176–178° C. |

| Example No. | Structure | Analytical Data |
|---|---|---|
| 168 | 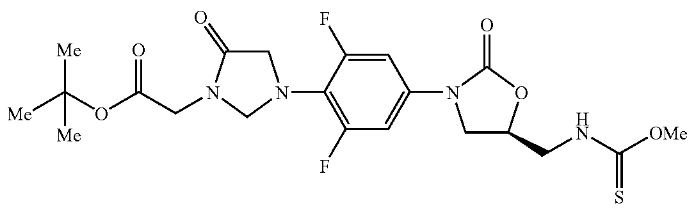 | ¹HNMR(200MHz, DMSO-d₆) δ: 9.53(bs, 1H), 7.32(d, J=11.8Hz, 2H), 4.90–4.80(m, 3H), 4.13–3.76(m, 8H), 3.33 (s, 3H), 1.43(s, 9H). |
| 169 | 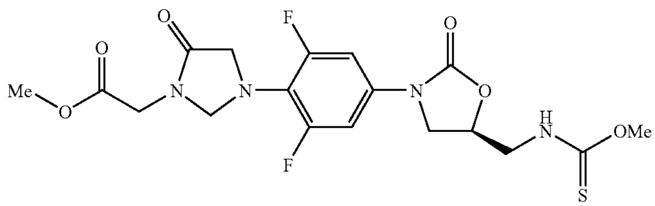 | ¹HNMR(400MHz, DMSO-d₆) δ: 9.50(bs, 1H), 7.29(d, J=12.2Hz, 2H), 4.84(m, 3H), 4.17–3.30(m, 14 H). |
| 170 | 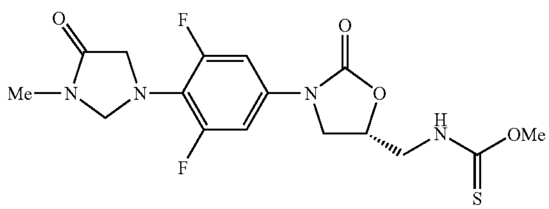 | ¹HNMR(200MHz, DMSO-d₆) δ: 9.53(bs, 1H), 7.29(d, J=12.4Hz, 2H), 4.88–4.76(m, 3H), 4.15–4.06(m, 1H), 3.91–3.74(m, 8H), 2.81(s, 3H). |
| 171 | 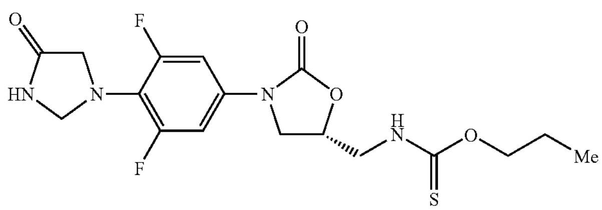 | ¹HNMR(400MHz, DMSO-d₆) δ: 9.47(bs, 1H), 8.53(s, 1H), 4.94–4.71(m, 3H), 4.35–4.22 (m, 2H), 4.14–4.08(m, 1H), 3.81–3.63(m, 4H), 3.52–3.45(m, 1H), 1.71–1.60(m, 2H), 0.93–0.84 (m, 3H). |
| 172 | 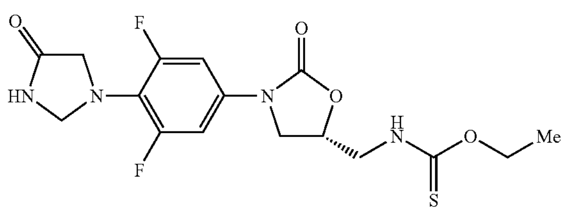 | ¹HNMR(400MHz, DMSO-d₆) δ: 9.42(t, J= 5.4 Hz, 1H), 8.51(s, 1H), 4.88(m, 1H), 4.69(s, 2H), 4.44–4.35(m, 2H), 4.19–4.02(m, 2H), 3.79–3.68(m, 4H), 3.49–3.46 (m, 1H), 3.37–3.33(m, 1H), 1.32–1.21(m, 3H). |
| 173 | 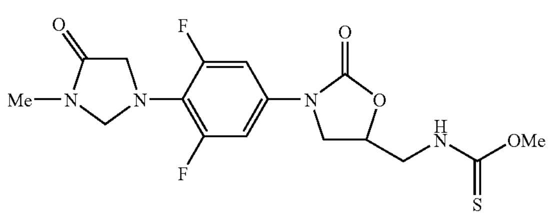 | ¹HNMR(200MHz, DMSO-d₆) δ: 9.53(bs, 1H), 7.29(d, J=12.4 Hz, 2H), 4.88–4.76(m, 3H), 4.15–4.06(m, 1H), 3.91–3.74(m, 8H), 2.81(s, 3H). |
| 174 | 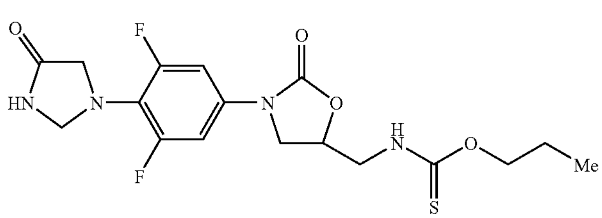 | ¹HNMR(400MHz, DMSO-d₆) δ: 9.47(bs, 1H), 8.53(s, 1H), 4.94–4.71(m, 3H), 4.35–4.22 (m, 2H), 4.14–4.08(m, 1H), 3.81–3.63(m, 4H), 3.52–3.45(m, 1H), 1.71–1.60(m, 2H), 0.93–0.84 (m, 3H). |

| Example No. | Structure | Analytical Data |
|---|---|---|
| 175 | 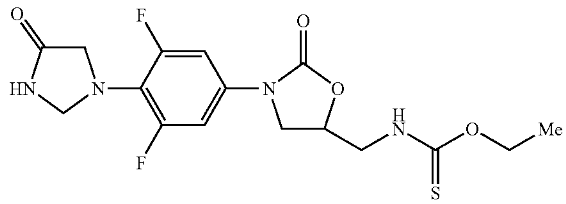 | $^1$HNMR(400MHz, DMSO-d$_6$) δ: 9.42(t, J= 5.4Hz, 1H), 8.51(s, 1H), 4.88(m, 1H), 4.69(s, 2H), 4.44–4.35(m, 2H), 4.19–4.02(m, 2H), 3.79–3.68(m, 4H), 3.49–3.46 (m, 1H), 3.37–3.33(m, 1H), 1.32–1.21(m, 3H). |

K. General procedure for the conversion of

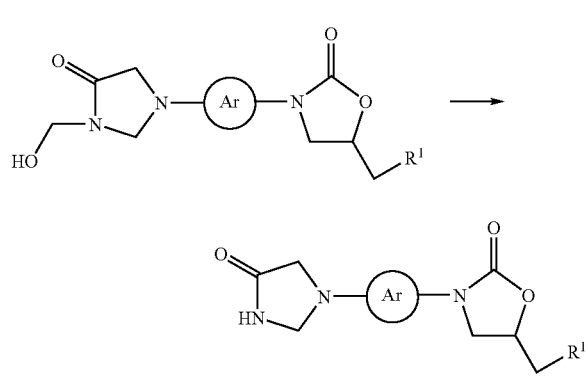

where R$^1$ is as defined for formula (I), where 'Ar' represents substituted or unsubstituted phenyl ring, the substituents are as defined on the phenyl ring of the formula (I).

Sodium hydride (360 mg, 7.5 mmol) was added to a solution of starting material (300 mg, 0.75 mmol) in dry THF (30 mL) and the resultant suspension was stirred at room temperature overnight. The reaction mixture was diluted with ethyl acetate (150 mL) and washed with water, brine and dried. The residue obtained upon evaporation of solvent was passed through a column of silica gel to afford the product as a colorless solid (150 mg, 54% yield).

Example 176 has been prepared by a person skilled in the art according to the methodology as described in the above Procedure K.

L. General procedure for the conversion of

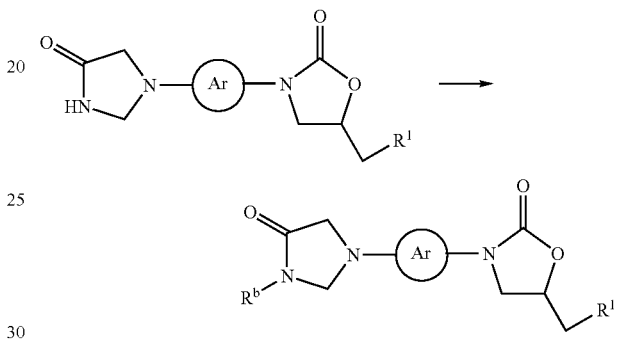

where R$^1$ is as defined for formula (I), where 'Ar' represents substituted or unsubstituted phenyl ring, the substituents are as defined on the phenyl ring of the formula (I); and R$^b$ represents (C$_1$–C$_{10}$)alkyl or aralkyl.

To a solution of starting material (1 eq) in dry DMF was added NaH (1.2 eq) at 0° C. under argon followed by appropriate alkyl halide or aralkyl halide (1.2 eq). The reaction mixture was stirred for 2–6 h while monitoring by TLC. After the consumption of starting material, the reaction mixture was diluted with ethyl acetate and washed with water, brine and dried. The residue obtained upon evaporation of solvent was passed through a column of silica gel to afford the product.

Examples 177–180 have been prepared by a person skilled in the art according to the methodology as described in the above procedure L.

| Example No. | Structure | Analytical Data |
|---|---|---|
| 176 | 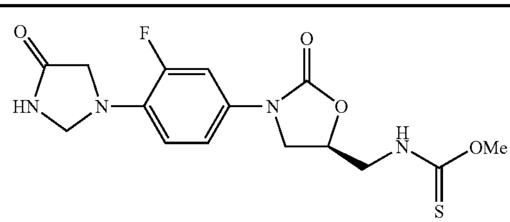 | $^1$HNMR(DMSO-d$^6$, 200MHz): δ 9.60–9.40(m, 1H), 8.62(s, 1H), 7.45(d, J=16.2Hz, 1H), 7.16(d, J=8.6Hz, 1H), 6.90–6.80(m, 1H), 4.90–4.75(m, 1H), 4.73(s, 2H), 4.20–3.40(m, 9H). Mp: 223° C. |

| Example No. | Structure | Analytical Data |
|---|---|---|
| 177 | 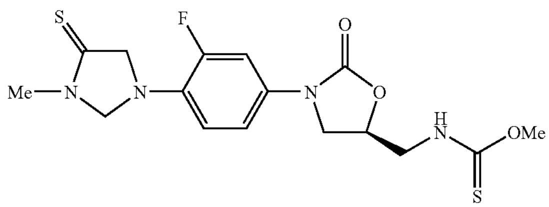 | ¹HNMR(DMSO-d⁶, 200MHz): δ 9.60–9.40(m, 1H), 7.49(dd, J=15.6, 2.4 Hz, 1H), 7.18(d, J=9.1 Hz, 1H), 6.95–6.80(m, 1H), 5.17 (s, 2H), 4.95–4.70(m, 1H), 4.42(s, 2H), 4.20–3.40(m, 7H). Mp: 195° C. |
| 178 | 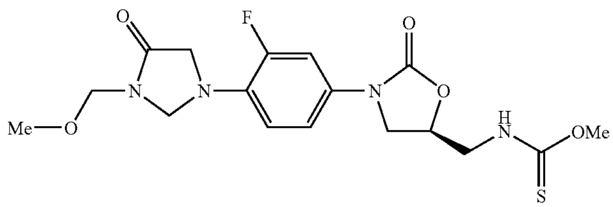 | ¹HNMR(CDCl₃, 200MHz): δ 7.46(dd, J=15.1, 2.4Hz, 1H), 7.10(d, J=8.8Hz, 1H), 6.77(bt, 1H), 6.65–6.56(m, 1H), 4.97(s, 2H), 4.97–4.80 (m, 1H), 4.84(s, 2H), 4.20–3.55(m, 9H), 3.37 (s, 3H). Mp: 160° C. |
| 179 | 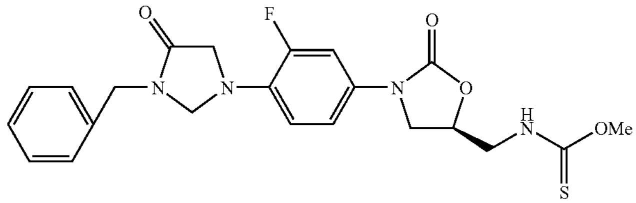 | ¹HNMR(CDCl₃+DMSO-d⁶, 200 MHz): δ 9.95–9.25(m, 1H), 7.55–7.25(m, 6H), 7.45(d, J=15.4 Hz, 1H), 6.63–6.54(m, 1H), 5.00–4.80 (m, 1H), 4.77(s, 2H), 4.60(s, 2H), 4.20–3.75 (m, 9H). Mp: 176° C. |
| 180 | 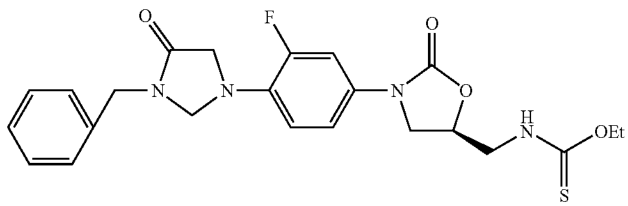 | ¹HNMR(CDCl₃, 200MHz): δ 7.50–7.20(m, 6H), 7.04(d, J=8.6 Hz, 1H), 6.78(bt, 1H), 6.58–6.49 (m, 1H), 5.00–4.35(m, 7H), 4.20–3.60(m, 6H), 1.31(t, J=7.0Hz, 3H). Mp: 184° C. |

M. General procedure for the conversion of

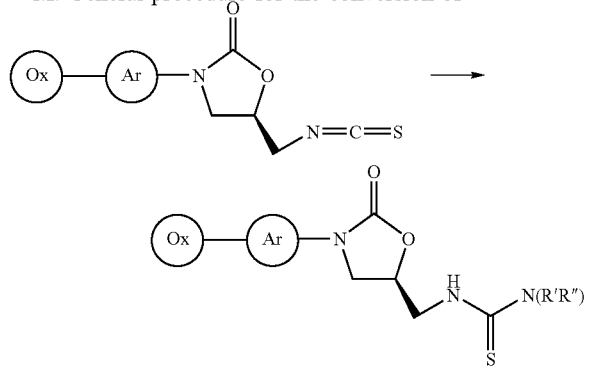

where 'Ox' represents a five membered heterocyclic group, containing at least one nitrogen atom and one more heteroatom selected from oxygen, nitrogen or sulfur. In which, the said atleast one nitrogen atom connecting said heterocyclic moiety 'Ox' to the 'Ar' moiety. The heterocyclic moiety is substituted by an ═O or ═S. The heterocycle may also be substituted by one or two additional substituents which are as defined on the heterocyclic moiety of formula (I). The heterocycle may also be fused with substituted or unsubstituted phenyl group. 'Ar' represents substituted or unsubstituted phenyl ring, the substituents are as defined on the phenyl ring of the formula (I); R' represents hydrogen, alkyl, alkenyl, substituted or unsubstituted aralkyl, heteroaralkyl, hydroxyalkyl and R" represents hydrogen or alkyl; or the two R' and R" groups together form a 5 or 6 membered cyclic structures containing one or two hetero atoms.

Reference Example of the Above Preparation

Example 181

(S)-1-{3-[3,5-Difluoro-4-(4-oxo-imidazolidin-1-yl)-phenyl]-2-oxo-oxazolidin-5-ylmethyl}-3-pyridin-2-yl-thiourea

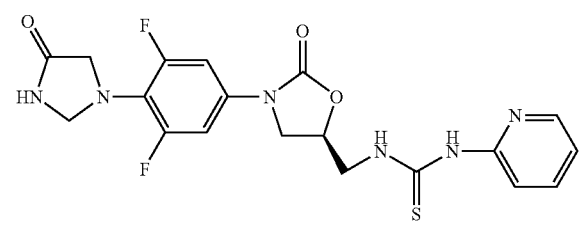

2-Amino pyridine (32 mg. 0.34 mmol) was added to a solution of isothiocyanate (100 mg, 0.3 mmol), obtained in step (i) of the example 116, in THF at 20 to 35° C. The resultant mixture was refluxed overnight. The residue obtained upon evaporation of the solvent was passed through a column of silica gel to afford the title compound (Yield: 50 mg, 40%).

$^1$H NMR (400 MHz, DMSO-$d_6$) δ: 11.99 (t, J=5.5 Hz, 1H), 10.71 (s, 1H), 8.51 (s, 1H), 8.11 (dd, $J_{2,3}$=5.1 Hz & $J_{1,2}$=1.6 Hz, 1H), 7.76 (m, 1H), 7.13 (d, J=8.2 Hz, 2H), 7.03 (m, 1H), 5.05–5.02 (m, 1H), 4.68 (s, 2H), 4.18–4.01 (m, 3H), 3.85–3.78 (m, 3H); Mp: 194–196° C.

Examples 182–195 have been prepared by a person skilled in the art according to the methodology as described in the above Example 181.

| Example No. | Structure | Analytical Data |
| --- | --- | --- |
| 182 | 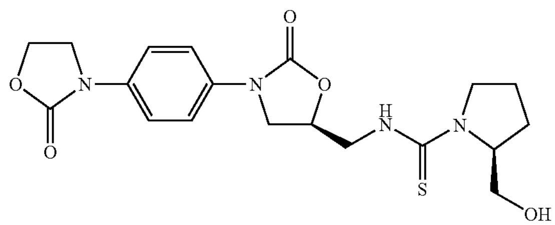 | $^1$HNMR(CDCl$_3$, 200MHz): δ 7.51 (s, 4H), 4.98–4.95(m, 1H), 4.49(t, J=7.8HZ, 2H), 4.17–3.88(m, 8H), 3.71–3.69(m, 3H), 1.93–1.78(m, 4H). Mp: 159° C. |
| 183 | 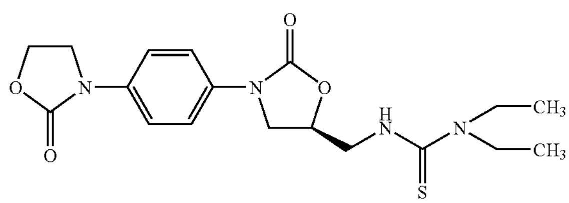 | $^1$HNMR(DMSO-$d^6$, 200MHz): δ 7.63(s, 1H), 7.57(s, 4H), 4.94–4.91 (m, 1H), 4.44(t, J=7.4Hz, 2H), 4.17–3.75(m, 6H), 3.66–3.56(q, J=6.8Hz, 4H), 1.07(t, J=6.8Hz, 6H). Mp: 103° C. |
| 184 | 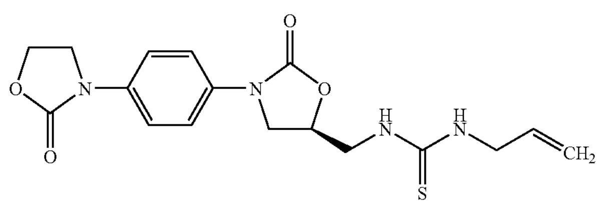 | $^1$HNMR(DMSO-$d^6$, 200MHz): δ 7.79(bs, 1H), 7.57(s, 4H), 5.80–5.75(m, 1H), 5.15–5.01(m, 2H), 4.86(m, 1H), 4.44(t, J=7.4Hz, 2H), 4.17–4.01 (m, 5H), 3.85(m, 2H). Mp: 171° C. |
| 185 | 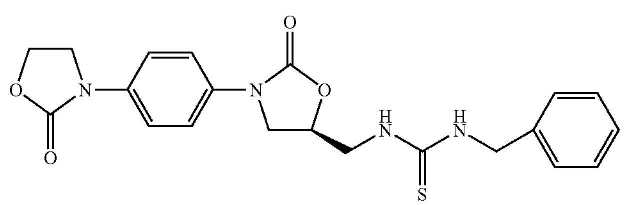 | $^1$HNMR(DMSO-$d^6$, 200MHz): δ 8.05(bs, 1H), 7.86(bs, 1H), 7.57(s, 4H), 7.25(s, 5H), 4.88–4.84(m, 1H), 4.67(s, 2H), 4.44(t, J=7.8Hz, 2H), 4.16–4.01(m, 3H), 3.89–3.86(m, 3H). Mp: 181° C. |
| 186 | 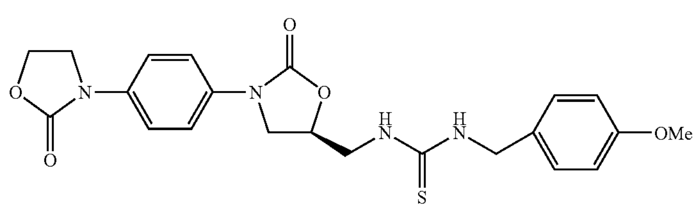 | $^1$HNMR(DMSO-$d^6$, 200MHz): δ 8.00(bs, 1H), 7.80(bs, 1H), 7.57(s, 4H), 7.19–7.15(d, J=8.4Hz, 2H), 6.84–6.80(d, J=8.2Hz, 2H), 4.86 (bs, 1H), 4.57(bs, 2H), 4.44(t, J=7.4Hz, 2H), 4.08–4.01(m, 3H), 3.88–3.85(m, 3H), 3.70(s, 3H). Mp: 169° C. |
| 187 | 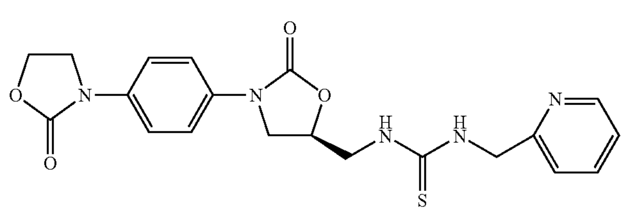 | $^1$HNMR(DMSO-$d^6$, 200MHz): δ 8.50–8.48(d, J=3.8Hz, 1H), 8.16 (m, 2H), 7.69(t, J=7.8Hz, 1H), 7.57 (s, 4H), 7.26–7.22(d, J=7.8Hz, 2H), 4.88(m, 1H), 4.75(bs, 2H), 4.44(t, J=7.2Hz, 2H), 4.18–4.01(m, 3H), 3.89–3.82(m, 3H). Mp: 165° C. |

-continued

| Example No. | Structure | Analytical Data |
|---|---|---|
| 188 | 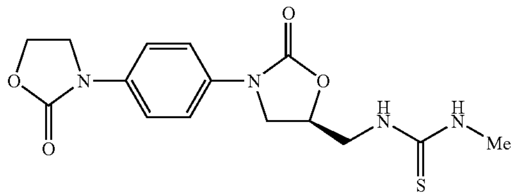 | ¹HNMR(DMSO-d⁶, 200MHz): δ 7.77(bs, 1H), 7.57(s, 5H), 4.86(m, 1H), 4.44(t, J=7.8Hz, 2H), 4.17–4.01(m, 3H), 3.81–3.33(m, 3H), 2.83(bs, 3H). Mp: 175° C. |
| 189 | 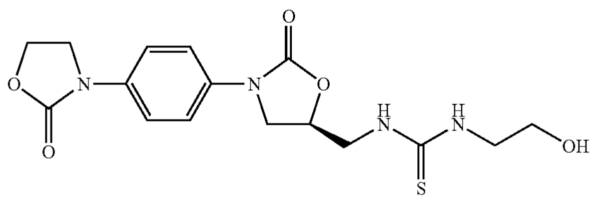 | ¹HNMR(DMSO-d⁶, 200MHz): δ 7.86(hump, 1H), 7.66(hump, 1H), 7.57(s, 4H), 4.78–4.68(m, 2H), 4.43 (t, J=7.2Hz, 2H), 4.12–4.01(m, 3H), 3.83(bs, 3H), 3.46–3.33(m, 4H). Mp: 161° C. |
| 190 | 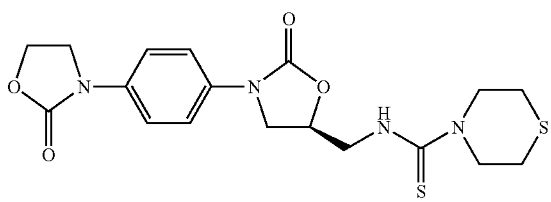 | ¹HNMR(DMSO-d⁶, 200MHz): δ 8.05(hump, 1H), 7.57(s, 4H), 4.95 (m, 1H), 4.43(t, J=7.2Hz, 2H), 4.08–3.89(m, 8H), 2.57(s, 4H), 2.49 (s, 4H). Mp: 159° C. |
| 191 | 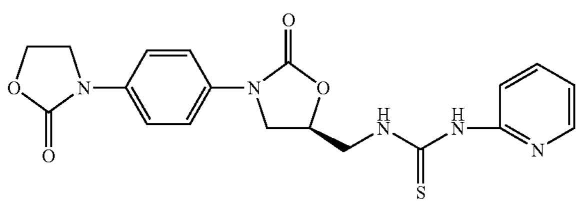 | ¹HNMR(DMSO-d⁶, 200MHz): δ 12.06(bs, 1H), 10.76(s, 1H), 8.14–8.11(d, J=5.0Hz, 1H), 7.77(t, J=8.2 Hz, 1H), 7.52(s, 4H), 7.17–7.13(d, J=3.2Hz, 1H), 7.04(t, J=5.8Hz, 1H), 5.05–5.03(m, 1H), 4.43(t, J=7.4Hz, 2H), 4.22(t, J=9.2Hz, 1H), 4.07–3.84(m, 5H). Mp: 189° C. |
| 192 | 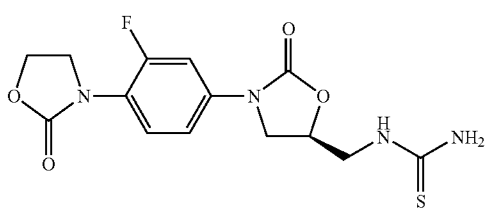 | ¹HNMR(CDCl₃+DMSO-d⁶, 200MHz): δ 8.07(bs, 1H), 7.62–7.40 (m, 2H), 7.16(d, J=7.8Hz, 1H), 6.65(bs, 1H), 4.85(bs, 1H), 4.48(t, J=8.0Hz, 2H), 4.04–3.96(m, 6H). Mp: 178° C. |
| 193 | 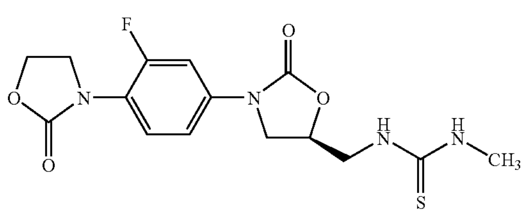 | ¹HNMR(CDCl₃+DMSO-d⁶, 200MHz): δ 7.68–7.19(m, 5H), 4.92 (hump, 1H), 4.53(t, J=7.8Hz, 2H), 4.08–3.98(m, 6H), 3.10(s, 3H). Mp: 144° C. |
| 194 | 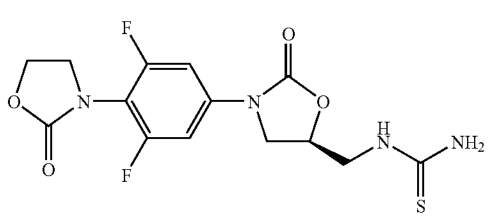 | ¹HNMR(CDCl+DMSO-d⁶, 200MHz): δ 8.10(bs, 1H), 7.35(d, J=8.4Hz, 2H), 6.58(bs, 1H), 4.91–4.89(m, 1H), 4.58(t, J=7.8Hz, 2H), 4.54–3.87(m, 6H). Mp: 92° C. |

| Example No. | Structure | Analytical Data |
|---|---|---|
| 195 | 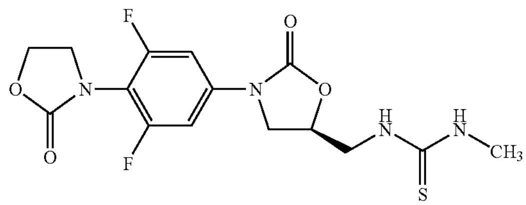 | ¹HNMR(CDCl₃, 200MHz): δ 7.26(s, 2H), 6.39(hump, 2H), 4.93(hump, 1H), 4.60(t, J=7.4Hz, 2H), 4.21–3.93(m, 6H), 2.99(d, J=4.8Hz, 3H). Mp: 113° C. |

Example 196

(S)-(3-{2,6-Difluoro-4-[5-(methoxythiocarbonylamino-methyl)-2-oxo-oxazolidin-3-yl]-phenyl}-5-oxo-imidazolidin-1-yl)-acetic acid

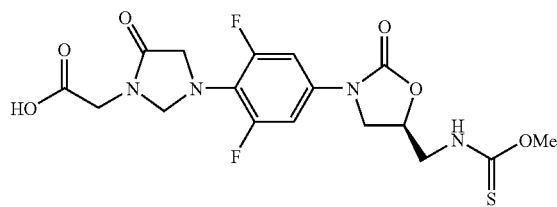

A solution of dioxane presaturated with dry HCl gas (2 mL) was added to a solution of compound (100 mg, 0.2 mmol), obtained in example 168, in dry dioxane (5 mL) at room temperature. The reaction mixture was stirred at room temperature for 15 h and then the mixture was concentrated at high vacuum pump. The residue obtained was washed a few times with toluene and the crystals were washed with ether to obtain the product.

¹H NMR (400 MHz, DMSO-d₆) δ: 12.93 (bs, 1H), 9.42 (bs, 1H), 7.31 (m, 2H), 4.88 (m, 3H), 4.15–3.20 (m, 11H).

Example 197

(S)-{3-[3,5-Difluoro-4-(3-methyl-4-oxo-imidazolidin-1-yl)-phenyl]-2-oxo-oxazolidin-5-ylmethyl}-methyl-thiocarbamic acid O-methyl ester

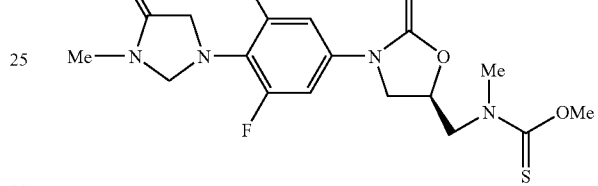

Sodium hydride (11 g, 60% in oil, 0.3 mmol) was added to a solution of the starting material (100 mg, 0.3 mmol), obtained in example 164, in dry DMF at room temperature. After stirring for a further 30 min, methyliodide (0.0.24 mmol, 0.4 mmol) was added and the reaction was continued for an additional 2 h. The reaction mixture was extracted with ethyl acetate after quenching with aq. NH₄Cl. The organic extracts were washed with water, brine and dried. The residue was passed through column to afford the title compound (40 g). Prolonged column afforded the 20 g of the title compound.

¹H NMR (200 MHz, DMSO-d₆) δ: 7.33 (d, J=12.4 Hz, 2H), 4.90–4.78 (m, 3H), 4.11 (t, J=8.9 Hz, 1H), 3.91 (s, 2H), 3.84–3.77 (m, 1H), 3.60 (s, 3H), 3.41–3.33 (m, 3H), 2.50 (s, 2H), 2.38 (s, 3H); Mp: 130° C.

Example 198 has been prepared by a person skilled in the art according to the methodology as described in the above Example 197.

| 198 | | ¹HNMR(400MHz, DMSO-d₆) δ: 8.56(s, 1H), 7.32(dd, J₂,₃=18.1Hz & J₁,₂=5.8 Hz, 2H), 4.91–4.86(m, 1H), 4.71(s, 2H), 4.11(t, J=8.8Hz, 1H), 3.81(s, 3H), 3.60(s, 3H), 3.42(d, J=3.9Hz, 1H), 3.41(d, J=3.9 Hz, 1H), 3.36(t, J=3.9 Hz, 1H), 2.39(s, 2H). MP: 154–156° C. |

Example 199

N1-((5S)-3-{3-Fluoro-4-[3-benzyl-4-oxo-1-imidazo-lidinyl]phenyl}-2-oxo-1,3-oxazolan-5-ylmethyl) ethylthiocarbamate hydrochloride

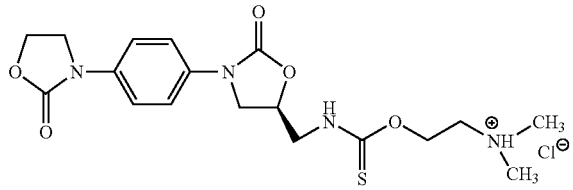

N1-((5S)-3-{3-fluoro-4-[3-benzyl-4-oxo-1-imidazolidi-nyl]phenyl}-2-oxo-1,3-oxazolan-5-ylmethyl)ethylthiocarbamate, obtained in example 152, was taken in methanol (100 mg) and was bubbled with HCl gas for 30 min. Then methanol was evaporated from the resultant mixture and washed with ether twice to obtain the title compound (Yield: 100%). Mp: 100° C. (hygroscopic).

$^1$H NMR (DMSO-d$^6$, 200 MHz): δ 10.60 (bs, 1H), 9.85–9.65 (m, 1H), 7.58 (s, 4H), 5.00–4.65 (m, 3H), 4.44 (t, J=7.6 Hz, 2H), 4.25–3.40 (m, 8H), 2.81 (s, 3H), 2.79 (s, 3H).

In vitro Data:

Minimum Inhibiton Concentrations (MICs) were determined by broth microdilution technique as per the guidelines prescribed in the fifth edition of Approved Standards, NCCLS document M7-A5 Vol 20-No 2, 2000 Villinova, Pa.

MIC is read as the lowest concentration of the compound that completely inhibits growth of the organism in the microdilution wells as detected by the unaided eye.

| Organism | Culture No. | DRCC No. |
|---|---|---|
| *Staphylococcus aureus* | ATCC 33591 | 019 |
| *Staphylococcus aureus* | ATCC 49951 | 213 |
| *Staphylococcus aureus* | ATCC 29213 | 035 |
| *Enterococcus faecalis* | ATCC 29212 | 034 |
| *Enterococcus faecalis* | NCTC 12201 | 153 |
| *Enterococcus faecium* | NCTC 12202 | 154 |
| *Escherichia coli* | ATCC 25922 | 018 |
| *Haemophilus influenzae* | ATCC 49247 | 432 |
| *Haemophilus influenzae* | ATCC 49766 | 433 |
| *Haemophilus influenzae* | ATCC 9006 | 529 |
| *Moraxella catarrhalis* | ATCC 25238 | 300 |
| *Streptococcus pneumoniae* | ATCC 6303 | 236 |
| *Streptococcus pneumoniae* | ATCC 49619 | 237 |
| *Streptococcus pneumoniae* | ATCC 700673 | 238 |
| *S. aureus* - MRSA and QRSA | — | 446 |
| *S. aureus* - MRSA and QRSA | — | 448 |
| *S. aureus* - MRSA and QRSA | — | 449 |
| *Corynebacterium jeikeium* | | |
| *Viridans Streptococci* | | |

ATCC: American Type Culture Collection, USA
NCTC: National Collections of Type Cultures, Colindale, UK
DRCC: Dr. Reddy's Culture Collection, Hyderabad, India.
The in vitro antibacterial activity data is shown in TABLE 1.

TABLE 1

In vitro Activity of Compounds against Gram positive and Gram negative bacteria

Antimicrobial Screening (MIC) µg/ml

| | *Staphylococcus aureus* | | | *Enterococcus* sp | | | | | *M. catarrhalis* | *H. influenzae* | | |
|---|---|---|---|---|---|---|---|---|---|---|---|---|
| Example | 019 | 213 | 035 | 034 | 153 | 154 | Mycobacterium | Salmorella | | | | |
| No. | MRSA | Smith S | S | S | R | R | MTCC 006 | TA 97 | 300 | 432 | 433 | 529 |
| 164 | 0.25 | 0.5 | 0.5 | 0.5 | 0.5 | 0.5 | 4 | 16 | 8 | 8 | 16 | 16 |
| 165 | 1 | 1 | 1 | 2 | 2 | 2 | 32 | 32 | >32 | >32 | >32 | >32 |
| 166 | 0.5 | 0.5 | 0.5 | 1 | 1 | 1 | 32 | 32 | 32 | >32 | >32 | >32 |
| 167 | 2 | 2 | 2 | 8 | 4 | 8 | 32 | 32 | >32 | >32 | >32 | >32 |
| 168 | 2 | 2 | 2 | 2 | 1 | 2 | 32 | 32 | — | — | — | — |
| 169 | 1 | 1 | 2 | 0.5 | 0.5 | 1 | 8 | 32 | — | — | — | — |

Initial stock solution of the test compound was prepared in DMSO. Subsequent two fold dilutions were carried out in sterile Mueller Hinton Broth (Difco) (MHB).

Frozen cultures stocks were inoculated into 50 ml sterile MHB in 250 ml Erlyn Meyer flasks.

Composition of MHB is as follows:

Beef Extract Powder—2.0 g/liter

Acid Digest of Casein—17.5 g/liter

Soluble Starch—1.5 g/liter

Final pH 7.3±0.1

Flasks were incubated for 4 to 5 h at 35° C. on a rotary shaker at 150 rpm. Inoculum was prepared by diluting the culture in sterile MHB to obtain a turbidity of 0.5 McFarland standard. This corresponds to 1–2×10$^8$ CFU/ml. The stock was further diluted in sterile broth to obtain 1–2×10$^6$ CFU/ml. 50 µl of the above diluted inoculum was added from 1–10 wells. The plates were incubated overnight at 37° C.

What is claimed is:

1. A compound that is an oxazolidinone derivative of the formula (I)

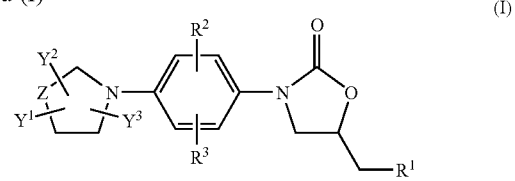

(I)

or a salt thereof, or a stereoisomer thereof, where

R$^1$ represents —NHR$^4$ wherein R$^4$ represents thio (C$_1$–C$_{10}$)acyl, —C(=S)-cyclo(C$_3$–C$_8$)alkoxy, —C(=S)—(C$_1$–C$_{10}$)alkoxy, —C(=S)—(C$_2$–C$_{10}$)alkenyloxy, —C(=S)-aryloxy, —C(=S)—S—(C$_1$–C$_{10}$) alkyl, —C(=S)—NH$_2$, —C(=S)—NH—(C$_1$–C$_{10}$) alkyl, —C(=S)—N—((C$_1$–C,o)alkyl)$_2$, —C(=S)—

NH—($C_2$–$C_{10}$)alkenyl, (C=S)—(C=O)—($C_1$–$C_{10}$) alkoxy, —(C=S)—(C=O)-aryloxy, —C(=S)—O—(C=O)—($C_1$–$C_{10}$)alkyl, C(=S)—C(=S)—($C_1$–$C_{10}$)alkyl, —C(=S)—C(=S)-aryl, —C(=S)-thiomorpholinyl or —C(=S)-pyrrolidinyl; $R^2$ and $R^3$, which may be the same or different, are each independently hydrogen, halogen, ($C_1$–$C_{10}$)alkyl, halogenated ($C_1$–$C_{10}$)alkyl, cyano, nitro, $SR^a$, $NR^a$ or $OR^a$, in which $R^a$ is hydrogen, ($C_1$–$C_{10}$)alkyl or halogenated ($C_1$–$C_{10}$)alkyl;

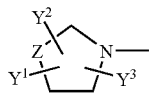

is a heterocyclic moiety in which

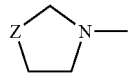

is a 5-membered heterocyclic skeleton, Z represents =CH, —$CH_2$ or $NR^b$, where $R^b$ is hydrogen or a moiety, which may be substituted or unsubstituted, straight chain or branched, selected from the group consisting of ($C_1$–$C_{10}$) alkyl, ($C_2$–$C_{10}$)alkenyl, ($C_3$–$C_8$)cycloalkyl, hydroxy ($C_1$–$C_{10}$)alkyl, ($C_1$–$C_{10}$)alkylhydroxy, ($C_1$–$C_{10}$)alkylamino, amino($C_1$–$C_{10}$)alkyl, ($C_1$–$C_{10}$)alkoxy, aryl, aralkyl, aryloxy, ($C_1$–$C_{10}$)alkylcarbonyl, arylcarbonyl, ($C_1$–$C_{10}$) alkoxycarbonyl and aryloxycarbonyl;

$Y^1$ represents =O or =S group and $Y^2$ and $Y^3$ independently represent hydrogen, halogen, cyano, nitro, formyl, hydroxy, amino, =O, =S group or substituted or unsubstituted groups selected from ($C_1$–$C_{10}$)alkyl, hydroxy($C_1$–$C_{10}$)alkyl, ($C_1$–$C_{10}$)alkylhydroxy, ($C_1$–$C_{10}$)alkoxy($C_1$–$C_{10}$)alkyl, ($C_1$–$C_{10}$)alkylcarbonyl, ($C_1$–$C_{10}$)alkoxycarbonyl, arylcarbonyl, carboxy ($C_1$–$C_{10}$)alkyl, ($C_1$–$C_{10}$)alkylsulfonyl, $C_1$–$C_{10}$)alkylcarbony($C_1$–$C_{10}$)alkyl, arylcarbonylamino($C_1$–$C_{10}$) alkyl, ($C_1$–$C_{10}$)alkylcarbonyloxy($C_1$–$C_{10}$)alkyl, amino ($C_1$–$C_{10}$)alkyl, mono($C_1$–$C_{10}$)alkylamino, di($C_1$–$C_{10}$) alkylamino, arylamino, ($C_1$–$C_{10}$)alkoxy, aryl, aryloxy, aralkyl, heteroaryl, heteroaralkyl, heterocyclyl or heterocycloalkyl; $Y^2$ and $Y^3$ when present on adjacent carbon atoms together may also form a substituted or unsubstituted 5 or 6 membered aromatic or non-aromatic cyclic structure, optionally containing one or two hetero atoms selected from oxygen, sulfur and nitrogen.

2. The compound of claim 1 having the structure

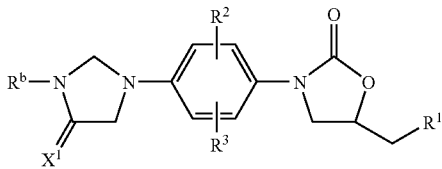

wherein $X^1$ is oxygen or sulfur.

3. The compound of claim 1 having the structure

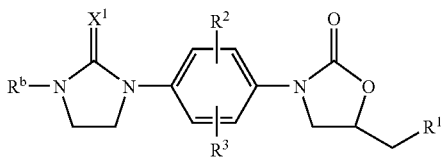

wherein $X^1$ is oxygen or sulfur.

4. The compound of claim 1 having the structure

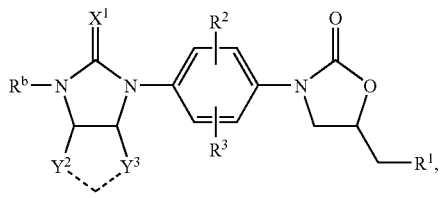

wherein $X^1$ is oxygen or sulfur, and

is a substituted or unsubstituted 5- or 6-membered aromatic or non-aromatic cyclic structure optionally having one or two hetero atoms, formed by $Y^2$ and $Y^3$.

5. The compound of claim 4, wherein said cyclic structure formed by $Y^2$ and $Y^3$ is benzene, pyridine, pyrrolidine, furan thiophene, morpholine, piperazine or pyrrole.

6. The compound of formula (I) as defined according to claim 1 which is selected from:

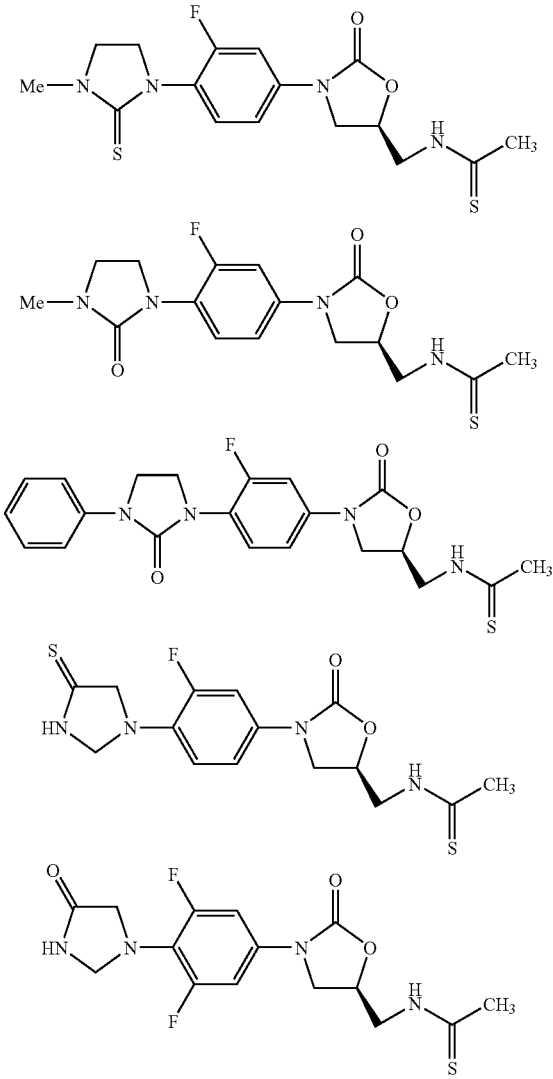

-continued
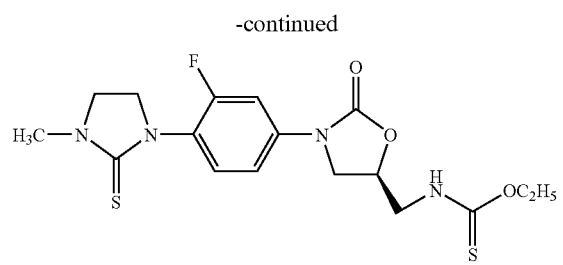
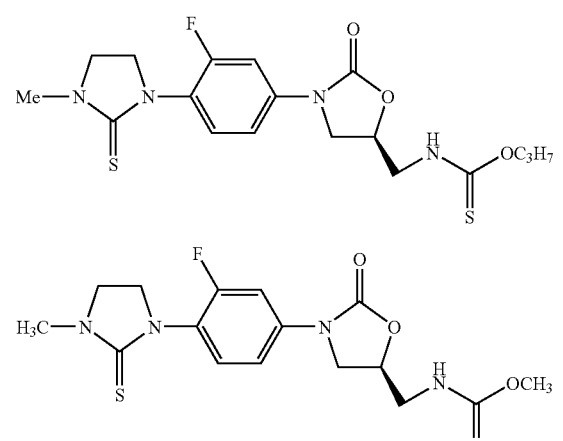
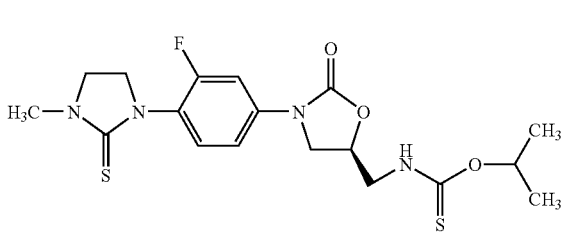
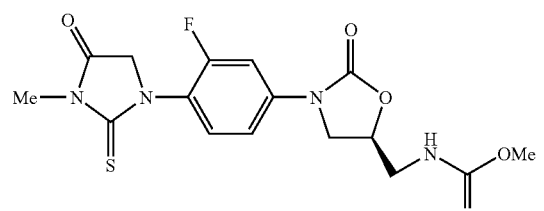
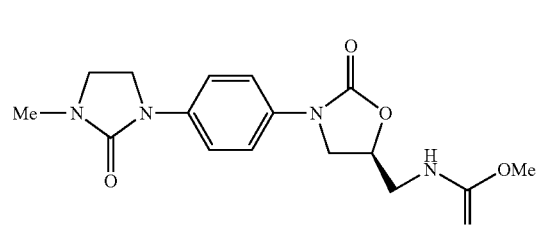
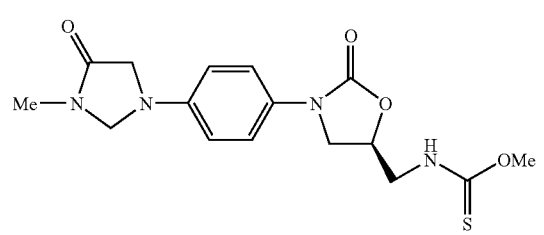
-continued
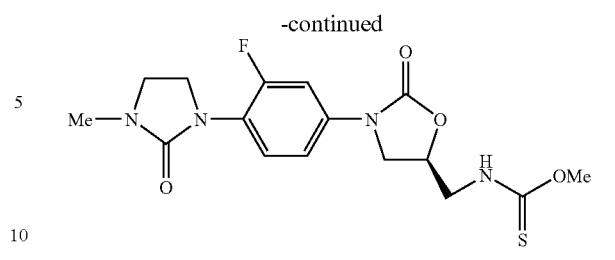
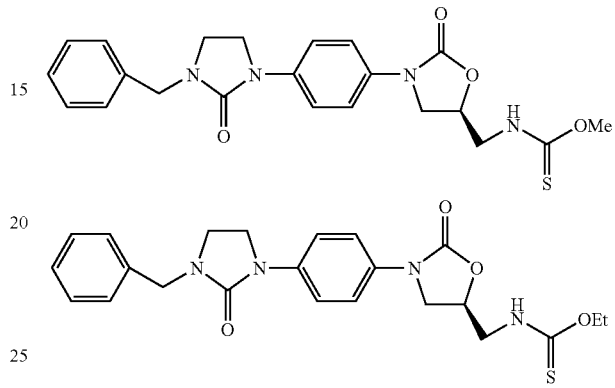
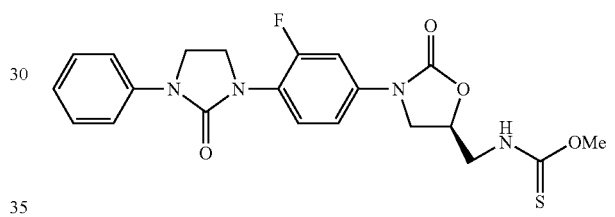
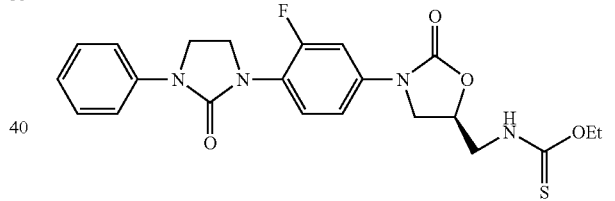
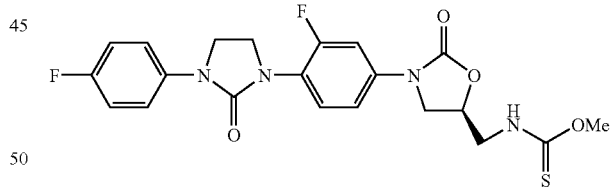
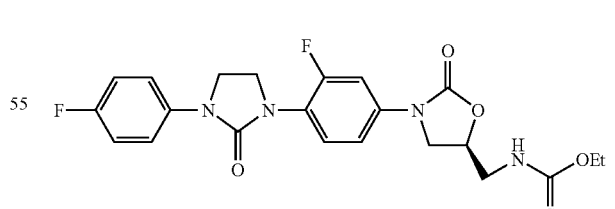
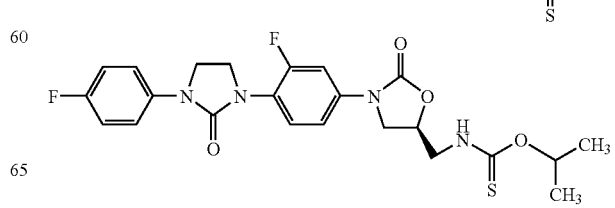

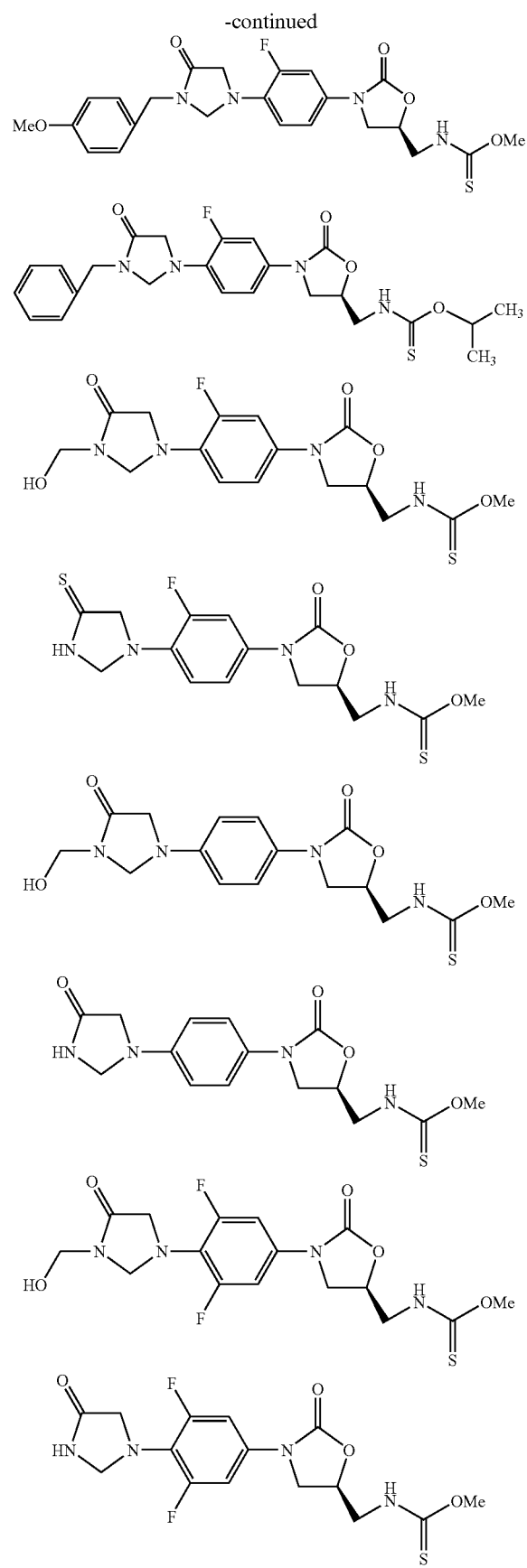
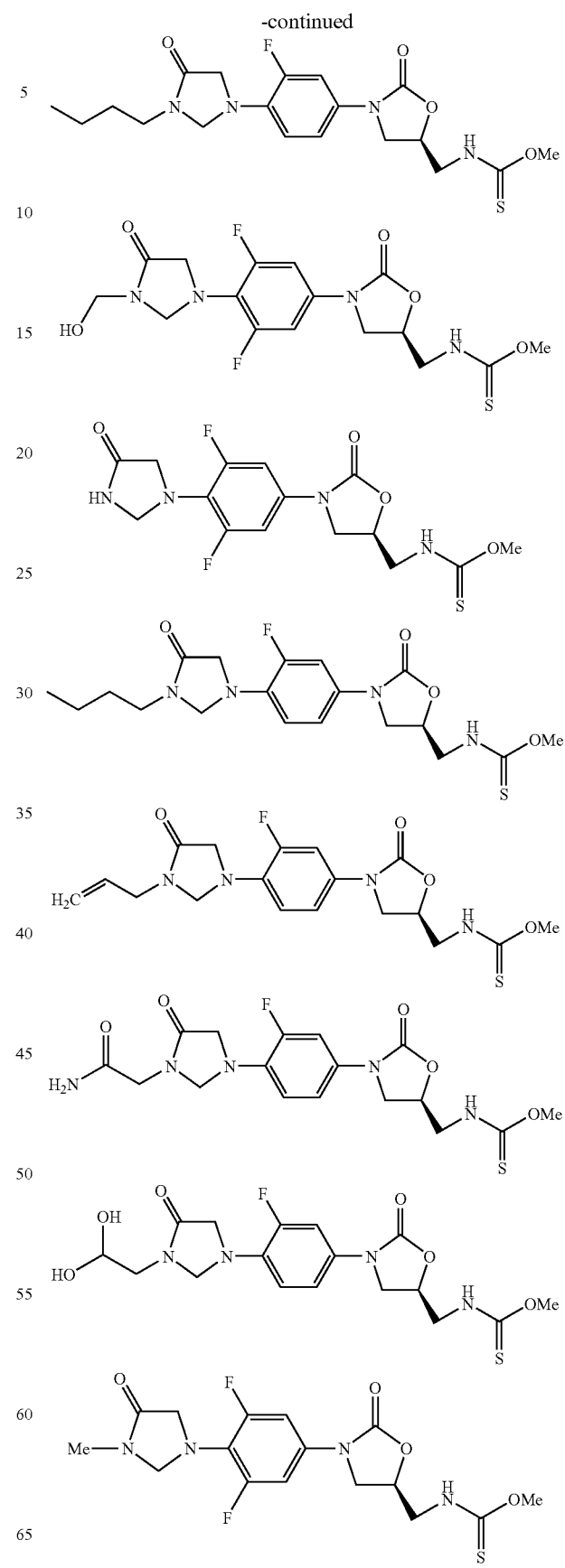

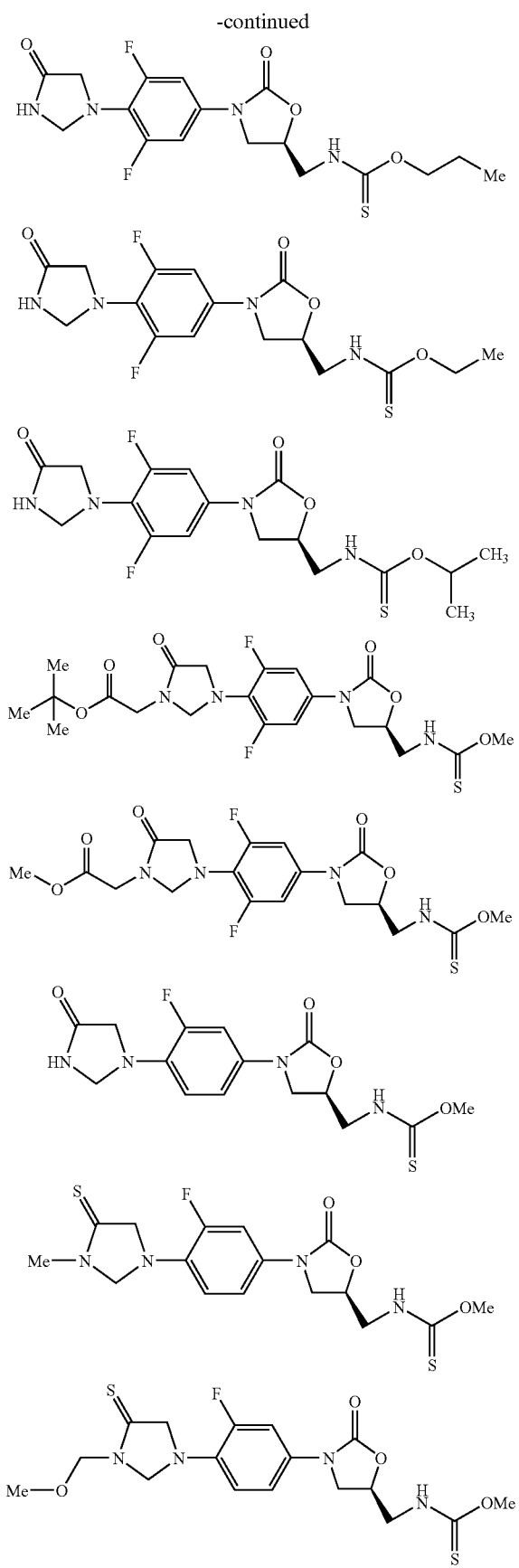
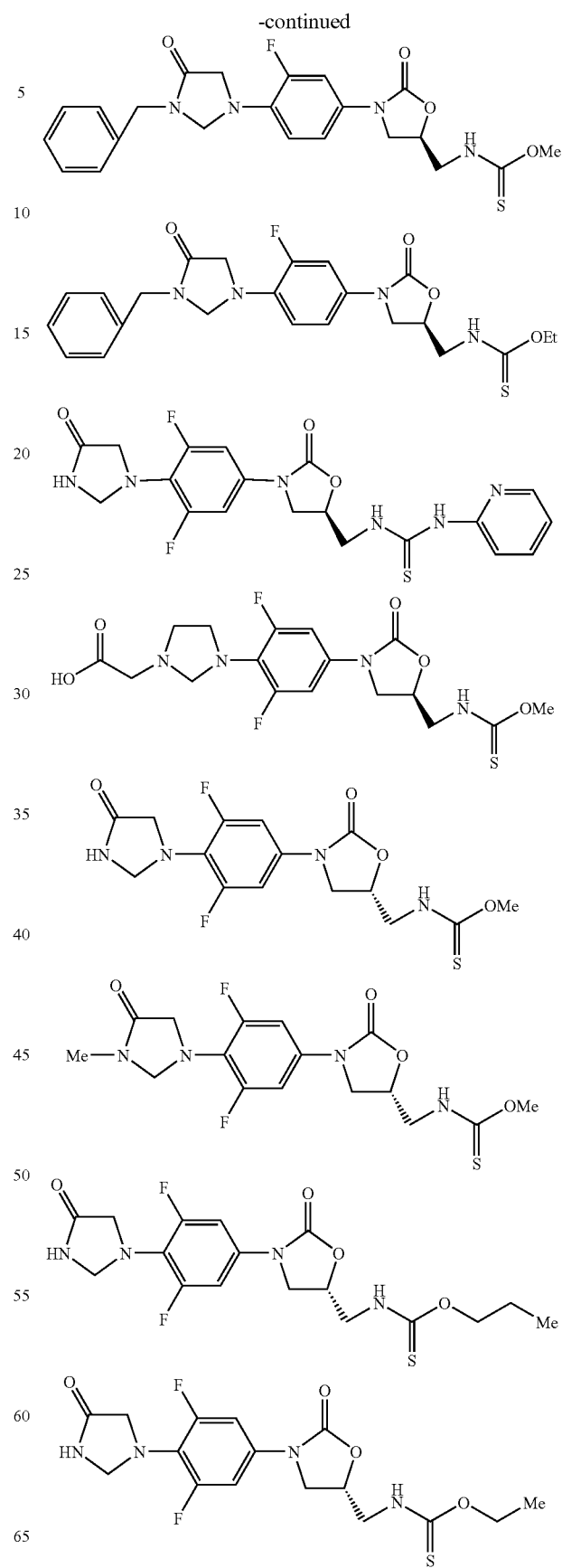

-continued

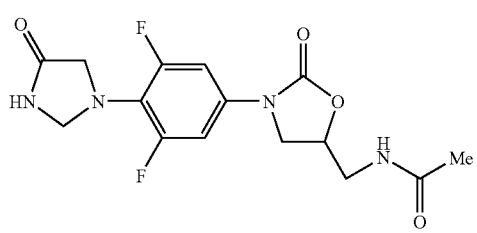

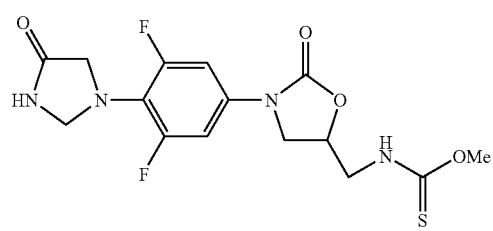

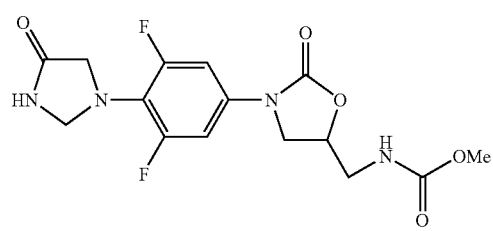

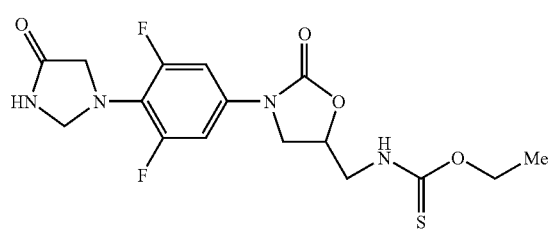

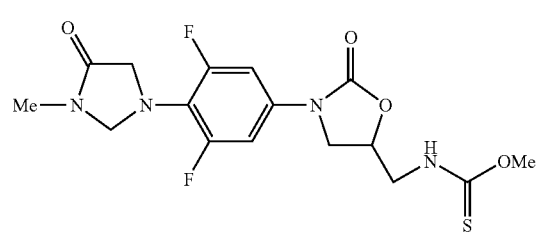

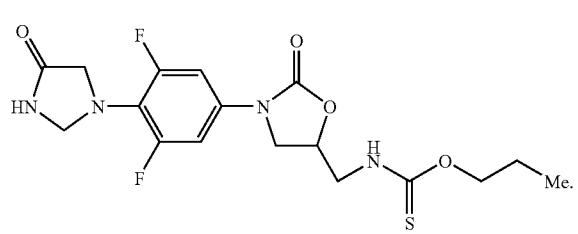

7. A pharmaceutical composition comprising a) an antibacterially effective amount of the compound of claim 1; and b) a pharmaceutically acceptable carrier.

8. The compound of claim 1, having the structure

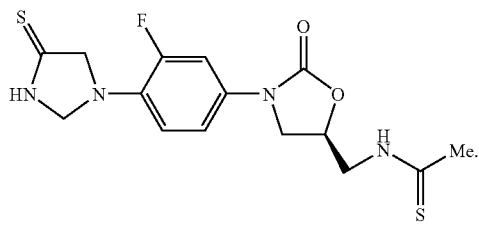

9. The compound of claim 1, having the structure

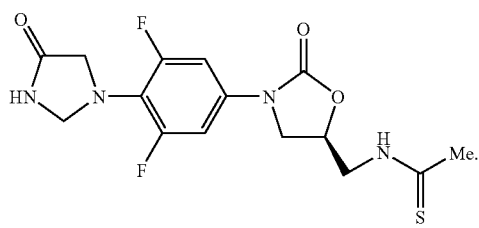

10. The compound of claim 1, having the structure

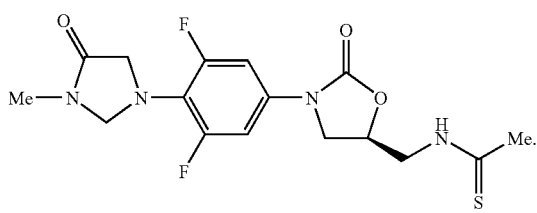

11. The compound of claim 1, having the structure

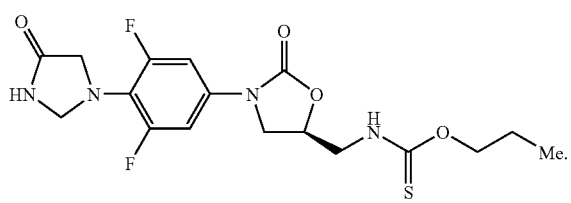

12. The compound of claim 1, having the structure

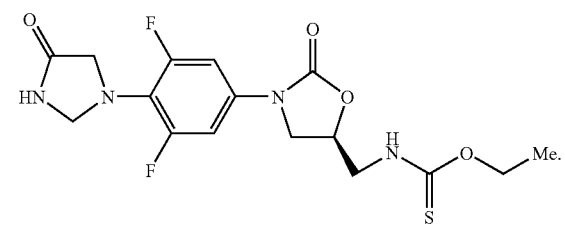

13. The compound of claim 1, having the structure

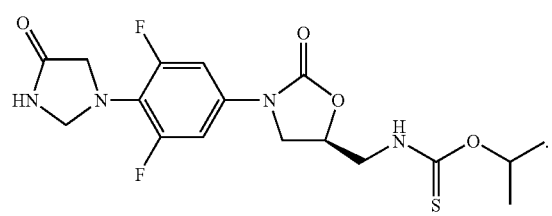

14. The compound of claim 1, having the structure

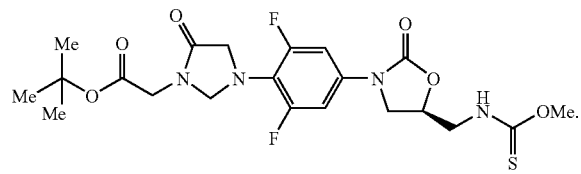

15. The compound of claim 1, having the structure

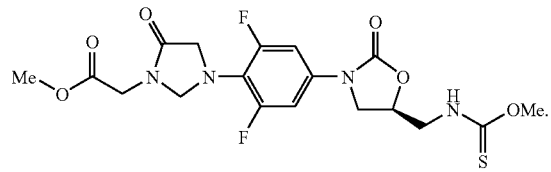

16. The compound of claim 1, having the structure

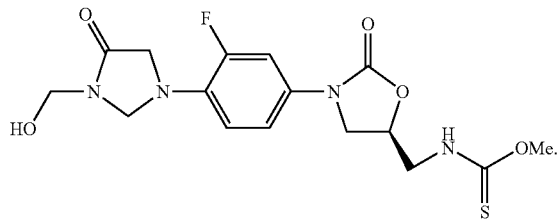

17. The compound of claim 1, having the structure

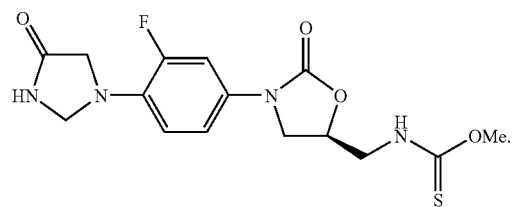

18. The compound of claim 1, having the structure

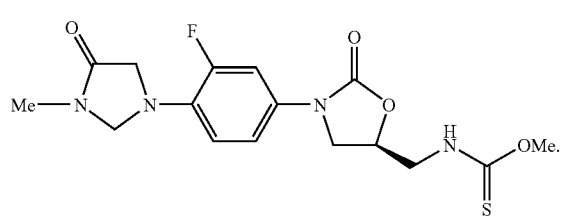

19. The compound of claim 1, having the structure

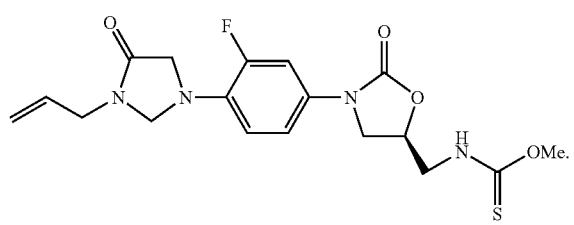

20. The compound of claim 1, having the structure

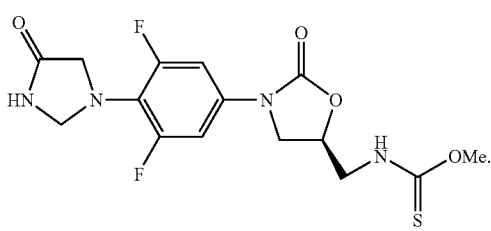

21. The compound of claim 1, having the structure

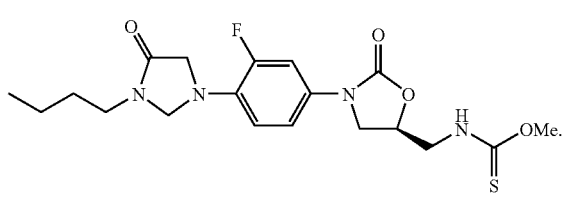

22. The compound of claim 1, having the structure

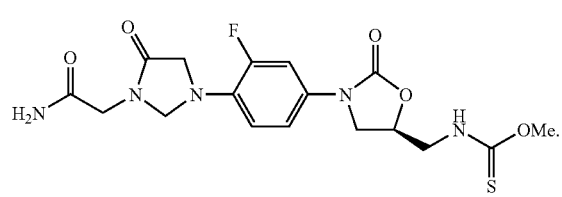

23. The compound of claim 1, having the structure

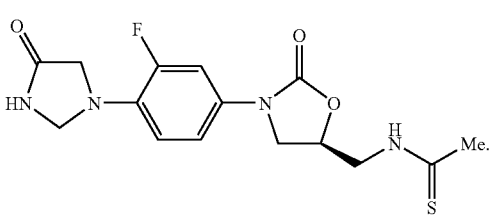

24. The compound of claim 1, having the structure

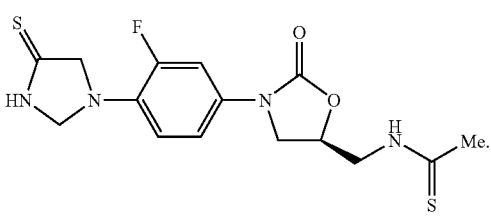

25. The compound of claim 1, having the structure

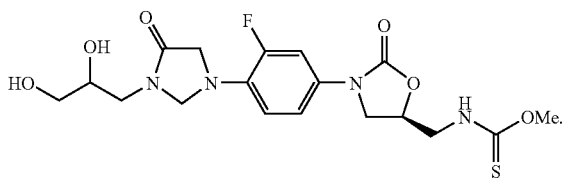

26. The compound of claim 1, having the structure
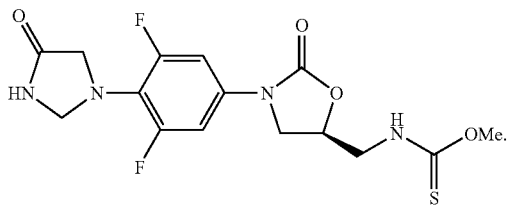
27. The compound of claim 1, having the structure
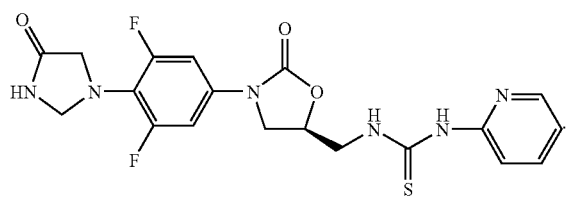
28. The compound of claim 1, having the structure
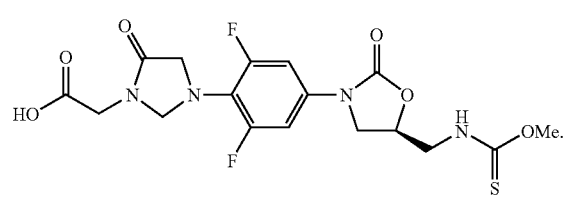
29. The compound of claim 1, having the structure
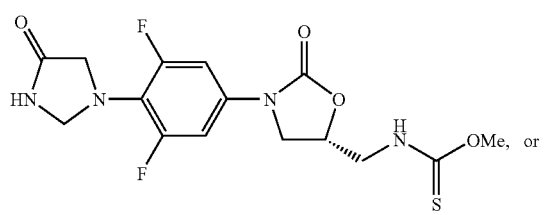
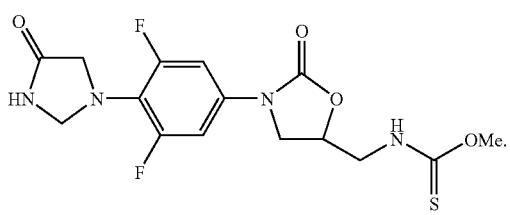
30. The compound of claim 1, having the structure
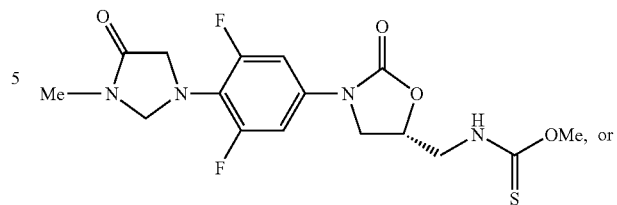
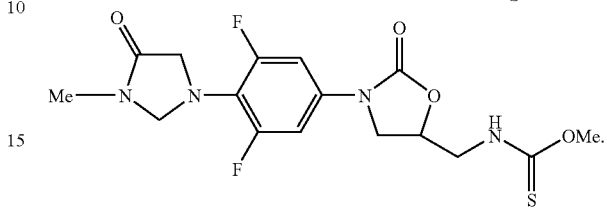
31. The compound of claim 1, having the structure
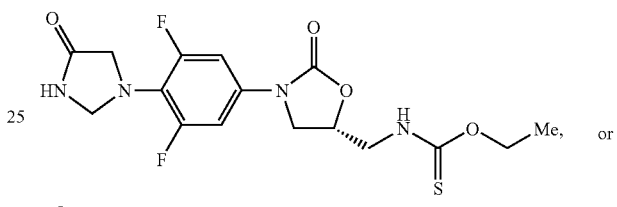
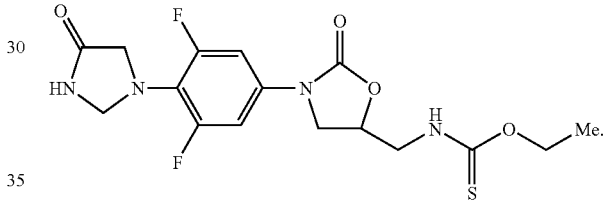
32. The compound of claim 1, having the structure
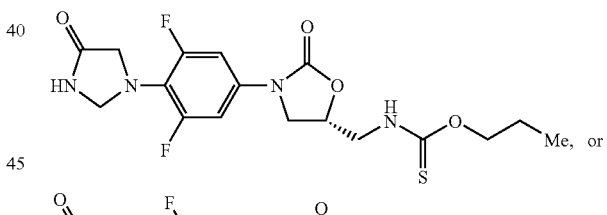
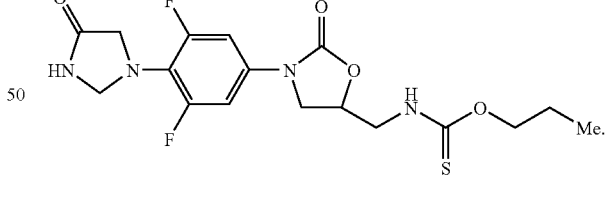
* * * * *